(12) United States Patent
Shin et al.

(10) Patent No.: US 9,583,718 B2
(45) Date of Patent: Feb. 28, 2017

(54) PYRENE-BASED COMPOUND AND ORGANIC LIGHT-EMITTING DIODE INCLUDING THE SAME

(71) Applicant: Samsung Display Co., Ltd., Yongin, Gyeonggi-Do (KR)

(72) Inventors: Dong-Woo Shin, Yongin (KR); O-Hyun Kwon, Yongin (KR); Mie-Hwa Park, Yongin (KR); Seul-Ong Kim, Yongin (KR); Byoung-Ki Choi, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 345 days.

(21) Appl. No.: 14/224,679

(22) Filed: Mar. 25, 2014

(65) Prior Publication Data
US 2014/0291646 A1    Oct. 2, 2014

(30) Foreign Application Priority Data

Mar. 27, 2013    (KR) .................. 10-2013-0033082

(51) Int. Cl.
*H01L 51/00* (2006.01)
*C07D 213/74* (2006.01)
(Continued)

(52) U.S. Cl.
CPC .......... *H01L 51/006* (2013.01); *C07D 213/74* (2013.01); *C07D 215/38* (2013.01);
(Continued)

(58) Field of Classification Search
None
See application file for complete search history.

(56) References Cited

U.S. PATENT DOCUMENTS

| 5,153,073 A | 10/1992 | Ohnuma et al. |
| 2010/0052526 A1 | 3/2010 | Je et al. |

(Continued)

FOREIGN PATENT DOCUMENTS

| KR | 10-2010-0017692 A | 2/2010 |
| KR | 10-2010-0024894 A | 3/2010 |

(Continued)

OTHER PUBLICATIONS

Takayoshi Suzuki, et al.; "Identification of G protein-coupled receptor 120-selective agonists derived from PPARγ agonists"; J. Med. Chem. 2008, 51, pp. 7640-7644.
(Continued)

*Primary Examiner* — J. L. Yang
(74) *Attorney, Agent, or Firm* — Lee & Morse, P.C.

(57) ABSTRACT

A pyrene-based compound and an organic light-emitting diode including the same, the pyrene-based compound being represented by Formula 1, below:

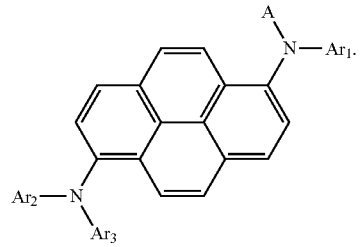

<Formula 1>

20 Claims, 1 Drawing Sheet

(51) Int. Cl.

| | |
|---|---|
| C07D 215/38 | (2006.01) |
| C07D 217/22 | (2006.01) |
| C07D 239/42 | (2006.01) |
| C07D 239/84 | (2006.01) |
| C07D 239/94 | (2006.01) |
| C07D 241/20 | (2006.01) |
| C07D 241/44 | (2006.01) |
| C07D 471/04 | (2006.01) |
| C09K 11/06 | (2006.01) |
| C07F 7/08 | (2006.01) |
| C09B 57/00 | (2006.01) |
| C09B 69/00 | (2006.01) |
| H01L 51/50 | (2006.01) |

(52) U.S. Cl.
CPC ......... *C07D 217/22* (2013.01); *C07D 239/42* (2013.01); *C07D 239/84* (2013.01); *C07D 239/94* (2013.01); *C07D 241/20* (2013.01); *C07D 241/44* (2013.01); *C07D 471/04* (2013.01); *C07F 7/0812* (2013.01); *C09B 57/001* (2013.01); *C09B 57/008* (2013.01); *C09B 69/008* (2013.01); *C09K 11/06* (2013.01); *H01L 51/0054* (2013.01); *H01L 51/0061* (2013.01); *C09K 2211/1007* (2013.01); *C09K 2211/1011* (2013.01); *C09K 2211/1029* (2013.01); *C09K 2211/1044* (2013.01); *H01L 51/0081* (2013.01); *H01L 51/5012* (2013.01)

(56) References Cited

U.S. PATENT DOCUMENTS

2010/0155714 A1*  6/2010  Seo ................. C09K 11/06
257/40
2011/0193064 A1  8/2011  Funahashi

FOREIGN PATENT DOCUMENTS

| KR | 10-2010-0075101 A | 7/2010 |
| KR | 10-2011-0015213 A | 2/2011 |
| KR | 10-2011-0072041 A | 6/2011 |

OTHER PUBLICATIONS

Song Eun Park, et al.; "Efficient Palladium-Catalyzed Amination of Aryl Chlorides Using Dicyclohexylamino[2,6-dimethyl_morpholino]phenylphosphine as a PN$_2$ Ligand" I Synthesis 1009, No. 5, pp. 0815-0823.

Raimo Saari, et al.; "Microwave-assisted synthesis of quinolone, isoquinoline, quinoxaline and quinazoline derivatives as CB2 receptor agonists"; Biorganic and Medicinal Chemistry 19 (2011) pp. 939-950.

* cited by examiner

PYRENE-BASED COMPOUND AND ORGANIC LIGHT-EMITTING DIODE INCLUDING THE SAME

CROSS-REFERENCE TO RELATED APPLICATION

Korean Patent Application No. 10-2013-0033082, filed on Mar. 27, 2013, in the Korean Intellectual Property Office, and entitled: "Pyrene-Based Compound and Organic Light-Emitting Diode Including the Same," is incorporated by reference herein in its entirety.

BACKGROUND

1. Field

Embodiments relates to a pyrene-based compound and an organic light-emitting diode including the same.

2. Description of the Related Art

Organic light-emitting diodes (OLEDs), which are self-emitting devices, may have advantages such as wide viewing angles, excellent contrast, quick response, high brightness, excellent driving voltage characteristics, and a may provide multicolored images.

SUMMARY

Embodiments are directed to a pyrene-based compound and an organic light-emitting diode including the same.

The embodiments may be realized by providing a pyrene-based compound represented by Formula 1, below:

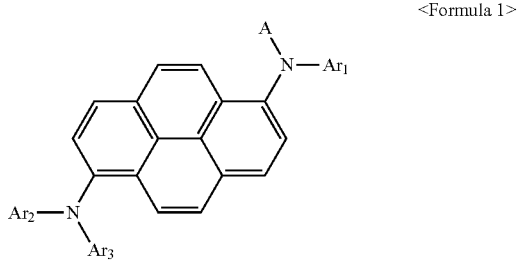

<Formula 1> wherein, in Formula 1, A is a substituted or unsubstituted $C_2$-$C_{30}$ heteroaromatic group including at least one nitrogen (N); and $Ar_1$, $Ar_2$, and $Ar_3$ are each independently a substituted or unsubstituted phenyl group or a substituted or unsubstituted naphthyl group.

A may be selected from a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted isoquinolinyl group, a substituted or unsubstituted quinolinyl group, a substituted or unsubstituted phthalazinyl group, a substituted or unsubstituted quinoxalinyl group, a substituted or unsubstituted quinazolinyl group, a substituted or unsubstituted cinnolinyl group, and a substituted or unsubstituted 1,10-phenanthrolinyl group.

A may be selected from a pyridinyl group, a pyrimidinyl group, a triazinyl group, a pyrazinyl group, a pyridazinyl group, an isoindolyl group, an indolyl group, an indazolyl group, an isoquinolinyl group, a quinolinyl group, a phthalazinyl group, a quinoxalinyl group, a cinnolinyl group, and a 1,10-phenanthrolinyl group; or a pyridinyl group, a pyrimidinyl group, a triazinyl group, a pyrazinyl group, a pyridazinyl group, an isoindolyl group, an indolyl group, an indazolyl group, an isoquinolinyl group, a quinolinyl group, a phthalazinyl group, a quinoxalinyl group, a cinnolinyl group, and a 1,10-phenanthrolinyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group, or —Si($Q_{11}$)($Q_{12}$)($Q_{13}$), in which $Q_{11}$ to $Q_{13}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group.

A may be a group represented by one of Formulae 2A to 2K below:

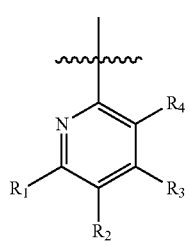

Formula 2A

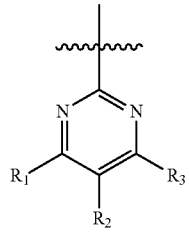

Formula 2B

Formula 2C
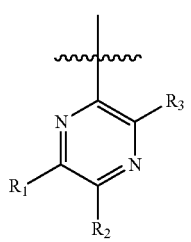

Formula 2D
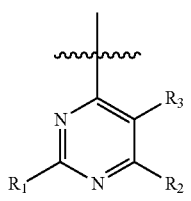

Formula 2E
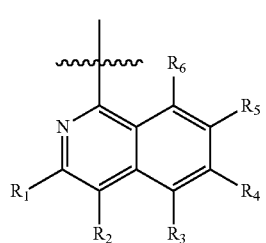

Formula 2F
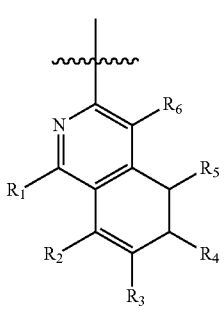

Formula 2G
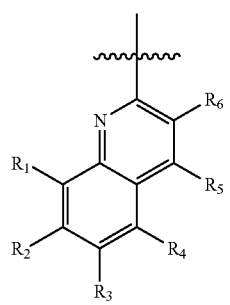

Formula 2H
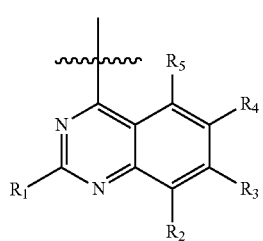

Formula 2I
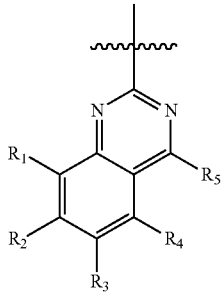

Formula 2J
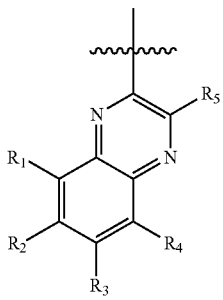

Formula 2K
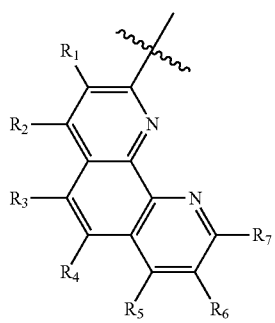

wherein, in Formulae 2A to 2K, $R_1$ to $R_7$ are each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof; a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group; a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group; and —Si($Q_{11}$)($Q_{12}$)($Q_{13}$), in which $Q_{11}$ to $Q_{13}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group.

$R_1$ to $R_7$ may each independently be selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a $C_1$-$C_{10}$ alkyl group; a $C_1$-$C_{60}$ alkyl group substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof; a $C_6$-$C_{16}$ aryl group, and a $C_2$-$C_{16}$ heteroaryl group; a $C_6$-$C_{16}$ aryl group or a $C_2$-$C_{16}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{10}$ alkyl group, phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group; and —Si($Q_{11}$)($Q_{12}$)($Q_{13}$), in which $Q_{11}$ to $Q_{13}$ are each independently a $C_1$-$C_{10}$ alkyl group, a $C_6$-$C_{16}$ aryl group, or a $C_2$-$C_{16}$ heteroaryl group.

$R_1$ to $R_7$ may each independently be selected from a hydrogen atom, a deuterium atom, F, Cl, Br, I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a methyl group, an ethyl group, a propyl group, a butyl group, a pentyl group, and a hexyl group; a phenyl group, a naphthyl group, and an anthracenyl group; and a phenyl group, a naphthyl group, and an anthracenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a methyl group, an ethyl group, a propyl group, a butyl group, a pentyl group, a hexyl group, phenyl group, a naphthyl group, an anthracenyl group, a fluorenyl group, a dimethylfluorenyl group, a diphenylfluorenyl group, a carbazolyl group, and a phenylcarbazolyl group.

A may have a structure selected from one of the following structures:

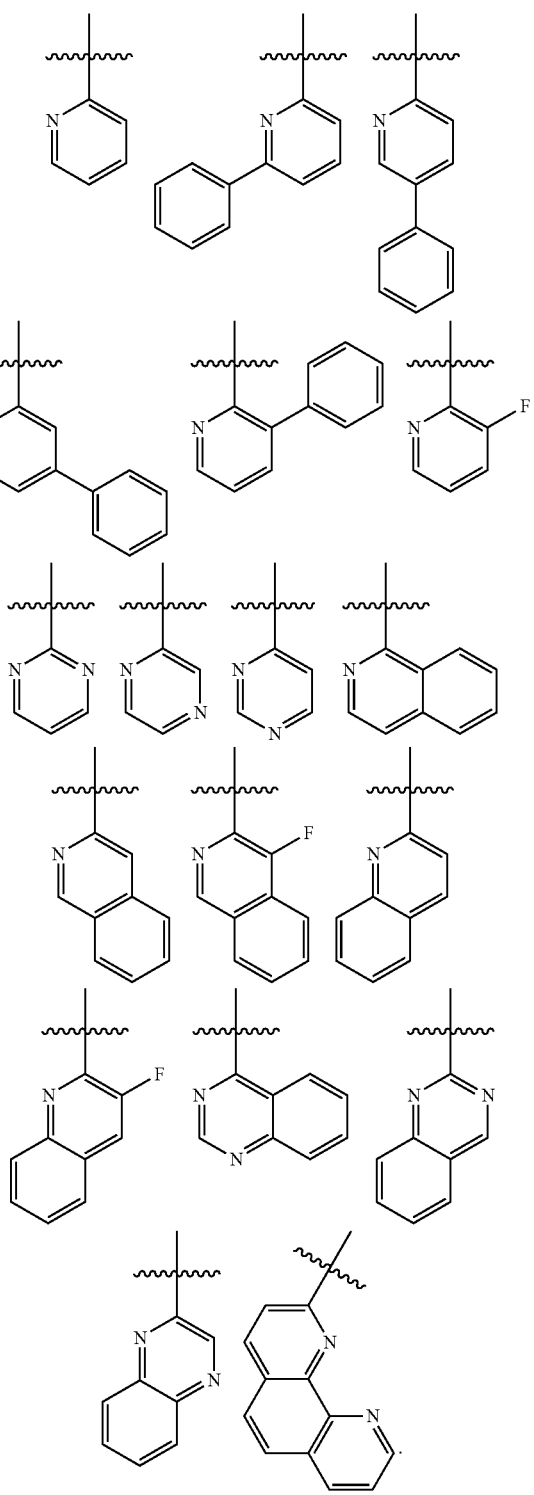

$Ar_1$, $Ar_2$, and $Ar_3$ may each independently be selected from a phenyl group and a naphthyl group; and a phenyl group and a naphthyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group, and $-Si(Q_{11})(Q_{12})(Q_{13})$, in which $Q_{11}$ to $Q_{13}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group.

$Ar_1$, $Ar_2$, and $Ar_3$ may each independently be selected from a phenyl group and a naphthyl group; and a phenyl group and a naphthyl group, each substituted with at least one of a deuterium atom, F, Cl, Br, I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof and a methyl group, an ethyl group, a propyl group, a butyl group, a pentyl group, and a hexyl group, a phenyl group, a naphthyl group, and an anthracenyl group, and a phenyl group, a naphthyl group, and an anthracenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a methyl group, an ethyl group, a propyl group, a butyl group, a pentyl group, a hexyl group, phenyl group, a naphthyl group, an anthracenyl group, a fluorenyl group, a dimethylfluorenyl group, a diphenylfluorenyl group, a carbazolyl group, and a phenylcarbazolyl group.

$Ar_1$ may be selected from one of the following structures:

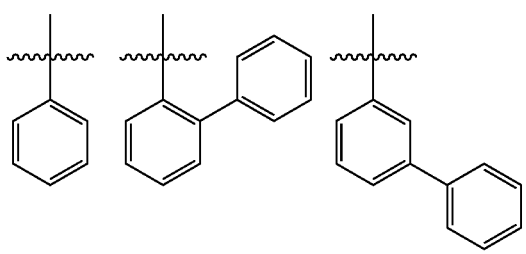

-continued

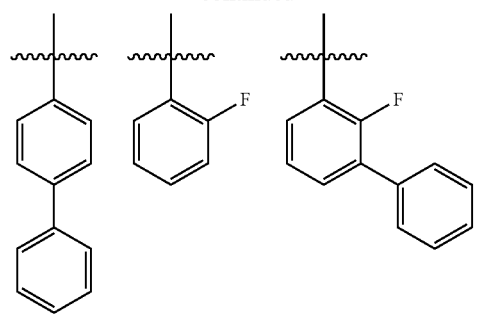

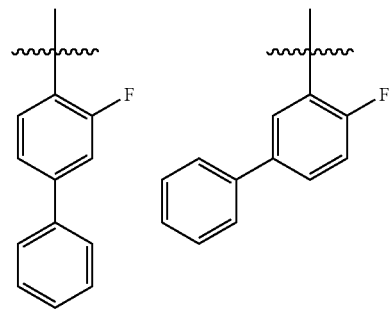

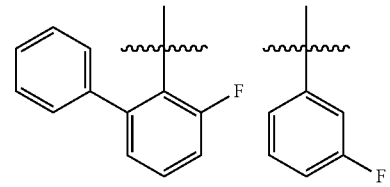

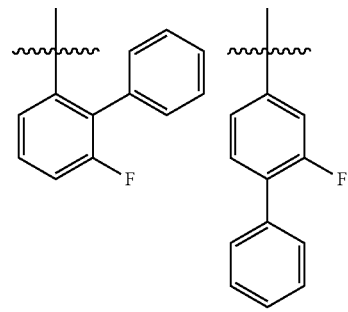

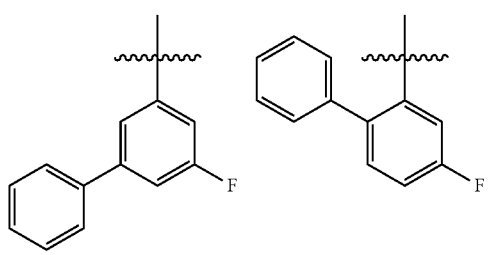

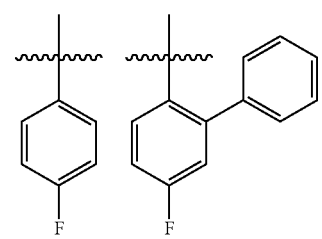

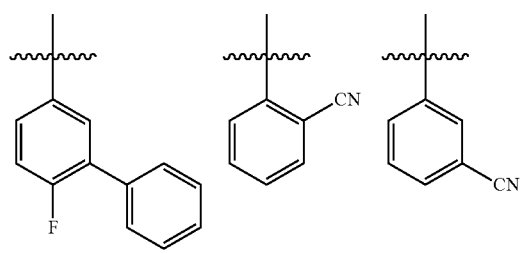
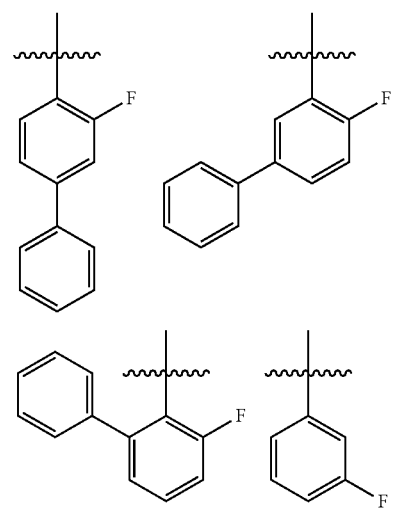
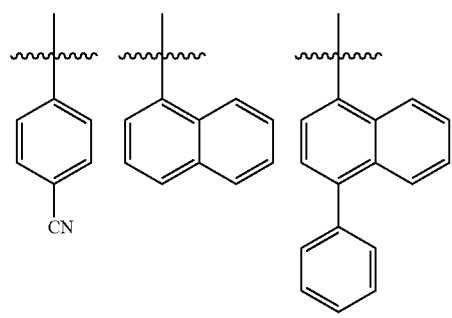
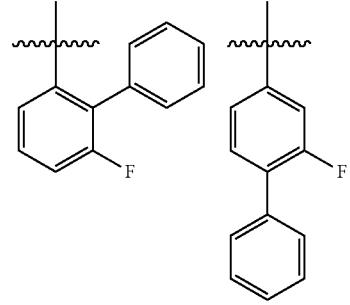
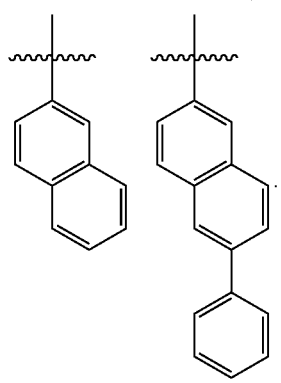
$Ar_2$ and $Ar_3$ may each independently be selected from one of the following structures:
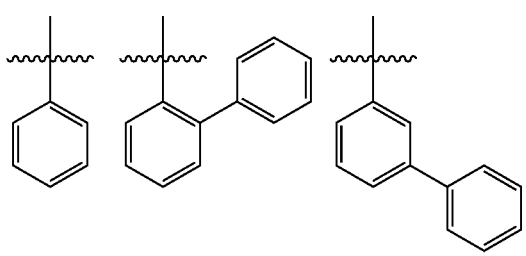
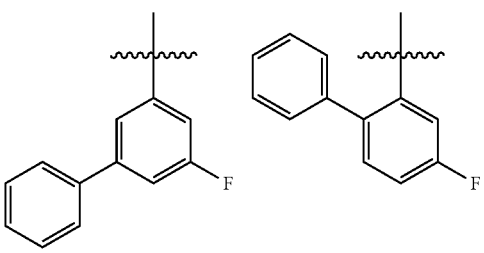
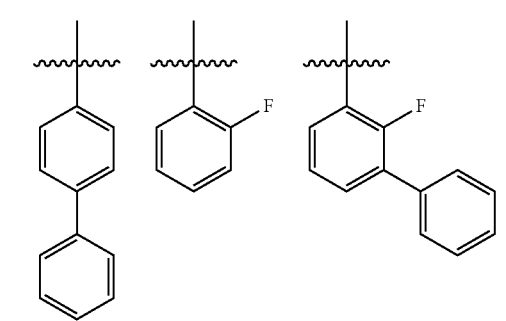
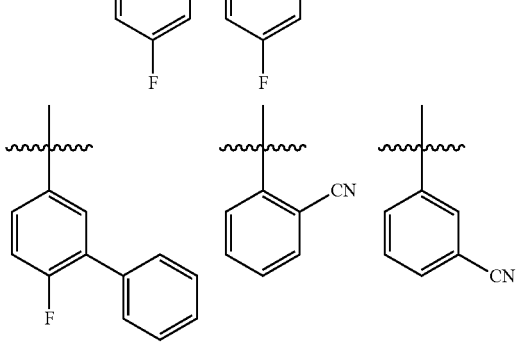

-continued

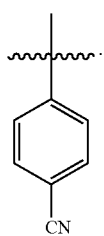

Ar₁ may be a substituted or unsubstituted phenyl group or a substituted or unsubstituted a naphthyl group, and Ar₂ and Ar₃ are a substituted or unsubstituted phenyl group.

The pyrene-based compound may be represented by one of Formulae 1A, 1B, or 1C, below:

<Formula 1A>

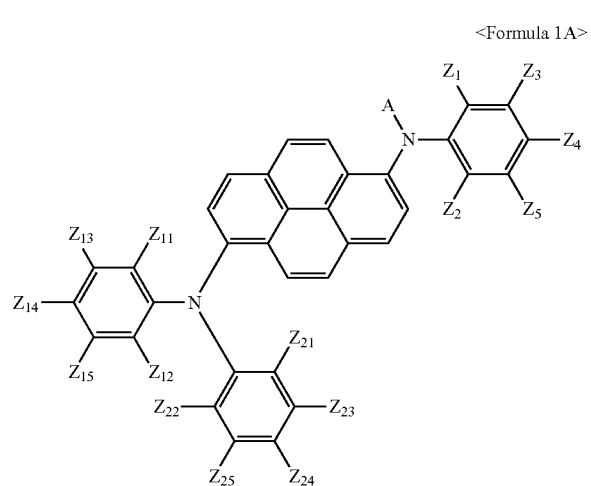

<Formula 1B>

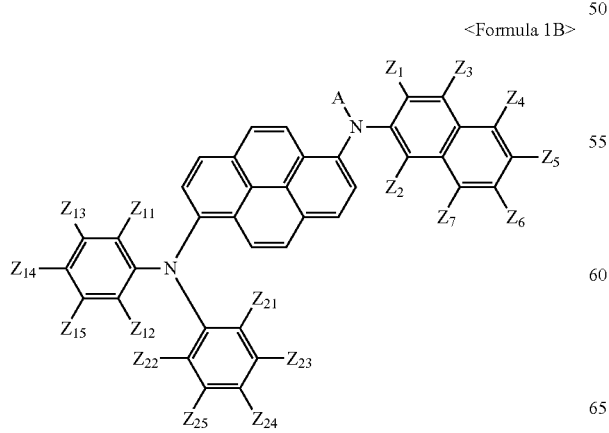

<Formula 1C>

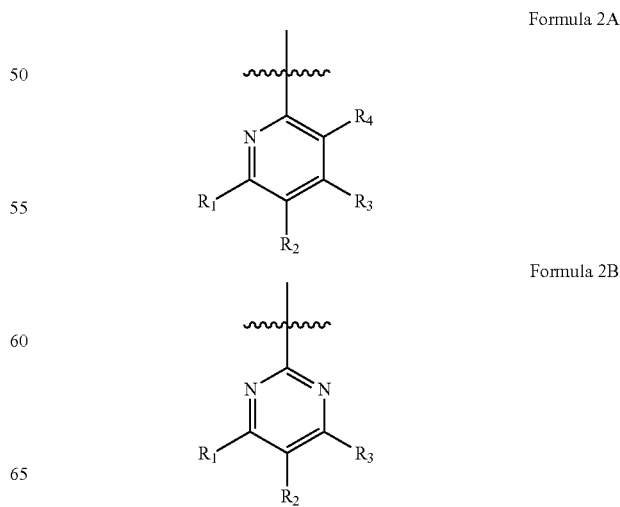

wherein, in Formulae 1A, 1B, and 1C, A is a substituted or unsubstituted $C_2$-$C_{30}$ heteroaromatic group including at least one nitrogen (N); and $Z_1$ to $Z_7$, $Z_{11}$ to $Z_{15}$ and $Z_{21}$ to $Z_{25}$ are each independently selected from a hydrogen atom, a deuterium atom, F, Cl, Br, I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a methyl group, an ethyl group, a propyl group, a butyl group, a pentyl group, and a hexyl group; a phenyl group, a naphthyl group, and an anthracenyl group; and a phenyl group, a naphthyl group, and an anthracenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a methyl group, an ethyl group, a propyl group, a butyl group, a pentyl group, a hexyl group, phenyl group, a naphthyl group, an anthracenyl group, a fluorenyl group, a dimethylfluorenyl group, a diphenylfluorenyl group, a carbazolyl group and a phenylcarbazolyl group.

A may be represented by one of Formulae 2A to 2K, below:

-continued

Formula 2C
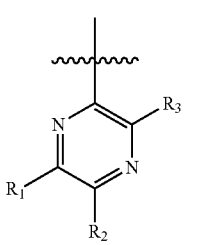

Formula 2D
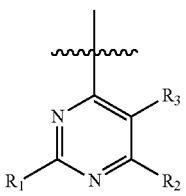

Formula 2E
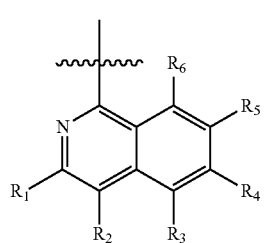

Formula 2F
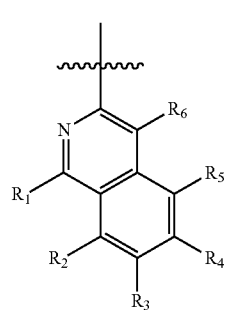

Formula 2G
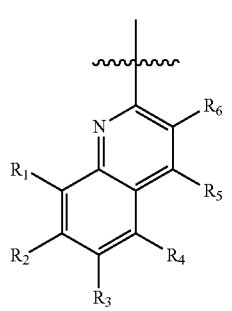

Formula 2H
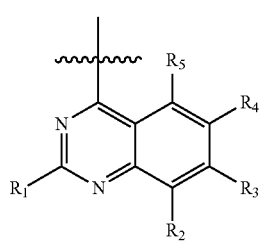

Formula 2I
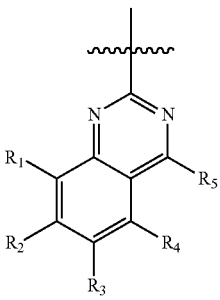

Formula 2J
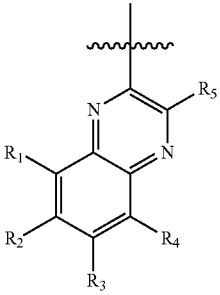

Formula 2K
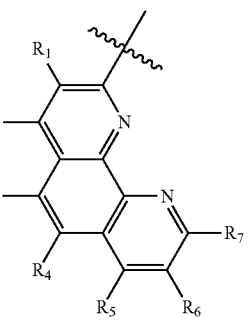

wherein, in Formulae 2A to 2K, $R_1$ to $R_7$ are each independently selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a $C_1$-$C_{10}$ alkyl group; a $C_1$-$C_{60}$ alkyl group substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof; a $C_6$-$C_{16}$ aryl group and a $C_2$-$C_{16}$ heteroaryl group; a $C_6$-$C_{16}$ aryl group and a $C_2$-$C_{16}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{10}$ alkyl group, phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group; and —Si($Q_{11}$)($Q_{12}$)($Q_{13}$), in which $Q_{11}$ to $Q_{13}$ are each independently a $C_1$-$C_{10}$ alkyl group, a $C_6$-$C_{16}$aryl group, or a $C_2$-$C_{16}$ heteroaryl group.

$R_1$ to $R_7$, $Z_1$ to $Z_7$, $Z_{11}$ to $Z_{15}$ and $Z_{21}$ to $Z_{25}$ may each independently be a hydrogen atom, a F atom, a cyano group, or a phenyl group.
The pyrene-based compound may be one of Compounds 1 to 96, below:
1
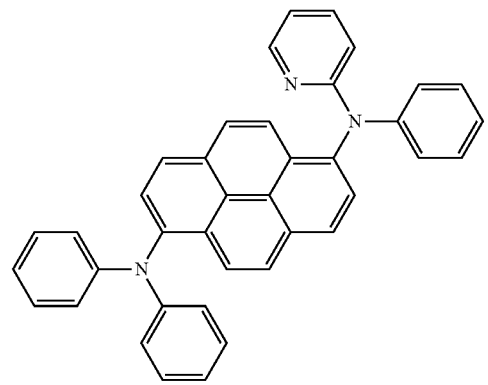
2
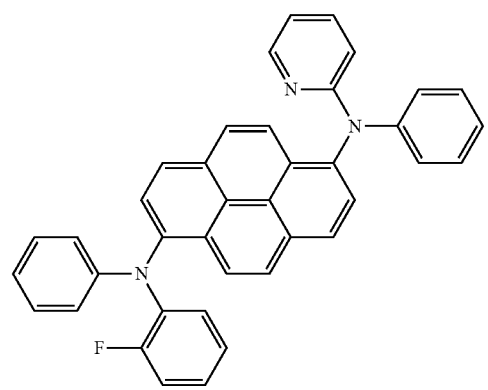
3
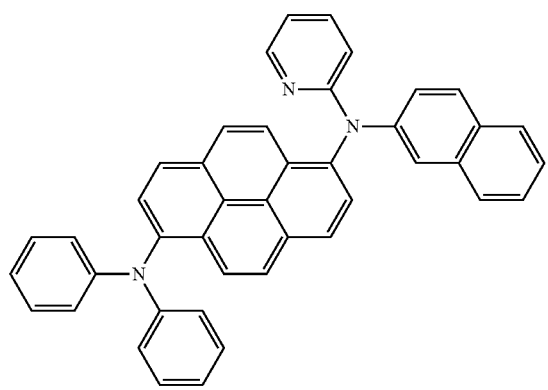
4
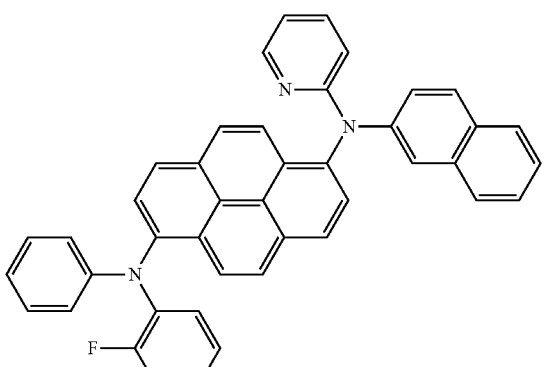
5
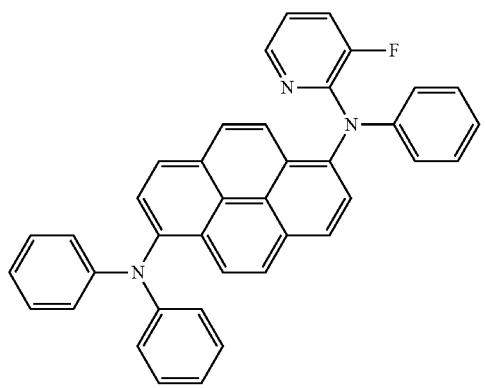
6
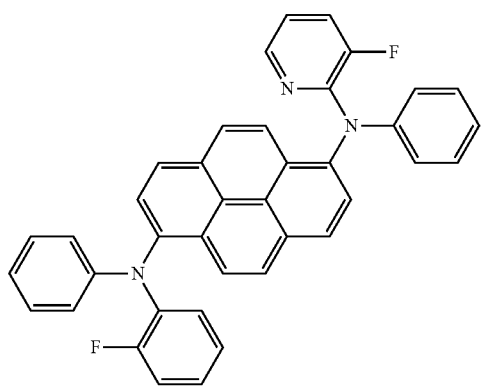
7
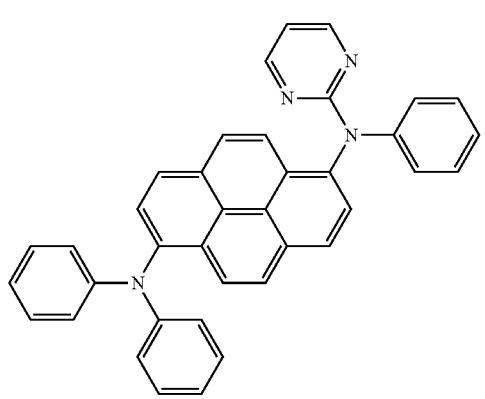

8
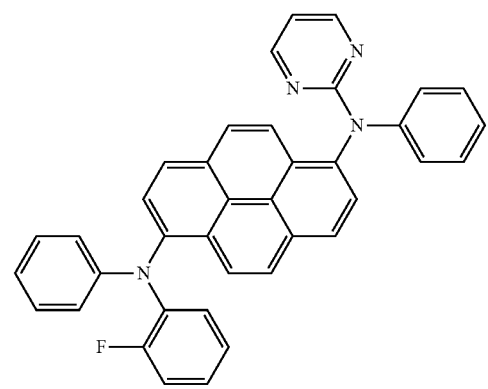
9
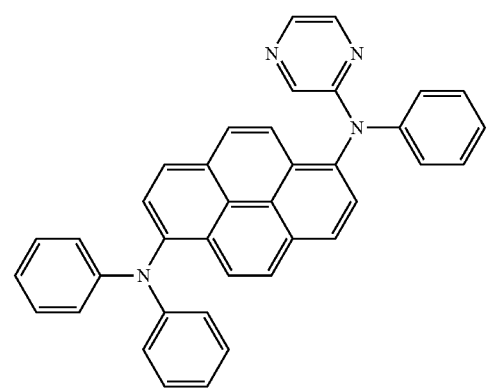
10
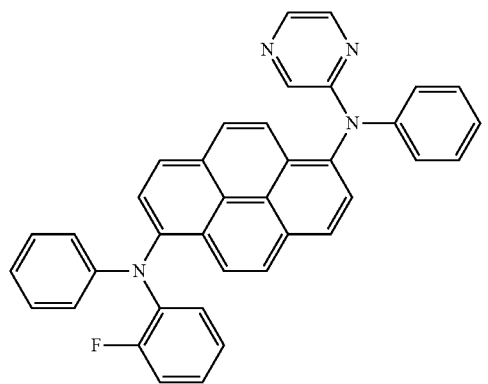
11
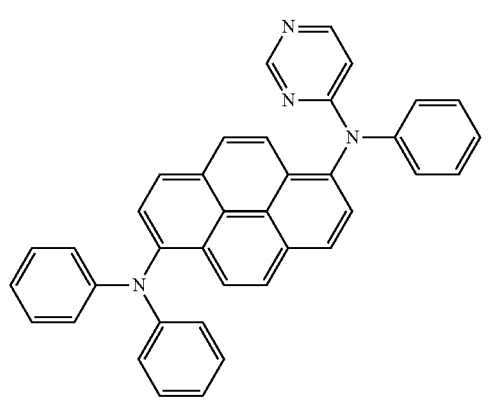
12
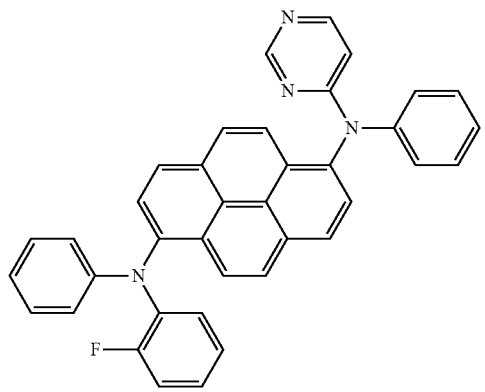
13
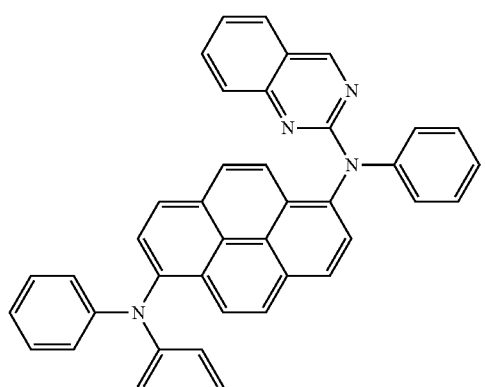
14
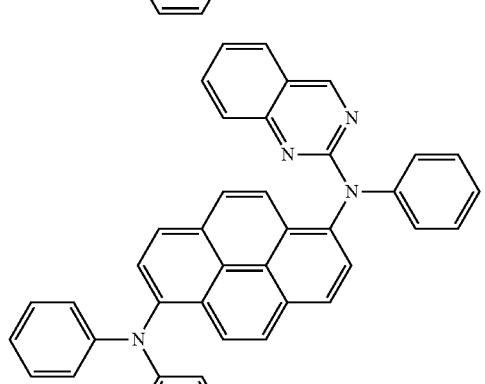
15
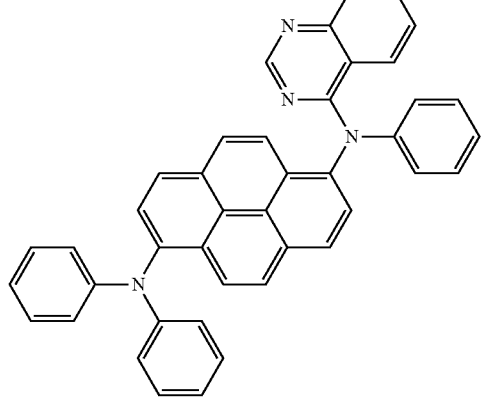

-continued
16
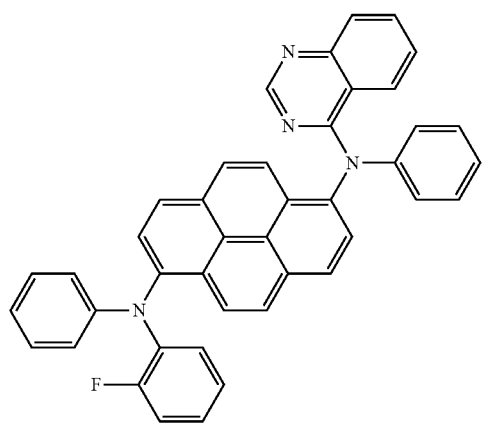
17
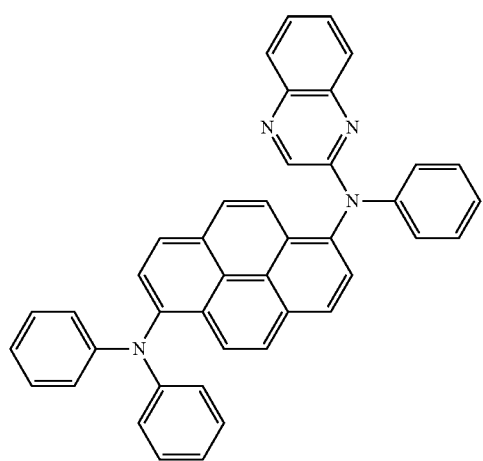
18
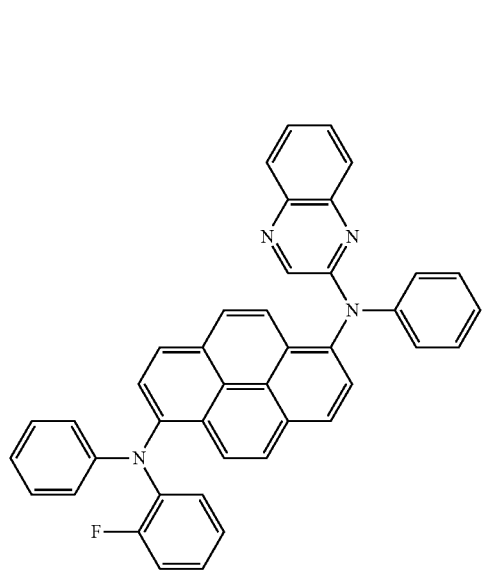
-continued
19
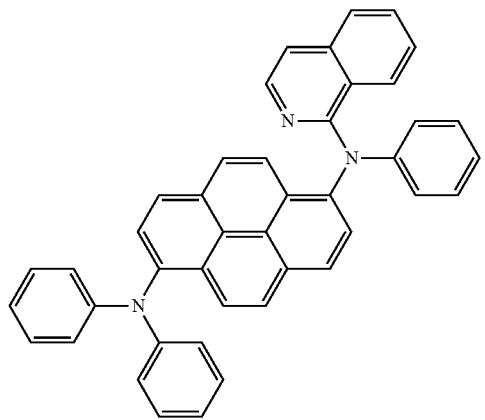
20
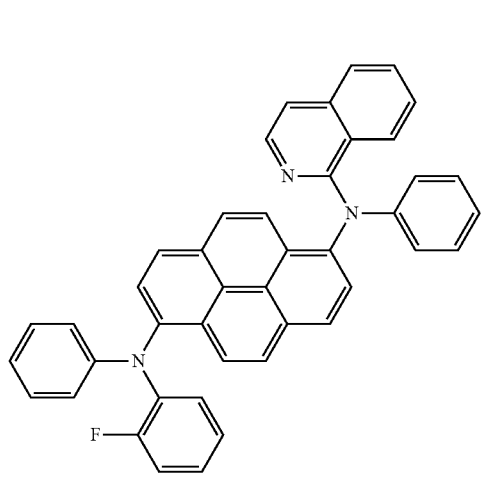
21
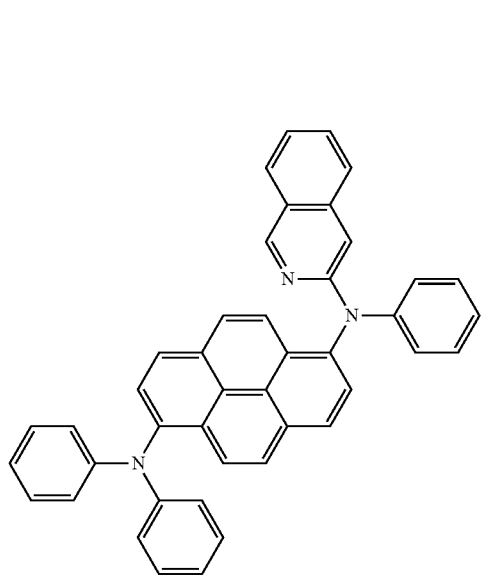

-continued
22
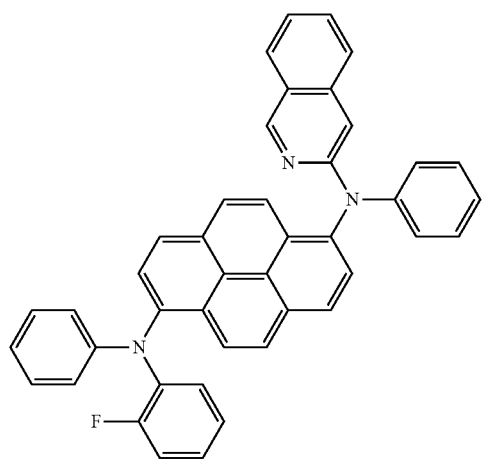
23
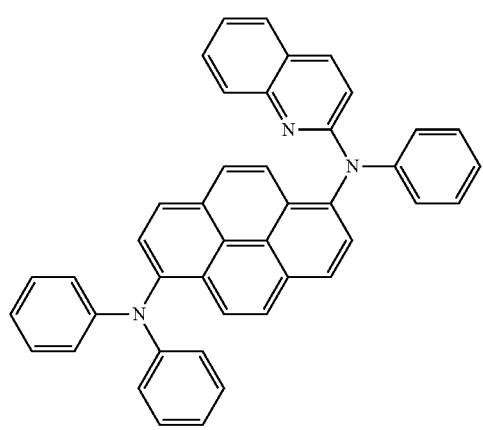
24
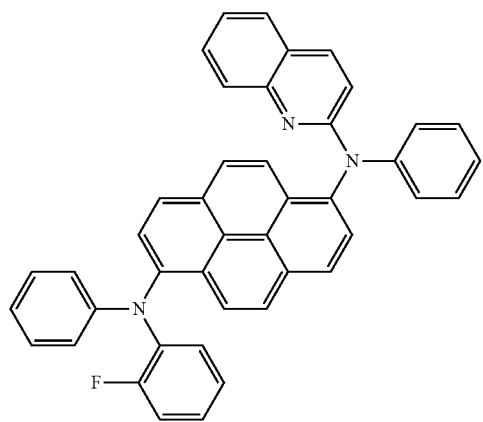
-continued
25
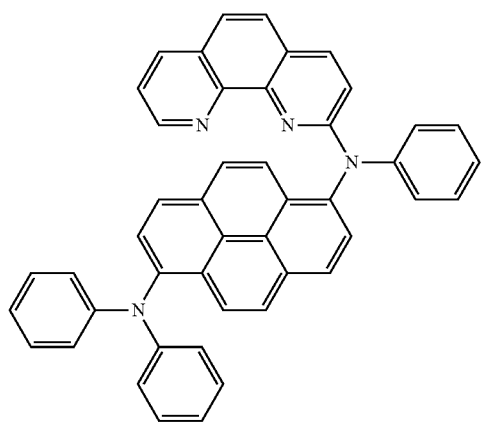
26
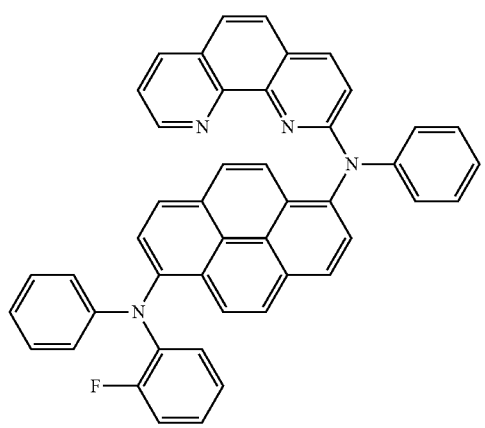
27
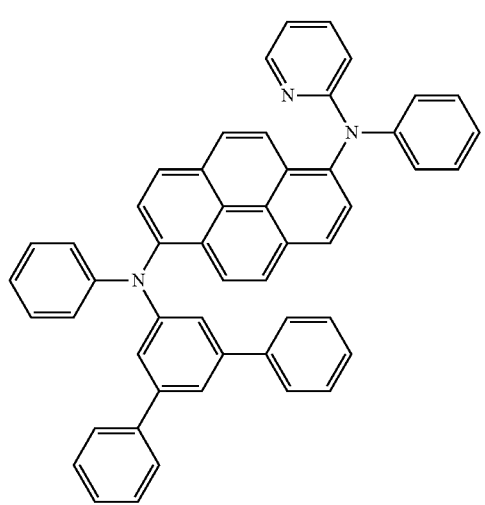

28
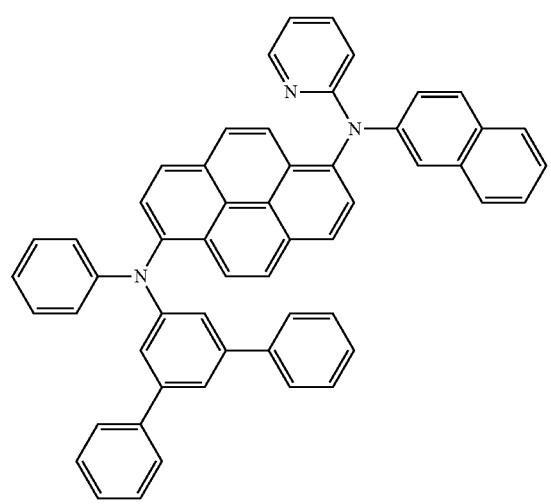
29
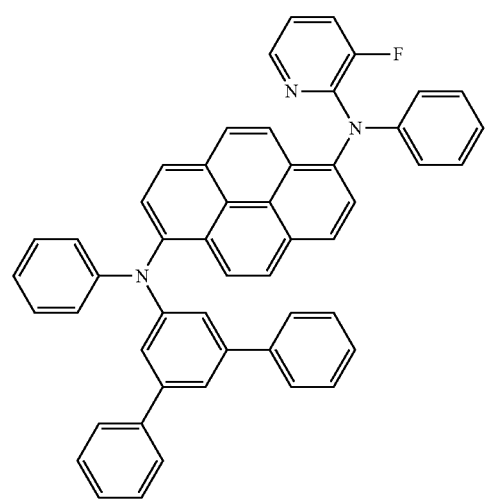
30
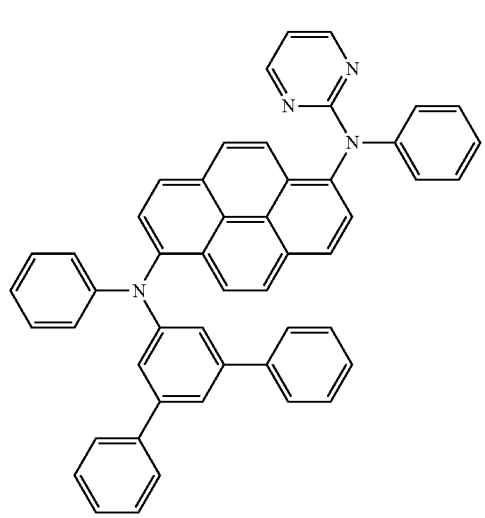
31
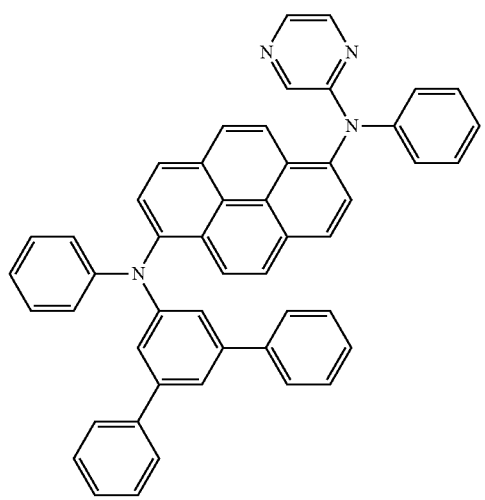
32
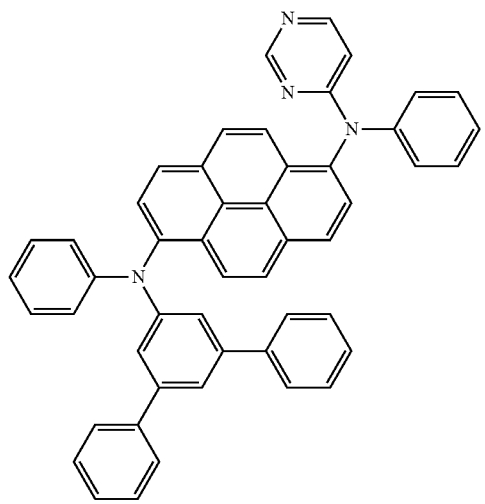
33
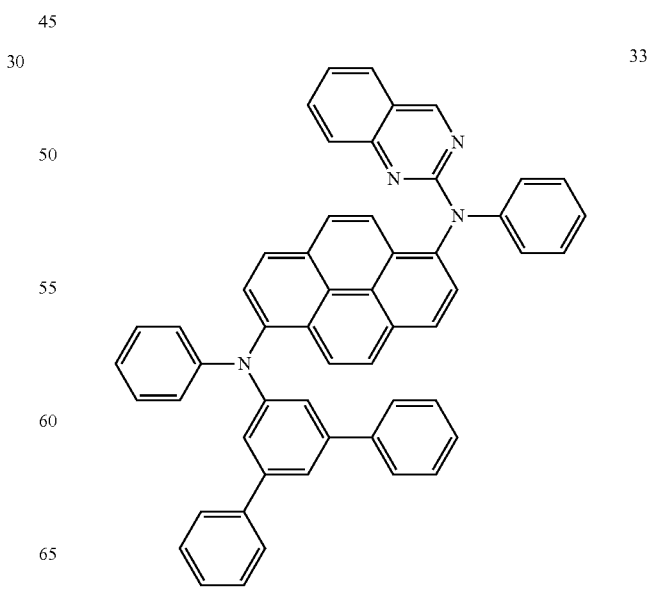

34
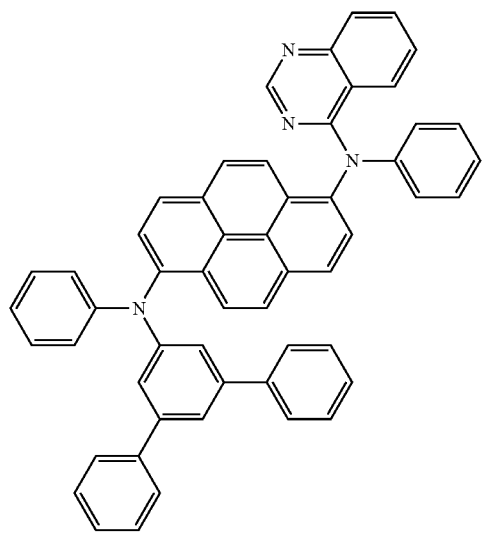
35
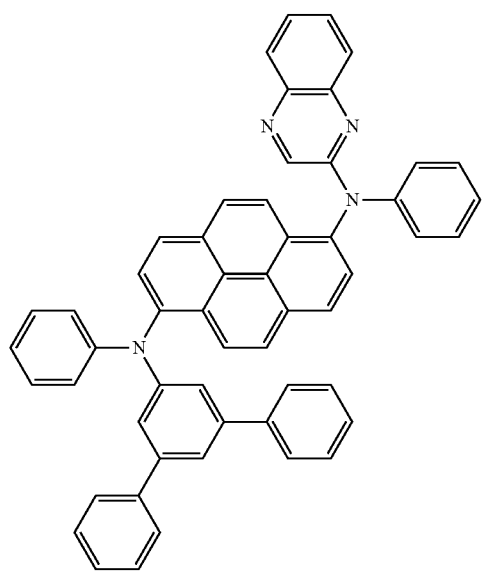
36
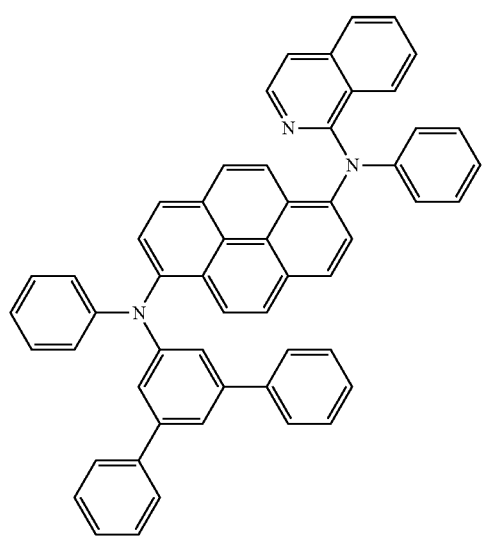
37
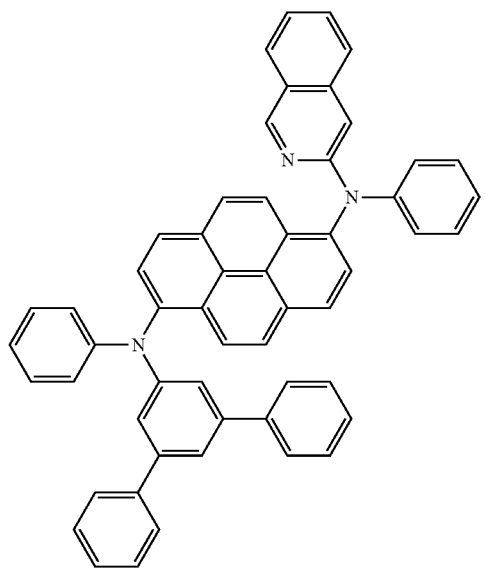
38
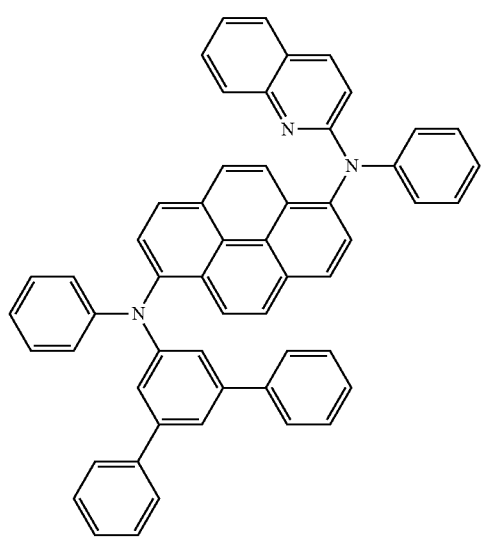
39
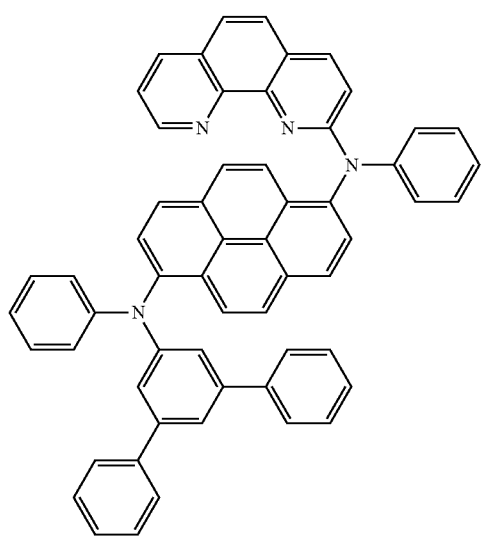

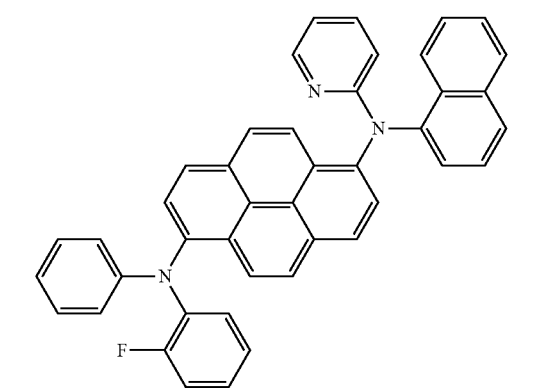
40
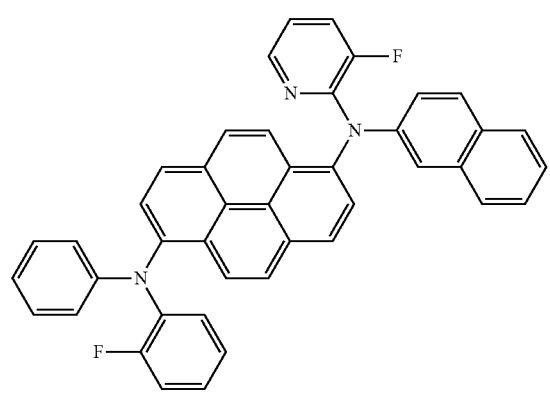
41
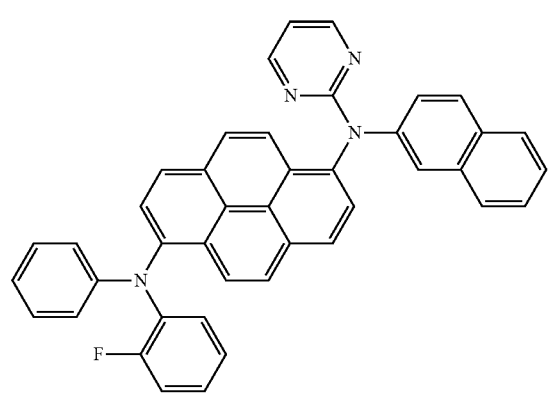
42
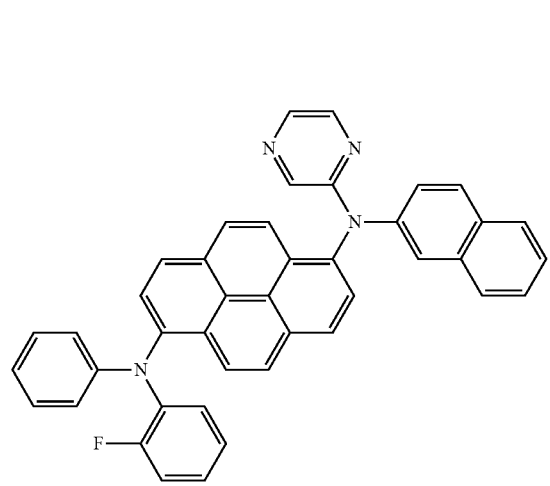
43
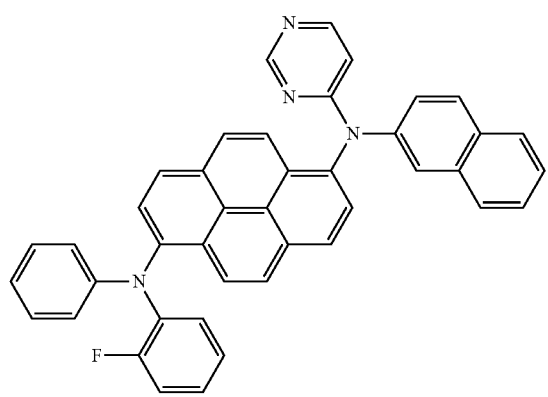
44
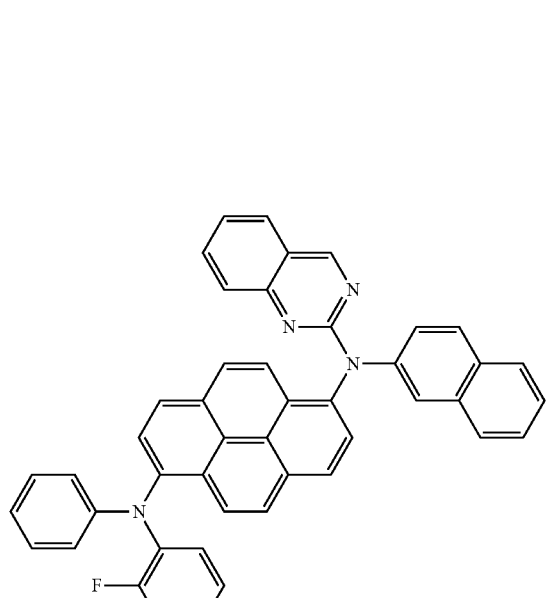
45
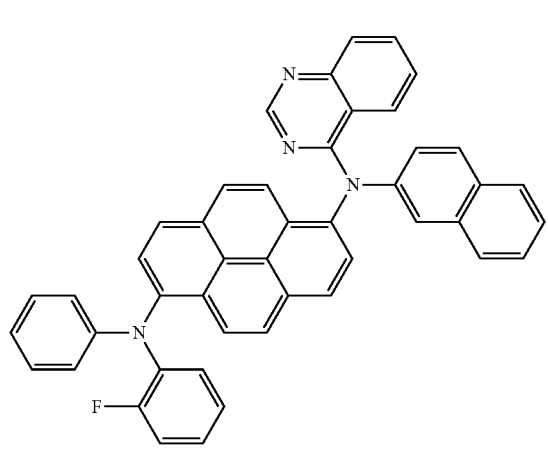
46

47
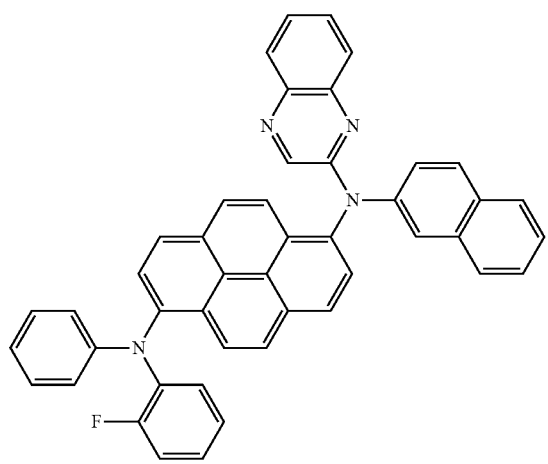
48
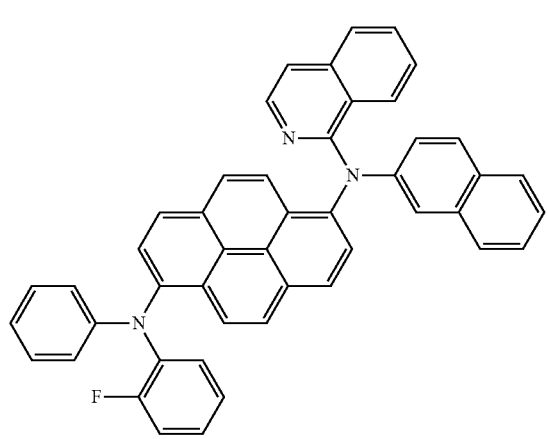
49
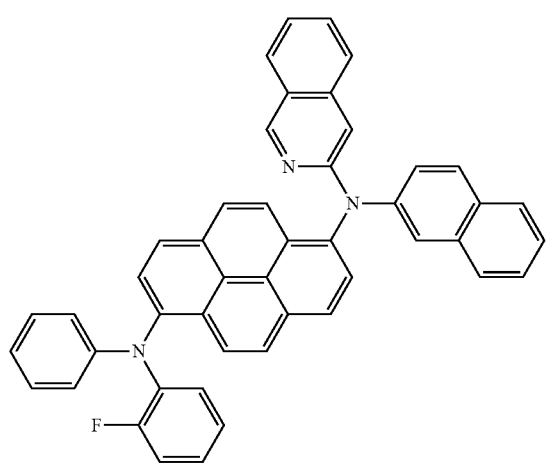
50
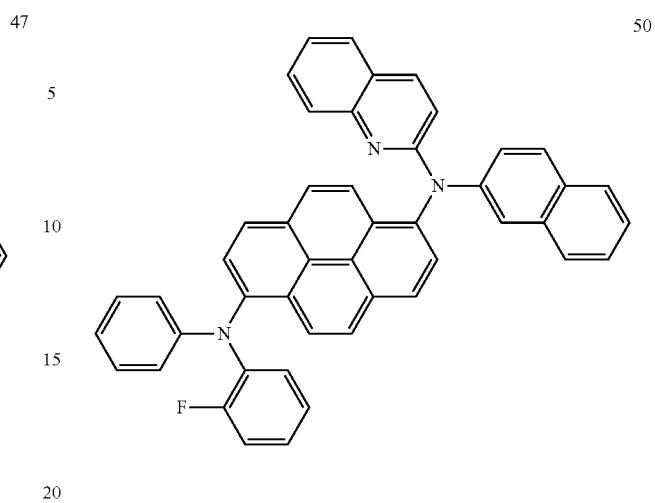
51
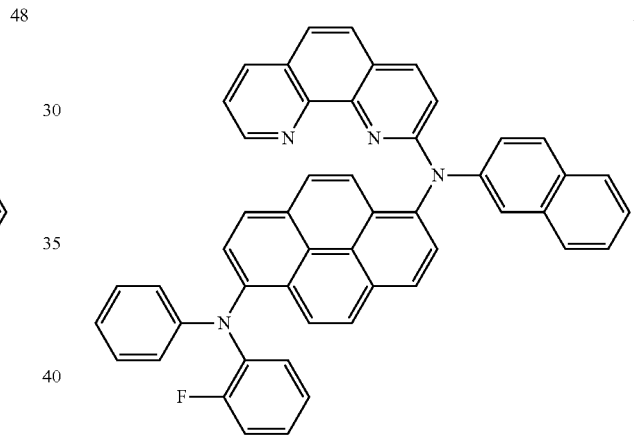
52
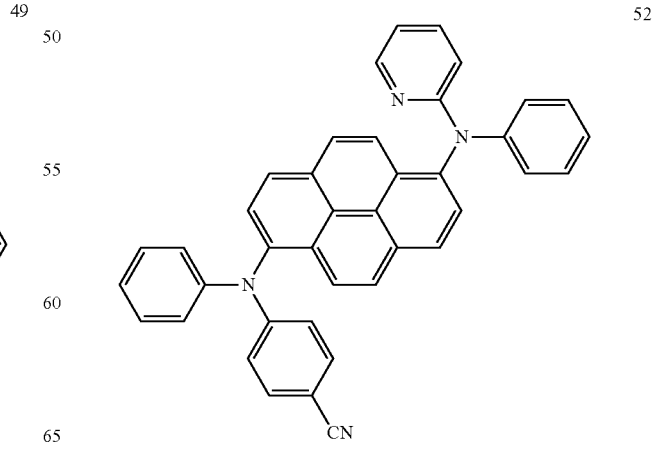

53
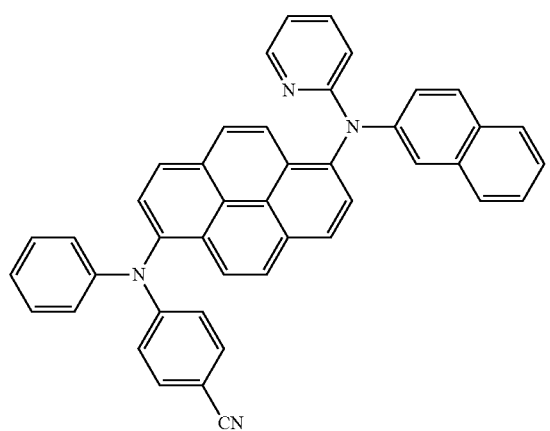
54
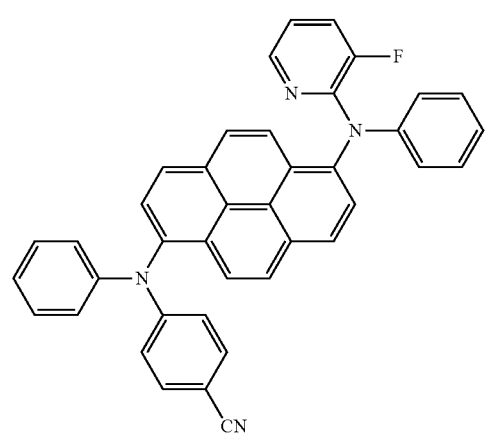
55
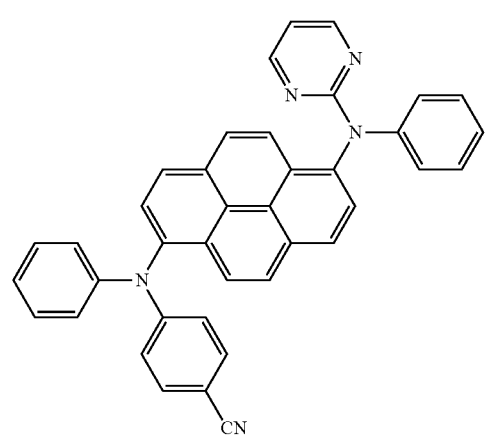
56
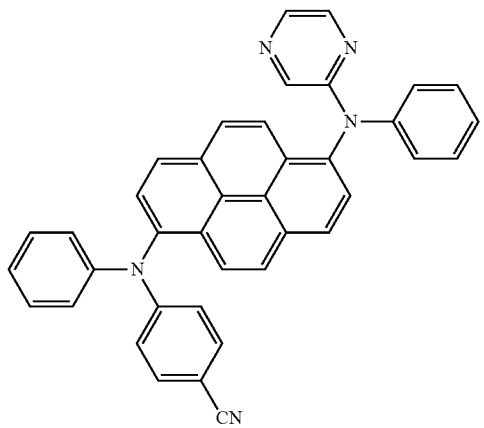
57
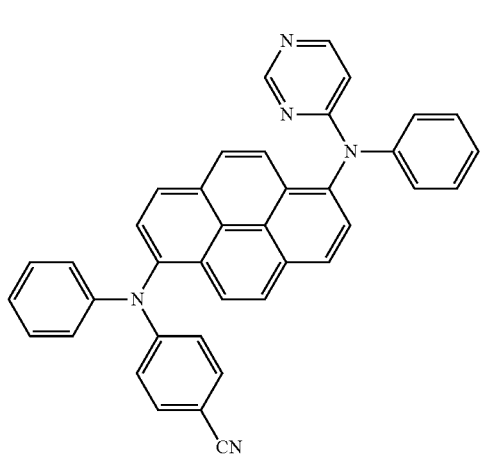
58
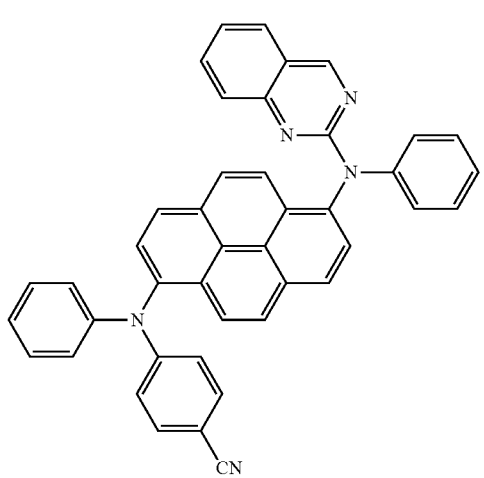

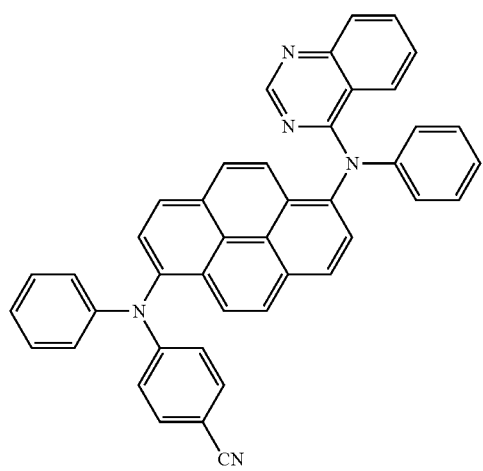
59
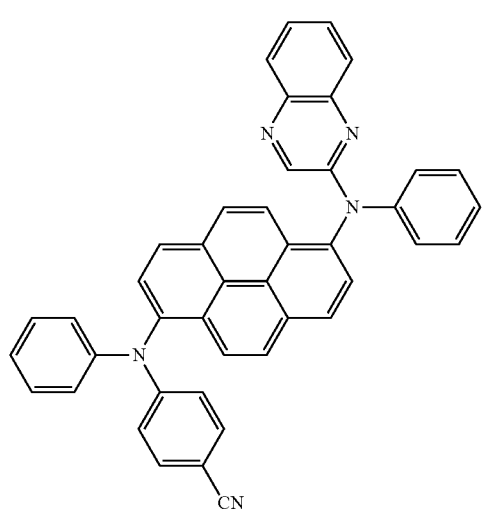
60
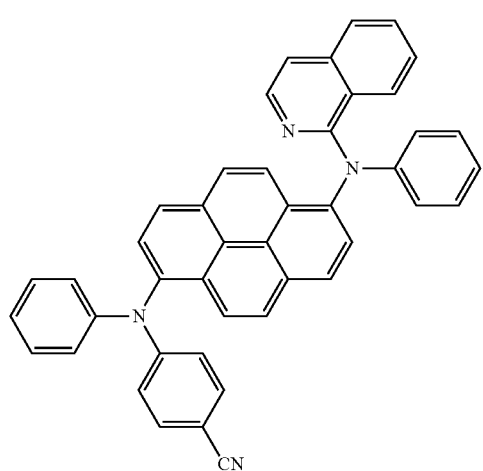
61
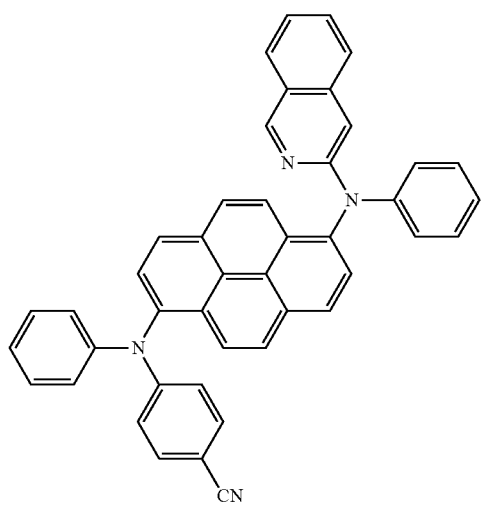
62
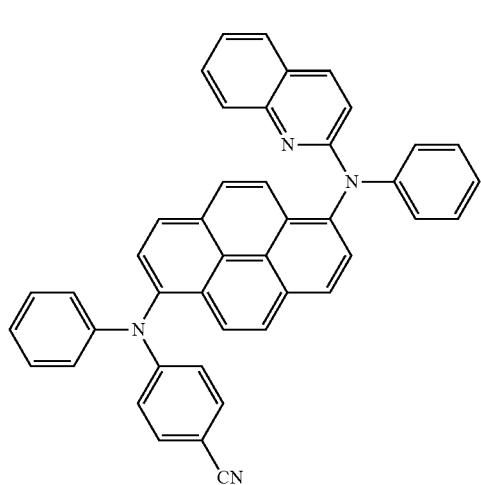
63
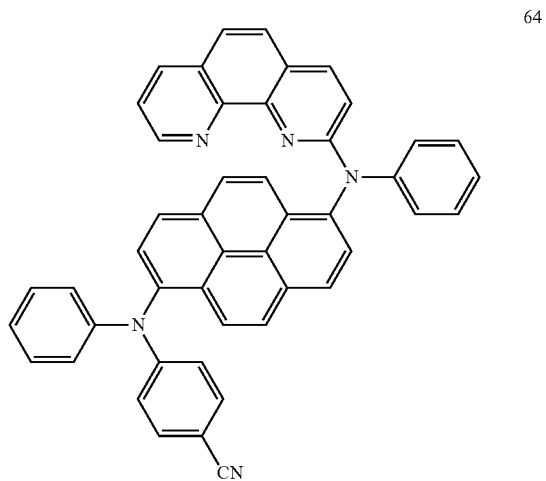
64

-continued
65
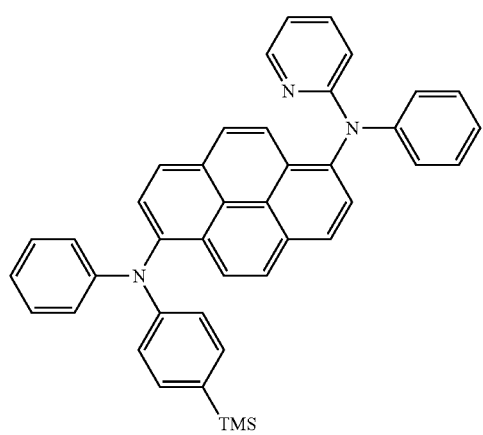
68
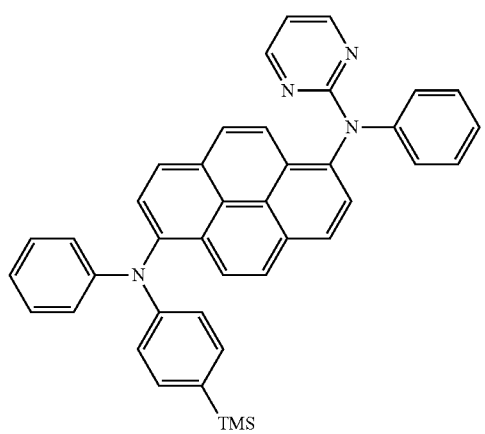
66
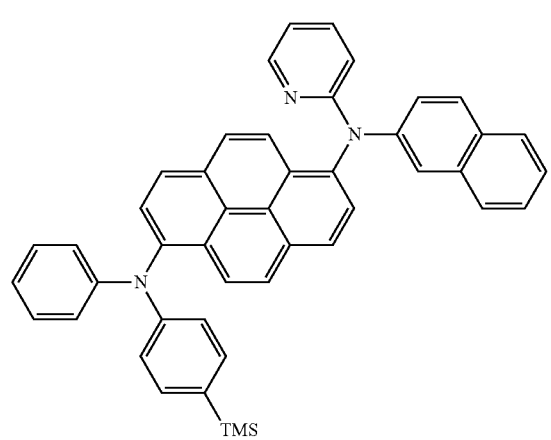
69
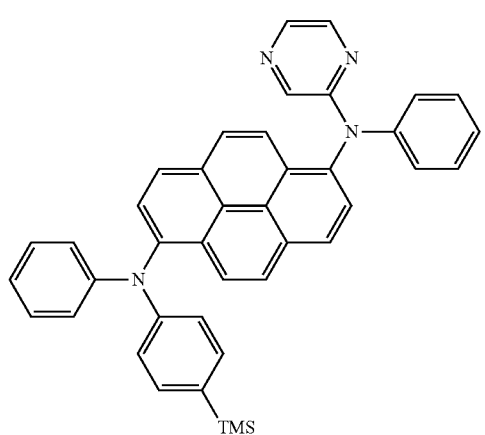
67
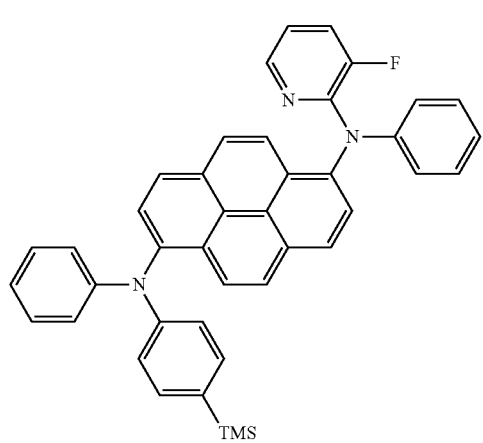
70
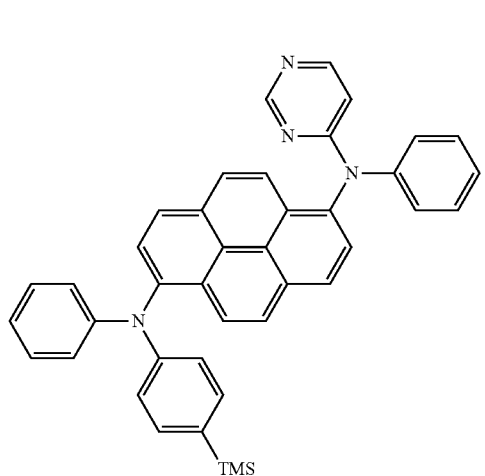

71
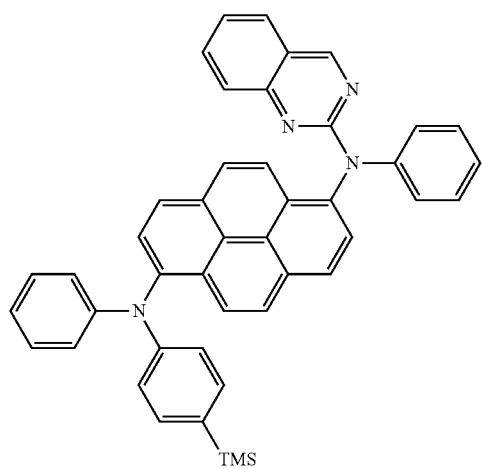
72
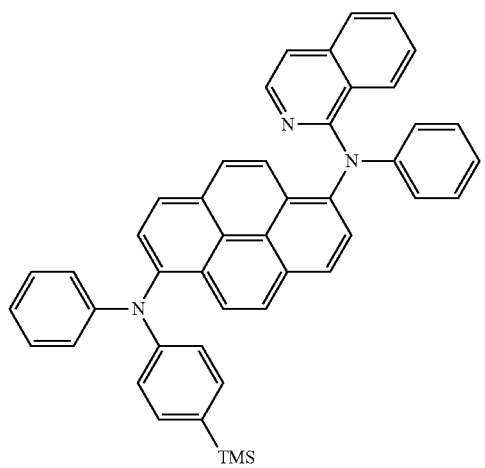
73
74
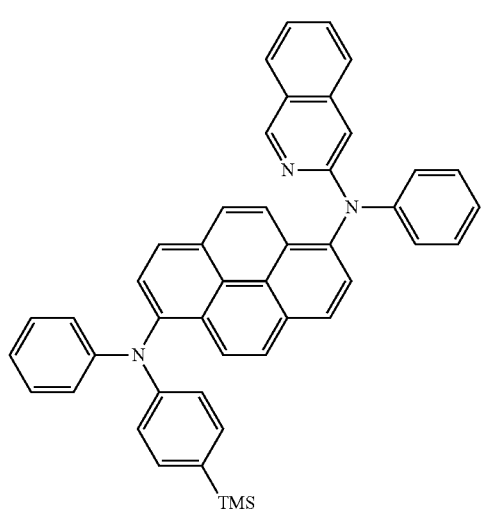
75
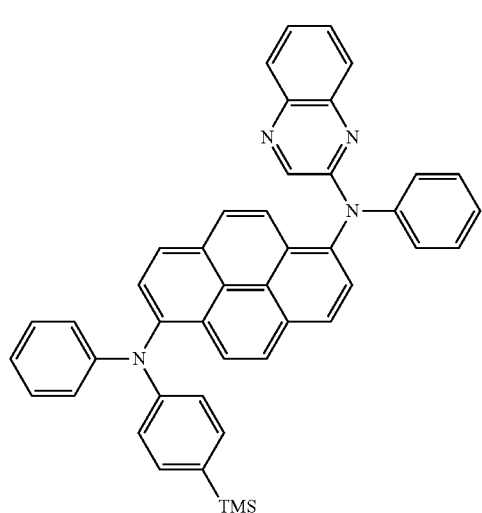
76
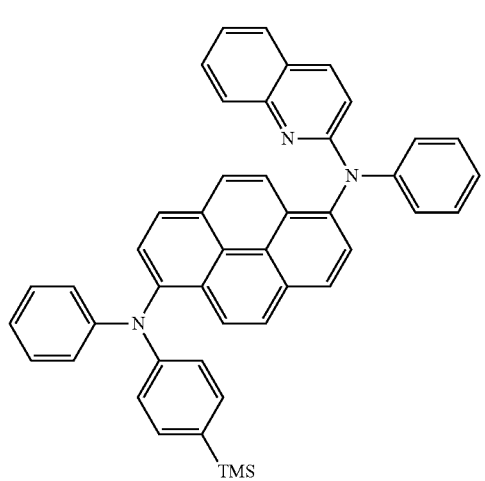

77
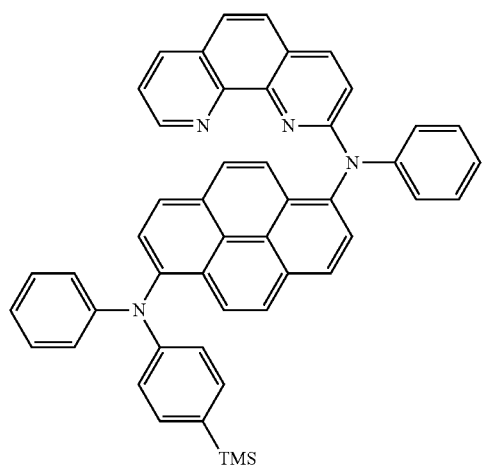
80
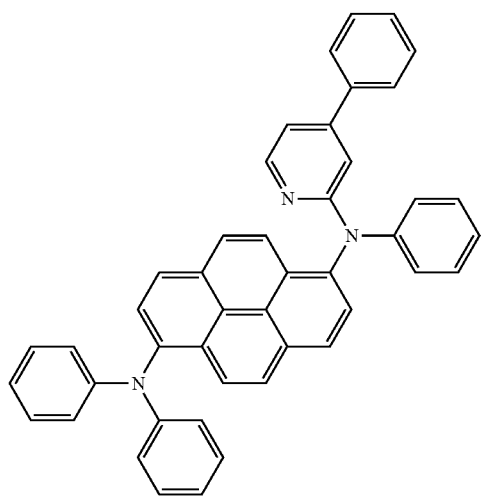
78
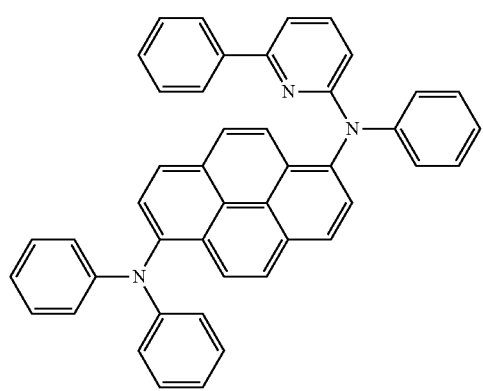
81
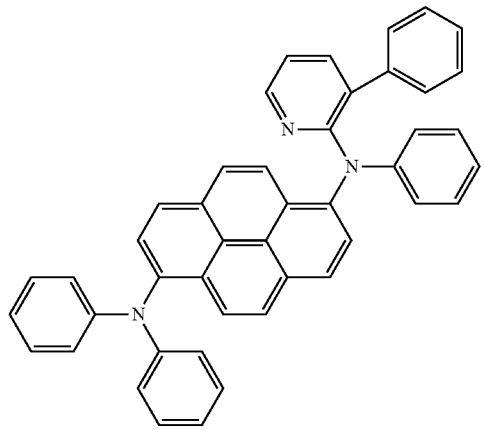
79
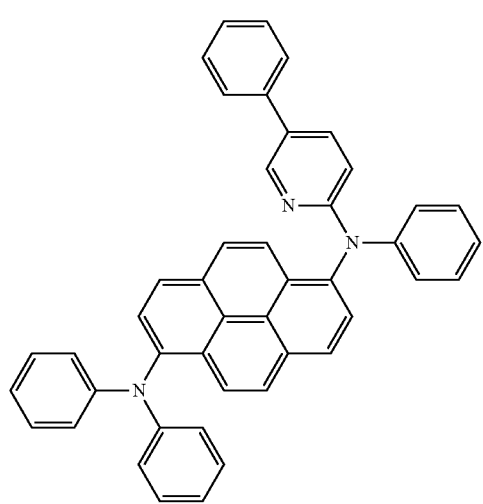
82
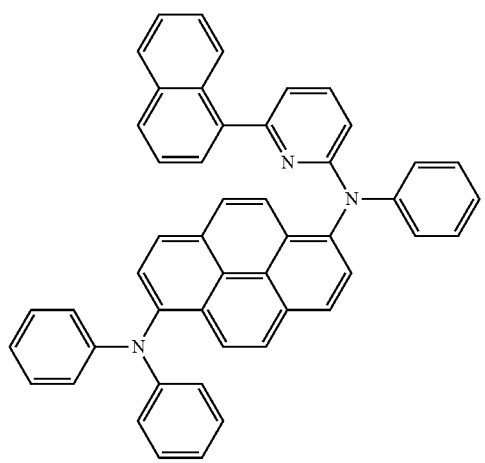

83
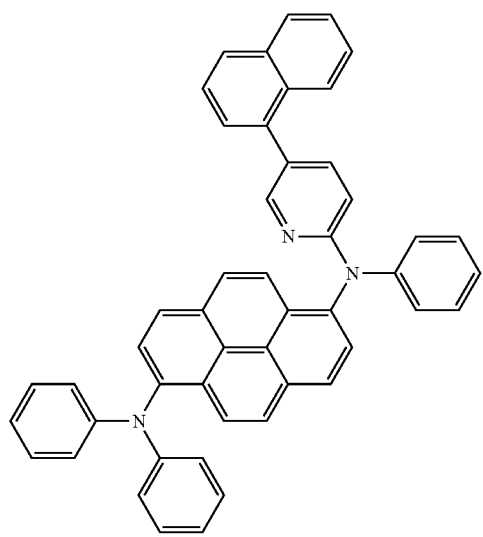
84
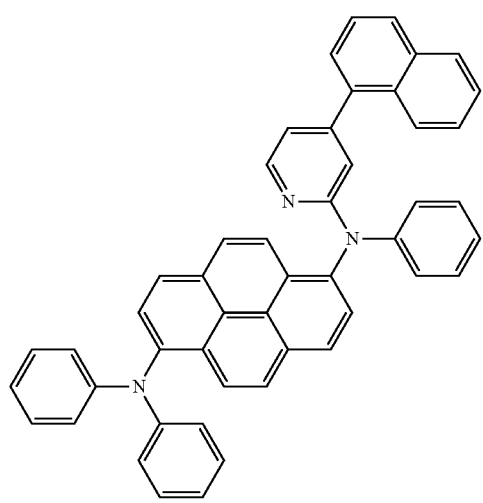
85
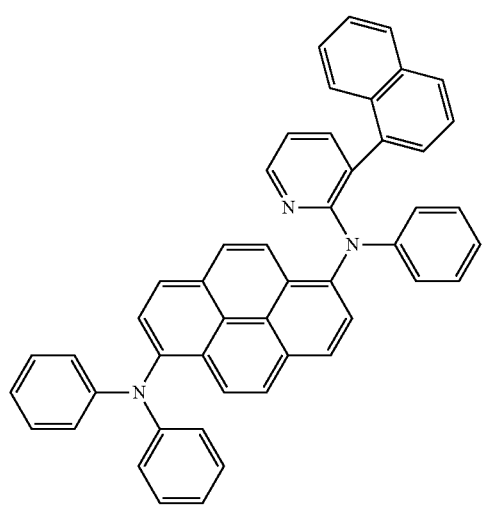
86
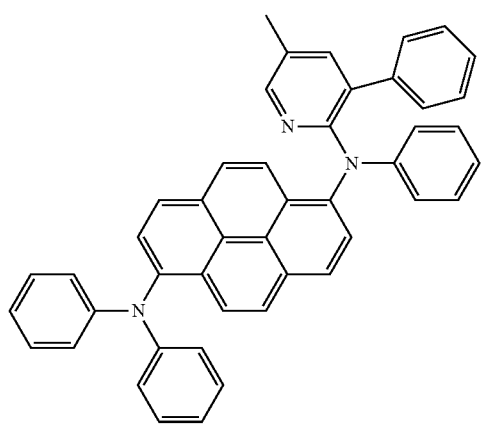
87
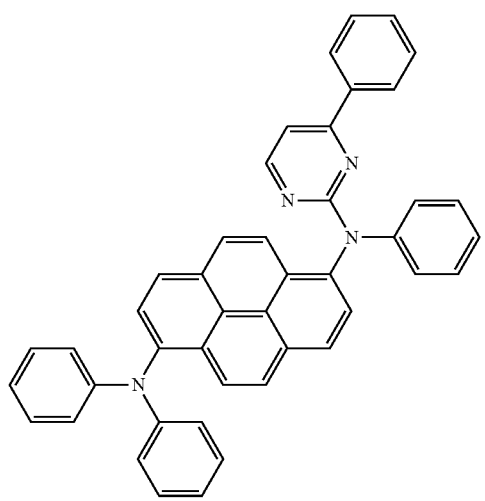
88
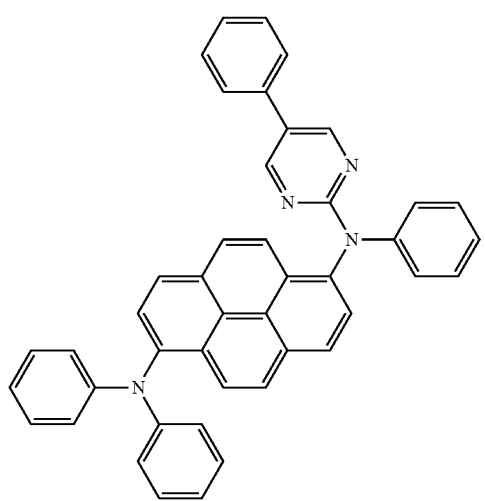

89
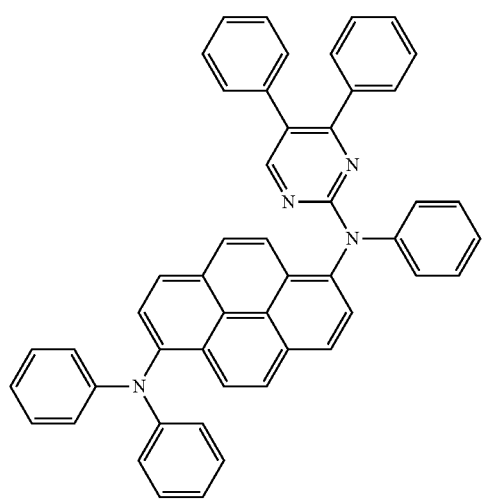
90
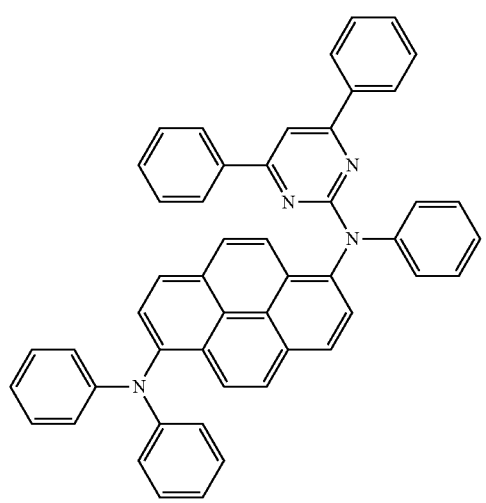
91
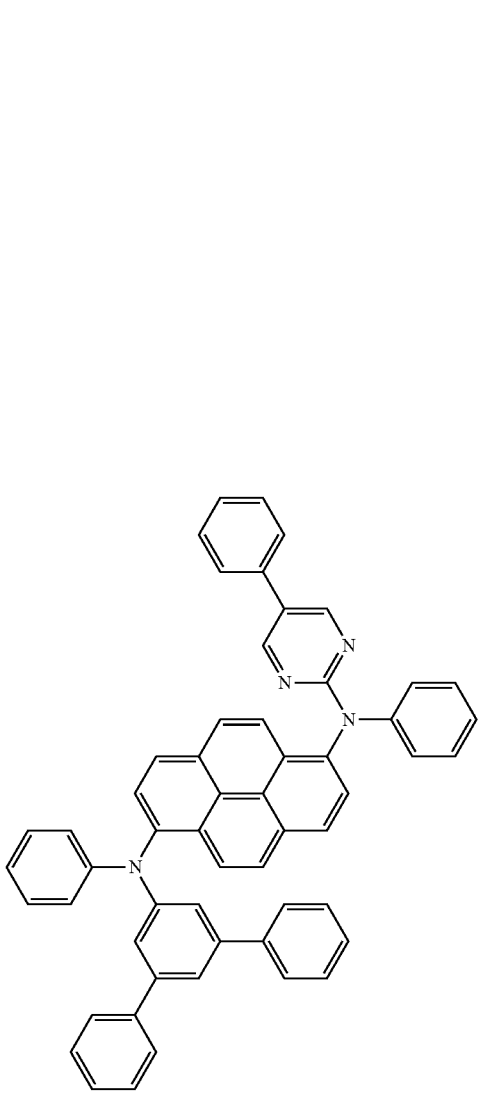
92
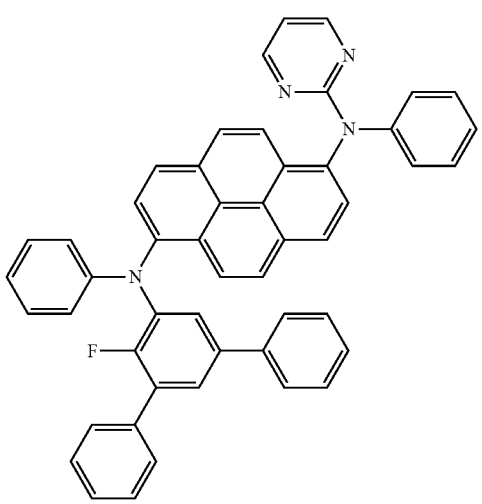
93

-continued

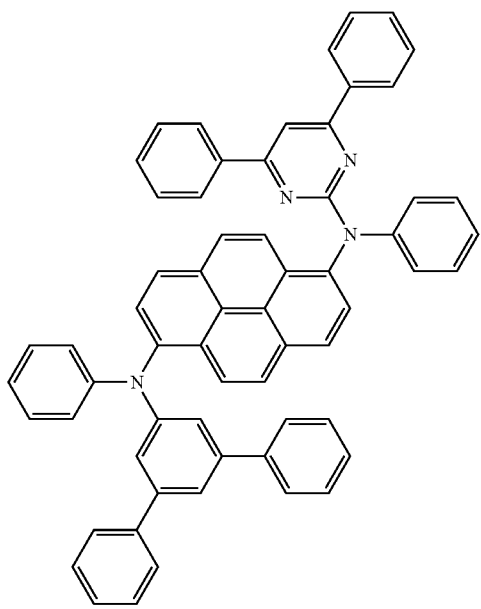

94

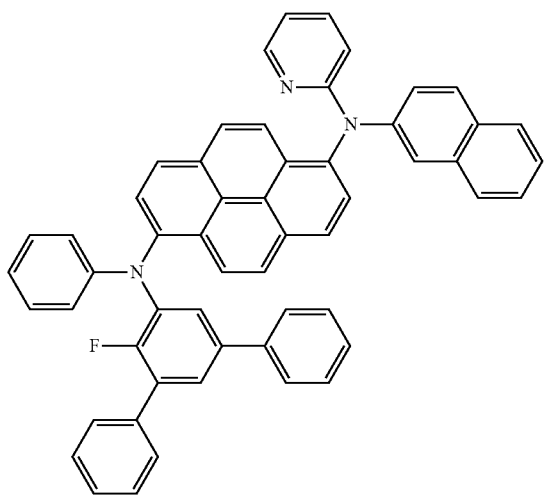

95

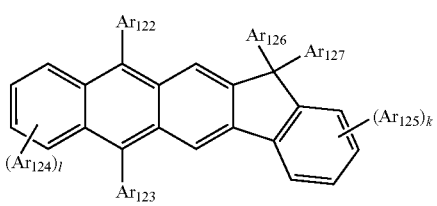

96

The embodiments may also be realized by providing an organic light-emitting diode including a first electrode; a second electrode facing the first electrode; and an organic layer between the first electrode and the second electrode and including an emission layer, wherein the organic layer includes the pyrene-based compound according to an embodiment.

The organic layer may further include a hole transportation region between the first electrode and the emission layer, the hole transportation region including at least one of a hole injection layer, a hole transportation layer, a functional layer having a hole injection capability and a hole transport capability, a buffer layer, and an electron blocking layer, and an electron transportation region between the emission layer and the second electrode, the electron transportation region including at least one of a hole blocking layer, an electron transportation layer, and an electron injection layer.

The pyrene-based compound may be in the emission layer, and a fluorescent dopant that emits light according to a fluorescence emission mechanism, the emission layer further including a host.

The host may include at least one of an anthracene-based compound represented by Formula 400, below, or an anthracene-based compound represented by Formula 401, below:

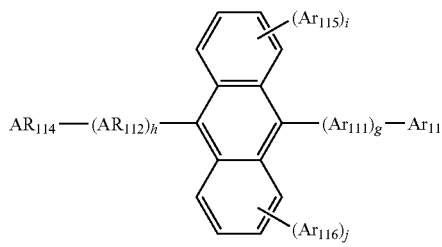

<Formula 400>

<Formula 401> wherein, in Formulae 400 and 401, $Ar_{111}$ and $Ar_{112}$ are each independently a substituted or unsubstituted $C_6$-$C_{60}$ arylene group; $Ar_{113}$ to $Ar_{116}$ and $Ar_{122}$ to $Ar_{125}$ are each independently a substituted or unsubstituted $C_1$-$C_{10}$ alkyl group or a substituted or unsubstituted $C_6$-$C_{60}$ aryl group; $Ar_{126}$ and $Ar_{127}$ are each independently a $C_1$-$C_{10}$ alkyl group; and g, h, i, j, k, and l are each independently an integer of 0 to 4.

BRIEF DESCRIPTION OF THE DRAWING

Features will be apparent to those of skill in the art by describing in detail exemplary embodiments with reference to the attached drawing in which.

DETAILED DESCRIPTION

Figure 1:
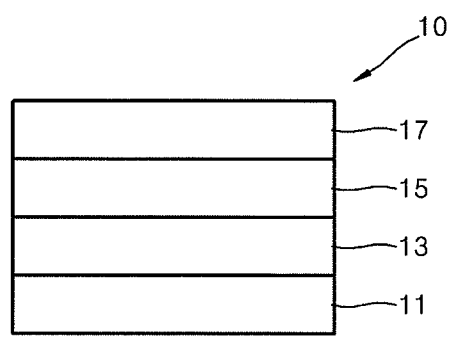
FIG. 1 illustrates a cross-sectional view of the structure of an organic light-emitting diode according to an embodiment.

Example embodiments will now be described more fully hereinafter with reference to the accompanying drawing;

however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

A pyrene-based compound according to an embodiment may be represented by Formula 1, below.

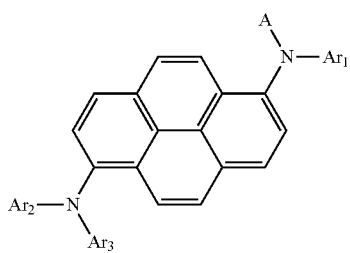

<Formula 1>

In Formula 1, ring A may be a substituted or unsubstituted $C_2$-$C_{30}$ heteroaromatic group including at least one nitrogen (N).

In Formula 1-1, ArIn an implementation, A may be selected from a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted isoquinolinyl group, a substituted or unsubstituted quinolinyl group, a substituted or unsubstituted phthalazinyl group, a substituted or unsubstituted quinoxalinyl group, a substituted or unsubstituted quinazolinyl group, a substituted or unsubstituted cinnolinyl group, or a substituted or unsubstituted 1,10-phenanthrolinyl.

For example, A may be selected from:
a pyridinyl group, a pyrimidinyl group, a triazinyl group, a pyrazinyl group, a pyridazinyl group, an isoindolyl group, an indolyl group, an indazolyl group, an isoquinolinyl group, a quinolinyl group, a phthalazinyl group, a quinoxalinyl group, a cinnolinyl group, and a 1,10-phenanthrolinyl group; and a pyridinyl group, a pyrimidinyl group, a triazinyl group, a pyrazinyl group, a pyridazinyl group, an isoindolyl group, an indolyl group, an indazolyl group, an isoquinolinyl group, a quinolinyl group, a phthalazinyl group, a quinoxalinyl group, a cinnolinyl group, and a 1,10-phenanthrolinyl group, each substituted with at least one of:

a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$aryl group, a $C_6$-$C_{60}$ aryloxy group, a $C_6$-$C_{60}$arylthio group, and a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group, and —Si($Q_{11}$)($Q_{12}$)($Q_{13}$) (in which $Q_{11}$ to $Q_{13}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group).

In an implementation, A in Formula 1 may be represented by one of Formulae 2A to 2K below, in which the broken line represents a bonding location with Formula 1.

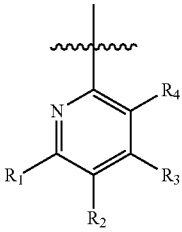

Formula 2A

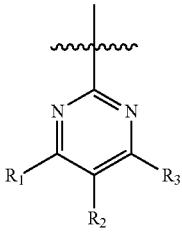

Formula 2B

-continued

Formula 2C
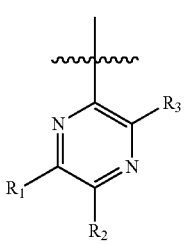

Formula 2D
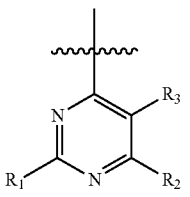

Formula 2E
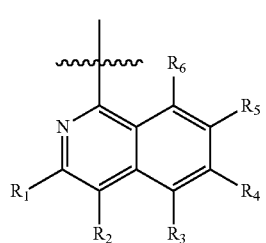

Formula 2F
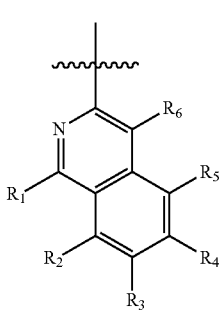

Formula 2G
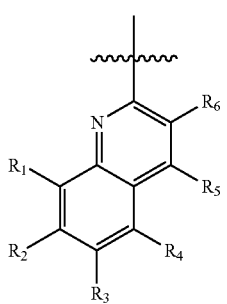

Formula 2H
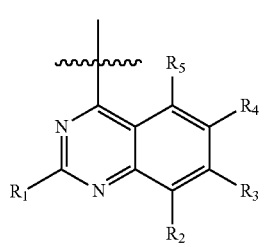

Formula 2I
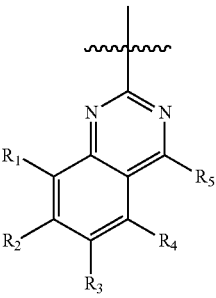

Formula 2J
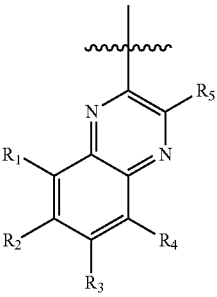

Formula 2K
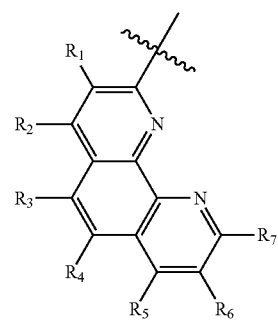

$R_1$ to $R_7$ in Formulae 2A to 2K may each independently selected from:

a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group; and —Si($Q_{11}$)($Q_{12}$)($Q_{13}$) (in which $Q_{11}$ to $Q_{13}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group).

In an implementation, $R_1$ to $R_7$ in Formulae 2A to 2K may each independently be selected from:

a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a $C_1$-$C_{10}$ alkyl group;

a $C_1$-$C_{60}$ alkyl group substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof;

a $C_6$-$C_{16}$ aryl group and a $C_2$-$C_{16}$ heteroaryl group;

a $C_6$-$C_{16}$ aryl group and a $C_2$-$C_{16}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{10}$ alkyl group, phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group; and —Si($Q_{11}$)($Q_{12}$)($Q_{13}$) (in which $Q_{11}$ to $Q_{13}$ are each independently a $C_1$-$C_{10}$ alkyl group, a $C_6$-$C_{16}$ aryl group, or a $C_2$-$C_{16}$ heteroaryl group), but are not limited thereto.

For example, $R_1$ to $R_7$ in Formulae 2A to 2K may each independently be selected from:

a hydrogen atom, a deuterium atom, F, Cl, Br, I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a methyl group, an ethyl group, a propyl group, a butyl group, a pentyl group, and a hexyl group;

a phenyl group, a naphthyl group, and an anthracenyl group; and a phenyl group, a naphthyl group, and an anthracenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a methyl group, an ethyl group, a propyl group, a butyl group, a pentyl group, a hexyl group, phenyl group, a naphthyl group, an anthracenyl group, a fluorenyl group, a dimethylfluorenyl group, a diphenylfluorenyl group, a carbazolyl group, and a phenylcarbazolyl group.

According to an embodiment, A in Formula 1 may have one of the following structures, in which the broken line represents a bonding location with Formula 1.

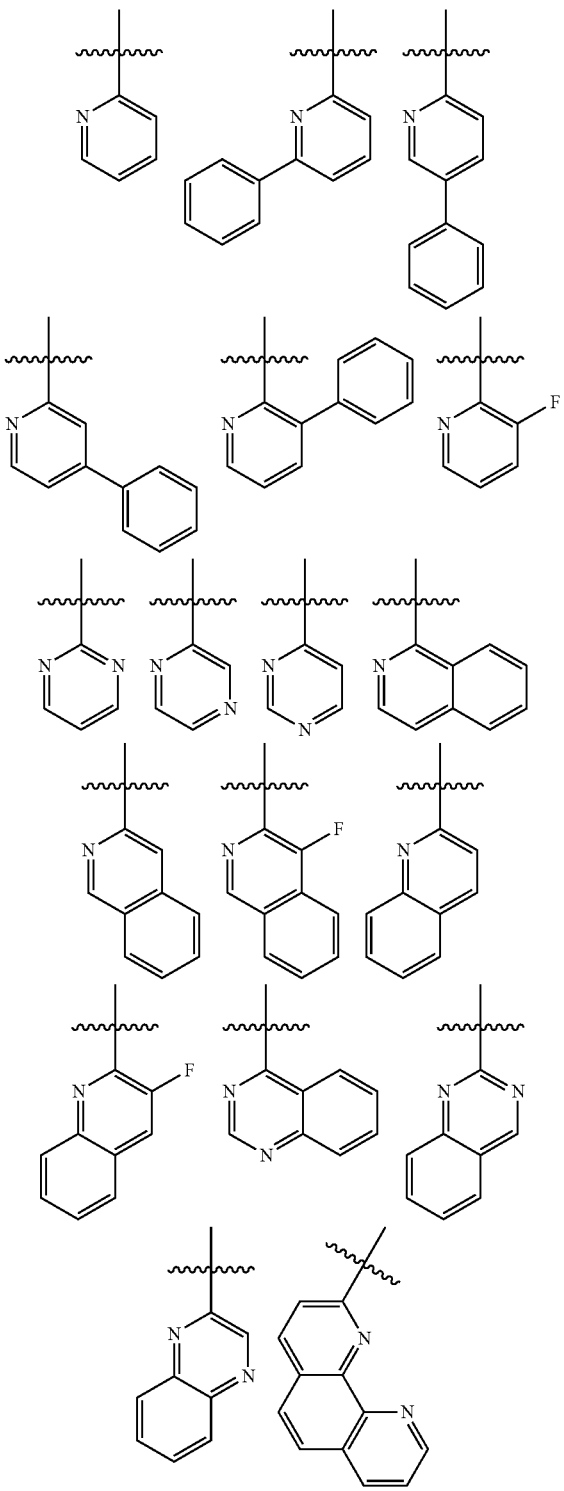

$Ar_1$, $Ar_2$, and $Ar_3$ in Formula 1 may each independently be selected from a substituted or unsubstituted phenyl group and a substituted or unsubstituted a naphthyl group.

For example, $Ar_1$, $Ar_2$ and $Ar_3$ in Formula 1 may each independently be selected from:

a phenyl group and a naphthyl group; and a phenyl group and a naphthyl group, each substituted with at least one of:

a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$aryl group, a $C_6$-$C_{60}$ aryloxy group, a $C_6$-$C_{60}$arylthio group, and a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group, and —Si($Q_{11}$)($Q_{12}$)($Q_{13}$) (in which $Q_{11}$ to $Q_{13}$ are each independently a $C_1$-$C_{60}$ alkyl group, a $C_1$-$C_{60}$ alkoxy group, a $C_6$-$C_{60}$aryl group, or a $C_2$-$C_{60}$ heteroaryl group).

For example, $Ar_1$, $Ar_2$ and $Ar_3$ in Formula 1 may each independently be selected from:

a phenyl group and a naphthyl group; and a phenyl group and a naphthyl group, each substituted with at least one of:

a deuterium atom, F, Cl, Br, I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof and a methyl group, an ethyl group, a propyl group, a butyl group, a pentyl group, and a hexyl group, a phenyl group, a naphthyl group, and an anthracenyl group, and a phenyl group, a naphthyl group, and an anthracenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a methyl group, an ethyl group, a propyl group, a butyl group, a pentyl group, a hexyl group, phenyl group, a naphthyl group, an anthracenyl group, a fluorenyl group, a dimethylfluorenyl group, a diphenylfluorenyl group, a carbazolyl group, and a phenylcarbazolyl group.

In an implementation, $Ar_1$ in Formula 1 may have one of the following structures, in which the broken line represents a bonding location with Formula 1.

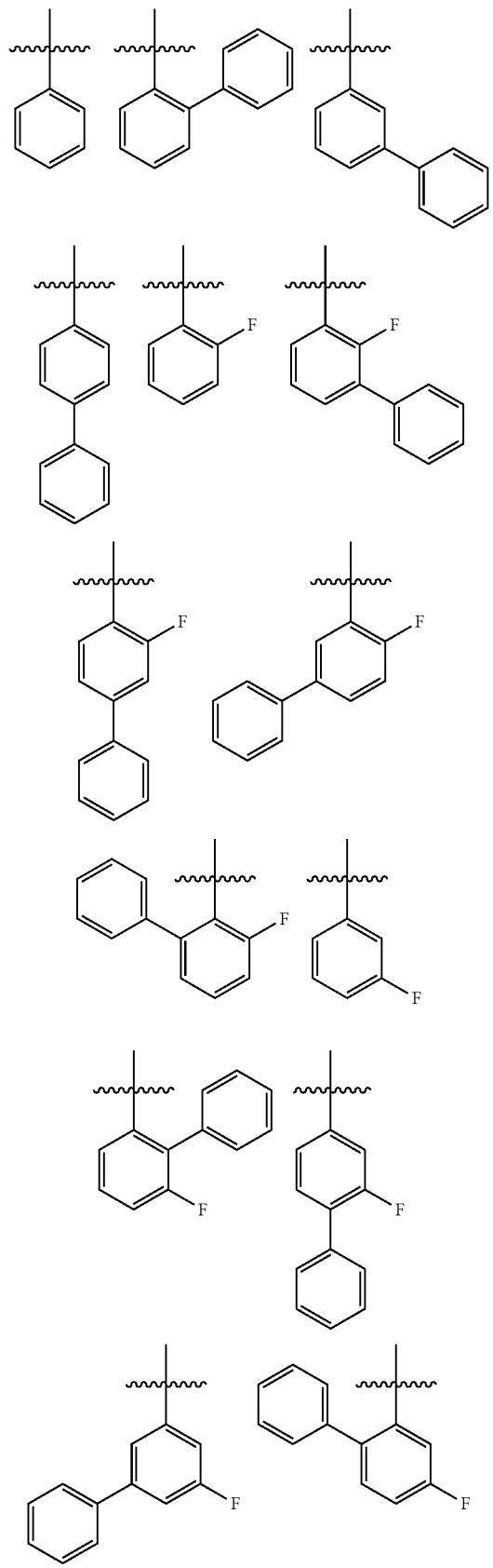

-continued
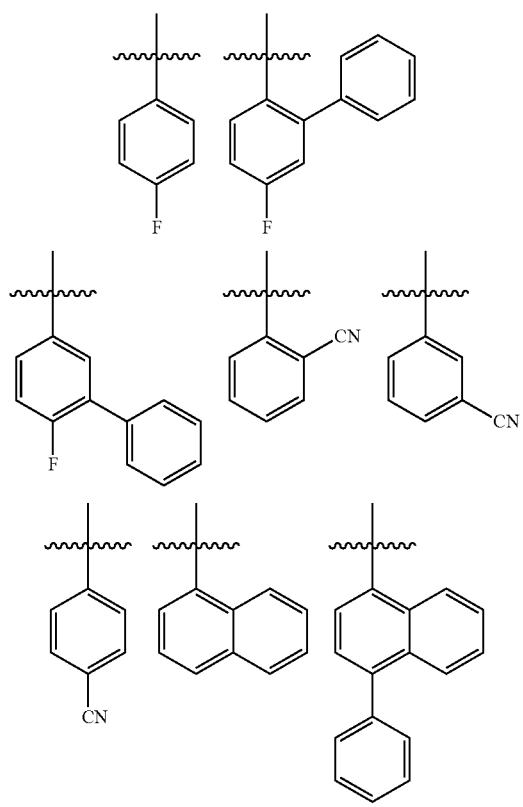
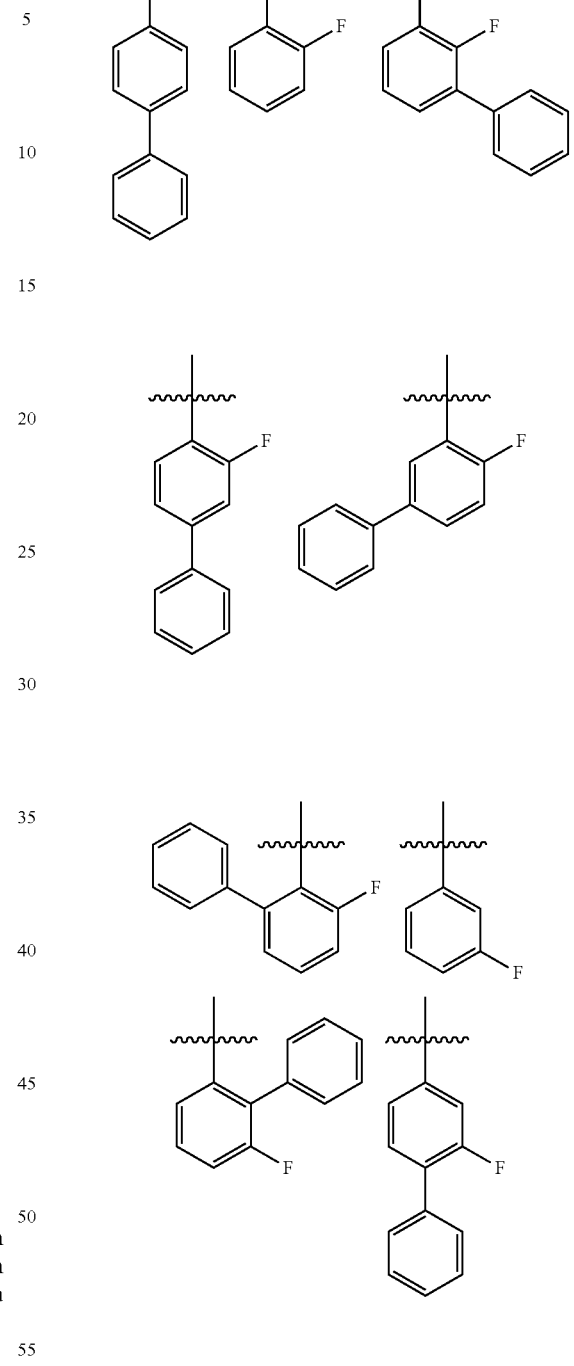
In an implementation, $Ar_2$ and $Ar_3$ in Formula 1 may each independently have one of the following structures, in which the broken line represents a bonding location with Formula 1.
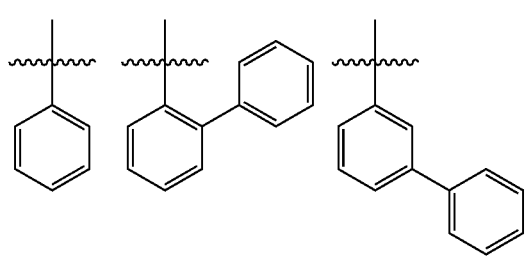

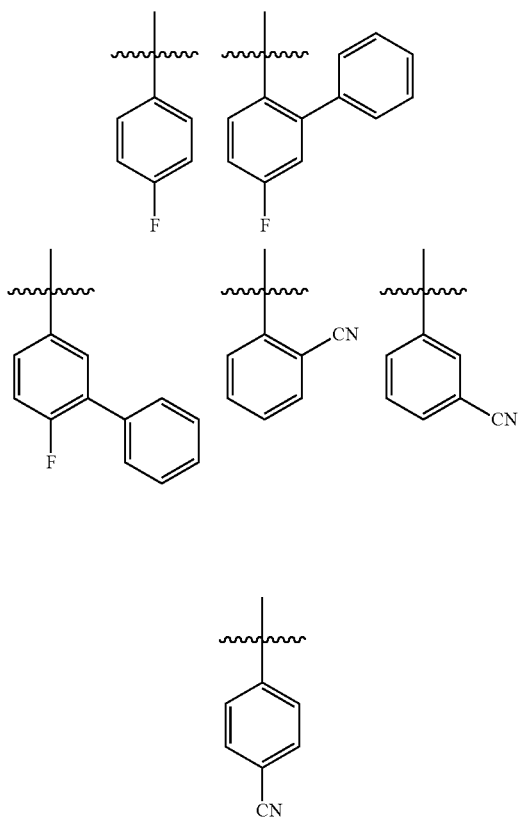

In Formula 1, Ar₁ may be a substituted or unsubstituted phenyl group or a substituted or unsubstituted a naphthyl group, and Ar₂ and Ar₃ may each independently be a substituted or unsubstituted phenyl group.

In an implementation, the pyrene-based compound represented by Formula 1 may be represented by Formula 1-1, below.

<Formula 1-1>

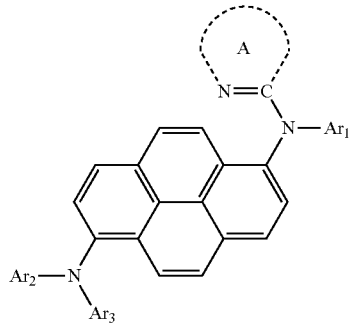

In Formula 1-1, $Ar_1$, $Ar_2$, and $Ar_3$ may be the same as described with respect to Formula 1, and A is shown as a partially formed heterocyclic ring.

According to an embodiment, the pyrene-based compound may be represented by one of Formulae 1A, 1B, or 1C, below.

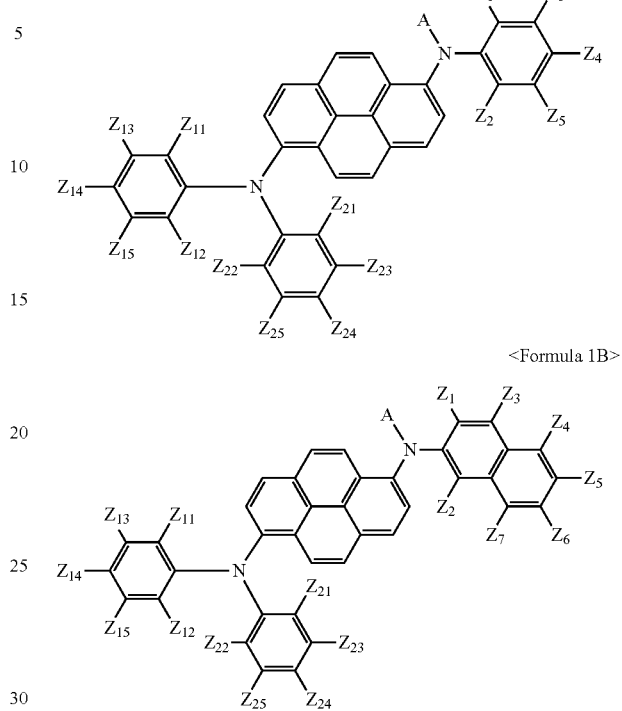

A in Formulae 1A, 1B, and 1C may be as described above with respect to Formula 1. For example, A in Formulae 1A, 1B, and 1C may be represented by one of Formulae 2A to 2K, above.

$Z_1$ to $Z_7$, $Z_{11}$ to $Z_{15}$, and $Z_{21}$ to $Z_{25}$ in Formulae 1A, 1B, and 1C may each independently be selected from a pyridinyl group, a pyrimidinyl group, a triazinyl group, a pyrazinyl group, a pyridazinyl group, an isoindolyl group, an indolyl group, an indazolyl group, an isoquinolinyl group, a quinolinyl group, a phthalazinyl group, a quinoxalinyl group, a cinnolinyl group, and a 1,10-phenanthrolinyl group. Each may be substituted with at least one of i) a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, and a $C_{60}$ alkoxy group; ii) a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof; iii) a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group and a $C_2$-$C_{60}$ heteroaryl group; iv) a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group and a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group; and v) —Si($Q_{11}$)($Q_{12}$)($Q_{13}$) (in which $Q_{11}$ to $Q_{13}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group).

For example, $Z_1$ to $Z_7$, $Z_{11}$ to $Z_{15}$, and $Z_{21}$ to $Z_{25}$ in Formulae 1A, 1B and 1C may each independently be selected from a phenyl group and a naphthyl group. Each may substituted with at least one of i) a hydrogen atom, a deuterium atom, F, Cl, Br, I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof and a methyl group, an ethyl group, a propyl group, a butyl group, a pentyl group, and a hexyl group; ii) a phenyl group, a naphthyl group, and an anthracenyl group; and iii) a phenyl group, a naphthyl group and an anthracenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a methyl group, an ethyl group, a propyl group, a butyl group, a pentyl group, a hexyl group, a phenyl group, a naphthyl group, an anthracenyl group, a fluorenyl group, a dimethylfluorenyl group, a diphenylfluorenyl group, a carbazolyl group, and a phenylcarbazolyl group.

According to an embodiment, the pyrene-based compound may be represented by Formula 1A, 1B, or 1C, A may be represented by one of Formulae 2A to 2K, and $R_1$ to $R_6$, $Z_1$ to $Z_7$, $Z_{11}$ to $Z_{15}$ and $Z_{21}$ to $Z_{25}$ may each independently be a hydrogen atom, a F atom, a cyano group, or a phenyl group in the Formula 1A, 1B, and 1C.

According to another embodiment, the pyrene-based compound may be one of Compounds 1 to 96 illustrated below.

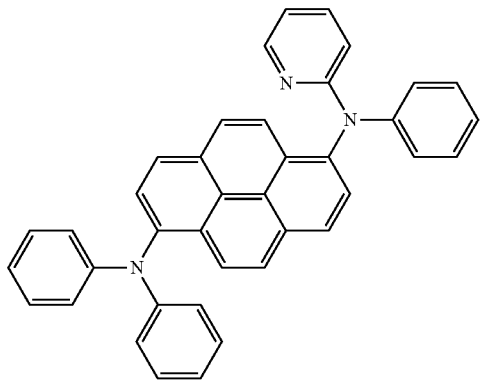

1

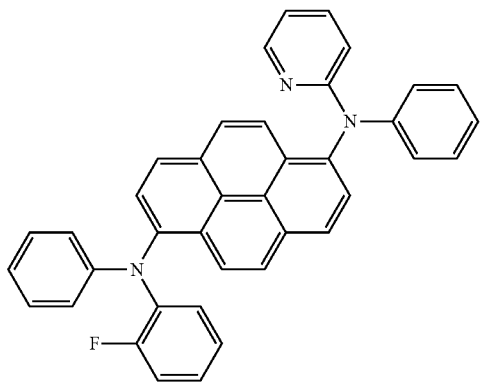

2

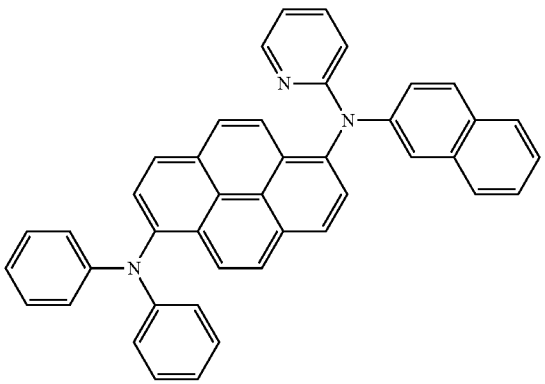

3

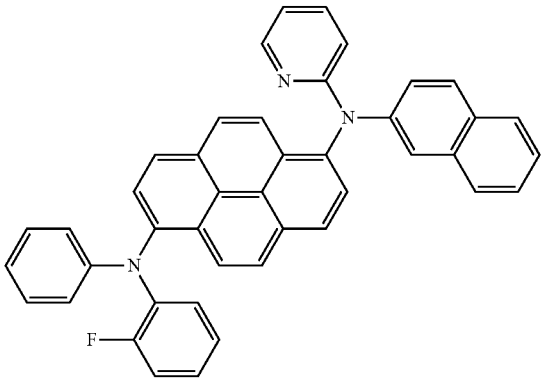

4

5
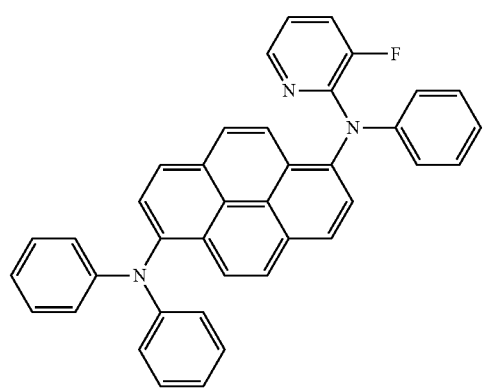
6
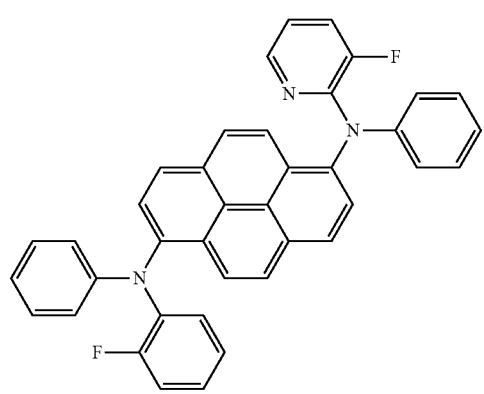
7
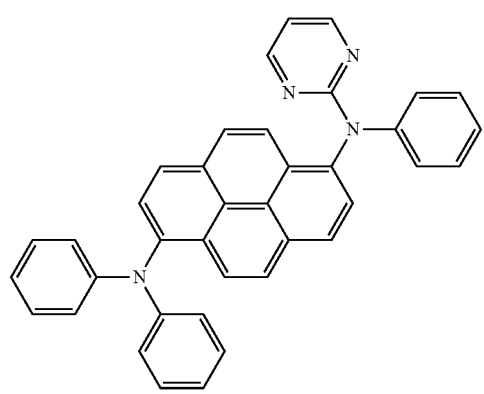
8
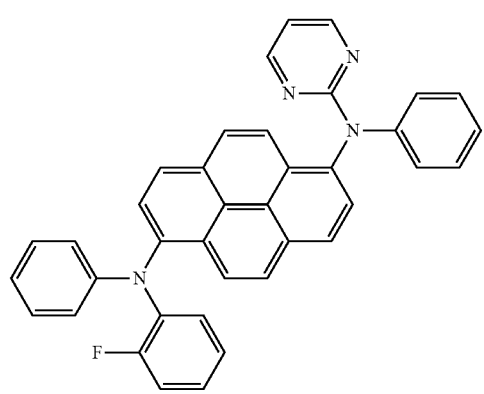
9
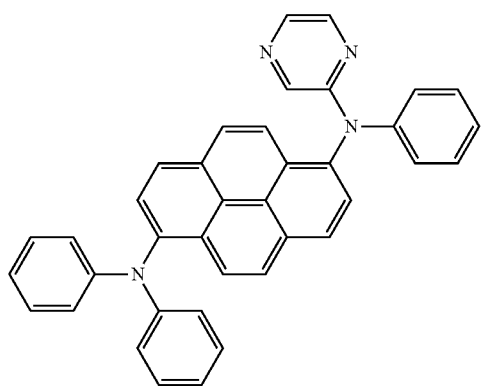
10
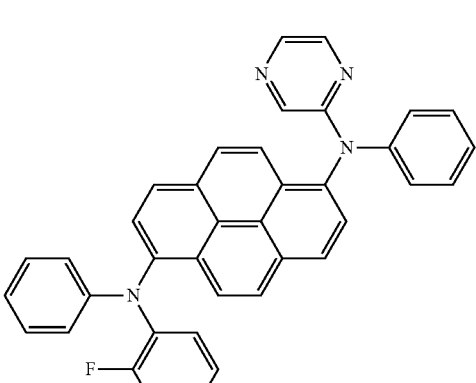
11
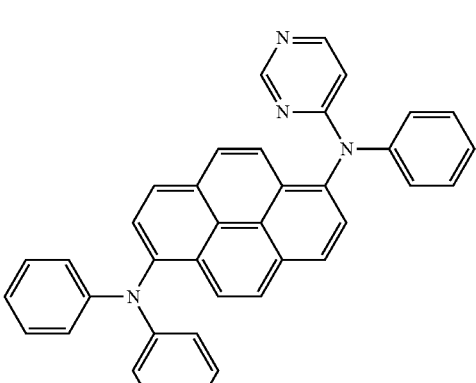
12
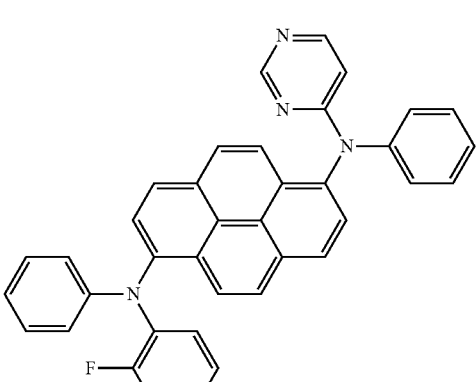

13
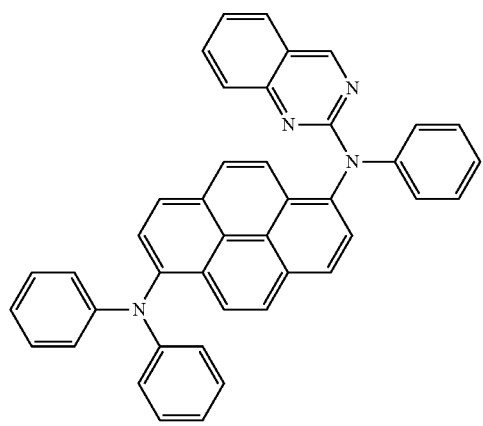
14
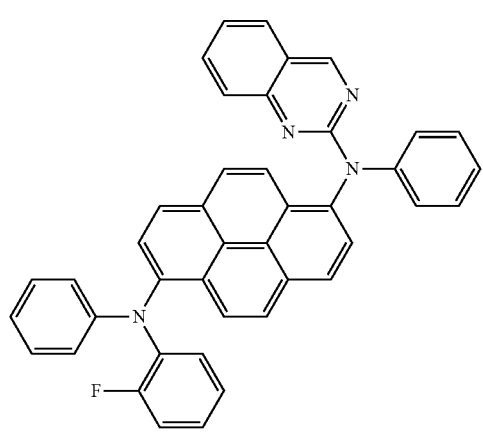
15
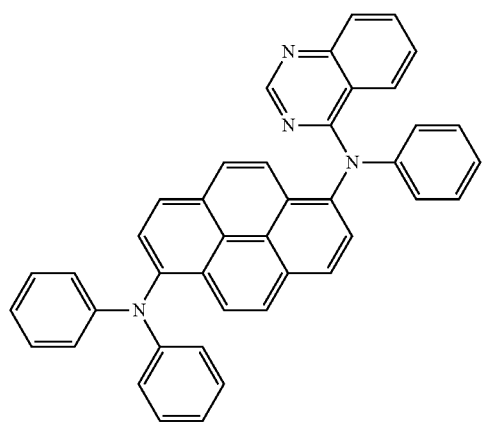
16
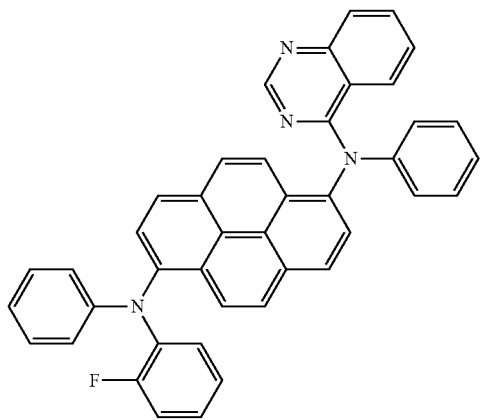
17
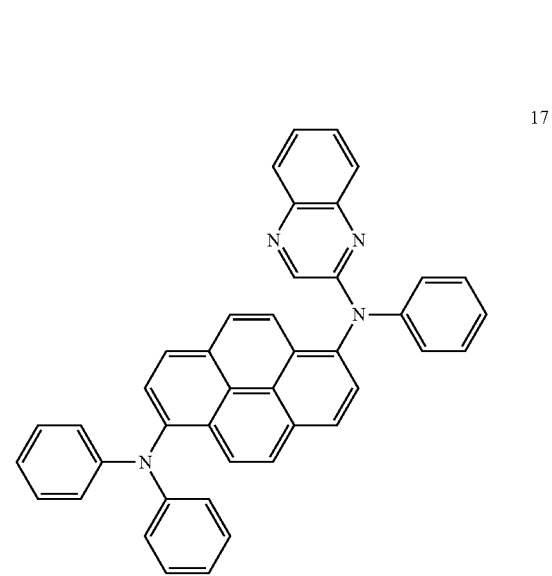
18
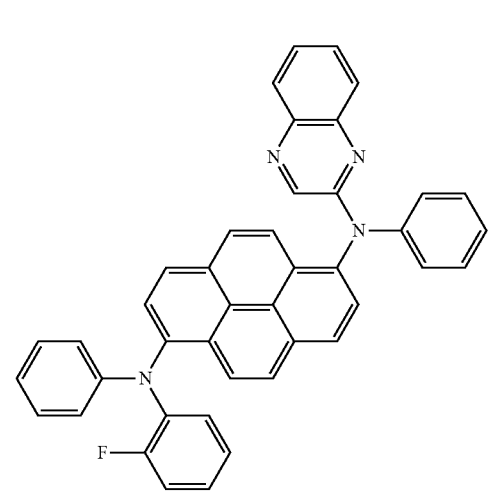

-continued
19
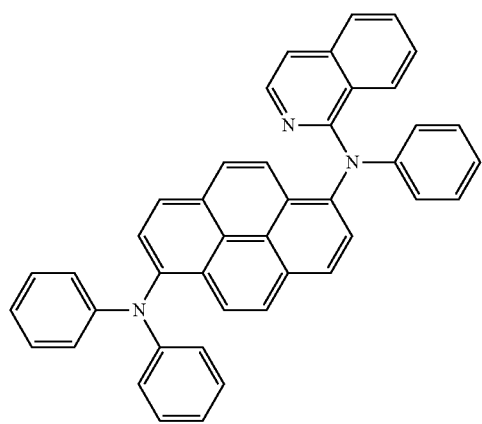
20
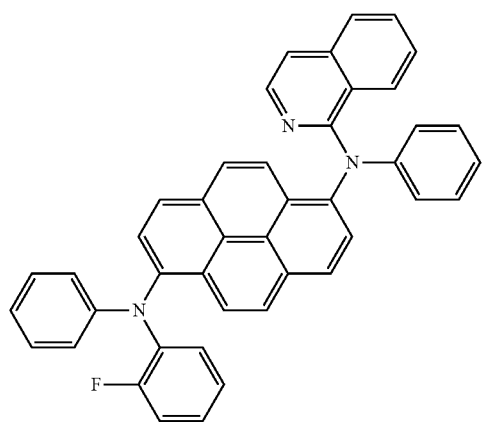
21
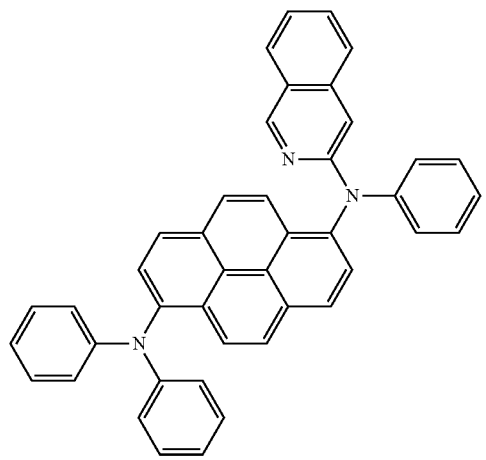
-continued
22
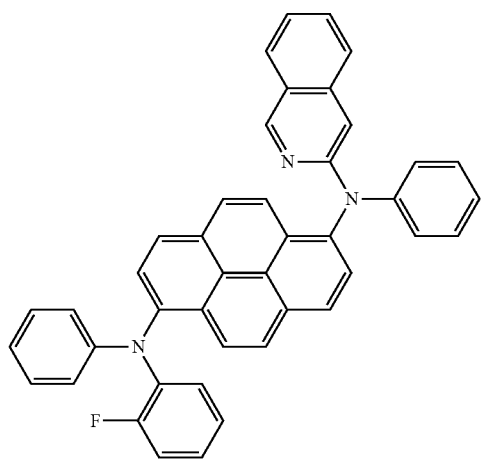
23
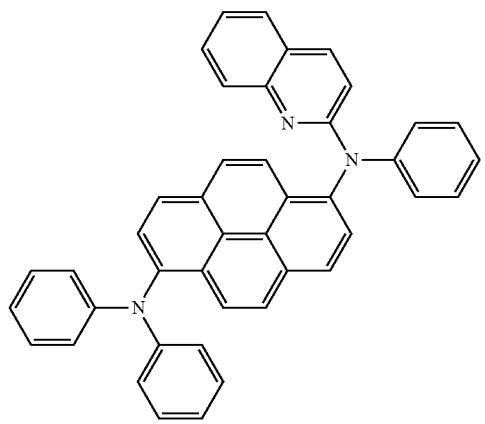
24
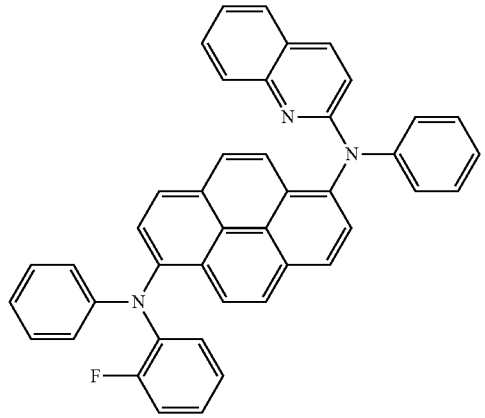

25
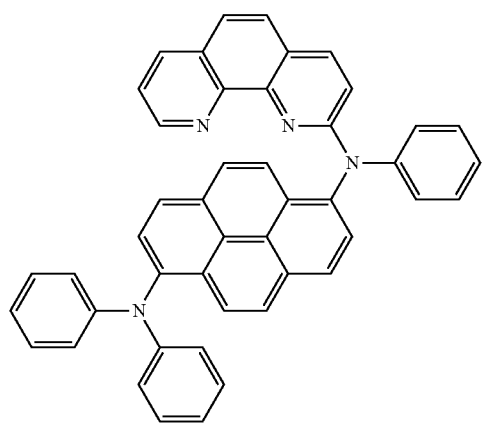
26
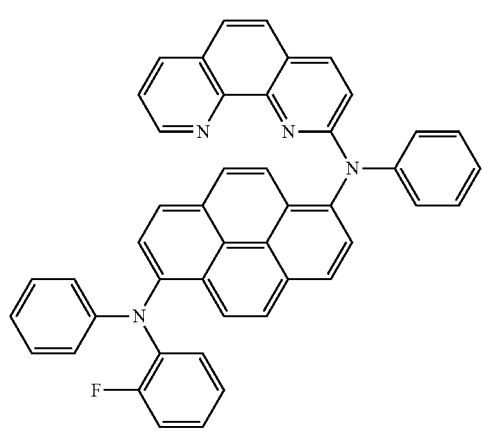
27
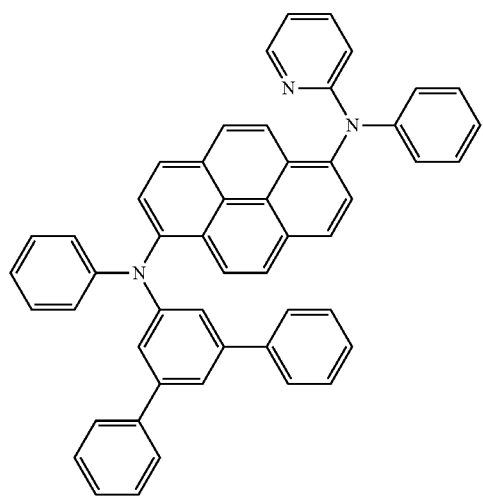
28
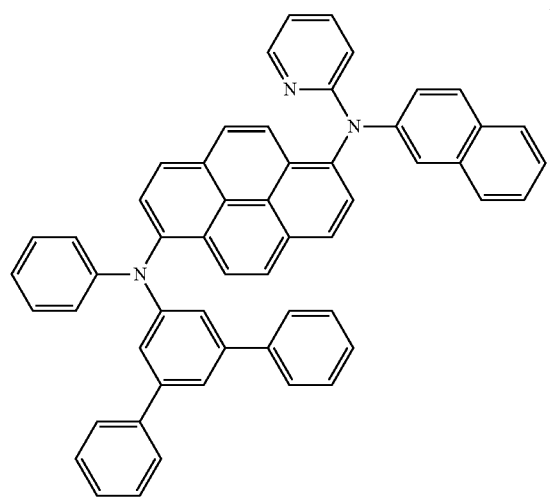
29
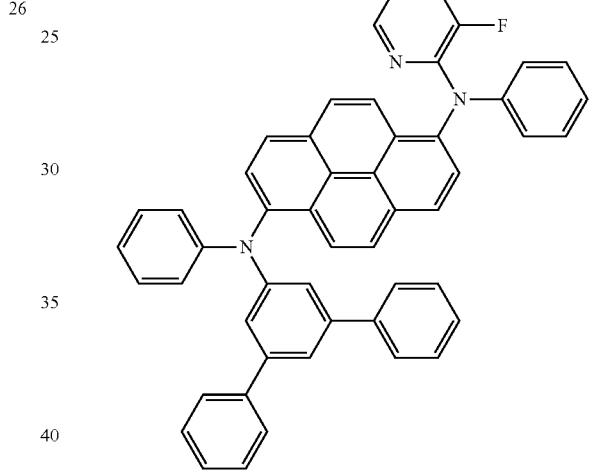
30
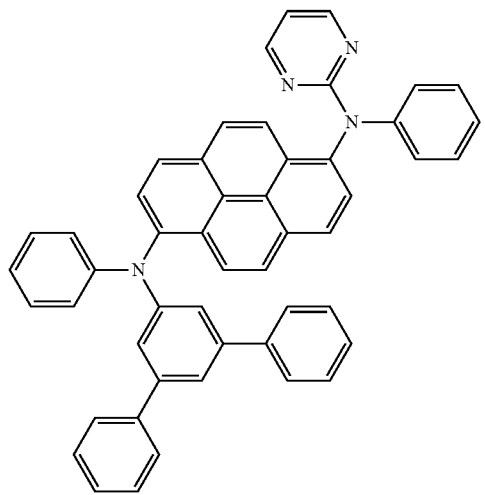

-continued
31
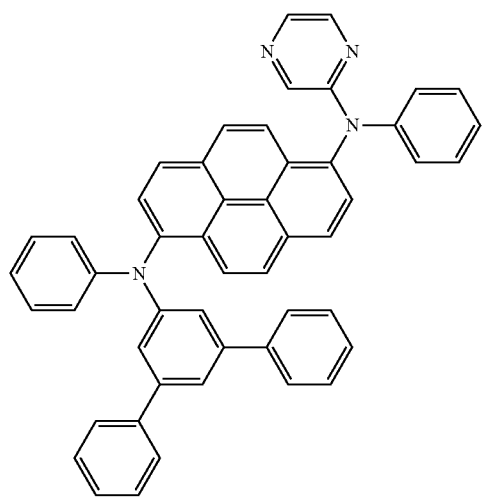
32
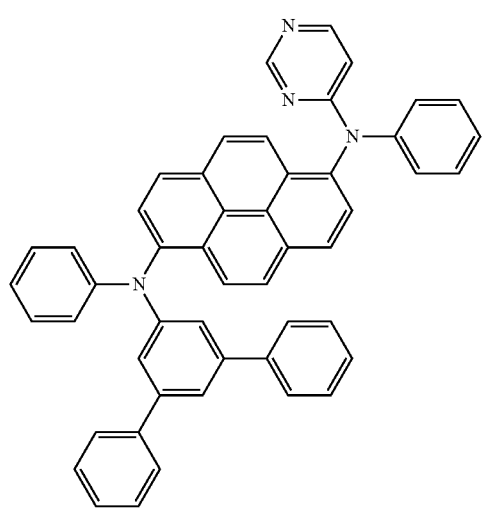
33
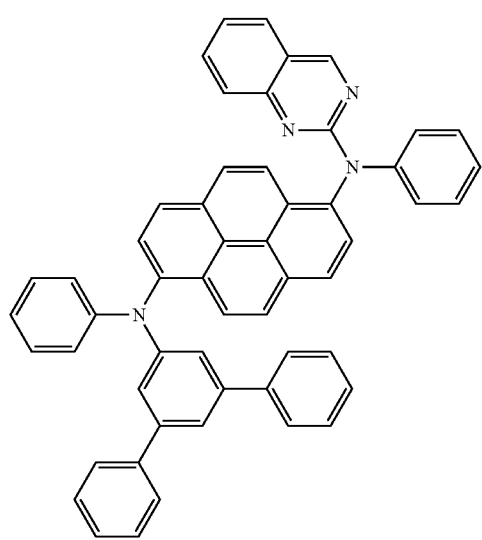
-continued
34
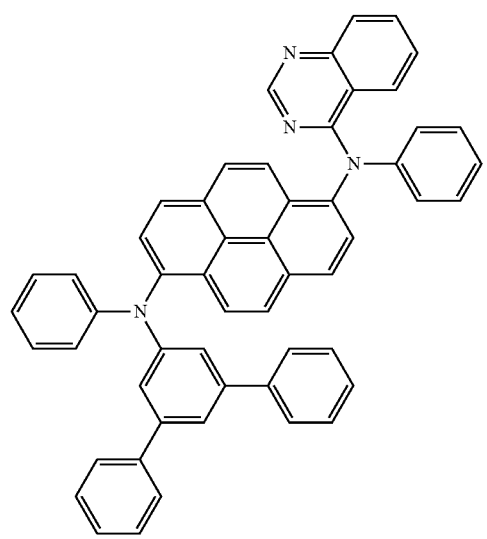
35
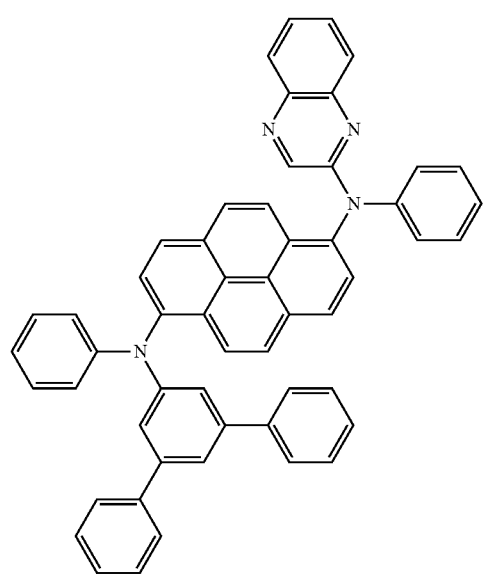
36
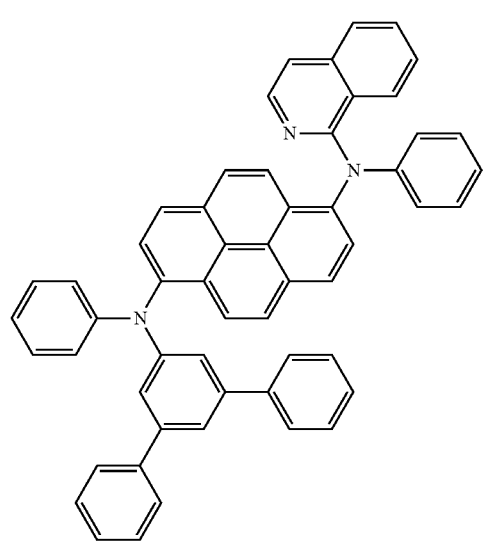

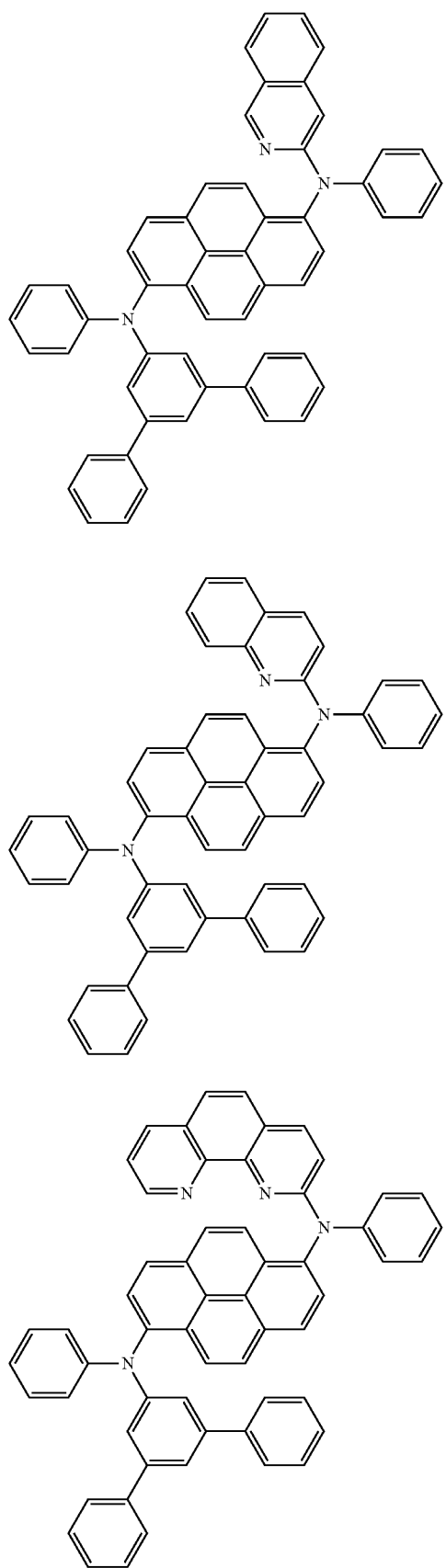
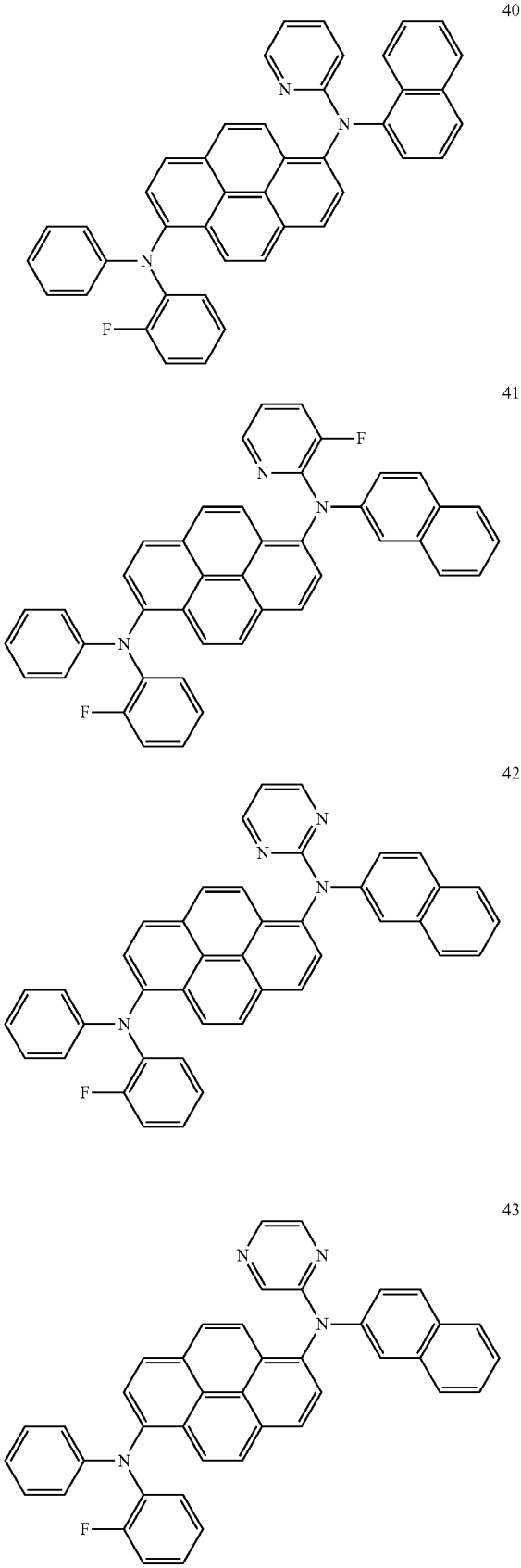

44
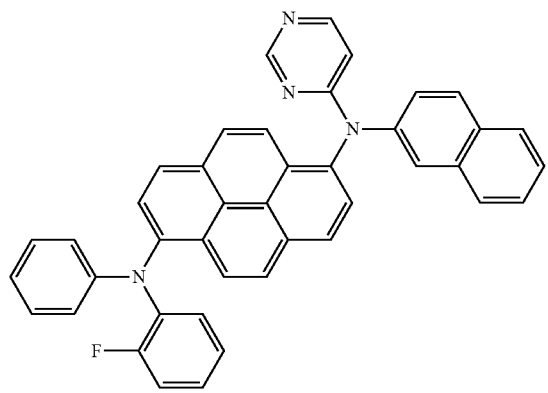
45
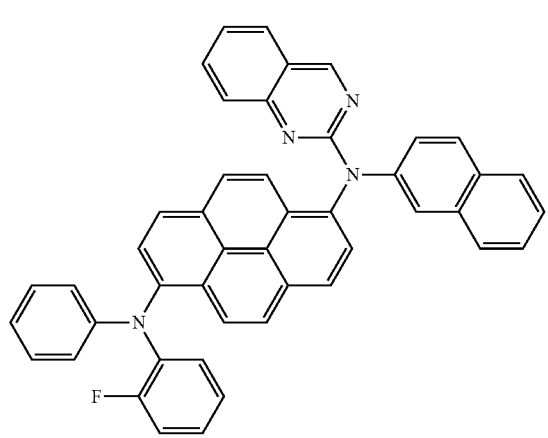
46
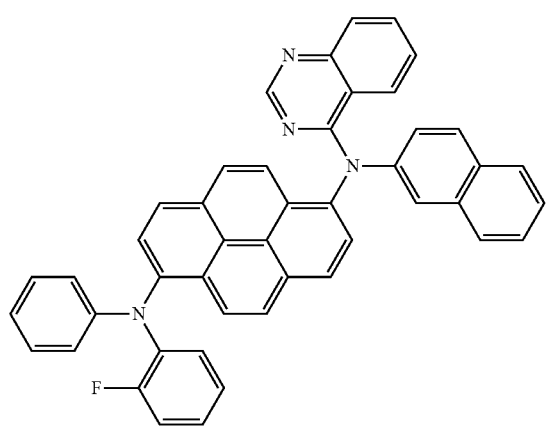
47
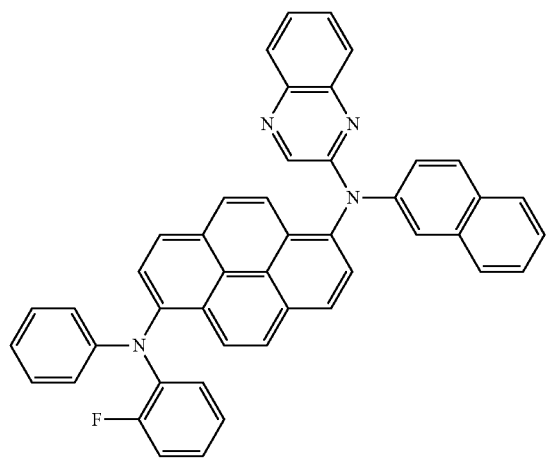
48
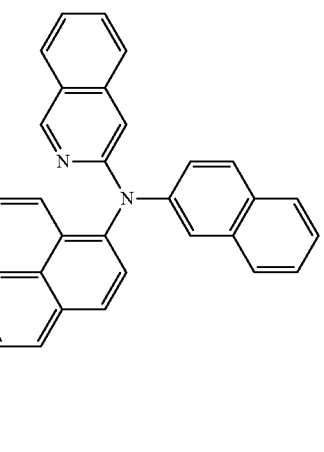
49

75
-continued
76
-continued
50
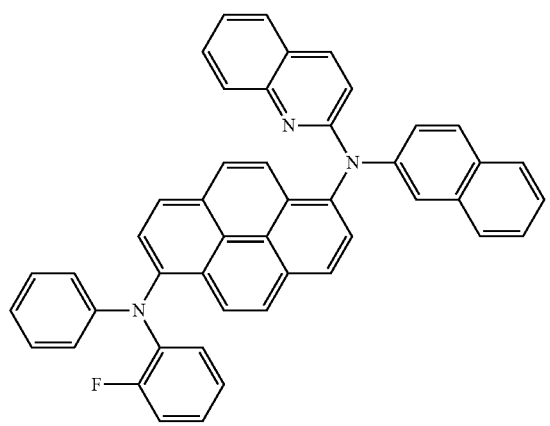
53
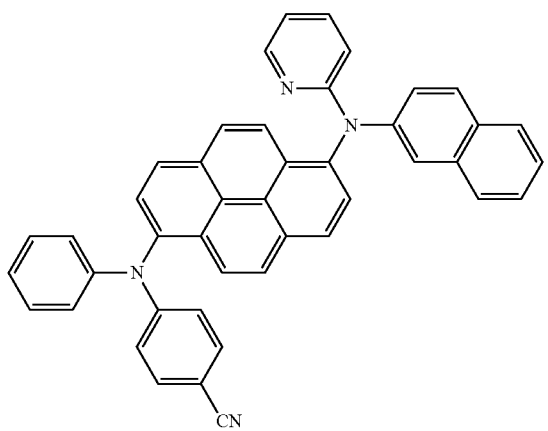
51
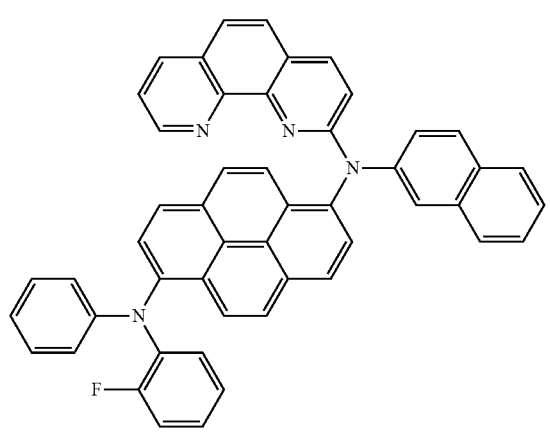
54
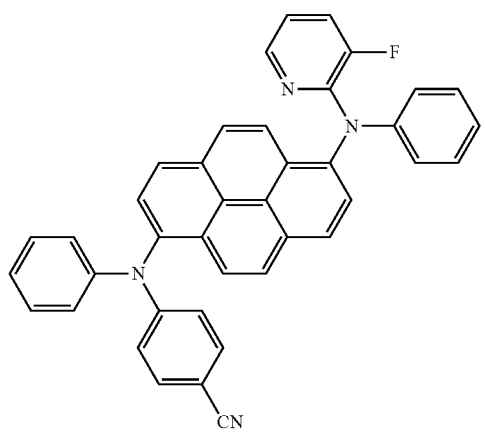
52
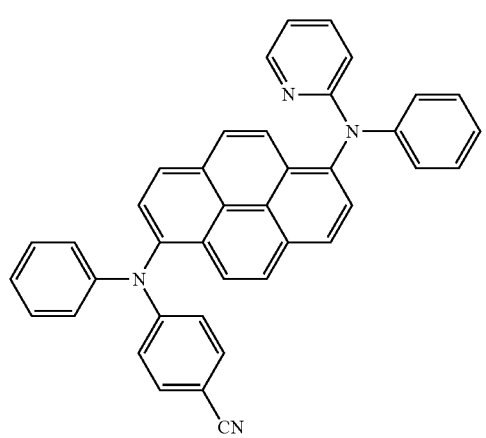
55
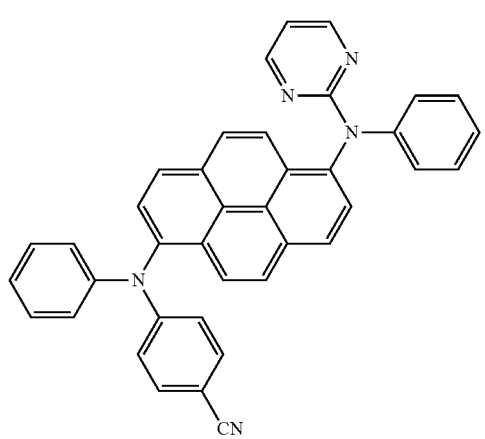

56
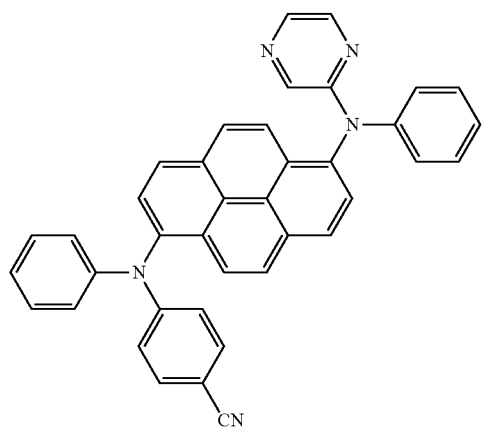
59
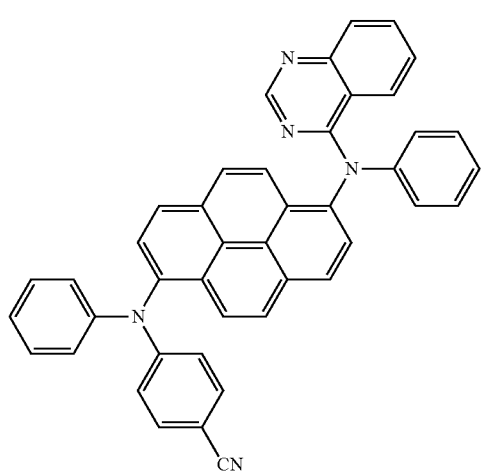
57
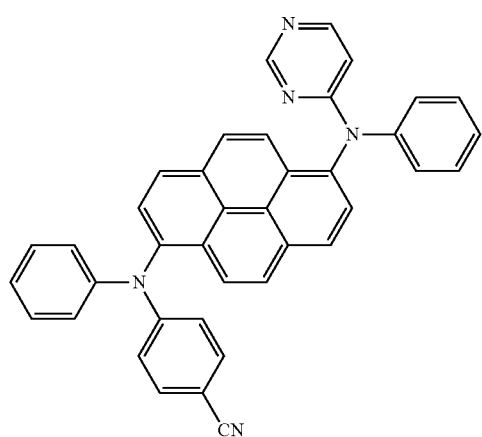
60
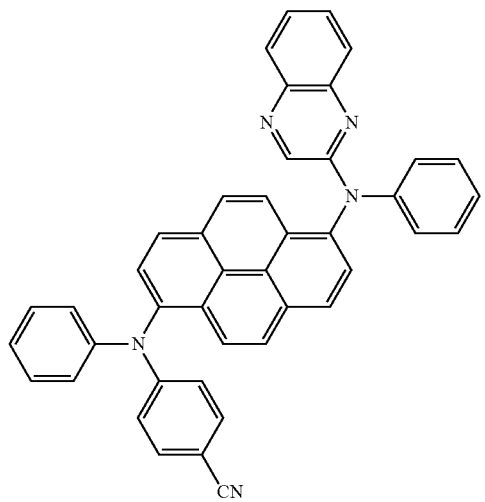
58
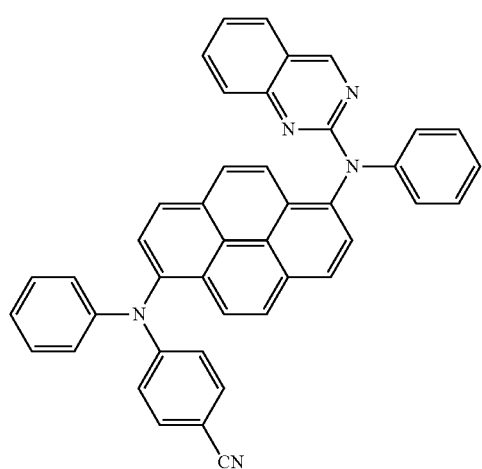
61
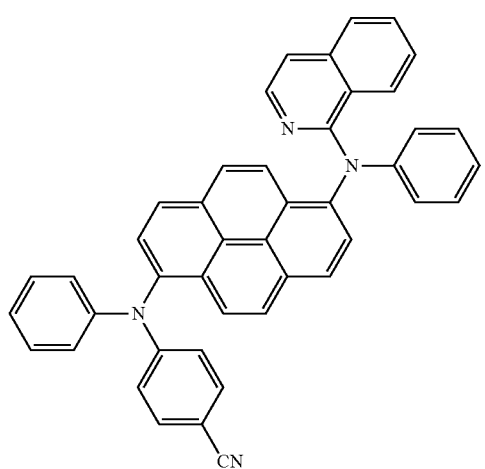

-continued
62
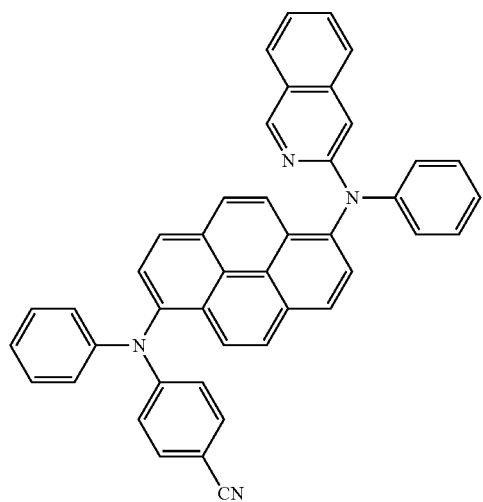
63
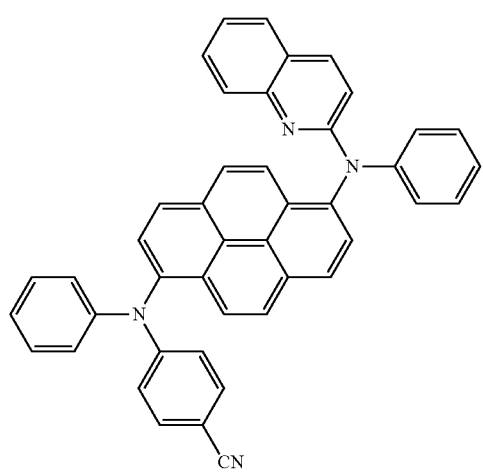
64
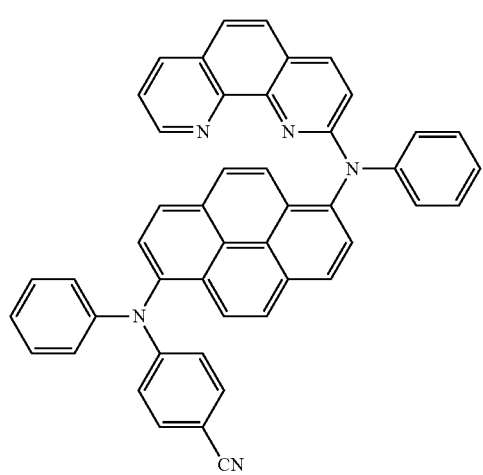
-continued
65
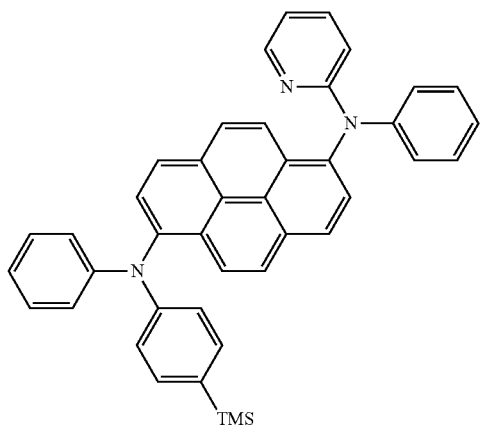
66
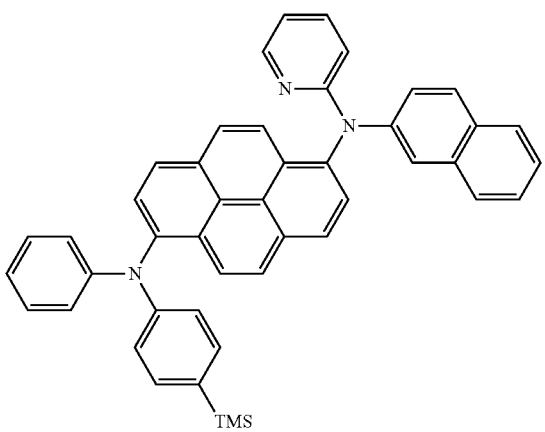
67
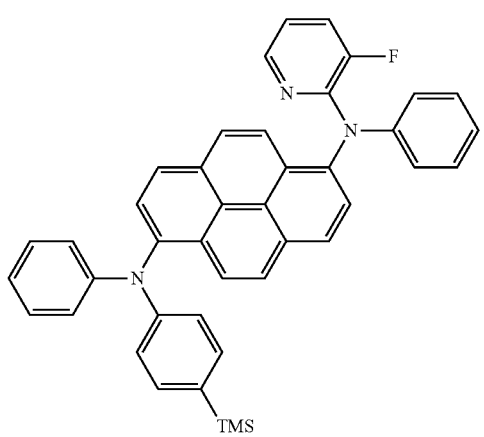

-continued
68
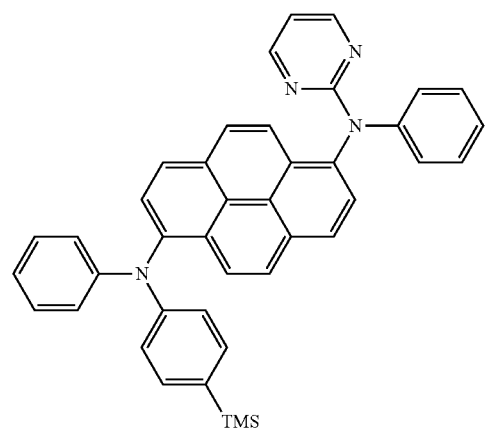
69
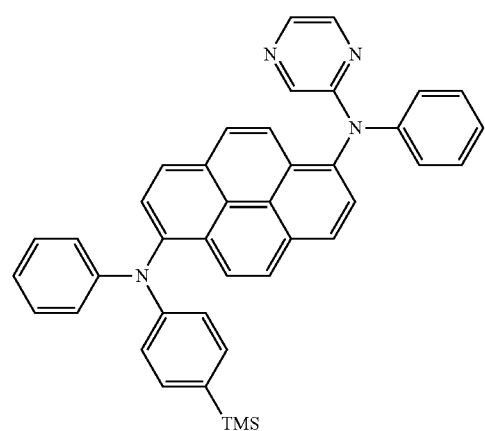
70
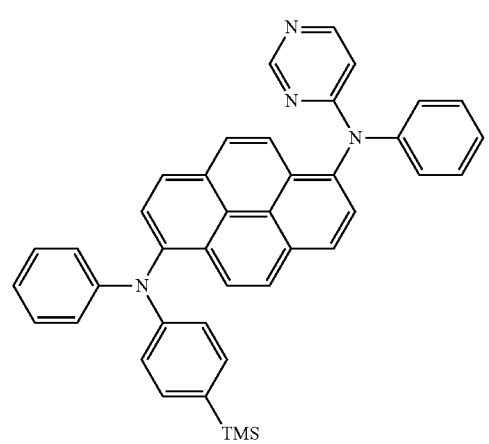
-continued
71
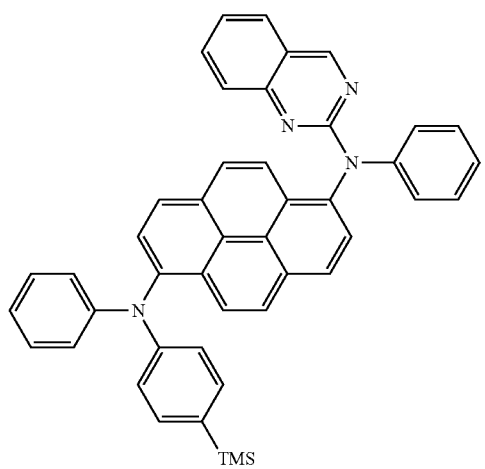
72
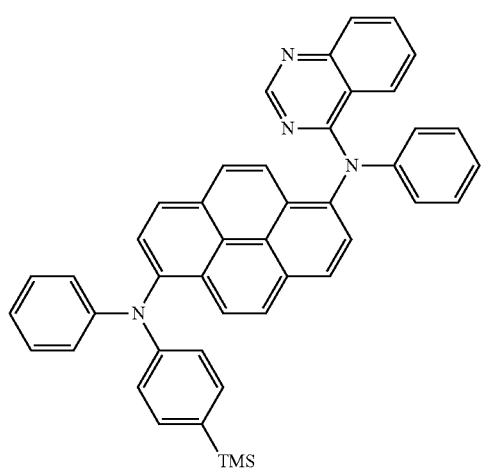
73
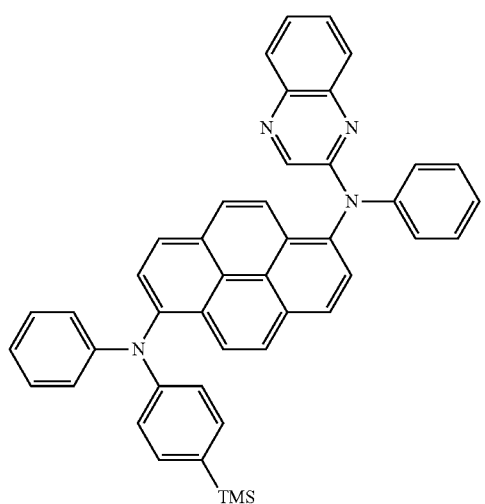

74
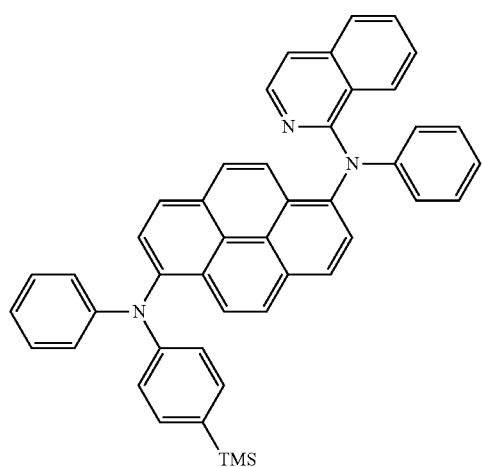
75
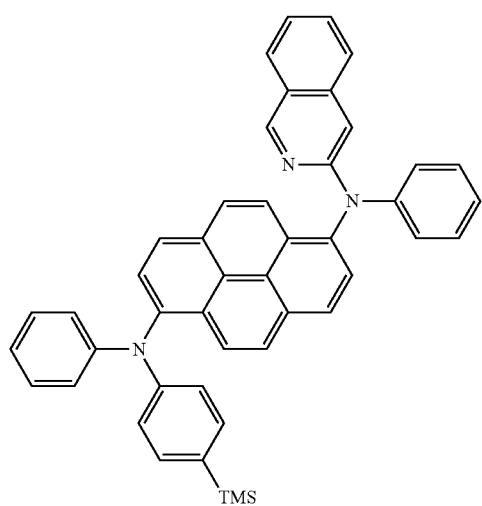
76
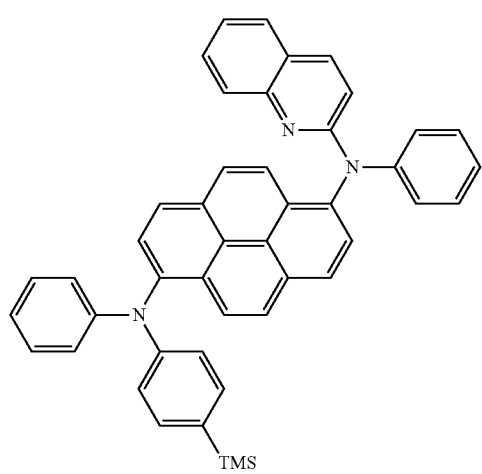
77
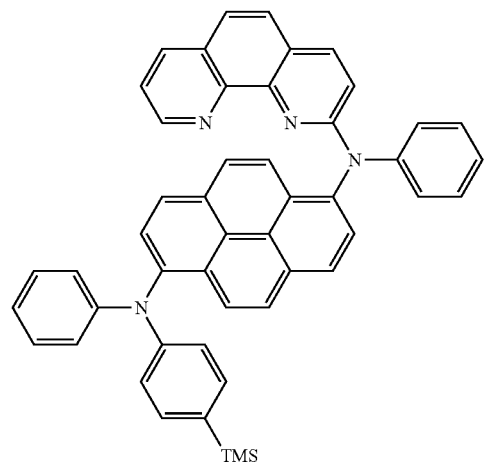
78
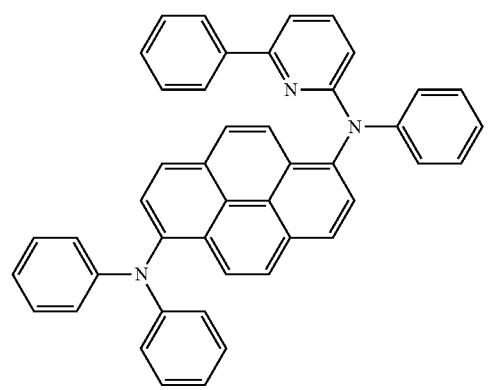
79
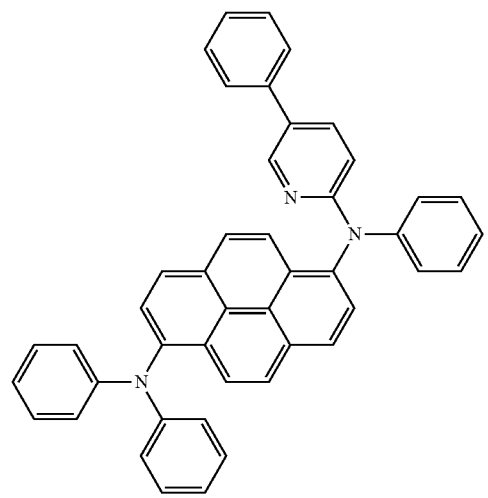

80
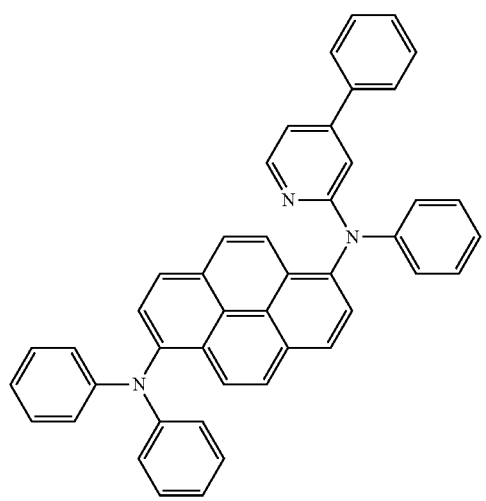
81
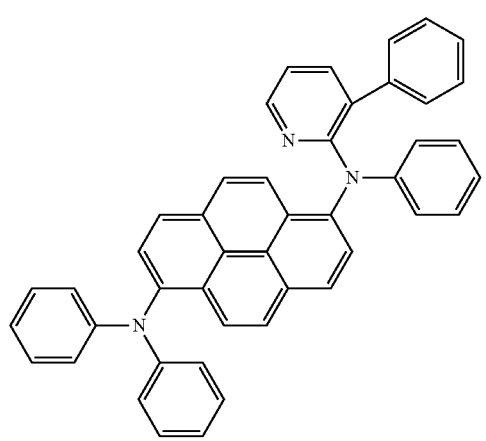
82
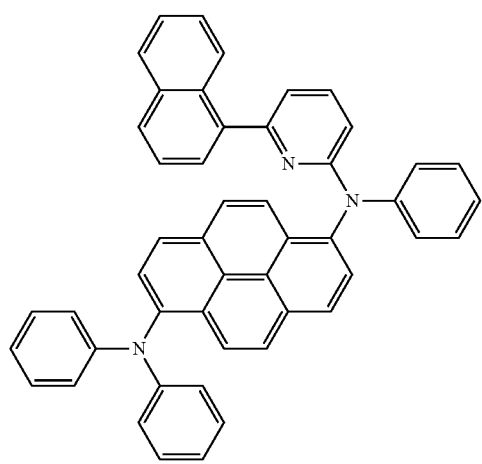
83
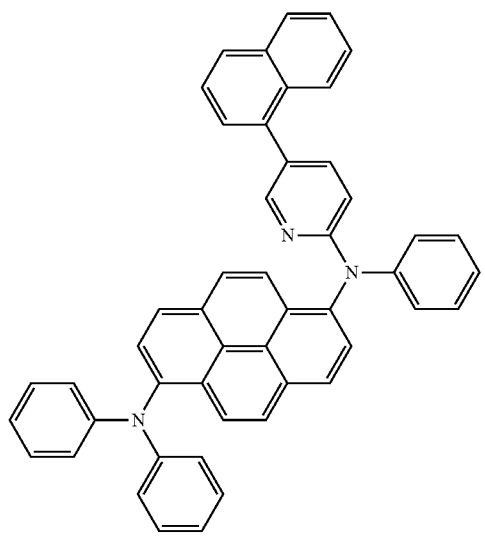
84
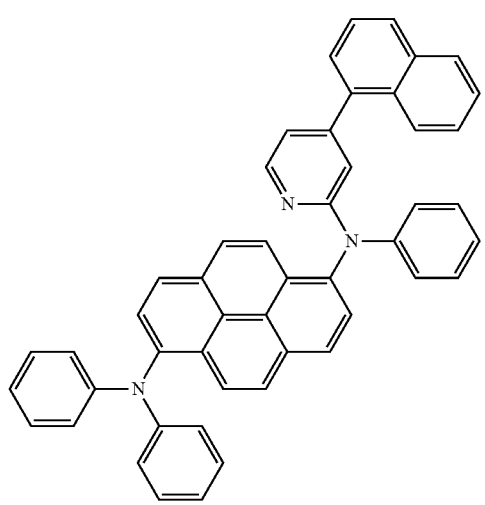
85
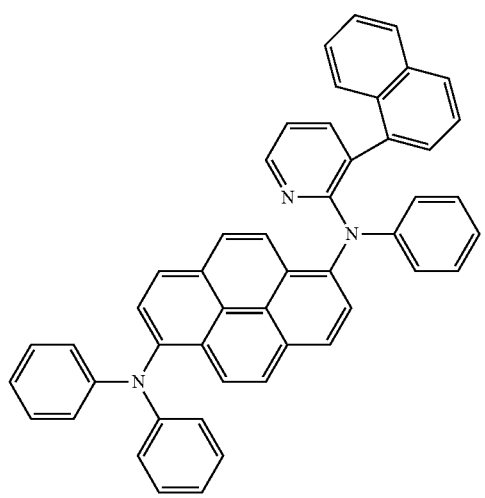

-continued
86
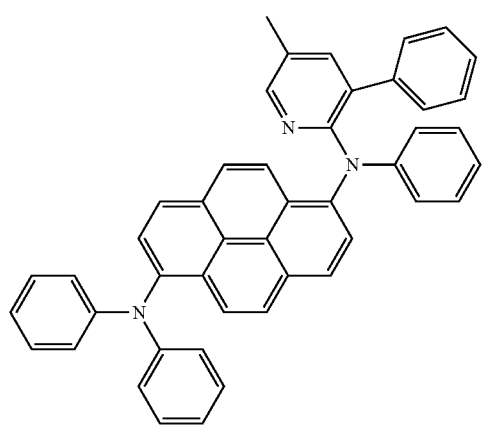
87
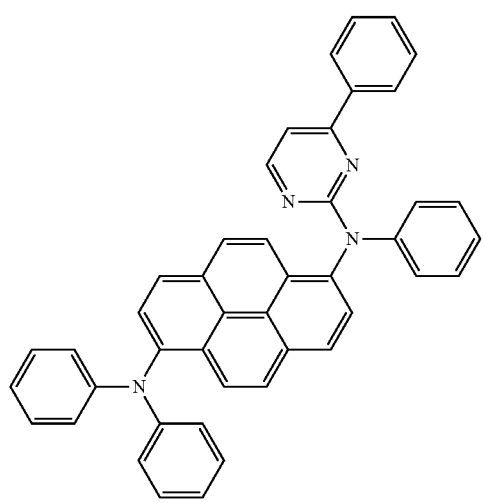
88
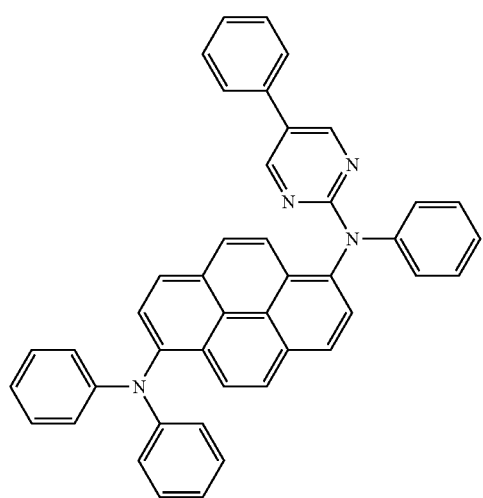
-continued
89
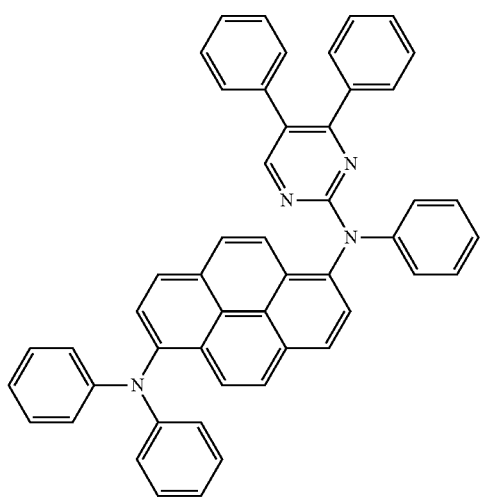
90
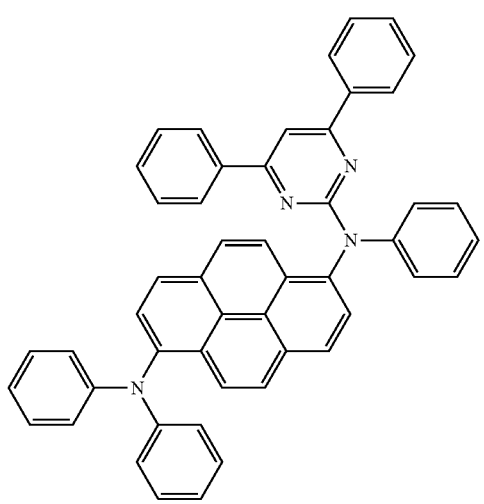
91
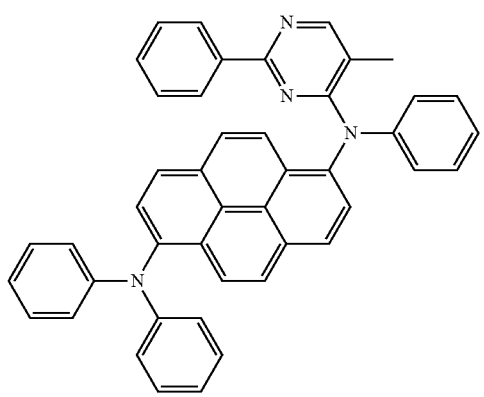

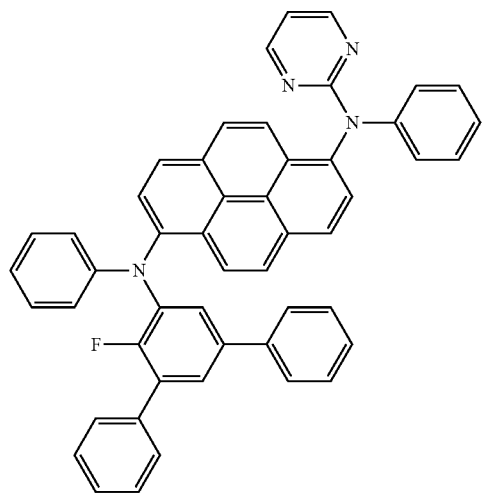
92
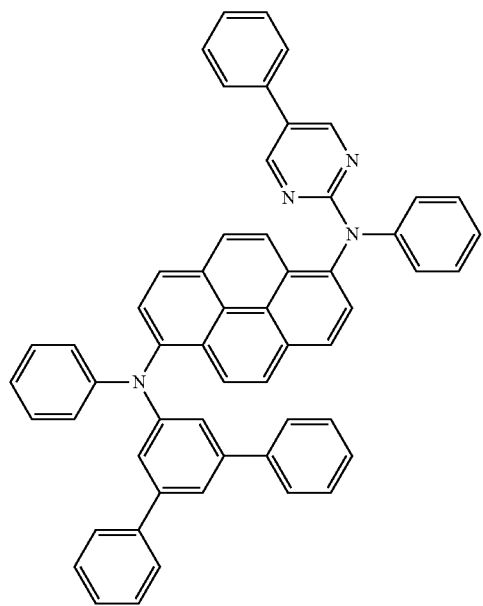
93
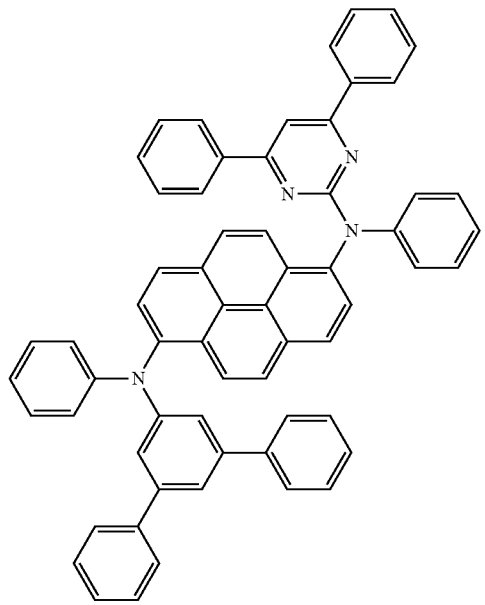
94
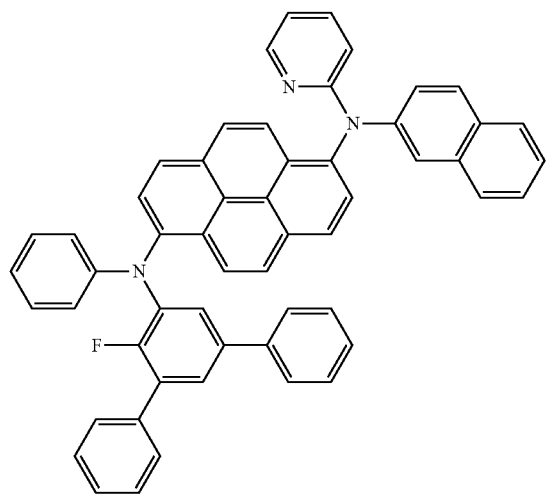
95
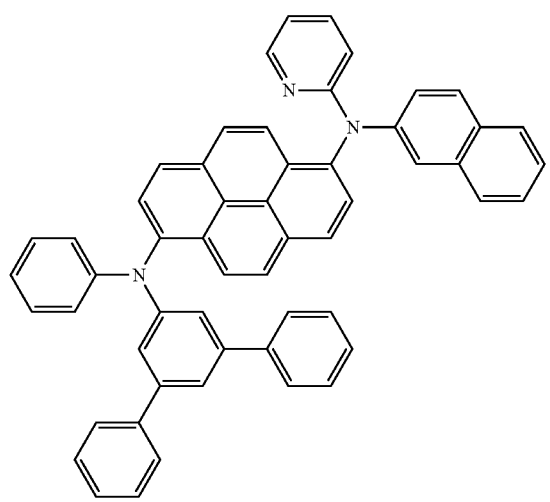
96

The pyrene-based compound represented by Formula 1 may have, as a substituent of two amino groups, A, $Ar_1$, $Ar_2$, and $Ar_3$, which are described above. In this regard, A may be a heteroaromatic group including at least one N, and $Ar_1$, $Ar_2$ and $Ar_3$ may each be a substituted or unsubstituted phenyl group or a substituted or unsubstituted naphthyl group. Accordingly, the pyrene-based compound may be a heteroaromatic group in which only one (e.g., A) of four substituents (e.g., A, $Ar_1$, $Ar_2$ and $Ar_3$) of two amino groups has a hetero atom (e.g., nitrogen) as a ring element. Accordingly, the pyrene-based compound may emit blue light with excellent color purity characteristics. For example, an organic light-emitting diode including the pyrene-based compound represented by Formula 1 may provide blue light with high color purity of which a y coordinate is 0.11 or less.

Although not limited to a particular theory, in the case of an organic light-emitting diode including, as a dopant of an emission layer, a compound (for example, Compound B which will be describe below) that has the same structure as the pyrene-based compound represented by Formula 1 except that two or more of four substituents of two amino groups are heteroaromatic groups, energy transition from an anthracen-based host to the dopant in the emission layer may not sufficiently occur and thus, performance of the organic light-emitting diode during operation may be rapidly decreased.

Also, two amino groups of the pyrene-based compound represented by Formula 1 may be different from each other. Thus, the pyrene-based compound represented by Formula 1 may be asymmetric. Accordingly, a film including the pyrene-based compound represented by Formula 1 may have high amorphous properties, and thus, the film including the pyrene-based compound represented by Formula 1 may have high electric stability. Thus, an organic light-emitting diode using the pyrene-based compound represented by Formula 1 may provide high brightness at low current.

Accordingly, an organic light-emitting diode employing the pyrene-based compound of Formula 1 may provide excellent electric characteristics (e.g., a low driving voltage, a high current density, a long lifespan, or the like) and excellent color purity characteristics.

The pyrene-based compound represented by Formula 1 may be synthesized by using suitable organic synthesis methods. Such synthesis methods of a pyrene-based compound may be seen by referring to examples below.

One or more of the pyrene-based compound of Formula 1 may be used between a pair of electrodes of an organic light-emitting diode. For example, one or more of the pyrene-based compound may be used in an emission layer.

Accordingly, provided is an organic light-emitting diode according to an embodiment including: a first electrode; a second electrode facing the first electrode; and an organic layer interposed between the first electrode and the second electrode, wherein the organic layer includes one or more pyrene-based compounds described above.

The wording that "(an organic layer) includes at least one pyrene-based compound" used herein means that "(an organic layer) may include one pyrene-based compound represented by Formula 1 or two or more pyrene-based compounds represented by Formula 1 being different from each other".

For example, the organic layer may include only Compound 3 as the pyrene-based compound. In this regard, Compound 3 may exist in an emission layer of the organic light-emitting diode. According to another embodiment, the organic layer may include Compound 3 and Compound 6 as the pyrene-based compound. In this regard, Compound 3 and Compound 6 may exist in an identical layer (for example, Compound 3 and Compound 6 may exist in an emission layer), or in different layers (for example, Compound 3 exists in an emission layer and Compound 6 exists in a hole transport layer.)

The organic layer may include at least one layer selected from a hole injection layer, a hole transport layer, a functional layer having a hole injection function and a hole transport function (hereinafter referred to as "H-functional layer"), a buffer layer, an electron blocking layer, an emission layer, a hole blocking layer, an electron transport layer, an electron injection layer, and/or a functional layer having an electron transport function and an electron injection function (hereinafter referred to as "E-functional layer").

The term "organic layer" used herein refers to a single layer and/or a plurality of layers disposed between a first electrode and a second electrode of an organic light-emitting diode.

The organic layer may include an emission layer, and the emission layer may include one or more pyrene-based compounds described above.

The pyrene-based compound included in the emission layer may act as a dopant. For example, the pyrene-based compound may act as a fluorescent dopant. An emission layer including the pyrene-based compound may emit blue light. In this regard, the emission layer may further include a host.

The host may include at least one compound selected from an anthracene-based compound represented by Formula 400 below and an anthracene-based compound represented by Formula 401 below:

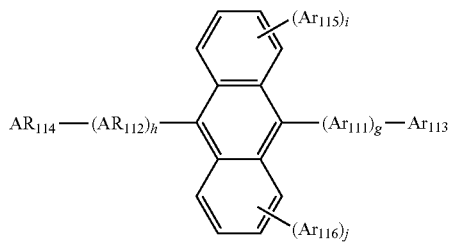

<Formula 400>

In Formula 400, $Ar_{111}$ and $Ar_{112}$ may each independently be a substituted or unsubstituted $C_6$-$C_{60}$ arylene group; $Ar_{113}$ to $Ar_{116}$ may each independently be a substituted or unsubstituted $C_1$-$C_{10}$ alkyl group or a substituted or unsubstituted $C_6$-$C_{60}$ aryl group; and g, h, i, and j may each independently be an integer of 0 to 4.

For example, $Ar_{111}$ and $Ar_{112}$ in Formula 400 may each independently be selected from a phenylene group, a naphthylene group, a phenanthrenylene group, or a pyrenylene group; and a phenylene group, a naphthylene group, a phenanthrenylene group, a fluorenyl group, and a pyrenylene group, each substituted with at least one of a phenyl group, a naphthyl group, and an anthracenyl group.

g, h, i, and j in Formula 400 may each independently be 0, 1, or 2.

$Ar_{113}$ to $Ar_{116}$ in Formula 400 may each independently be selected from a $C_1$-$C_{10}$ alkyl group, each substituted with at least one of a phenyl group, a naphthyl group, and an anthracenyl group; a phenyl group, a naphthyl group, an anthracenyl group, a pyrenyl group, a phenanthrenyl group and a fluorenyl group; and a phenyl group, a naphthyl group, an anthracenyl group, a pyrenyl group, a phenanthrenyl group, and a fluorenyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, a fluorenyl group, and

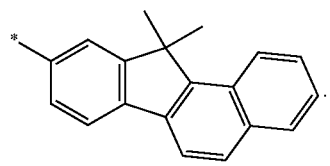 [SMILES: *c1ccc2c(c1)C(C)(C)c1c-2ccc2ccccc12]

For example, the anthracene-based compound represented by Formula 400 may be one of the following compounds:

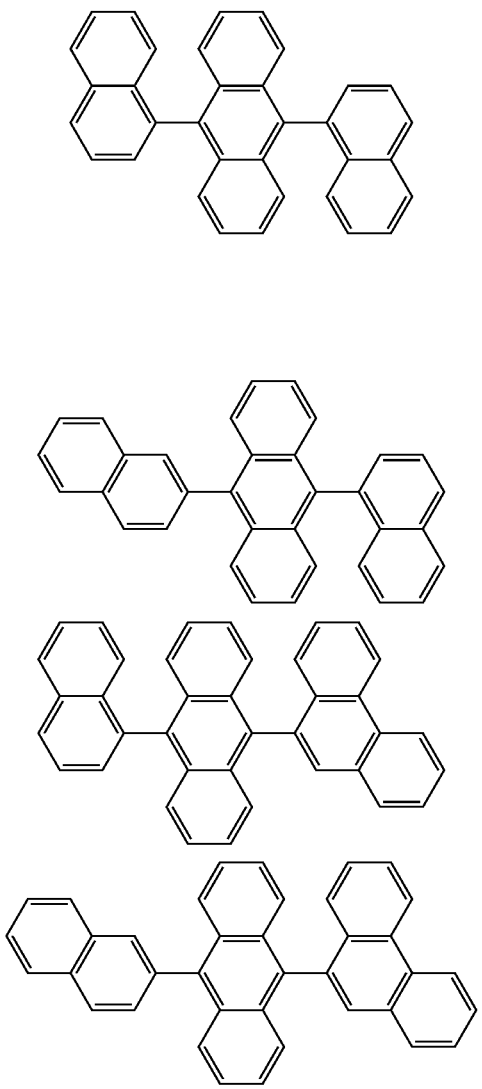

-continued

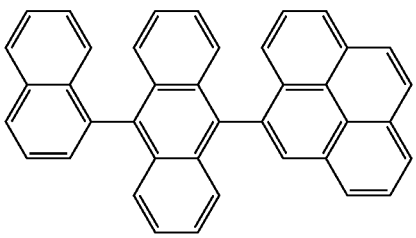

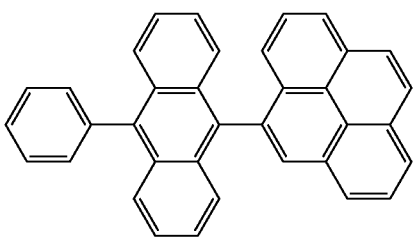

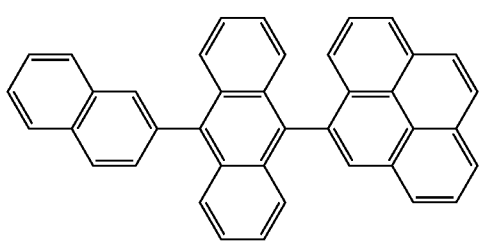

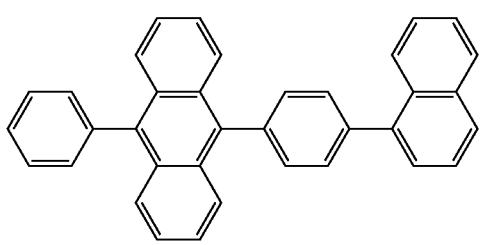

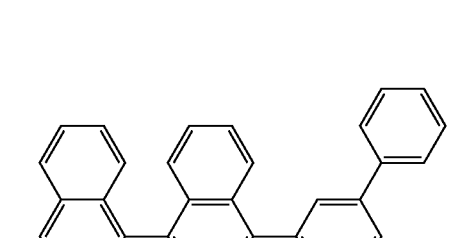

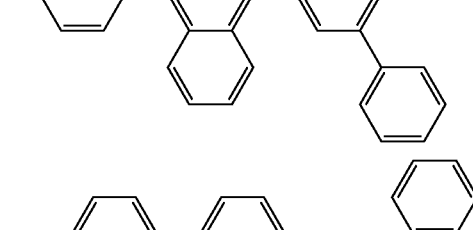

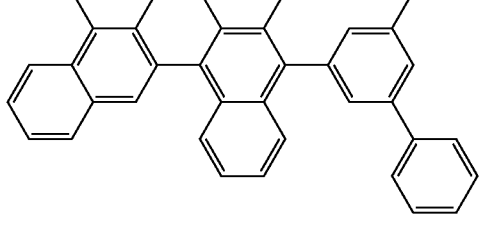

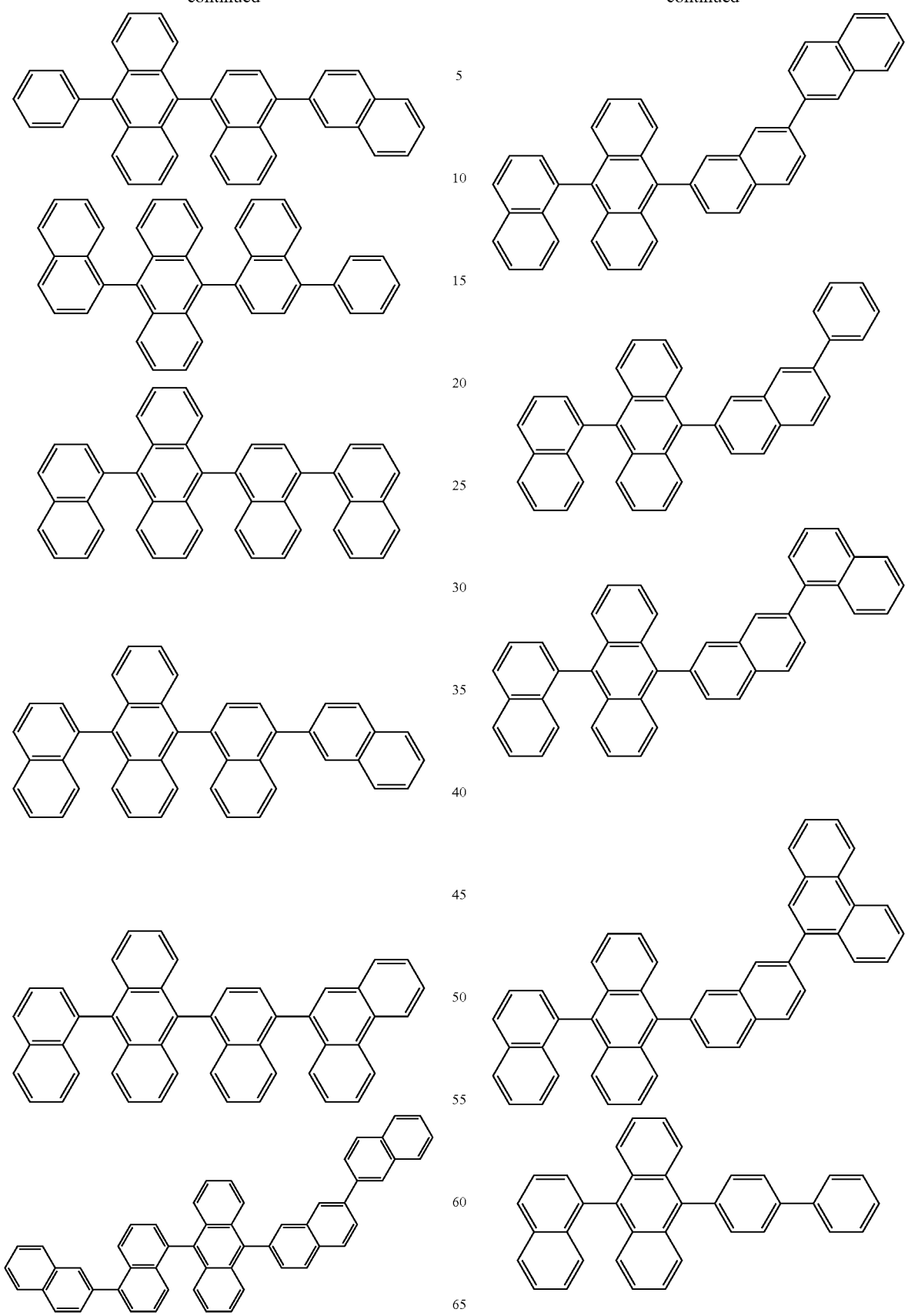

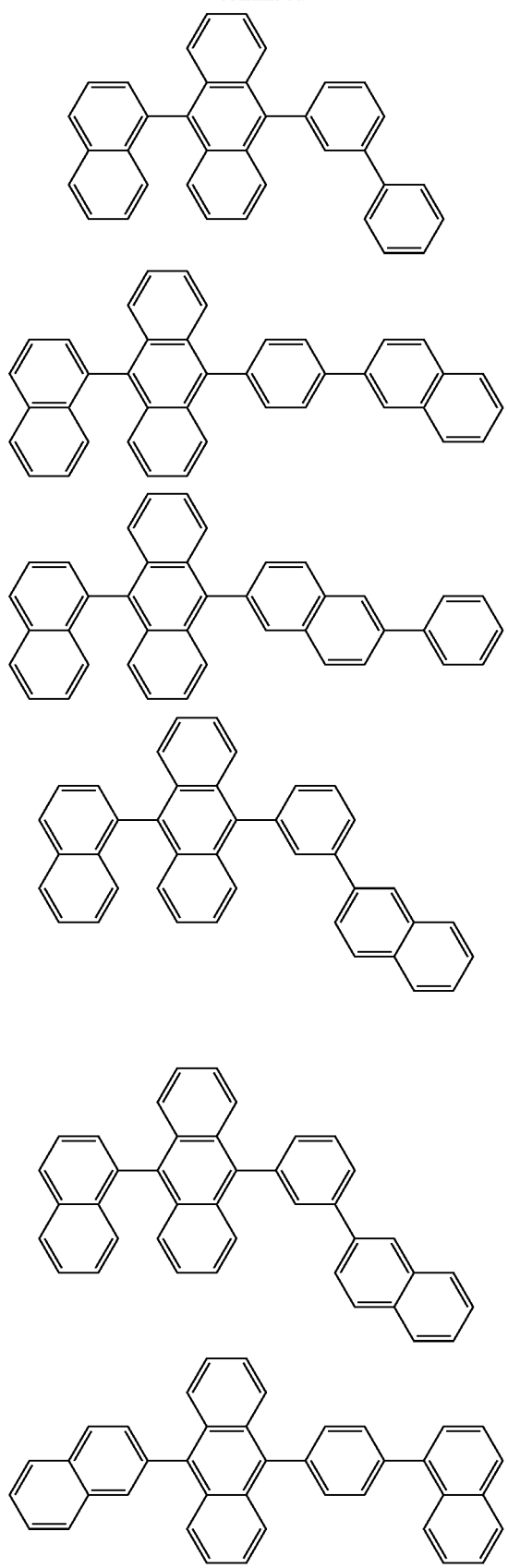

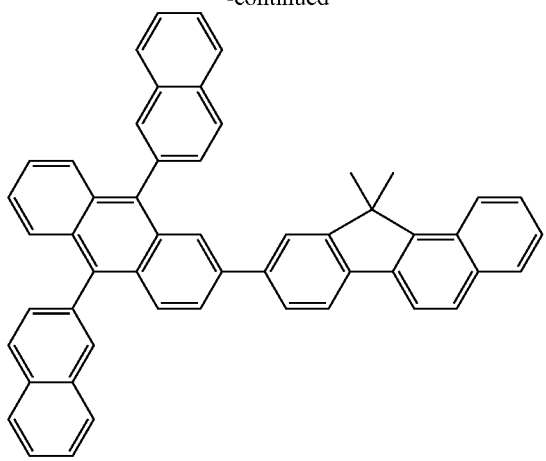

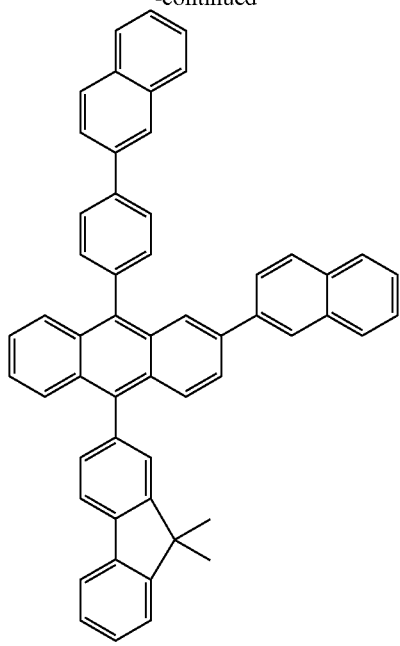

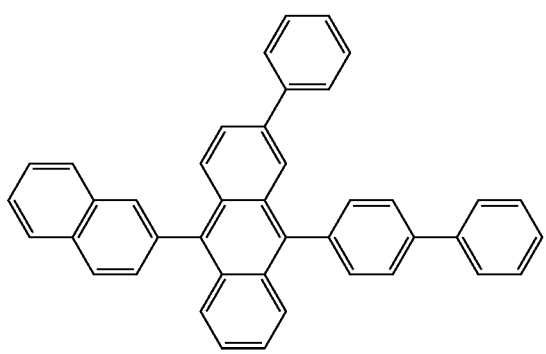

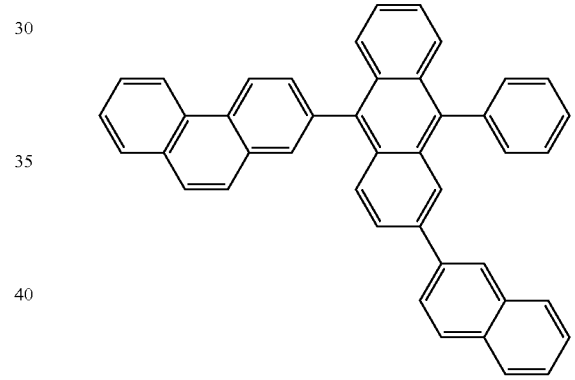

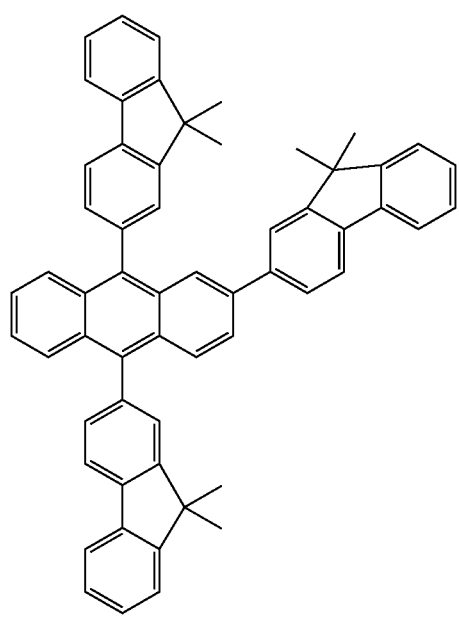

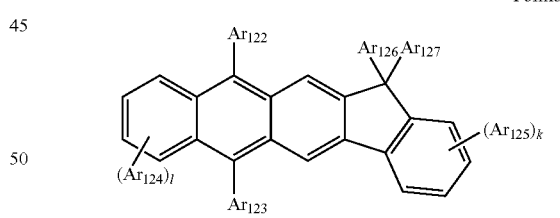

<Formula 401>

Ar$_{122}$ to Ar$_{125}$ in Formula 401 may be understood by referring to the description presented in connection to Ar$_{113}$ in Formula 400.

Ar$_{126}$ and Ar$_{127}$ in Formula 401 may each independently be a $C_1$-$C_{10}$ alkyl group (e.g., a methyl group, an ethyl group, or a propyl group).

k and l in Formula 401 may each independently be an integer of 0 to 4. For example, k and l may each independently be 0, 1, or 2.

For example, the anthracene-based compound represented by Formula 401 may be one of the following compounds.

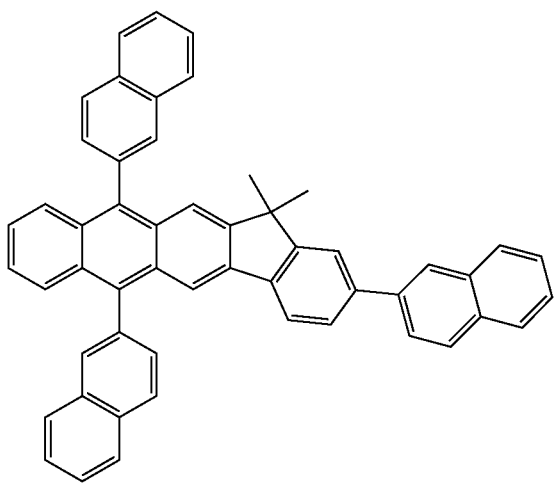

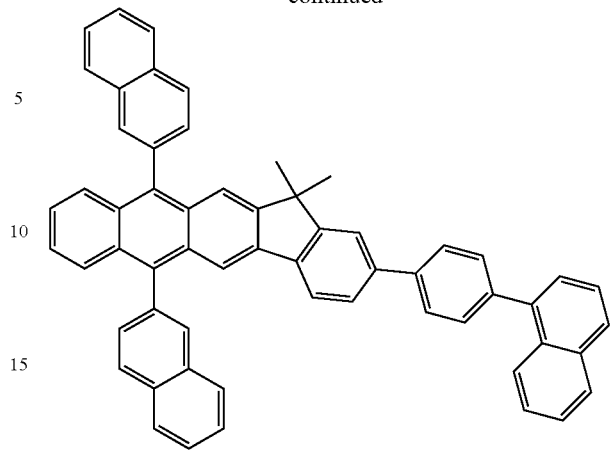

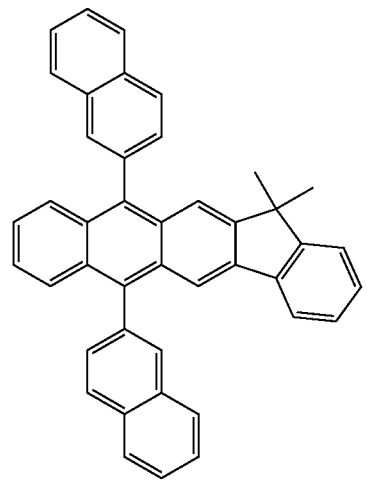

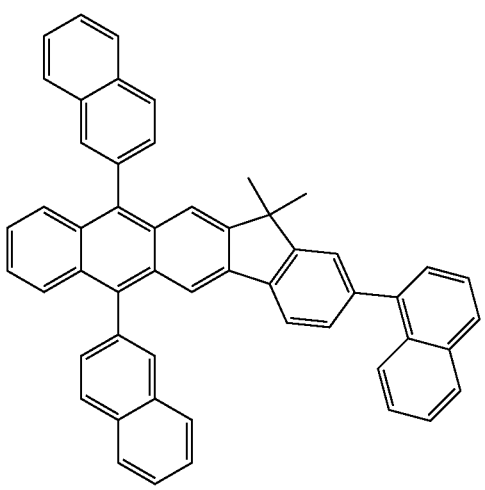

An organic light-emitting diode employing the pyrene-based compound of Formula 1 may emit blue light that satisfies sRGB standard. Accordingly, the organic light-emitting diode may be used in a large full-color display device (e.g., an organic light-emitting display (OLED) TV, or the like.).

FIG. 1 illustrates a schematic sectional view of an organic light-emitting diode 10 according to an embodiment. Hereinafter, the structure of an organic light-emitting diode according to an embodiment and a method of manufacturing a pyrene-based compound according to an embodiment will be described in connection with FIG. 1.

A substrate 11, which may be a suitable substrate that is used for OLEDs, may be e.g., a glass substrate or a transparent plastic substrate, each with excellent mechanical strength, thermal stability, transparency, surface smoothness, ease of handling, and water resistance.

A first electrode 13 may be formed by depositing or sputtering a material for a first electrode on the substrate 11. When the first electrode 13 is an anode, the material for the first electrode may be selected from materials with a high work function to facilitate hole injection. The first electrode 13 may be a reflective electrode, a semi-transmissive electrode, or a transmissive electrode. For example, when the organic light-emitting diode is used for a large full-color display, the second electrode 13 of the organic light-emitting diode may be a reflective electrode or a semi-transmissive electrode. The material for the first electrode may be a transparent material with high conductivity, and examples of such a material may include indium tin oxide (ITO), indium zinc oxide (IZO), tin oxide ($SnO_2$), and zinc oxide (ZnO). When magnesium (Mg), aluminum (Al), aluminum-lithium (Al—Li), calcium (Ca), magnesium-indium (Mg—In), magnesium-silver (Mg—Ag), or the like is used, the first electrode 13 may be used as a reflective electrode.

The first electrode 13 may have a single-layer structure or a multi-layer structure including at least two layers. For example, the first electrode 13 may have a three-layered structure of ITO/Ag/ITO.

An organic layer may be disposed of the first electrode 13.

The organic layer 15 may include a hole injection layer, a hole transport layer, a buffer layer, an emission layer, an electron transport layer, and an electron injection layer.

The hole injection layer (HIL) may be formed on the first electrode 13 by using various methods, e.g., vacuum deposition, spin coating, casting, Langmuir-Blodgett (LB) deposition.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec.

When a HIL is formed using spin coating, the coating conditions may vary according to the compound that is used to form the HIL, and the desired structure and thermal properties of the HIL to be formed. For example, the coating rate may be in the range of about 2,000 rpm to about 5,000 rpm, and a temperature at which heat treatment is performed to remove a solvent after coating may be in the range of about 80° C. to about 200° C.

For use as a hole injection material, a suitable hole injection material may be used. Examples of such a hole material may include N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (pani/DBSA), poly(3,4-ethylenedioxythiophene)/poly(4-styrenesulfonate) (PEDOT/PSS), polyaniline/camphor sulfonicacid (pani/CSA), or (polyaniline)/poly(4-styrenesulfonate) (PANI/PSS).

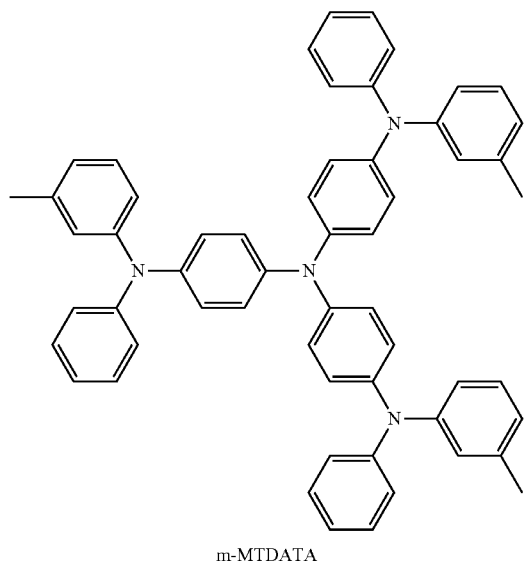

m-MTDATA

-continued

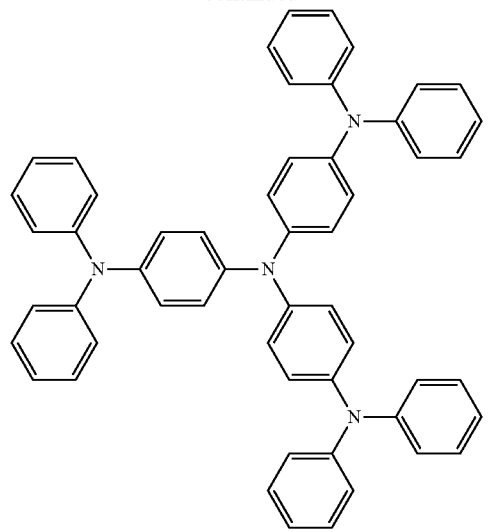

TDATA

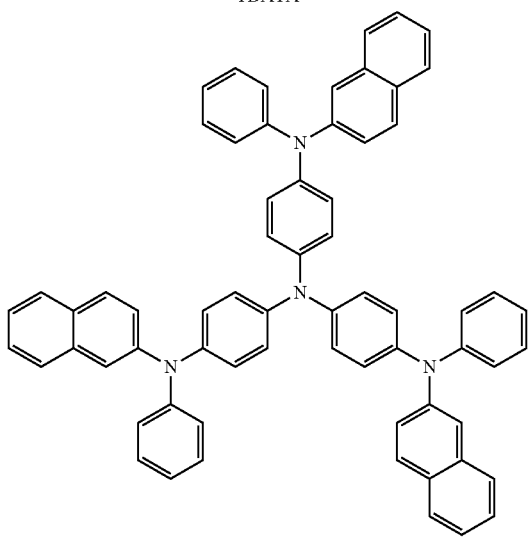

2-TNATA

A thickness of the HIL may be in a range of about 100 Å to about 10,000 Å, e.g., about 100 Å to about 1,000 Å. When the thickness of the HIL is within these ranges, the HIL may have satisfactory hole injection ability without a substantial increase in driving voltage.

Then, a hole transportation layer (HTL) may be formed on the HIL by using vacuum deposition, spin coating, casting, Langmuir-Blodgett (LB) deposition, or the like. When a HTL is formed using vacuum deposition or spin coating, the deposition and coating conditions may be similar to those for the formation of the HIL, though the conditions for deposition and coating may vary according to the material that is used to form the HTL.

A material that is used to form the HTL may be a suitable hole transport material. Examples of the material that is used to form the HTL may include a carbazol derivative, such as N-phenylcarbazol or polyvinylcarbazol; N,N'-bis(3-methylphenyl)-N,N'-diphenyl-[1,1-biphenyl]-4,4'-diamine (TPD); 4,4',4''-tris(N-carbazolyl)triphenylamine (TCTA), and alpha (α)-NPD.

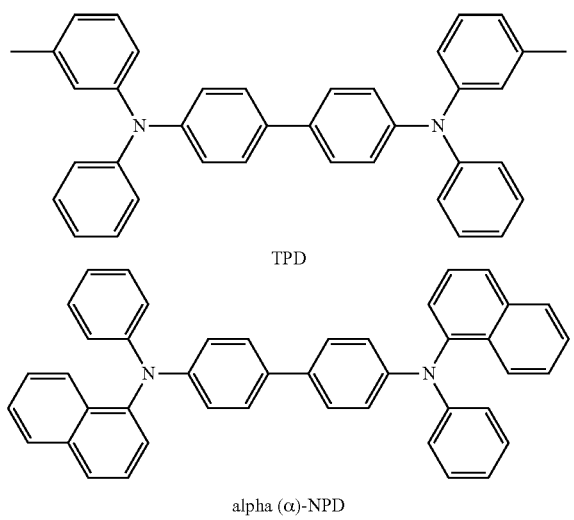

TPD alpha (α)-NPD

A thickness of the HTL may be in a range of about 50 Å to about 20,000 Å, e.g., about 100 Å to about 1,500 Å. When the thickness of the HTL is within these ranges, the HTL may have satisfactory hole transporting ability without a substantial increase in driving voltage.

The H-functional layer (a functional layer having a hole injection ability and a hole transport ability) may include one or more materials selected from the materials for the HIL and the materials for the HTL. A thickness of the H-functional layer may be in a range of about 100 Å to about 10,000 Å, e.g., about 100 Å to about 1,000 Å. When the thickness of the H-functional layer is within these ranges, the H-functional layer may have satisfactory hole injection and transport characteristics without a substantial increase in driving voltage.

Also, at least one layer selected from the hole injection layer, the hole transport layer, and the H-functional layer may include at least one selected from a compound represented by Formula 300 below and a compound represented by Formula 350 below:

<Formula 300>

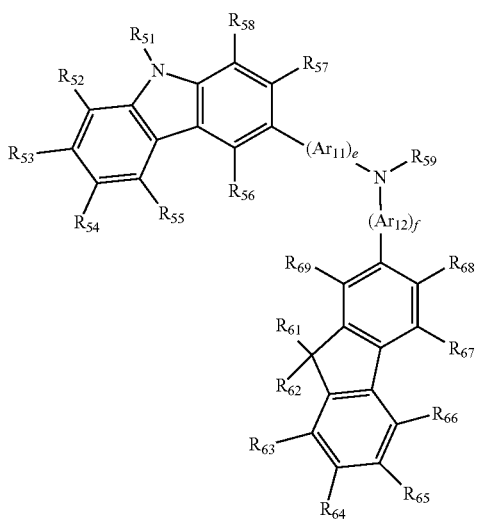

<Formula 350>

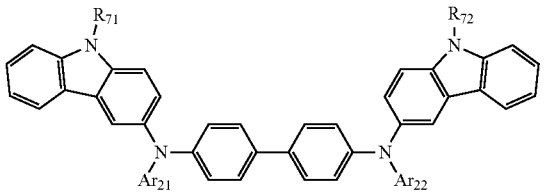

$Ar_{11}$ and $Ar_{12}$ in Formula 300 may each independently be a substituted or unsubstituted $C_6$-$C_{60}$ arylene group.

For example, $Ar_{11}$ and $Ar_{12}$ may be each independently selected from:

a phenylene group, a pentalenylene group, an indenylene group, a naphthylene group, an azulenylene group, an acenaphthylene group, a fluorenylene group, a phenalenylene group, a phenanthrenylene group, an anthracenylene group, a fluorantenylene group, a triphenylenylene group, a pyrenylene group, a chrysenylenylene group, a naphthacenylene group, a pycenylene group, a perylenylene group and a pentacenylene group; and a phenylene group, a pentalenylene group, an indenylene group, a naphthylene group, an azulenylene group, an acenaphthylene group, a fluorenylene group, a phenalenylene group, a phenanthrenylene group, an anthracenylene group, a fluorantenylene group, a triphenylenylene group, a pyrenylene group, a chrysenylenylene group, a naphthacenylene group, a pycenylene group, a perylenylene group and a pentacenylene group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_1$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group.

e and f in Formula 300 may each independently be an integer of 0 to 5, or 0, 1, or 2. In an implementation, e may be 1 and f may be 0.

$R_{51}$ to $R_{58}$, $R_{61}$ to $R_{69}$ and $R_{71}$ to $R_{72}$ in Formulae 300 and 350 may each independently be selected from a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, and a substituted or unsubstituted $C_6$-$C_{60}$ arylthio group.

For example, $R_{51}$ to $R_{58}$, $R_{61}$ to $R_{69}$, and $R_{71}$ to $R_{72}$ may each independently be selected from:

a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{10}$ alkyl group (for example, a methyl group, an ethyl group, a propyl group, a butyl group, a pentyl group, or a hexyl group), and a $C_1$-$C_{10}$ alkoxy group (for example, a methoxy group, an ethoxy group, a propoxy group, a butoxy group, a pentoxy group, or the like);

a $C_1$-$C_{10}$ alkyl group and a $C_1$-$C_{10}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{10}$ alkyl group, and a $C_1$-$C_{10}$ alkoxy group, and is not limited thereto.

$R_{59}$, $Ar_{21}$, and $Ar_{22}$ in Formulae 300 and 350 may each independently be selected from a phenyl group, a naphthyl group, an anthracenyl group, biphenyl group, and a pyridyl group; and a phenyl group, a naphthyl group, an anthracenyl group, biphenyl group, and a pyridyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a substituted or unsubstituted $C_1$-$C_{20}$ alkyl group, and a substituted or unsubstituted $C_1$-$C_{20}$ alkoxy group.

In an implementation, the compound represented by Formula 300 may be represented by Formula 300A below.

<Formula 300A>

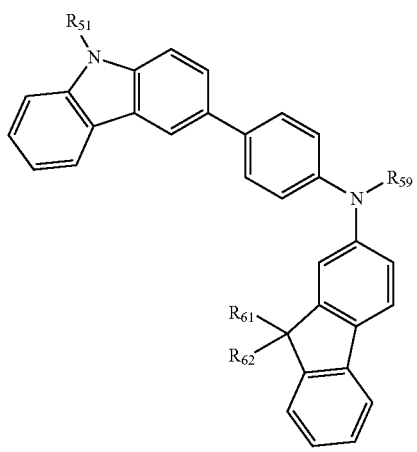

$R_{51}$, $R_{61}$, $R_{62}$ and $R_{59}$ in Formula 300A are already described in detail above.

For example, at least one layer selected from the HIL, the HTL, and the H-functional layer may include at least one selected from Compounds 301 to 320. In an implementation, these layers may instead or additionally include other compounds:

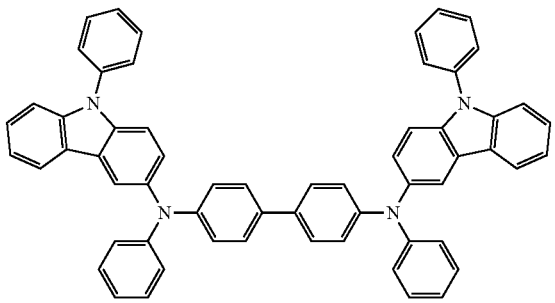
301

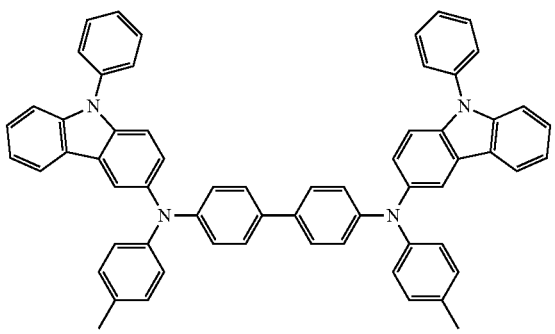
302

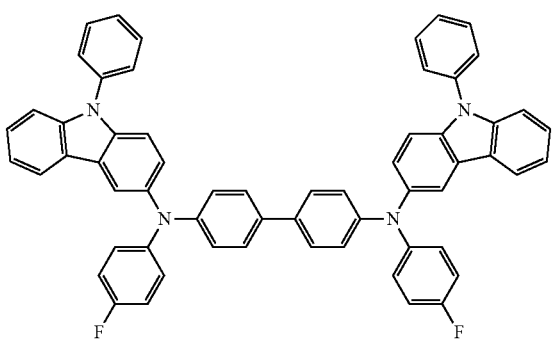
303

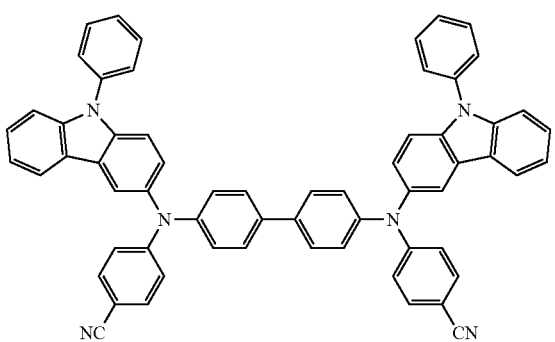
304

305
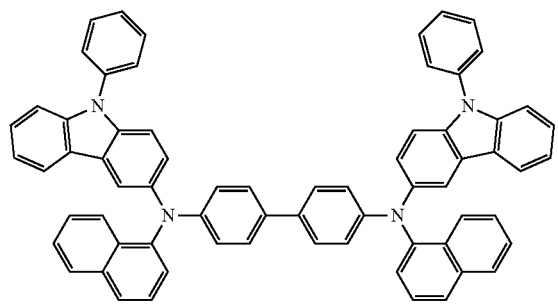
306
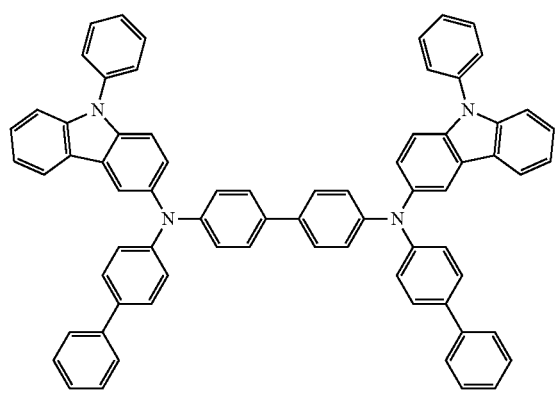
307
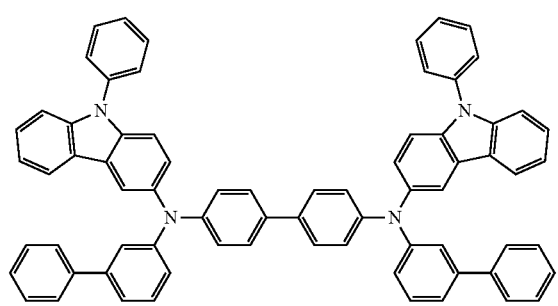
308
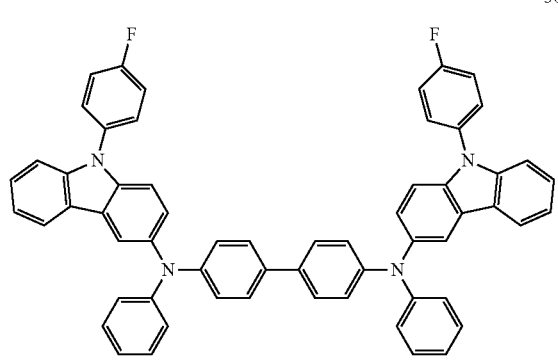
309
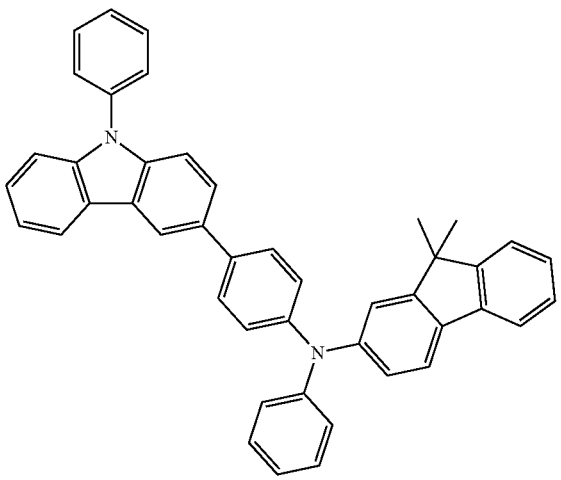
310
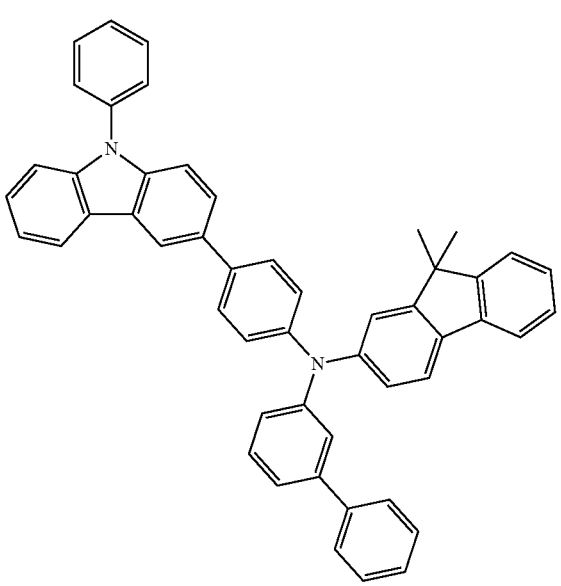

111
-continued
312
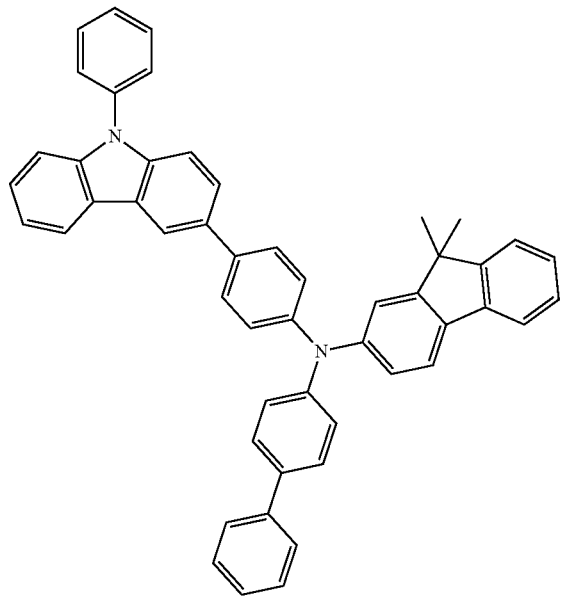
311
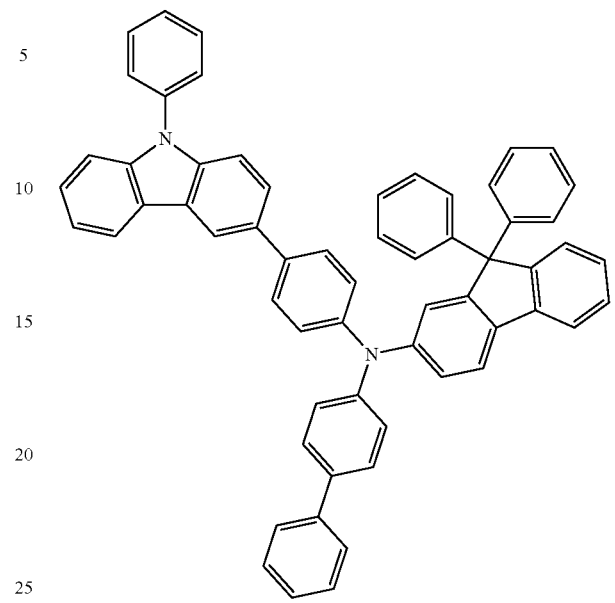
112
-continued
313
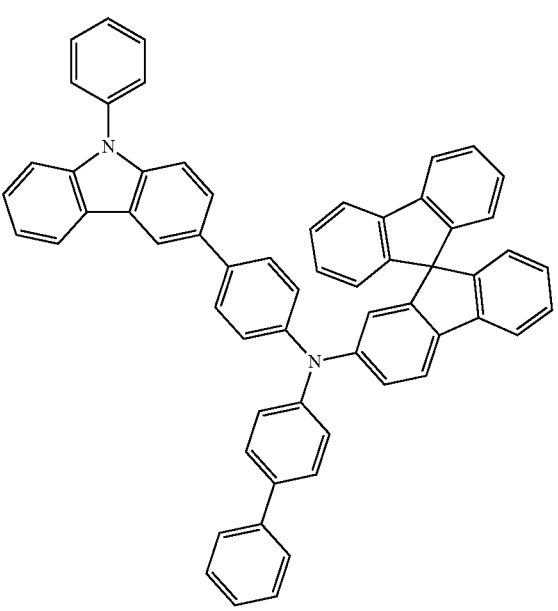
314

113
-continued
315
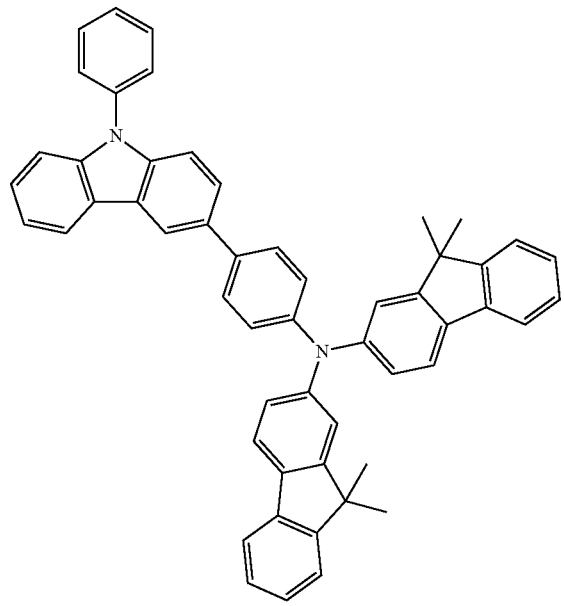
316
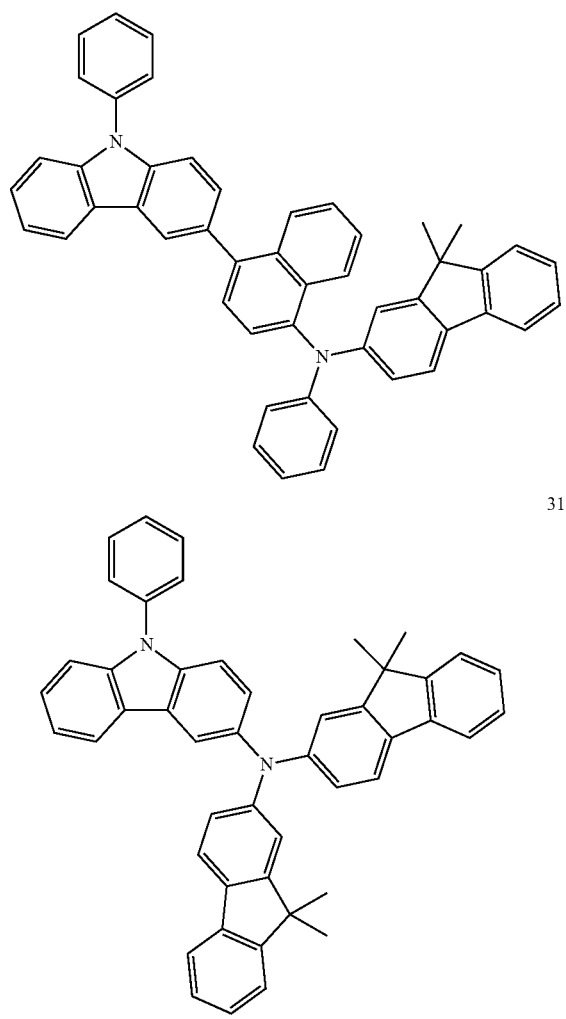
114
-continued
318
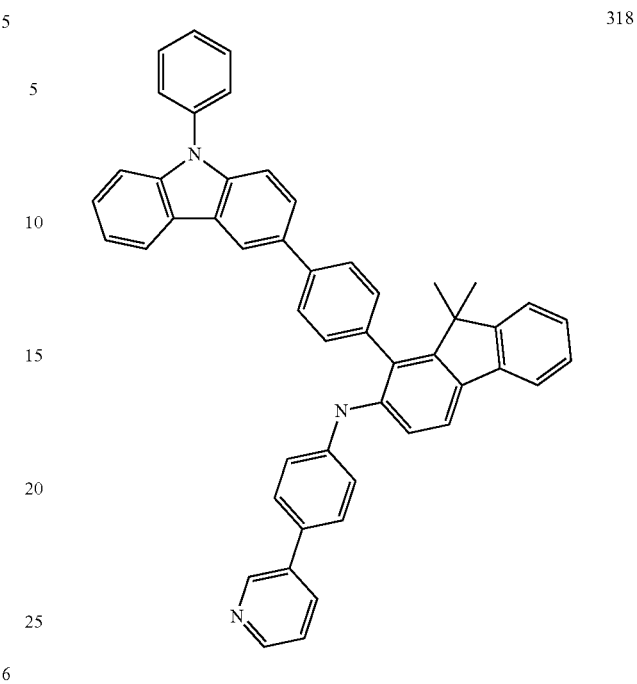
319
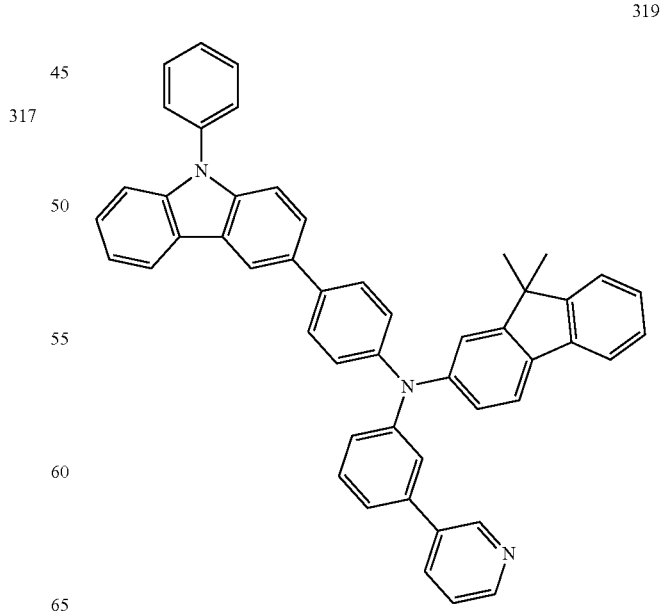
317

-continued

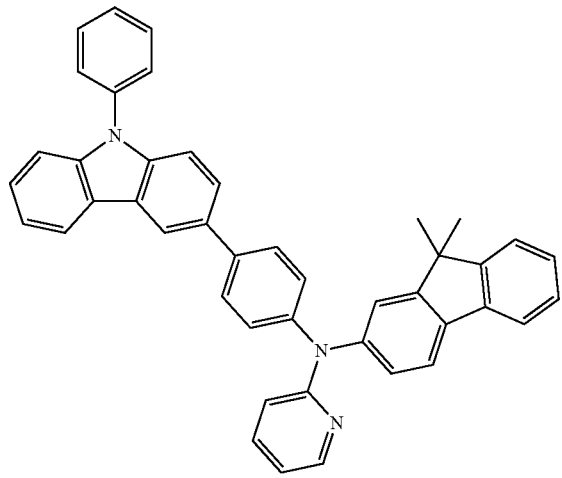

At least one layer selected from the hole injection layer, the hole transport layer, and the H-functional layer may further include, in addition to suitable hole injection materials, suitable hole transport materials, and/or suitable materials having a hole injection function and a hole transport function, a charge-generating material to help increase conductivity of the corresponding layer.

The charge-generating material may be, e.g., a p-dopant. The p-dopant may be one of quinine derivatives, metal oxides, and compounds with a cyano group, but is not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-CTNQ); a metal oxide, such as tungsten oxide or molybdenium oxide; and a cyano group-containing compound, such as Compound 200 below.

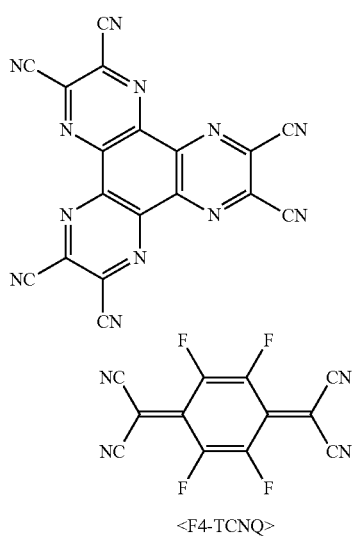

<Compound 200>

<F4-TCNQ>

When the HIL, the HTL, or the H-functional layer further includes a charge-generating material, the charge-generating material may be homogeneously dispersed or non-homogeneously distributed in the HIL, the HTL, or the H-functional layer.

A buffer layer may be disposed between the EML and at least one of the HIL, the HTL, and the H-functional layer. The buffer layer may help compensate for an optical resonance distance of light according to a wavelength of the light emitted from an emission layer, and thus may help increase efficiency. The butter layer may include suitable hole injecting materials or hole transporting materials. In an implementation, the buffer layer may include the same material as one of the materials included in the HIL, the HTL, and the H-functional layer that are disposed under the buffer layer.

Then, an emission layer (EML) may be formed on the HIL, the HTL, or the H-functional layer by, e.g., vacuum deposition, spin coating, casting, LB deposition, or the like. When the EML is formed using vacuum deposition or spin coating, the deposition and coating conditions may be similar to those for the formation of the HIL, though the conditions for deposition and coating may vary according to the material that is used to form the EML.

The EML may include one or more of the pyrene-based compounds described above.

The pyrene-based compound included in the EML may act as a dopant (e.g., a blue fluorescent dopant). For example, the EML may further include, in addition to the pyrene-based compound, a host.

As the host, $Alq_3$, 4,4'-N,N'-dicarbazol-biphenyl (CBP), poly(n-vinylcarbazole) (PVK), 9,10-di(naphthalen-2-yl)anthracene (ADN), TCTA, 1,3,5-tris(N-phenylbenzimidazole2-yl)benzene (TPBI), 3-tert-butyl-9,10-di(naphth-2-yl)anthracene (TBADN), E3, distyryl arylene (DSA), dmCBP (illustrated below), Compounds 501 to 509 below, or the like may be used.

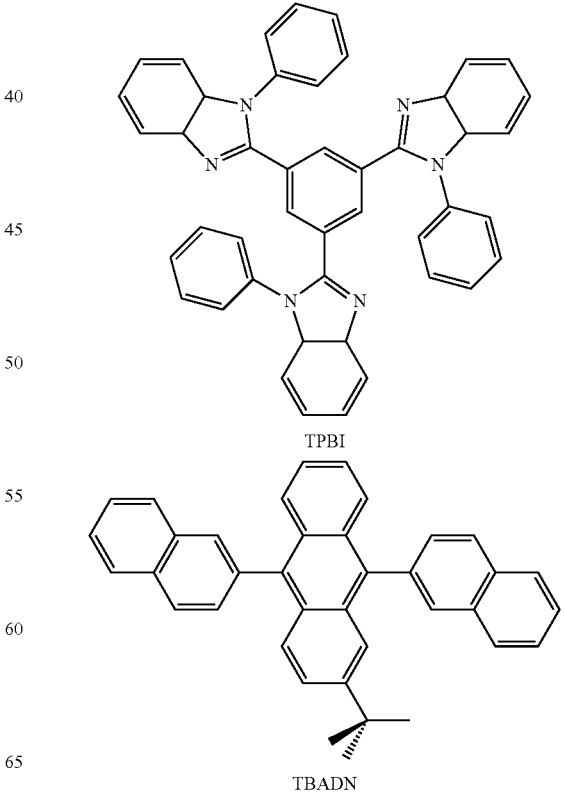

TPBI

TBADN

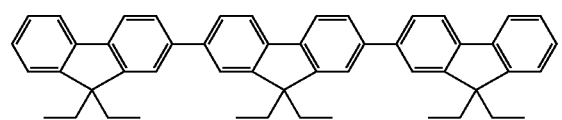
E3
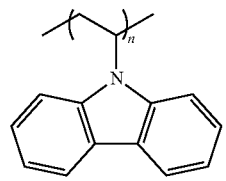
PVK
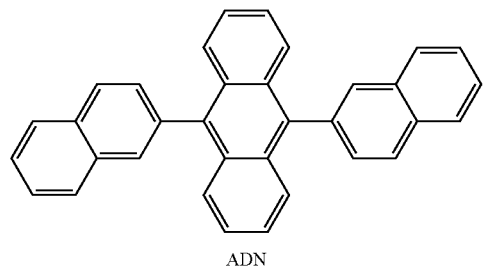
ADN
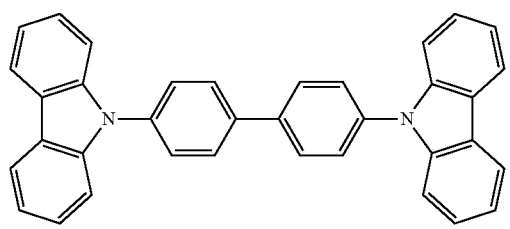
CBP
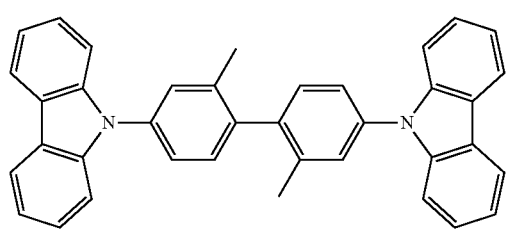
dmCBP
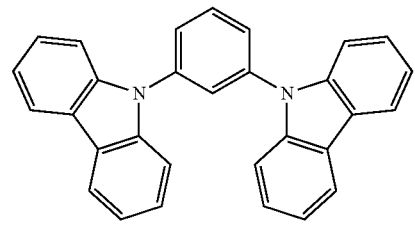
501
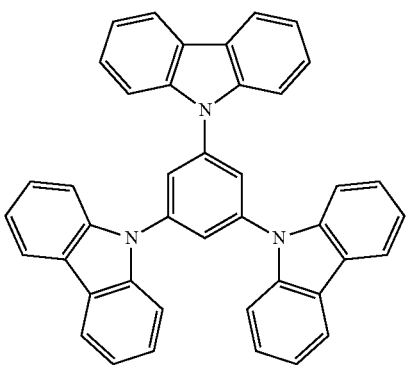
502
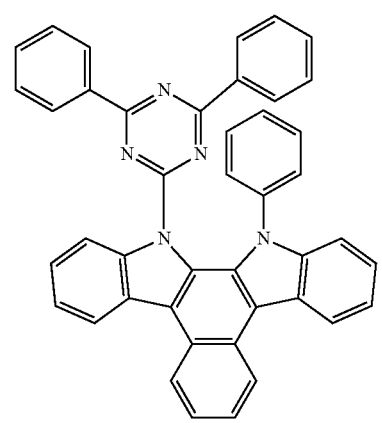
503
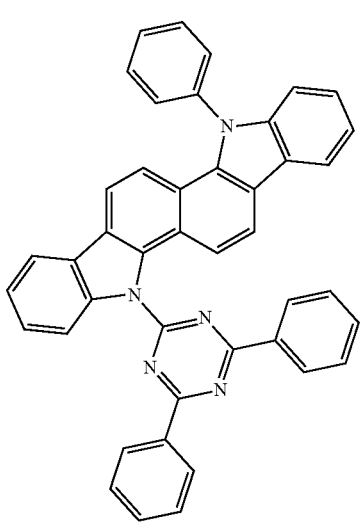
504

505

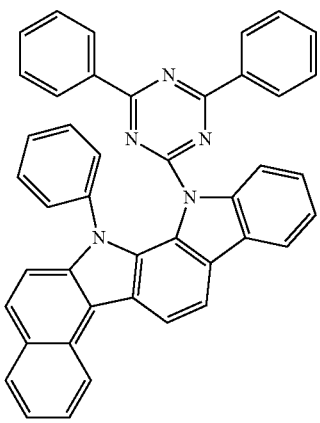

506

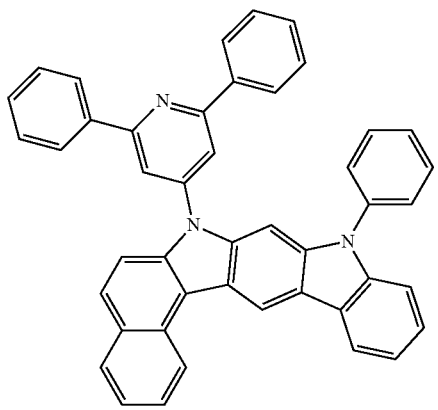

507

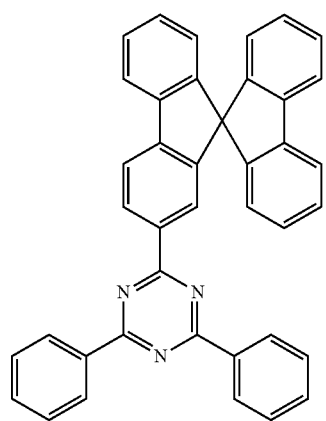

508

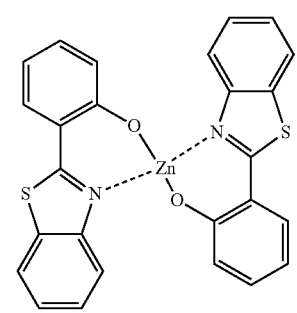

509

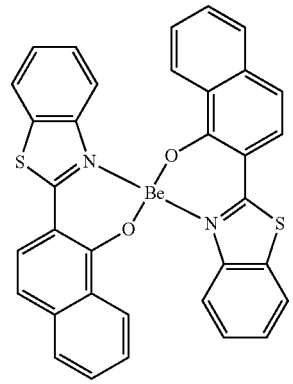

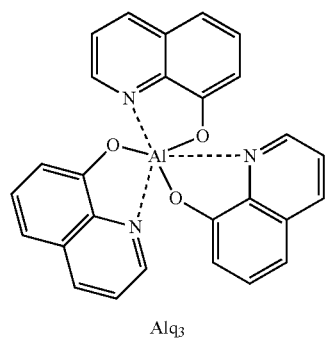

Alq$_3$

Alternatively, the EML may include as the host at least one compound selected from an anthracene-based compound represented by Formula 400 below and an anthracene-based compound represented by Formula 401.

The organic light-emitting diode may include a blue sub-pixel that emits blue light, a green sub-pixel that emits green light, and a red sub-pixel that emits red light. The blue sub-pixel may include a blue EML that emits blue light, and the blue EML may include the pyrene-based compound represented by Formula 1. According to another embodiment, due to a stack structure including a red EML, a green EML, and/or a blue EML, the EML may emit white light.

Also, the blue EML may further include compounds illustrated below as the blue dopant, but other materials may further be included in the blue EML.

121
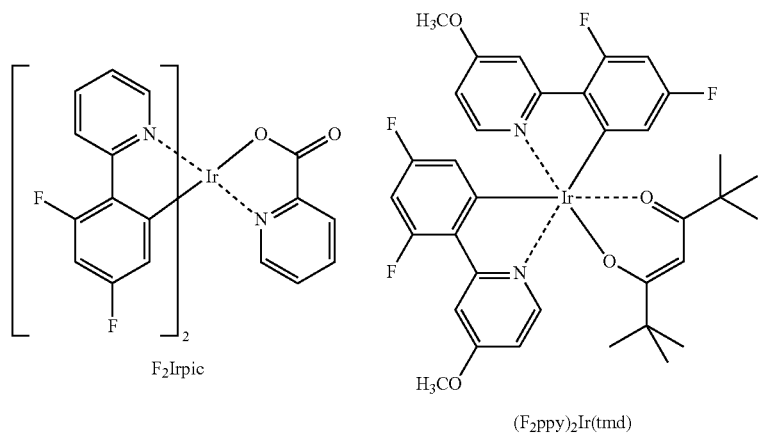
122
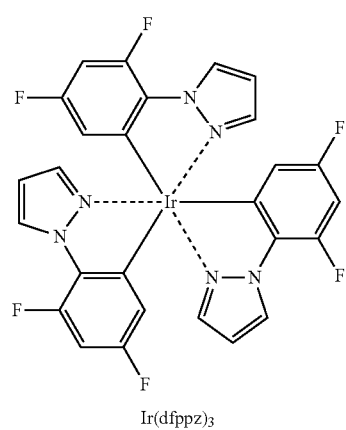
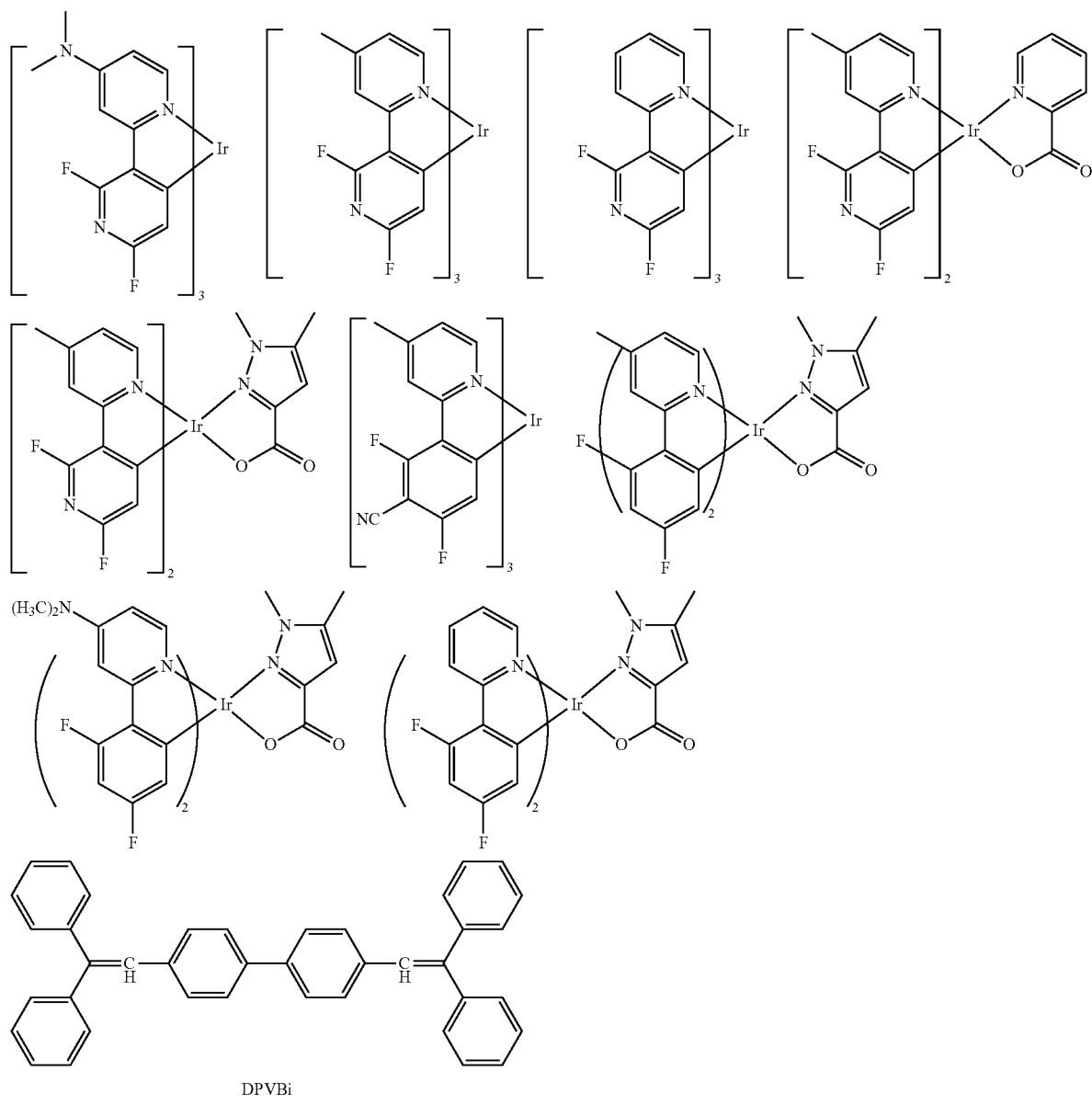

-continued
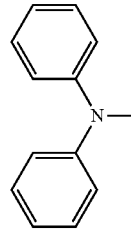
DPAVBi
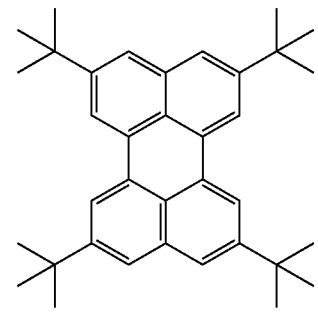
TBPe
For example, the red EML of the red sub-pixel may include compounds illustrated below as a red dopant. In an implementation, DCM or DCJTB may be used as the red dopant.
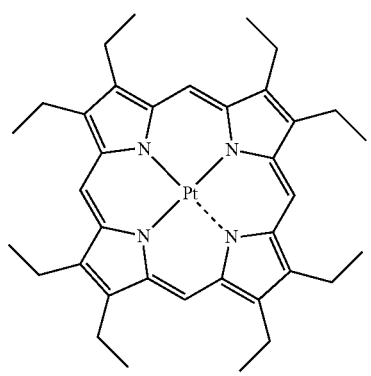
PtOEP
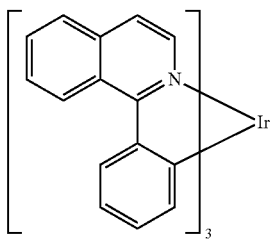
Ir(piq)₃
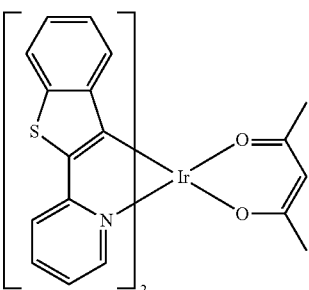
Btp₂Ir(acac)
-continued
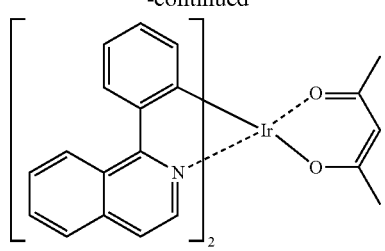
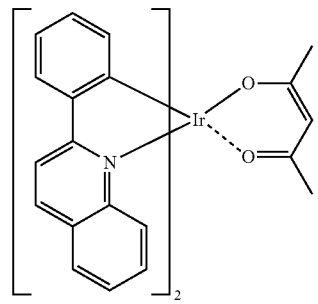
Ir(pq)₂(acac)
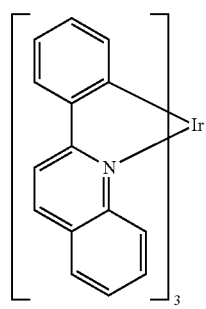
Ir(2-phq)₃

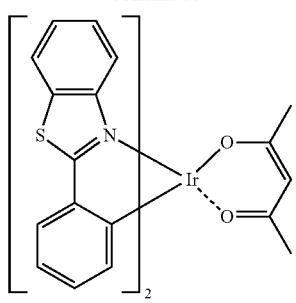
Ir(BT)₂(acac)
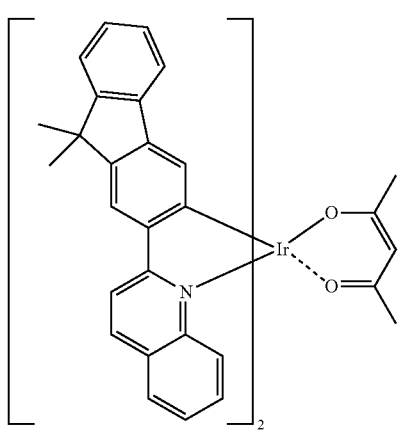
Ir(flq)₂(acac)
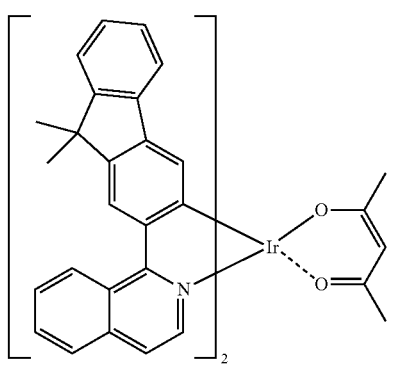
Ir(fliq)₂(acac)
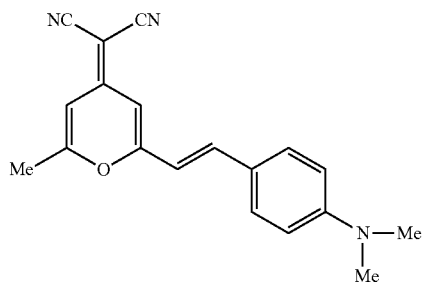
DCM
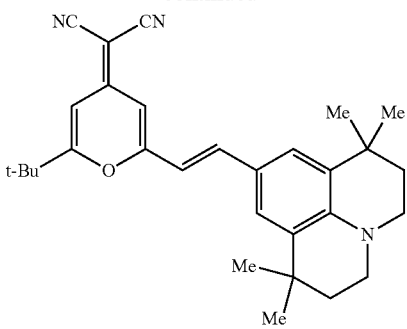
DCJTB
For example, the green EML of the green sub-pixel may include compounds illustrated below as a green dopant. In an implementation, a C545T below may be used as a green dopant.
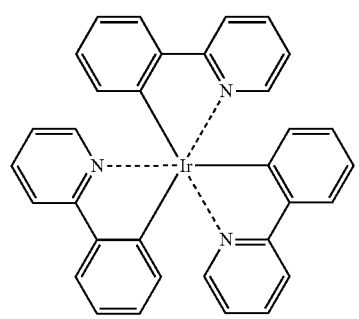
Ir(ppy)₃
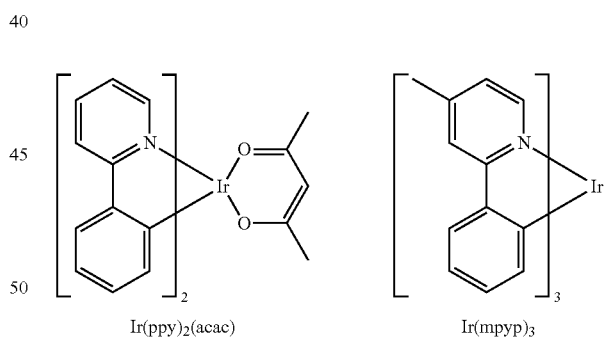
Ir(ppy)₂(acac)    Ir(mpyp)₃
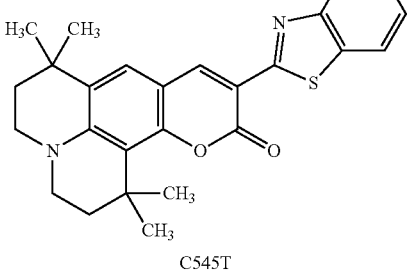
C545T
Another example of the dopant included in the EML may include a complex below.

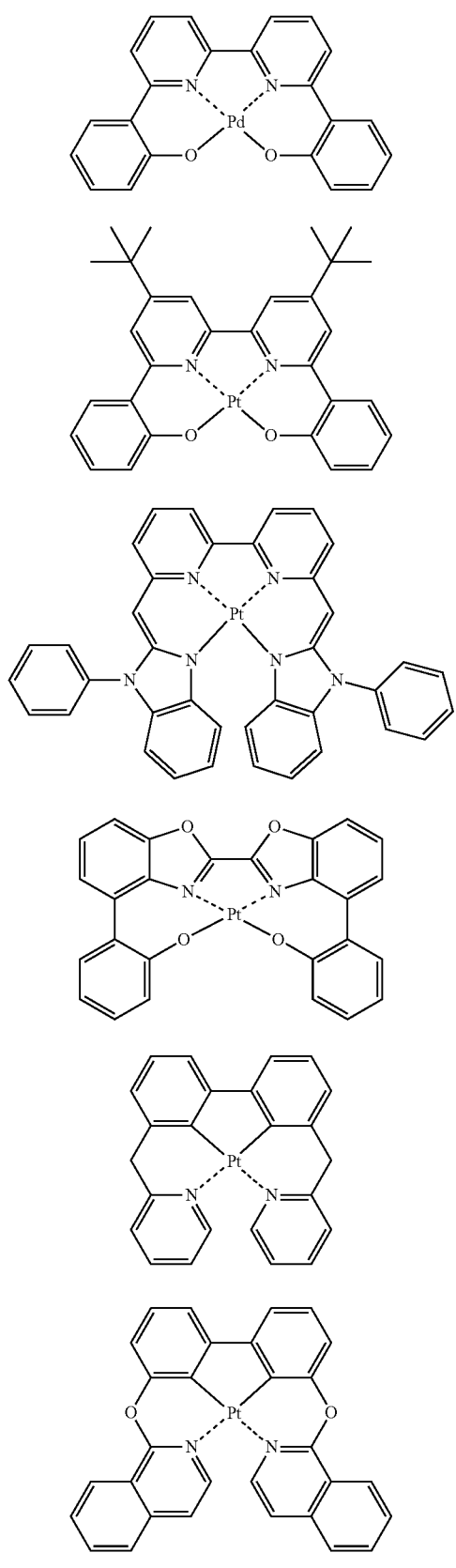

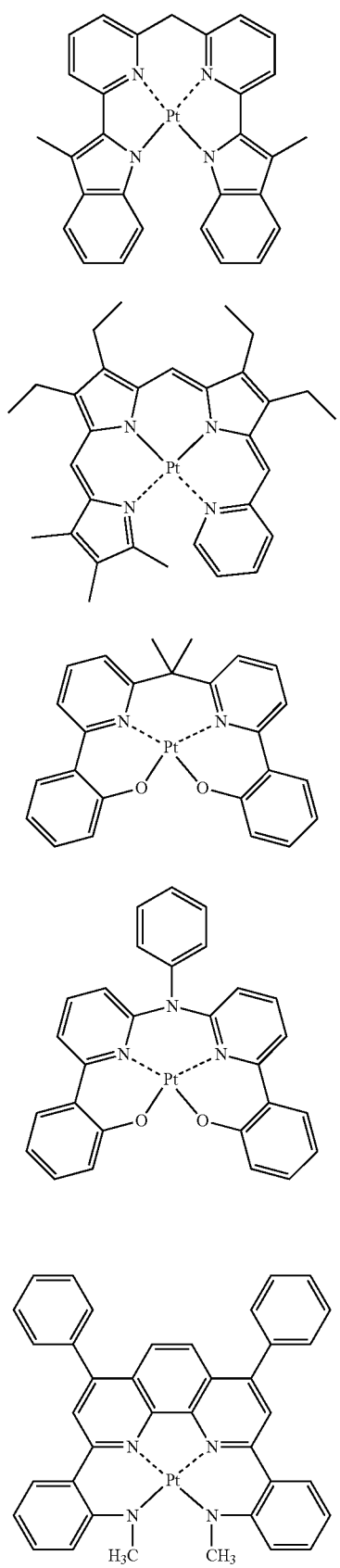
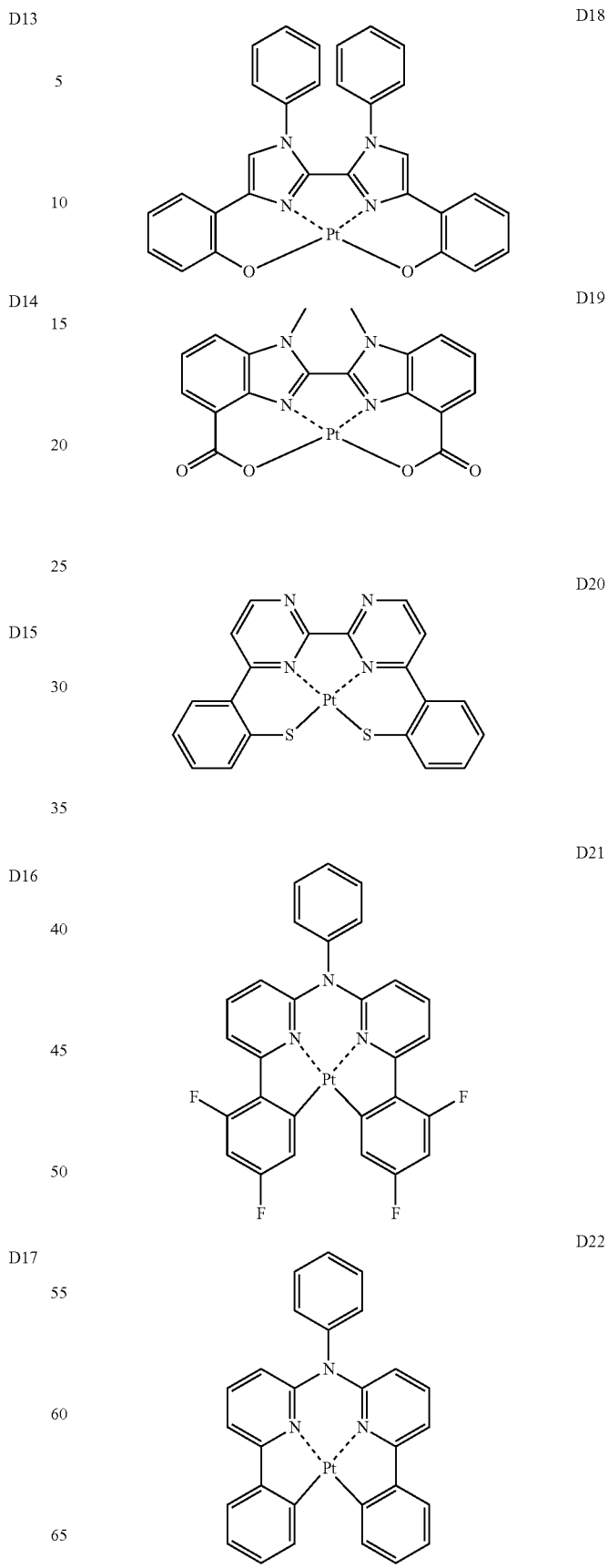

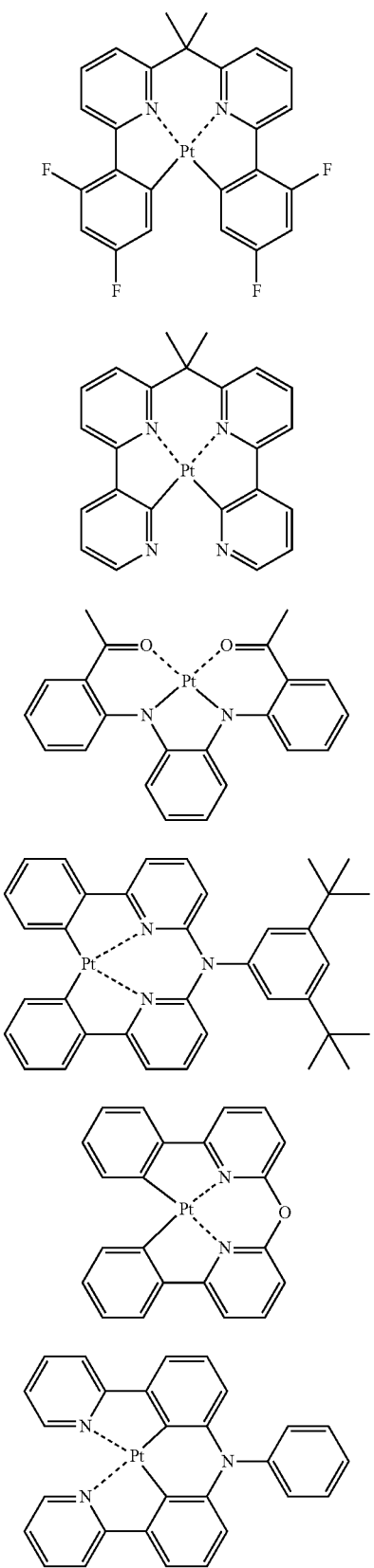
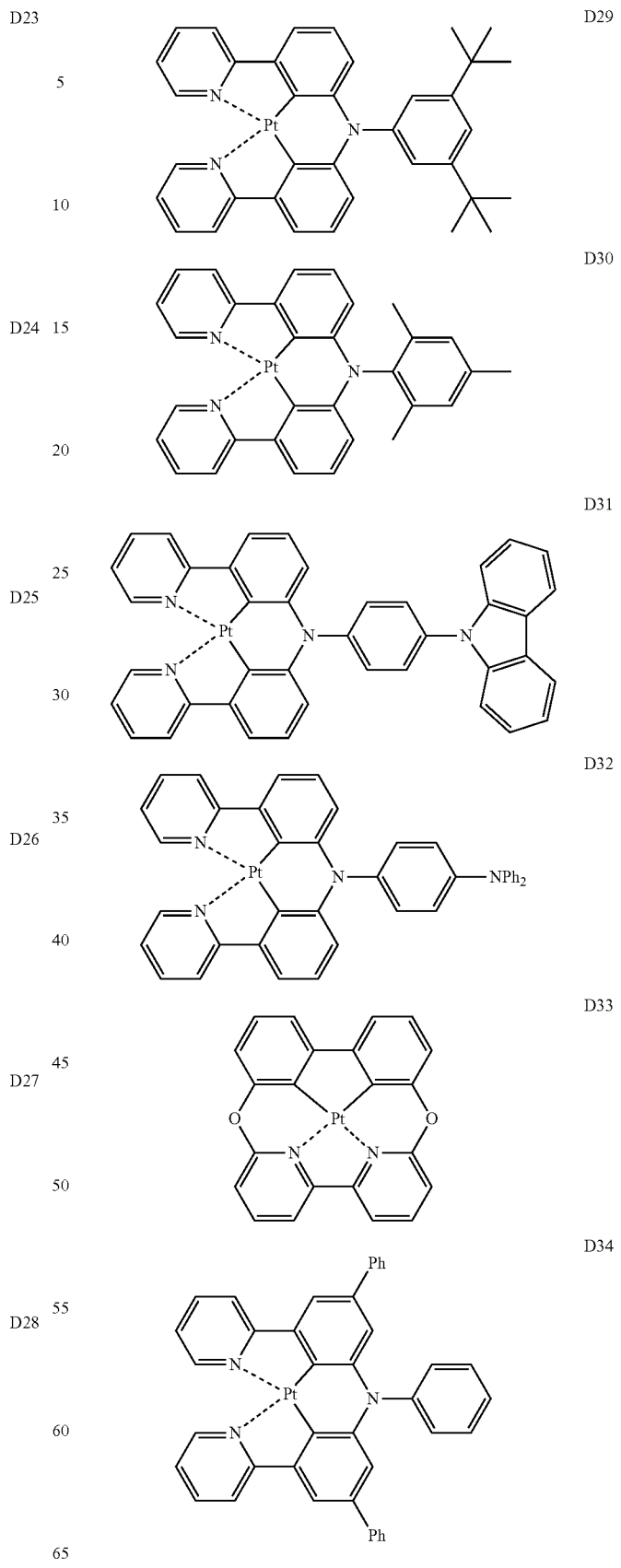

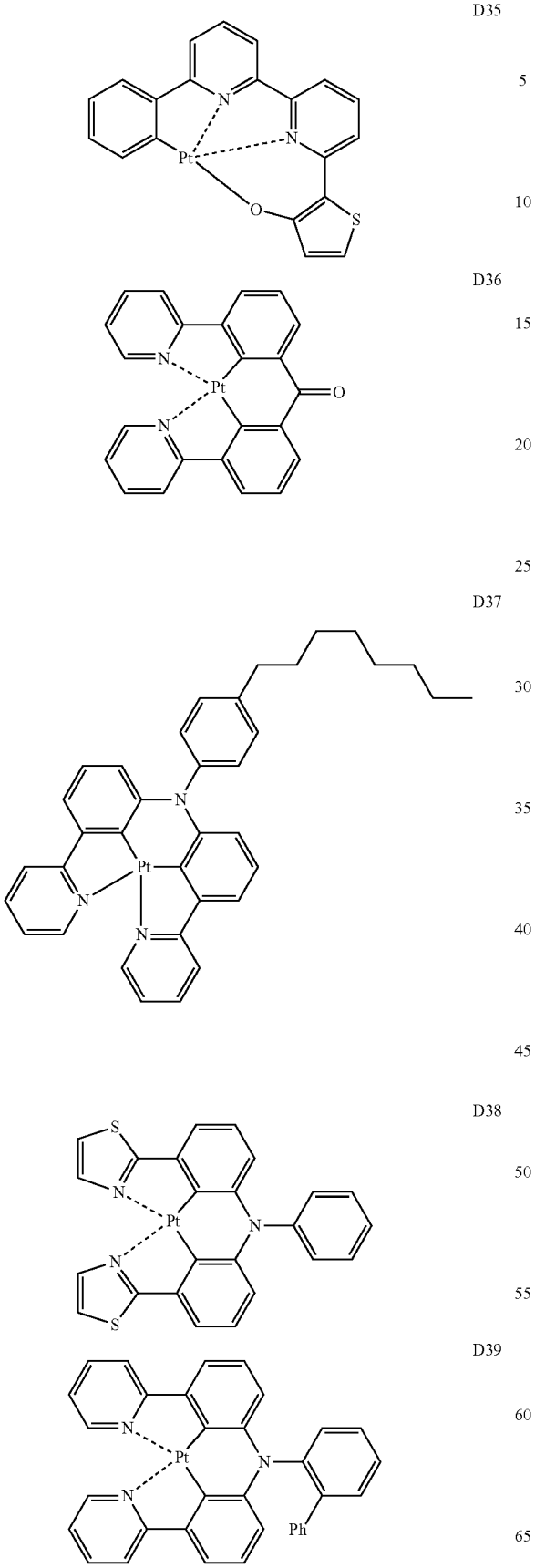

-continued
D45 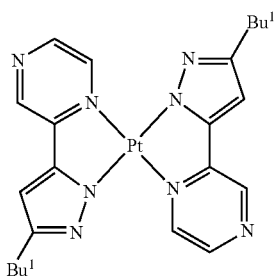
D46 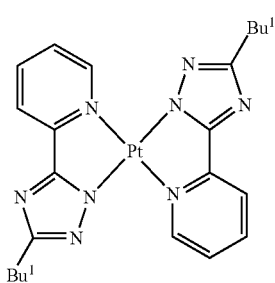
D47 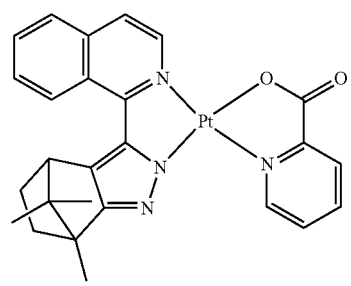
D48 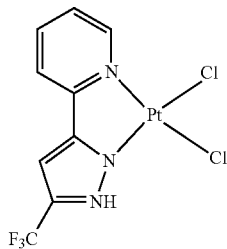
D49 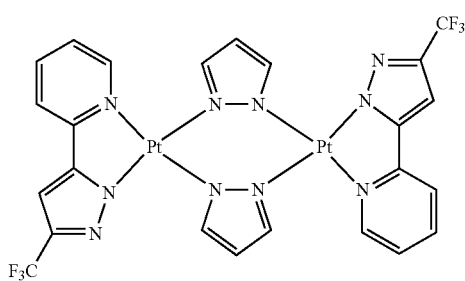
-continued
D50 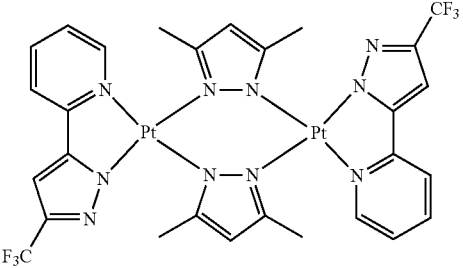
Another example of the dopant included in the EML may include a Os-complex below.
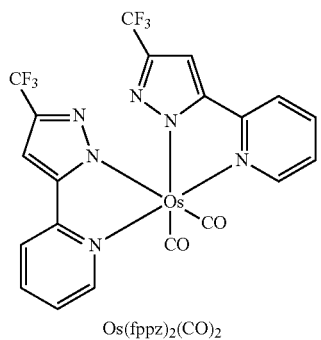
Os(fppz)$_2$(CO)$_2$
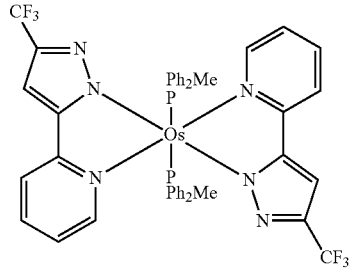
Os(fppz)$_2$(PPh$_2$Me)$_2$
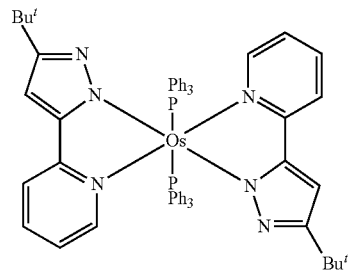
Os(bppz)$_2$(PPh$_3$)$_2$
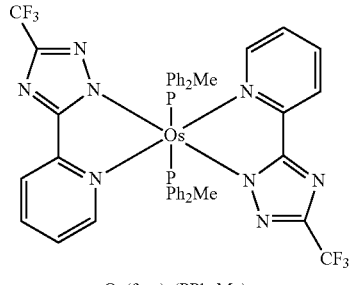
Os(fptz)$_2$(PPh$_2$Me)$_2$ -continued

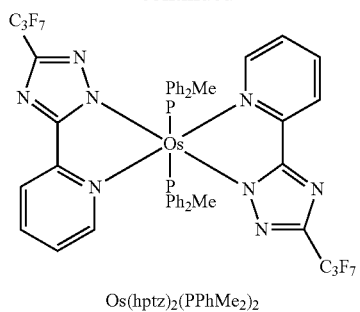

Os(hptz)₂(PPhMe₂)₂

When the EML includes both a host and a dopant, an amount of the dopant may be from about 0.01 parts to about 15 parts by weight, based on 100 parts by weight of the host.

A thickness of the EML may be in a range of about 100 Å to about 1,000 Å, e.g., about 100 Å to about 600 Å. When the thickness of the EML is within these ranges, the EML may have improved luminescent ability without a substantial increase in driving voltage.

Next, an electron transport layer (ETL) may be formed on the EML using a suitable method, e.g., by vacuum deposition, spin coating, casting, or the like. When the ETL is formed using vacuum deposition or spin coating, the deposition and coating conditions may be similar to those for the formation of the HIL, though the conditions for deposition and coating may vary according to the material that is used to form the ETL. A material for an ETL may include suitable electron transporting materials that stably transport electrons injected from an electron injection electrode (cathode). Examples of the material for the ETL may include a quinoline derivative, such as tris(8-quinolinolate)aluminium (Alq3), TAZ, Balq, beryllium bis(benzoquinolin-10-olate) (Bebq2), ADN, Compound 201, and Compound 202.

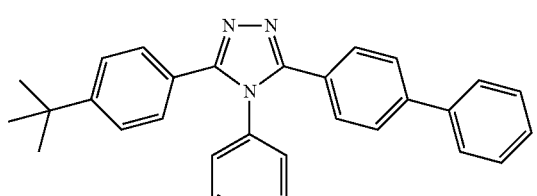

TAZ

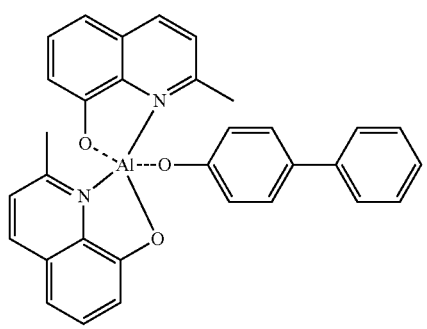

BAlq

-continued

<Compound 201>

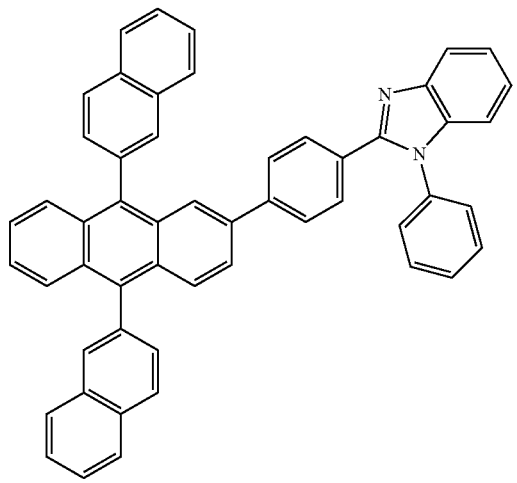

<Compound 202>

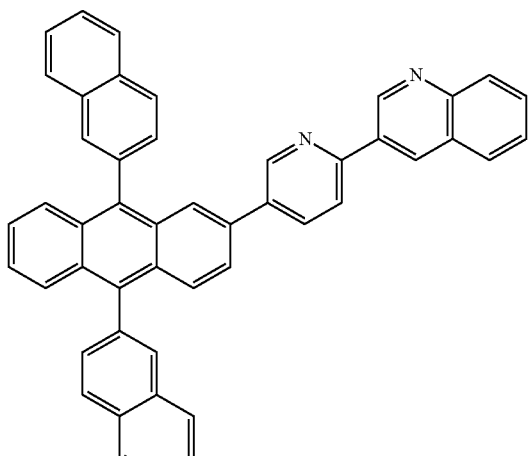

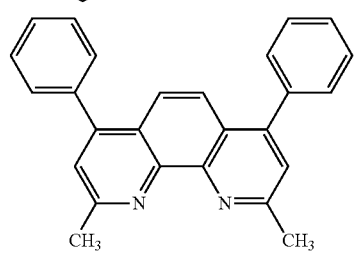

BCP

A thickness of the ETL may be in a range of about 100 Å to about 1,000 Å, e.g., about 150 Å to about 500 Å. When the thickness of the ETL is within these ranges, the ETL may have satisfactory electron transporting ability without a substantial increase in driving voltage.

The ETL may further include a metal-containing material, in addition to a suitable electron transporting inorganic material.

The metal-containing material may include a lithium (Li) complex. Examples of the Li complex may include lithium quinolate (Liq) and Compound 203 below.

Compound 203

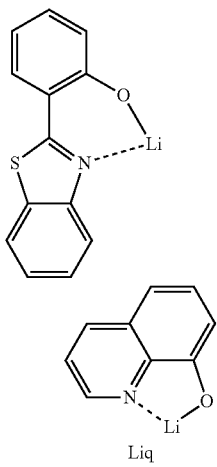

Liq

Then, an EIL, which facilitates injection of electrons from the cathode, may be formed on the ETL. A suitable electron-injecting material may be used to form the EIL.

Examples of materials for forming the EIL may include LiF, NaCl, a CsF, $Li_2O$, and BaO. The deposition conditions of the EIL may be similar to those used to form the HIL, although the deposition conditions may vary according to the material that is used to form the EIL.

The thickness of the EIL may be from about 1 Å to about 100 Å, e.g., may be from about 3 Å to about 90 Å. When the thickness of the EIL is within these ranges, the EIL may have satisfactory electron injection ability without a substantial increase in driving voltage.

A second electrode 17 may be disposed on the organic layer 15. The second electrode 17 may be a cathode, which is an electron injecting electrode. A metal for forming the second electrode may be a metal, an alloy, an electrically conductive compound, which have a low-work function, or a mixture thereof. For example, lithium (Li), magnesium (Mg), aluminum (Al), aluminum (Al)-lithium (Li), calcium (Ca), magnesium (Mg)-indium (In), magnesium (Mg)-silver (Ag), or the like may be formed as a thin film to obtain a thin film-type reflective, semi-reflective, or a transmissive electrode. In an implementation, to manufacture a top-emission light-emitting device, a transmissive electrode formed of indium tin oxide (ITO) or indium zinc oxide (IZO) may be used. When the organic light-emitting diode is used in a large full-color display device, the second electrode (cathode) may be a reflective electrode.

In addition, when a phosphorescent dopant is used in the EML, a triplet exciton or a hole may diffuse to an ETL. To prevent the diffusion, a hole blocking layer (HBL) may be formed between the HTL and the EML or between the H-functional layer and the EML by vacuum deposition, spin coating, casting, LB deposition, or the like. When the HBL is formed using vacuum deposition or spin coating, the deposition and coating conditions may be similar to those for the formation of the HIL, though the conditions for deposition and coating may vary according to the material that is used to form the HBL. A suitable hole-blocking material may be used. Examples of hole-blocking materials may include oxadiazole derivatives, triazole derivatives, and phenanthroline derivatives. For example, BCP illustrated below may be used as the hole-blocking material.

BCP

A thickness of the HBL may be in a range of about 20 Å to about 1,000 Å, e.g., about 30 Å to about 300 Å. When the thickness of the HBL is within these ranges, the HBL may have improved hole blocking ability without a substantial increase in driving voltage.

The organic light-emitting diode may be used in a full color display apparatus, a lamp, or the like. For example, the organic light-emitting diode may be a full color display apparatus.

Accordingly, provided is an organic light-emitting apparatus according to an embodiment including: a substrate including a first sub-pixel, a second sub-pixel, and a third sub-pixel; a first electrode formed in each of the first sub-pixel, second sub-pixel and third sub-pixel of the substrate; a second electrode that commonly faces the first electrodes in the first sub-pixel, the second sub-pixel, and the third sub-pixel; a first EML that is formed between the first electrode of the first sub-pixel and the second electrode and emits a first color light; a second EML that is formed between the first electrode of the second sub-pixel and the second electrode and emits a second color light; and a third EML that is formed between the first electrode of the third sub-pixel and the second electrode and emits a third color light, wherein the first EML includes one or more of the pyrene-based compounds described above. According to an embodiment, the first electrode may be a transmissive electrode or a semi-transmissive electrode, and the second electrode may be a reflective electrode. According to another embodiment, the first electrode may be a reflective electrode, and the second electrode may be a transmissive electrode or a semi-transmissive electrode.

A mixed light of the first light, the second light, and the third light of the organic light-emitting diode may be white light. Accordingly, the organic light-emitting diode may be a full-color display apparatus. The first light may be blue light. Also, the second light may be green light and the third light may be red light.

The first EML of the organic light-emitting apparatus may include the pyrene-based compound of Formula 1. Due to the inclusion of the pyrene-based compound, the emitted first color light (blue light) may have excellent color purity characteristics (e.g., a y color coordinate may be 1.0 or less) that satisfy NTSC or sRGB standards. Accordingly, the organic light-emitting apparatus may be used as a large high-quality TV.

According to an embodiment, the organic light-emitting apparatus may be a bottom emission type organic light-emitting apparatus in which the first electrode is a transmissive electrode or a semi-transmissive electrode, and the second electrode is a reflective electrode.

According to another embodiment, the organic light-emitting apparatus may be a top emission type organic light-emitting apparatus in which the first electrode is a reflective electrode, and the second electrode is a transmissive electrode or a semi-transmissive electrode.

The organic light-emitting apparatus may include the pyrene-based compound of Formula 1. Due to the inclusion of the pyrene-based compound, blue light having excellent color purity characteristics (e.g., a y color coordinate may be 1.0 or less) that satisfy a sRGB standard may be emitted. Accordingly, a complicated resonance structure that compensates for color purity of blue light is not needed, and thus, manufacturing costs may be reduced.

The full color display may be used in a television (TV), a personal computer monitor, a mobile communication terminal, an MP3 player, a navigation device for use in vehicles, or the like.

The unsubstituted $C_1$-$C_{60}$ alkyl group (or a $C_1$-$C_{60}$ alkyl group) used herein may be a $C_1$-$C_{60}$ linear or branched alkyl group, such as methyl group, ethyl group, propyl group, isobutyl group, sec-butyl group, pentyl group, iso-amyl group, or hexyl group, and a substituent of a substituted $C_1$-$C_{60}$ alkyl group may be selected from a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkyn, yl group, and a $C_1$-$C_{60}$ alkoxy group; a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a ahydrazine group, a hydrazone group, a carboxyl group or a salt thereof, a sulfonic acid or a salt thereof, and a phosphoric acid or a salt thereof; a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group; a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group; and —N($Q_{11}$)($Q_{12}$); and —Si($Q_{13}$)($Q_{14}$)($Q_{15}$) (in which $Q_{11}$ and $Q_{12}$ are each independently a $C_6$-$C_{60}$ aryl group, or a $C_2$-$C_{60}$ heteroaryl group, and $Q_{13}$ to $Q_{15}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group).

The unsubstituted $C_1$-$C_{60}$ alkoxy group (or $C_1$-$C_{60}$ alkoxy group) used herein may have a formula of —OA (where A is the unsubstituted $C_1$-$C_{60}$ alkyl group described above), and detailed examples thereof are methoxy, ethoxy, and isopropyloxy, and detailed examples of substituents of the unsubstituted $C_1$-$C_{60}$ alkoxy group may be understood by referring to the detailed examples of substituents of the substituted $C_1$-$C_{60}$ alkyl group.

The unsubstituted $C_2$-$C_{60}$ alkenyl group (or $C_2$-$C_{60}$ alkenyl group) used herein may refer to an unsubstituted $C_2$-$C_{60}$ alkyl group having one or more carbon double bonds at a center or end thereof. Examples of the unsubstituted $C_2$-$C_{60}$ alkenyl group are ethenyl group, prophenyl group, and butenyl. Detailed examples of substituents of the substituted $C_2$-$C_{60}$ alkenyl groups may be understood by referring to the detailed examples of substituents of the substituted $C_1$-$C_{60}$ alkyl group.

The unsubstituted $C_2$-$C_{60}$ alkynyl group (or $C_2$-$C_{60}$ alkynyl group) used herein refers to an unsubstituted $C_2$-$C_{60}$ alkyl group having one or more carbon triple bonds at a center or end thereof. Examples of the unsubstituted $C_2$-$C_{60}$ alkynyl group are ethynyl group, propynyl group, and the like. Detailed examples of substituents of the substituted $C_2$-$C_{60}$ alkynyl groups may be understood by referring to the detailed examples of substituents of the substituted $C_1$-$C_{60}$ alkyl group.

The unsubstituted $C_3$-$C_{10}$ cyclo alkyl group used herein may refer to a cyclic saturated hydrocarbon monovalent group, and examples thereof are cyclopropyl group, cyclobutyl group, cyclopentyl group, cyclohexyl group, cyclooctyl group, etc. Detailed examples of substituents of the substituted $C_3$-$C_{10}$ alkynyl groups may be understood by referring to the detailed examples of substituents of the substituted $C_1$-$C_{60}$ alkyl group.

The unsubstituted $C_3$-$C_{10}$ cycloalkenyl group may refer to a cyclic unsaturated hydrocarbon group that has one or more carbon double bonds and is not an aromatic cycle, and detailed examples thereof are cyclopropenyl group, cyclobutenyl group, cyclopentenyl group, cyclohexenyl group, cycloheptenyl group, 1,3-cyclohexadienyl group, 1,4-cyclohexadienyl group, 2,4-cycloheptadienyl group, and 1,5-cycloctadienyl. Detailed examples of substituents of the substituted $C_3$-$C_{10}$ cycloalkenyl groups may be understood by referring to the detailed examples of substituents of the substituted $C_1$-$C_{60}$ alkyl group.

The unsubstituted $C_6$-$C_{60}$ aryl group may be a monovalent group having a carbocyclic aromatic system having 6 to 60 carbon atoms including at least one aromatic ring. The unsubstituted $C_6$-$C_{60}$ arylene group may be a divalent group having a carbocyclic aromatic system having 6 to 60 carbon atoms including at least one aromatic ring. When the aryl group and or the arylene group have at least two rings, they may be fused to each other via a single bond. Detailed examples of substituents of the substituted $C_6$-$C_{60}$ aryl group and $C_6$-$C_{60}$ arylene group may be understood by referring to the detailed examples of substituents of the substituted $C_1$-$C_{60}$ alkyl group.

Examples of the substituted or unsubstituted $C_6$-$C_{60}$ aryl group may include a phenyl group, a $C_1$-$C_{10}$ alkylphenyl group (for example, ethylphenyl group), a $C_1$-$C_{10}$ alkylbiphenyl group (for example, ethylbiphenyl group), a halophenyl group (for example, an o-, m- or p-fluorophenyl group, a dichlorophenyl group), a dicyanophenyl group, a trifluoromethoxyphenyl group, o-, m-, and p-tolyl groups, o-, m- and p-cumenyl groups, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, halonaphthyl group (for example, a fluoronaphthyl group), a $C_1$-$C_{10}$ alkylnaphthyl group (for example, a methylnaphthyl group), a $C_1$-$C_{10}$ alkoxynaphthyl group (for example, a methoxynaphthyl group), an anthracenyl group, azrenyl group, an acenaphthylenyl group, a phenalenyl group, a fluorenyl group, anthraquinolinyl group, a methylanthracenyl group, a phenanthrenyl group, a triphenylenyl group, a pyrenyl group, a chrysenyl group, an ethyl-chrysenyl group, a picenyl group, perylenyl group, a chloroperylenyl group, a pentaphenyl group, a pentasenyl group, a tetraphenylenyl group, a hexaphenyl group, a hexacenyl group, a rubicenyl group, a coroneryl group, a trinaphthylenyl group, a heptaphenyl group, a heptacenyl group, a piranthrenyl group, and an obarenyl group Examples of the substituted or unsubstituted $C_6$-$C_{60}$ arylene group may be easily understood by referring to examples of the substituted or unsubstituted $C_6$-$C_{60}$ aryl group.

The unsubstituted $C_2$-$C_{60}$ heteroaryl group used herein may refer to a monovalent group having a system composed of one or more aromatic rings having at least one hetero atom selected from nitrogen (N), oxygen (O), phosphorous (P), and sulfur (S) and carbon atoms as the remaining ring atoms. The unsubstituted $C_2$-$C_{60}$ heteroarylene group used herein may refer to a divalent group having a system composed of one or more aromatic rings having at least one hetero atom selected from nitrogen (N), oxygen (O), phosphorous (P), and sulfur (S) and carbon atoms as the remaining ring atoms. In this regard, when the heteroaryl group and the heteroarylene group each include two or more rings, the rings may be fused to each other. Detailed examples of substituents of the substituted $C_2$-$C_{60}$ heteroaryl group and $C_2$-$C_{60}$ heteroarylene group may be understood by referring to the detailed examples of substituents of the substituted $C_1$-$C_{60}$ alkyl group.

Examples of the unsubstituted $C_2$-$C_{60}$ heteroaryl group may include a pyrazolyl group, an imidazolyl group, a oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, benzoan imidazolyl group, an imidazo pyridinyl group, and an imidazo pyrimidinyl group. Examples of the substituted or unsubstituted $C_2$-$C_{60}$ heteroarylene group may be easily understood by referring to examples of the substituted or unsubstituted $C_2$-$C_{60}$ heteroaryl group.

The substituted or unsubstituted $C_6$-$C_{60}$ aryloxy group may be represented by —$OA_2$ (wherein $A_2$ indicates the substituted or unsubstituted $C_6$-$C_{60}$ aryl group), and the substituted or unsubstituted $C_6$-$C_{60}$ arylthio group may be represented by —$SA_3$ (wherein $A_3$ indicates a substituted or unsubstituted $C_6$-$C_{60}$ aryl group).

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Intermediates 1 to 14 were synthesized by using methods disclosed in i) Journal of Medicinal Chemistry, 51(23), 7640-7644, 2008, ii) Synthesis (5), 815-823, 2009, and iii) Bioorganic & Medicinal Chemistry 19(2), 939-950, 2011, which are incorporated by references herein in their entirety.

Synthesis Example 1

Synthesis of Compound 4

Synthesis of Intermediate PY1

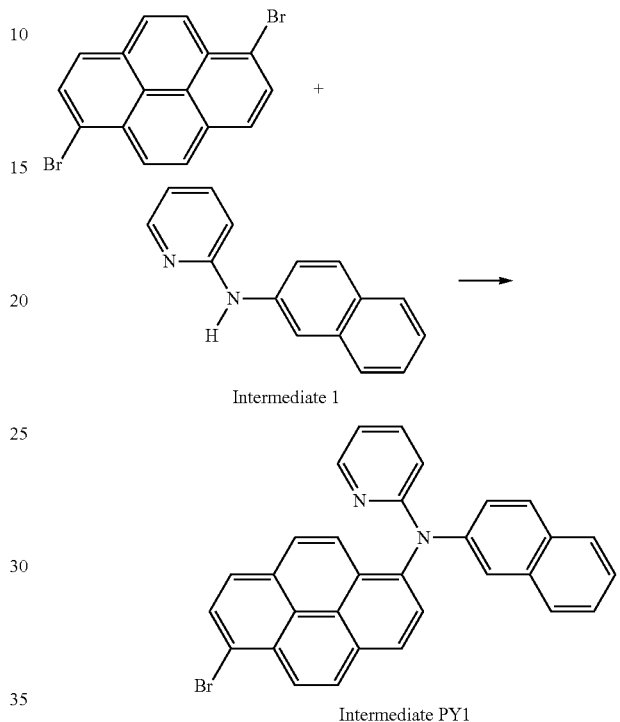

Intermediate 1

Intermediate PY1

Under nitrogen atmosphere, 3.6 g (10 mmol) of 1,6-dibromopyrene, 2.2 g (10 mmol) of Intermediate 1, 287 mg (0.5 mmol) of bis(dibenzylideneacetone)palladium (Pd(dba)$_2$), 303 mg (1.5 mmol) of P(tert-Bu)$_3$, and 2.9 g (30 mmol) of sodium t-butoxide were added to 500 ml of toluene, and then, the mixture was refluxed for 12 hours. When the reaction was completed, a solvent was removed by evaporation, and then, 500 ml of methylene chloride and 500 ml of water were respectively added thereto and the mixture was washed to collect an organic layer which was then dried with an anhydrous magnesium sulfate. Subsequently, the result was subjected to recrystallization and silica gel chromatography to obtain Intermediate PY1 (1 g, yield of 20%).

Synthesis of Compound 1

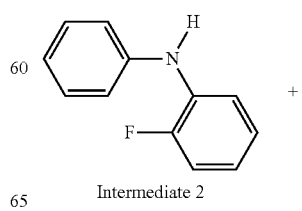

Intermediate 2

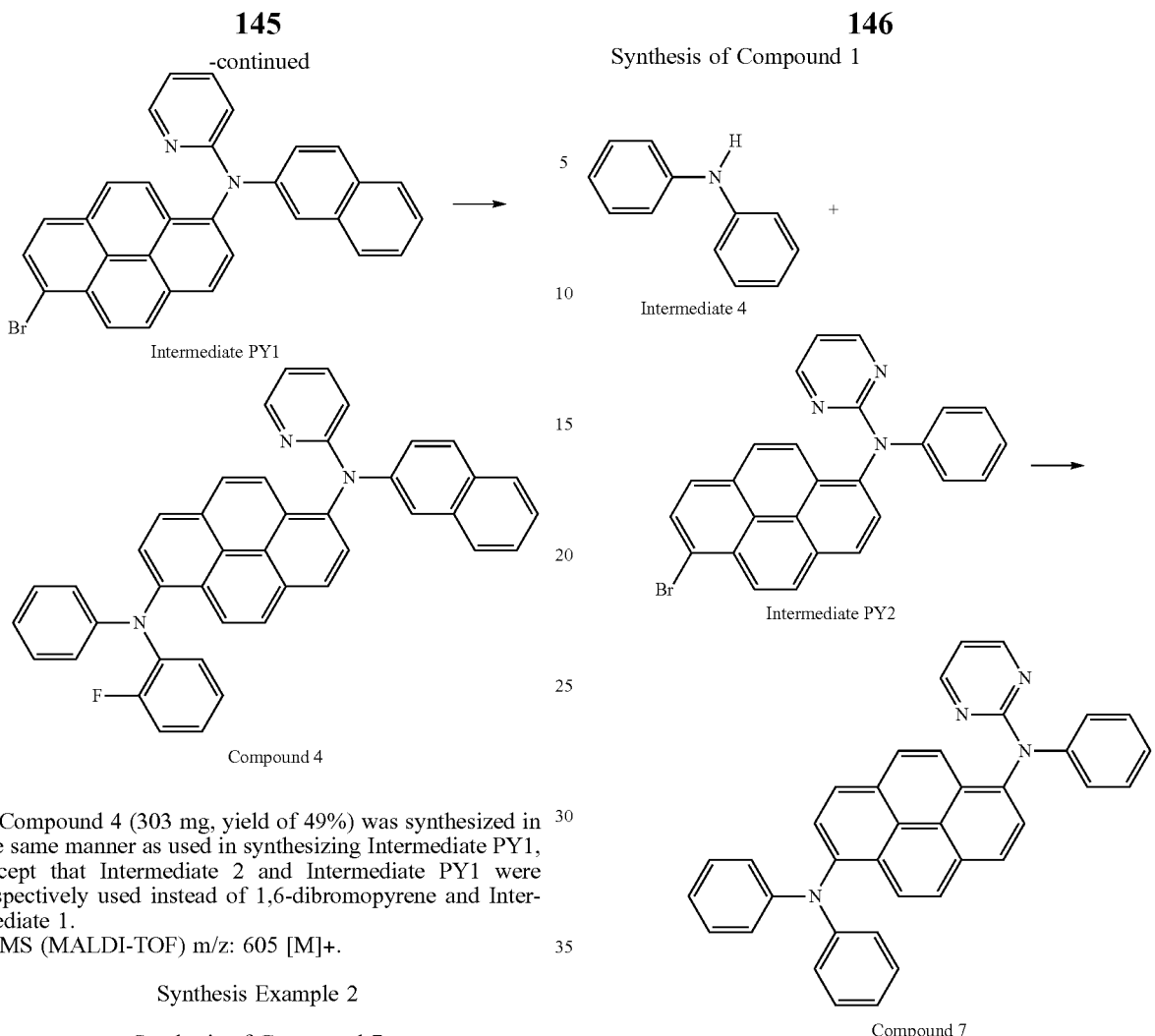

Compound 4 (303 mg, yield of 49%) was synthesized in the same manner as used in synthesizing Intermediate PY1, except that Intermediate 2 and Intermediate PY1 were respectively used instead of 1,6-dibromopyrene and Intermediate 1.

MS (MALDI-TOF) m/z: 605 [M]+.

Synthesis Example 2

Synthesis of Compound 7

Synthesis of Intermediate PY2

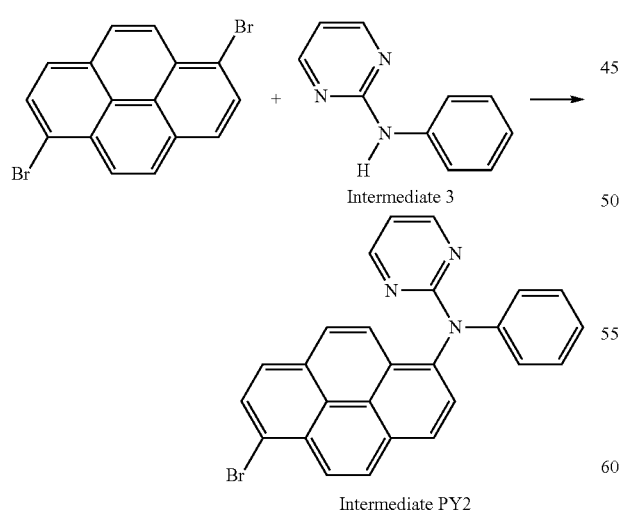

Intermediate PY2 (502 mg, yield of 12%) was synthesized in the same manner as used in synthesizing Intermediate PY1, except that Intermediate 3 was used instead of Intermediate 1.

Synthesis of Compound 1

Compound 7 (298 mg, yield of 48%) was synthesized in the same manner as used in synthesizing Intermediate PY1, except that Intermediate 4 and Intermediate PY2 were respectively used instead of 1,6-dibromopyrene and Intermediate 1.

MS (MALDI-TOF) m/z: 538 [M]+.

Synthesis Example 3

Synthesis of Compound 8

Synthesis of Compound 8

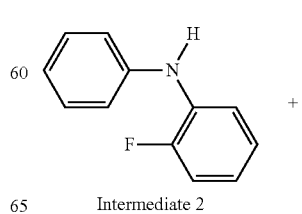

Intermediate 2

-continued

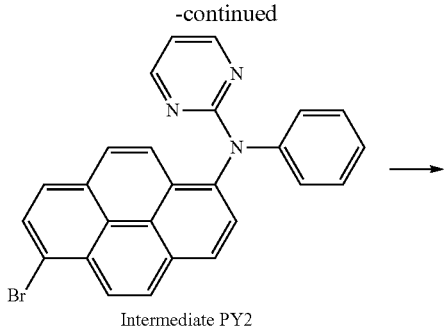
Intermediate PY2

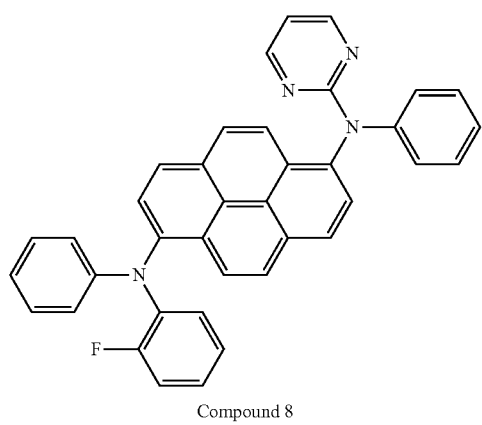
Compound 8

Compound 8 (338 mg, yield of 43%) was synthesized in the same manner as used in synthesizing Intermediate PY1, except that Intermediate 2 and Intermediate PY2 were respectively used instead of 1,6-dibromopyrene and Intermediate 1. MS (MALDI-TOF) m/z: 556 [M]+.

Synthesis Example 4

Synthesis of Compound 13

Synthesis of Intermediate PY3

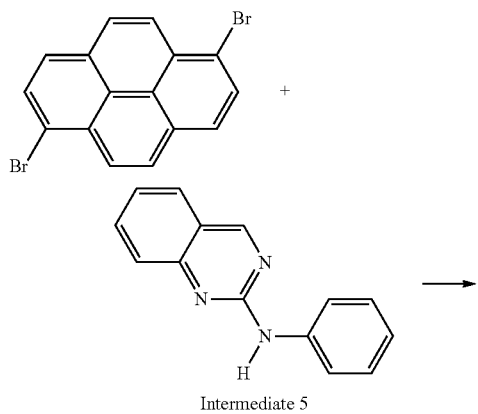
Intermediate 5

-continued

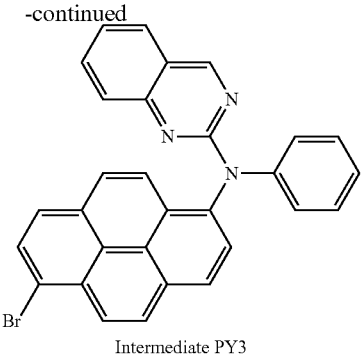
Intermediate PY3

Intermediate PY3 (278 mg, yield of 10%) was synthesized in the same manner as used in synthesizing Intermediate PY1, except that Intermediate 5 was used instead of Intermediate 1.

Synthesis of Compound 13

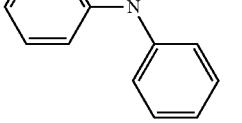
Intermediate 4

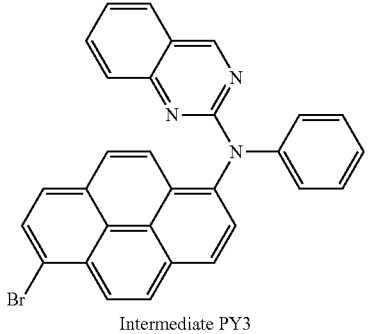
Intermediate PY3

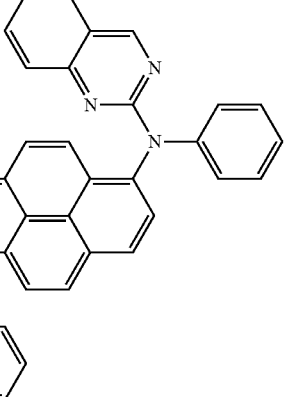
Compound 13

Compound 13 (502 mg, yield of 44%) was synthesized in the same manner as used in synthesizing Intermediate PY1, except that Intermediate 4 and Intermediate PY3 were respectively used instead of 1,6-dibromopyrene and Intermediate 1.

MS (MALDI-TOF) m/z: 588 [M]+.

Synthesis Example 5

Synthesis of Compound 15

Synthesis of Intermediate PY4

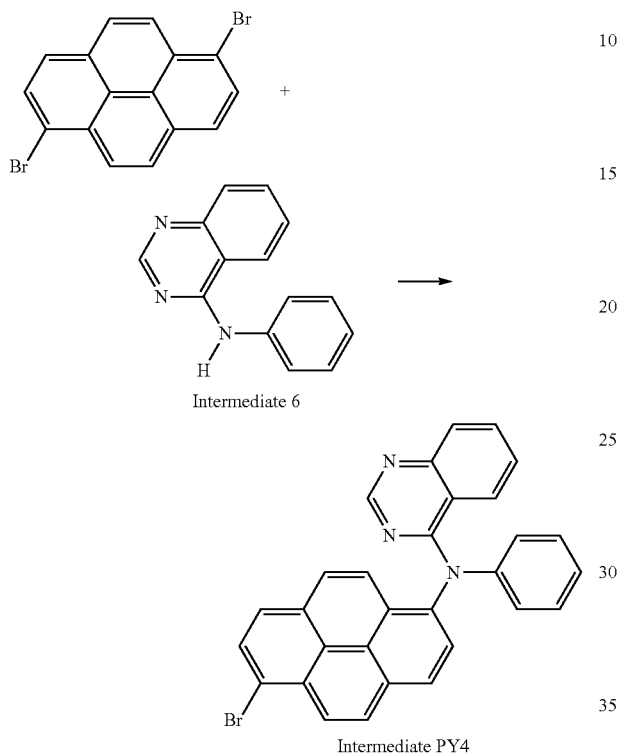

Intermediate PY4 (444 mg, yield of 13%) was synthesized in the same manner as used in synthesizing Intermediate PY1, except that Intermediate 6 was used instead of Intermediate 1.

Synthesis of Compound 15

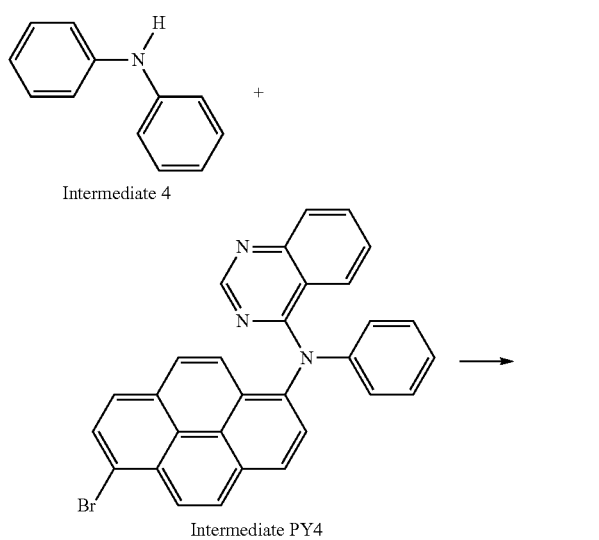

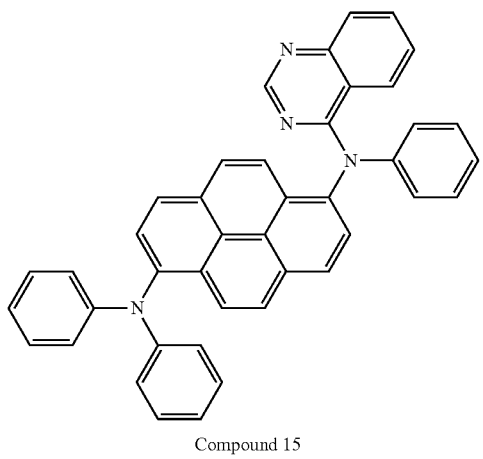

Compound 15 (679 mg, yield of 35%) was synthesized in the same manner as used in synthesizing Intermediate PY1, except that Intermediate 4 and Intermediate PY4 were respectively used instead of 1,6-dibromopyrene and Intermediate 1.

MS (MALDI-TOF) m/z: 588 [M]+.

Synthesis Example 6

Synthesis of Compound 32

Synthesis of Intermediate PY5

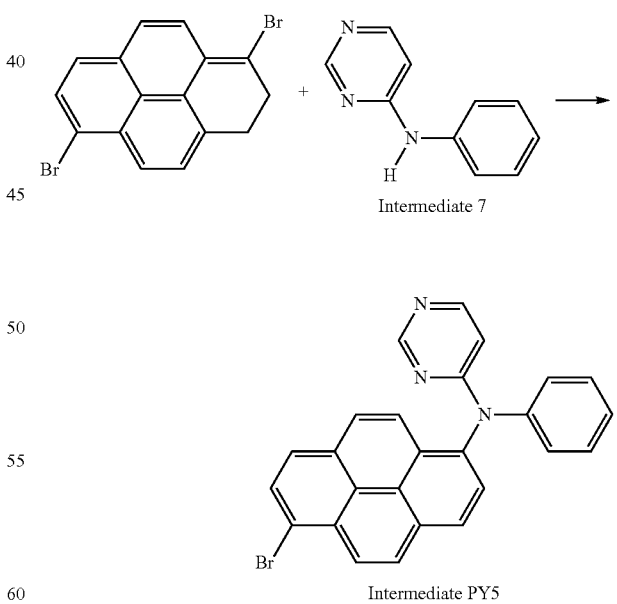

Intermediate PY5 (275 mg, yield of 12%) was synthesized in the same manner as used in synthesizing Intermediate PY1, except that Intermediate 7 was used instead of Intermediate 1.

Synthesis of Compound 32

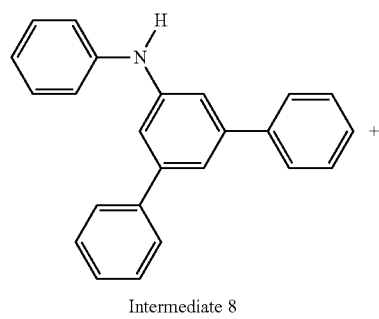

Intermediate 8

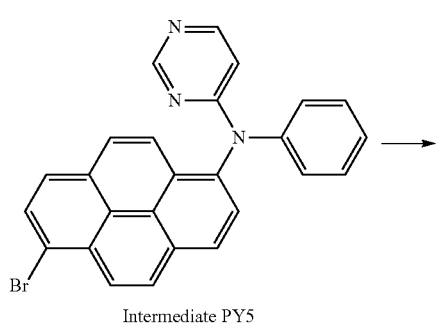

Intermediate PY5

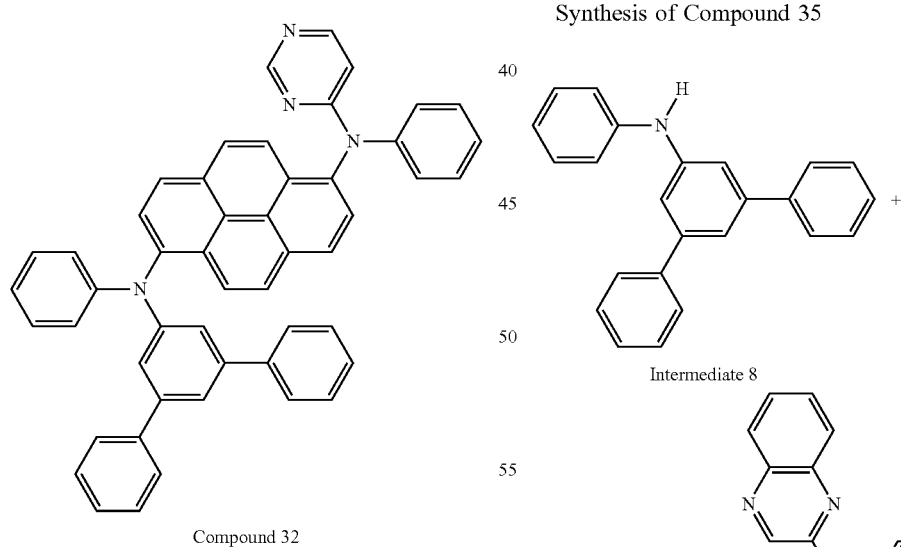

Compound 32

Compound 32 (459 mg, yield of 39%) was synthesized in the same manner as used in synthesizing Intermediate PY1, except that Intermediate 8 and Intermediate PY5 were respectively used instead of 1,6-dibromopyrene and Intermediate 1.

MS (MALDI-TOF) m/z: 690 [M]+.

Synthesis Example 7

Synthesis of Compound 35

Synthesis of Intermediate PY6

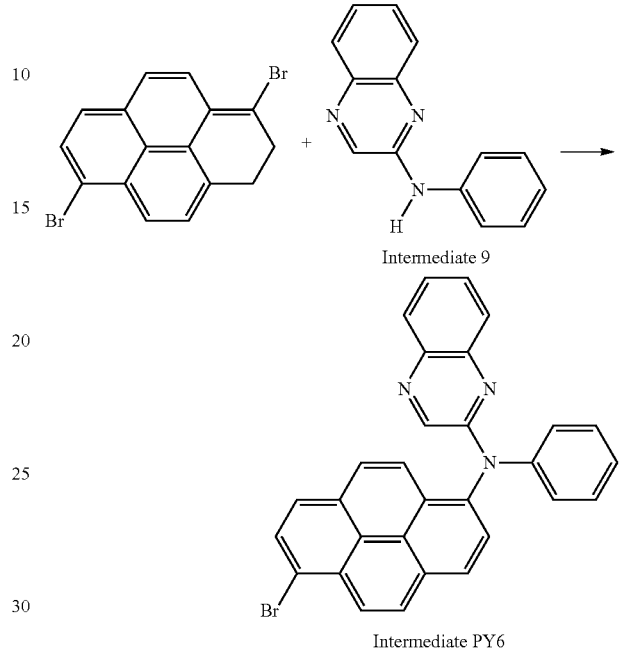

Intermediate 9

Intermediate PY6

Intermediate PY6 (351 mg, yield of 13%) was synthesized in the same manner as used in synthesizing Intermediate PY1, except that Intermediate 9 was used instead of Intermediate 1.

Synthesis of Compound 35

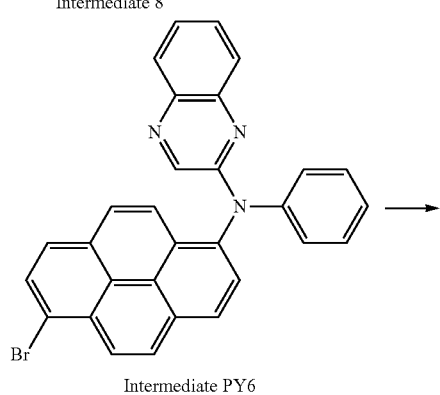

Intermediate 8

Intermediate PY6

-continued

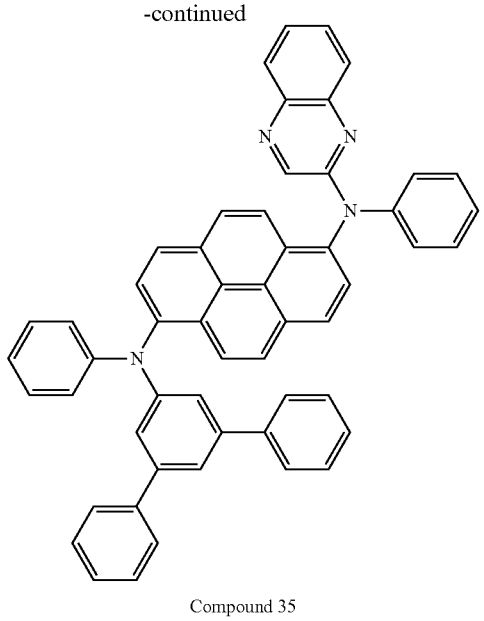

Compound 35

Compound 35 (672 mg, yield of 46%) was synthesized in the same manner as used in synthesizing Intermediate PY1, except that Intermediate 8 and Intermediate PY6 were respectively used instead of 1,6-dibromopyrene and Intermediate 1.
MS (MALDI-TOF) m/z: 740 [M]+.

Synthesis Example 8

Synthesis of Compound 44

Synthesis of Intermediate PY7

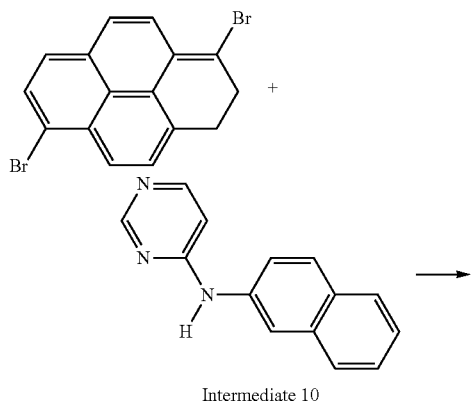

Intermediate PY7

Intermediate PY7 (358 mg, yield of 11%) was synthesized in the same manner as used in synthesizing Intermediate PY1, except that Intermediate 10 was used instead of Intermediate 1.

Synthesis of Compound 44

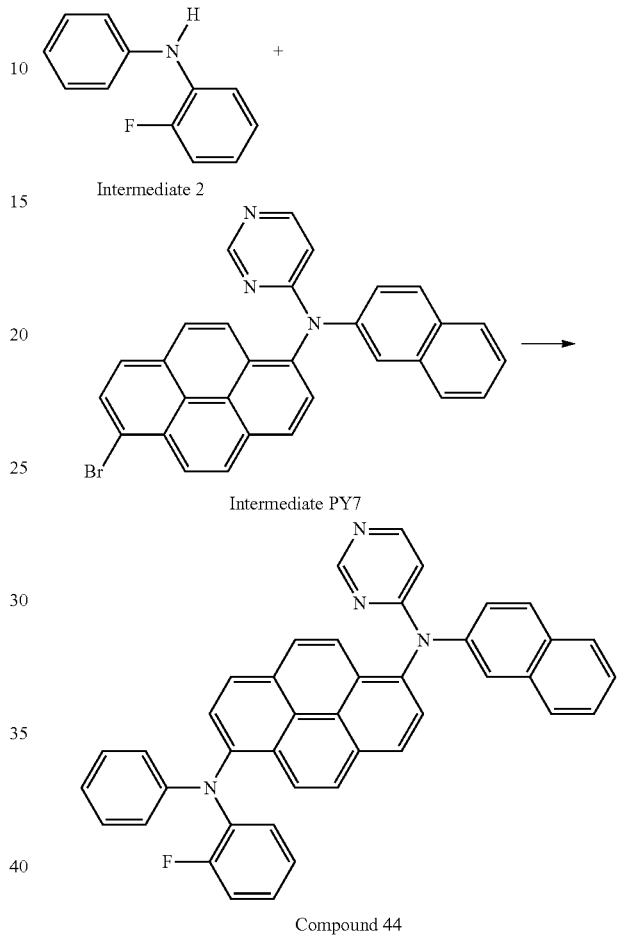

Compound 44

Compound 44 (521 mg, yield of 43%) was synthesized in the same manner as used in synthesizing Intermediate PY1, except that Intermediate 2 and Intermediate PY7 were respectively used instead of 1,6-dibromopyrene and Intermediate 1.
MS (MALDI-TOF) m/z: 606 [M]+.

Synthesis Example 9

Synthesis of Compound 69

Synthesis of Intermediate PY8

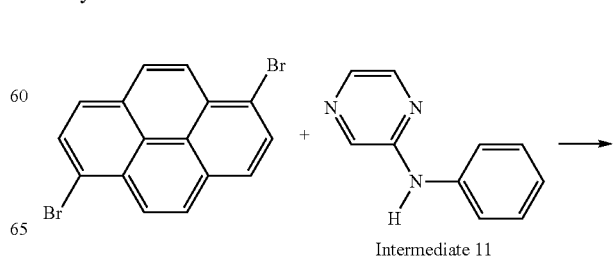

Intermediate 11

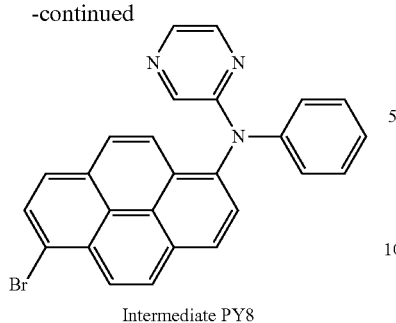

Intermediate PY8

Intermediate PY8 (498 mg, yield of 12%) was synthesized in the same manner as used in synthesizing Intermediate PY1, except that Intermediate 11 was used instead of Intermediate 1.

Synthesis of Compound 69

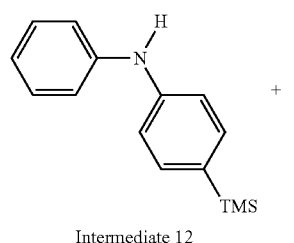

Intermediate 12

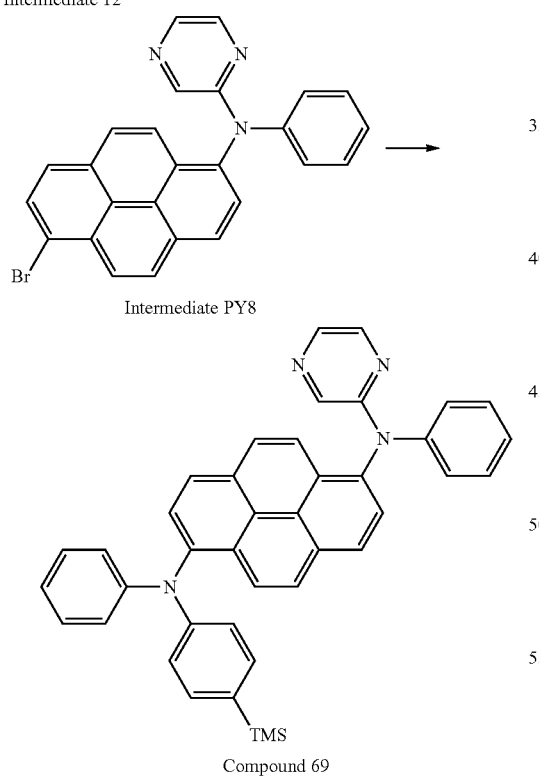

Intermediate PY8

Compound 69

Compound 69 (475 mg, yield of 41%) was synthesized in the same manner as used in synthesizing Intermediate PY1, except that Intermediate 12 and Intermediate PY8 were respectively used instead of 1,6-dibromopyrene and Intermediate 1.

MS (MALDI-TOF) m/z: 610 [M]+.

Synthesis Example 10

Synthesis of Compound 87

Synthesis of Intermediate PY9

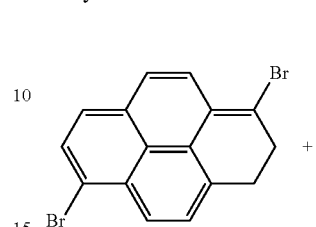

+

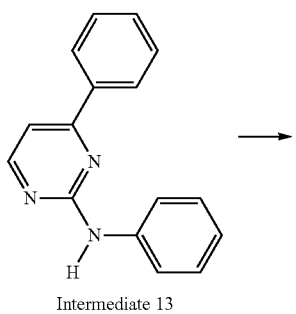

Intermediate 13

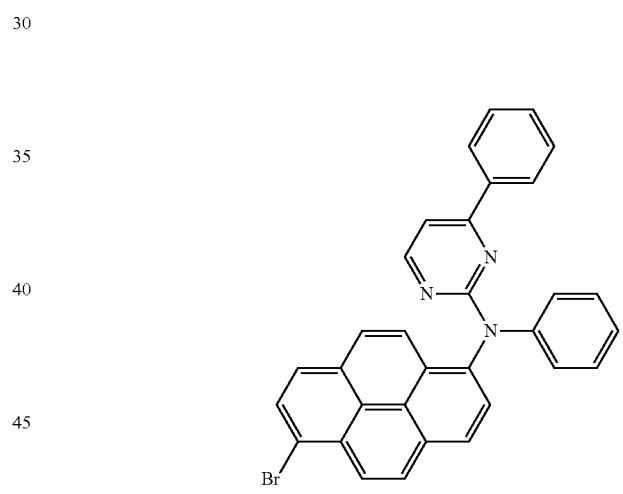

Intermediate PY9

Intermediate PY9 (277 mg, yield of 9%) was synthesized in the same manner as used in synthesizing Intermediate PY1, except that Intermediate 13 was used instead of Intermediate 1.

Synthesis of Compound 87

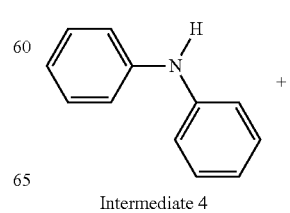

Intermediate 4

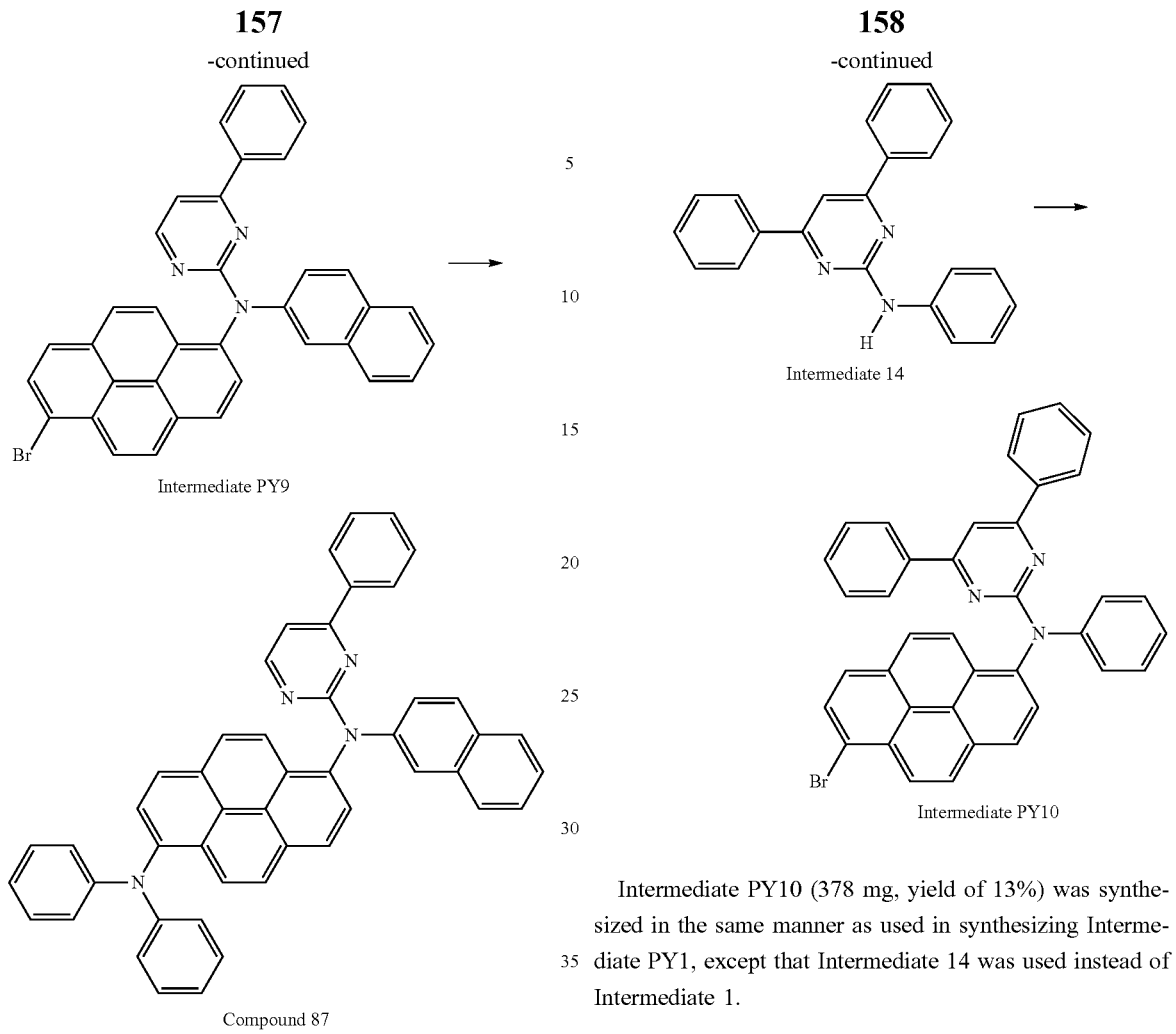

Compound 87 (535 mg, yield of 47%) was synthesized in the same manner as used in synthesizing Intermediate PY1, except that Intermediate 4 and Intermediate PY9 were respectively used instead of 1,6-dibromopyrene and Intermediate 1.

MS (MALDI-TOF) m/z: 664 [M]+.

Synthesis Example 11

Synthesis of Compound 90

Synthesis of Intermediate PY10

Intermediate PY10 (378 mg, yield of 13%) was synthesized in the same manner as used in synthesizing Intermediate PY1, except that Intermediate 14 was used instead of Intermediate 1.

Synthesis of Compound 90

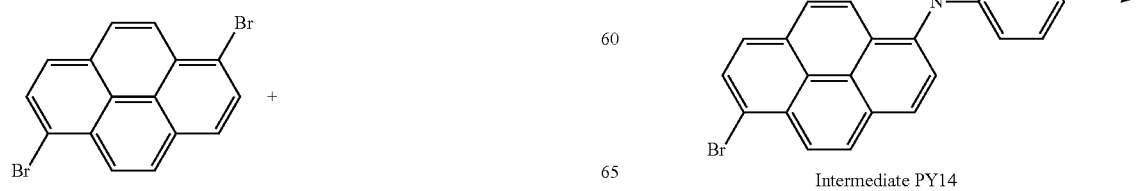

-continued

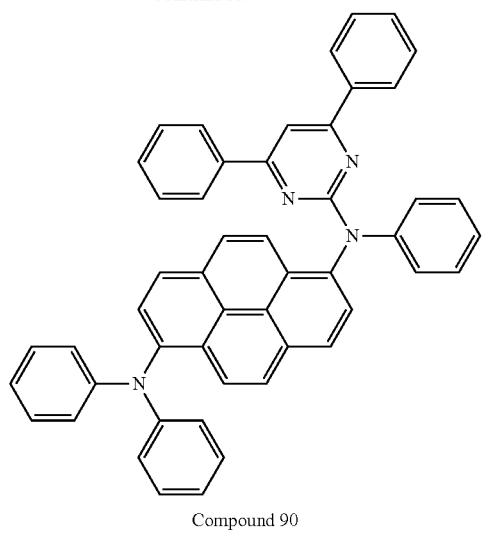

Compound 90

Compound 90 (423 mg, yield of 41%) was synthesized in the same manner as used in synthesizing Intermediate PY1, except that Intermediate 4 and Intermediate PY14 were respectively used instead of 1,6-dibromopyrene and Intermediate 1.

MS (MALDI-TOF) m/z: 690 [M]+.

Evaluation Example 1

PL Spectrum Evaluation

Compound 7 was dissolved at a concentration of $1\times10^{-5}$ M in $CHCl_3$, and a photolumineccscence (PL) spectrum thereof was measured by using ISC PC1 spectroflorometer equipped with a Xenon lamp. The same experiment was performed with Compound 8 and Compounds A and B below to obtain PL spectrum maximum wavelengths, and results thereof are shown in Table 1, below.

TABLE 1

|  | Compound A | Compound 7 | Compound 8 | Compound B |
|---|---|---|---|---|
| PL maximum wavelength (nm) | 456 | 452 | 437 | 419 |

<Compound A>

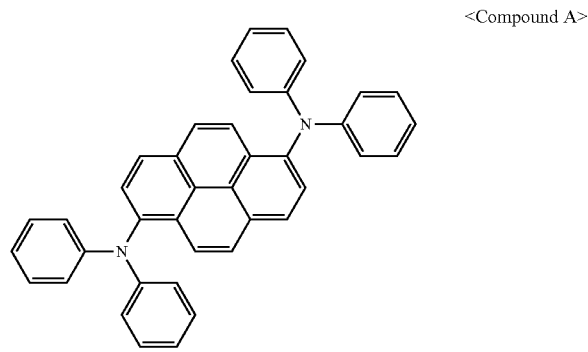 [SMILES: c1ccc(N(c2ccccc2)c2ccc3ccc4c(N(c5ccccc5)c5ccccc5)ccc5ccc2c3c54)cc1]

TABLE 1-continued

|  | Compound A | Compound 7 | Compound 8 | Compound B |
|---|---|---|---|---|

<Compound B>

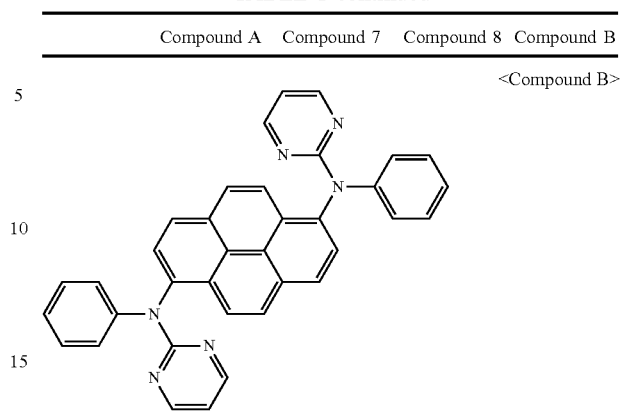

Referring to Table 1, it may be seen that Compounds 7 and 8 exhibited better blue color purity characteristics than Compound A, and Compound B exhibited PL characteristics with a relatively short wavelength region.

Example 1

A Corning 15 $\Omega cm^2$ (1,200 Å) ITO glass substrate was cut to a size of 50 mm×50 mm×0.5 mm, and then, the ITO glass substrate was sonicated with isopropyl alcohol and pure water each for 5 minutes, and then cleaned by exposure to UV light for 30 minutes and to ozone. Then, the ITO glass substrate was mounted on a vacuum deposition apparatus.

m-MTDATA was deposited on the ITO glass substrate functioning as an anode at a deposition rate of 1 Å/sec to form a hole injection layer having a thickness of 600 Å, and then alpha-NPD was deposited on the hole injection layer at a deposition rate of 1 Å/sec to form a hole transport layer having a thickness of 300 Å.

Then, Compound 4 (dopant) and 9,10-di-naphthalene-2-yl-anthracene (ADN, host) were co-deposited on the hole transport layer at deposition rates of 0.05 Å/sec and 1 Å/sec, respectively, to form an emission layer having a thickness of 200 Å.

Thereafter, $Alq_3$ was deposited on the emission layer to form an electron transport layer having a thickness of 300 Å, and LiF was deposited on the electron transport layer to form an electron injection layer having a thickness of 10 Å, and then, Al was deposited on the electron injection layer to form a second electrode (cathode) having a thickness of 2,000 Å, thereby completing manufacturing of an organic light-emitting diode.

Example 2

An organic light-emitting diode was manufactured in the same manner as in Example 1, except that as a dopant, Compound 7 was used instead of Compound 4 in forming the emission layer.

Example 3

An organic light-emitting diode was manufactured in the same manner as in Example 1, except that as a dopant, Compound 8 was used instead of Compound 4 in forming the emission layer.

Example 4

An organic light-emitting diode was manufactured in the same manner as in Example 1, except that as a dopant, Compound 13 was used instead of Compound 4 in forming the emission layer.

Example 5

An organic light-emitting diode was manufactured in the same manner as in Example 1, except that as a dopant, Compound 15 was used instead of Compound 4 in forming the emission layer.

Example 6

An organic light-emitting diode was manufactured in the same manner as in Example 1, except that as a dopant, Compound 32 was used instead of Compound 4 in forming the emission layer.

Example 7

An organic light-emitting diode was manufactured in the same manner as in Example 1, except that as a dopant, Compound 35 was used instead of Compound 4 in forming the emission layer.

Example 8

An organic light-emitting diode was manufactured in the same manner as in Example 1, except that as a dopant, Compound 44 was used instead of Compound 4 in forming the emission layer.

Example 9

An organic light-emitting diode was manufactured in the same manner as in Example 1, except that as a dopant, Compound 69 was used instead of Compound 4 in forming the emission layer.

Example 10

An organic light-emitting diode was manufactured in the same manner as in Example 1, except that as a dopant, Compound 87 was used instead of Compound 4 in forming the emission layer.

Example 11

An organic light-emitting diode was manufactured in the same manner as in Example 1, except that as a dopant, Compound 90 was used instead of Compound 4 in forming the emission layer.

Comparative Example A

An organic light-emitting diode was manufactured in the same manner as in Example 1, except that as a dopant, Compound A was used instead of Compound 4 in forming the emission layer.

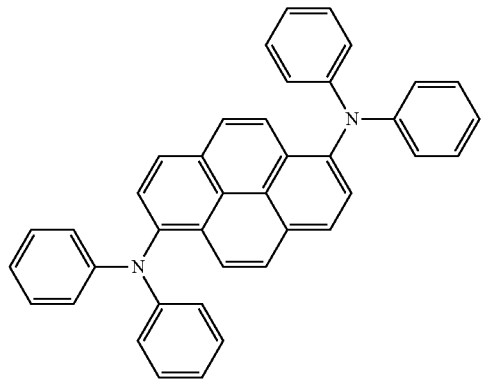

<Compound A>

Comparative Example B

An organic light-emitting diode was manufactured in the same manner as in Example 1, except that as a dopant, Compound B was used instead of Compound 4 in forming the emission layer.

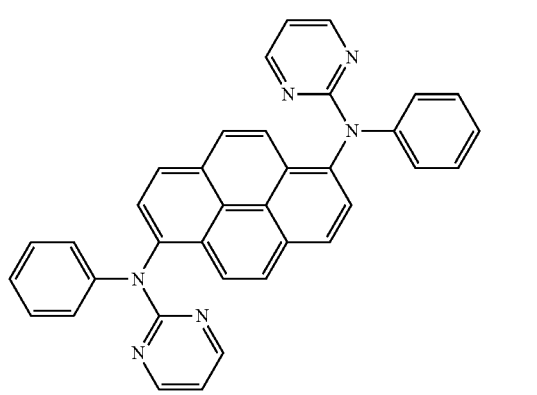

<Compound B>

Evaluation Example 2

The driving voltage, current density, brightness, and a Color coordinate of the organic light-emitting diodes manufactured according to Examples 1 to 11 and a Comparative Examples A and B were evaluated by using a PR650 Spectroscan Source Measurement Unit. (Product of Photo-Research Company). Results thereof are shown in Table 2, below. A IS90 lifespan refers to a time required when brightness reduces to 90% of its initial brightness.

TABLE 2

| | Emission layer host | Emission layer dopant | Brightness (cd/m$^2$) | Current density (cd/A) | Driving voltage (V) | Color coordinate (CIE) |
|---|---|---|---|---|---|---|
| Example 1 | ADN | Compound 4 | 700 | 12 | 4.2 | (0.14, 0.091) |
| Example 2 | ADN | Compound 7 | 700 | 13 | 4.1 | (0.14, 0.099) |
| Example 3 | ADN | Compound 8 | 700 | 12 | 4.3 | (0.14, 0.085) |
| Example 4 | ADN | Compound 13 | 700 | 13 | 4.3 | (0.14, 0.109) |
| Example 5 | ADN | Compound 15 | 700 | 13 | 4.2 | (0.14, 0.085) |
| Example 6 | ADN | Compound 32 | 700 | 14 | 4.4 | (0.14, 0.095) |
| Example 7 | ADN | Compound 35 | 700 | 12 | 4.3 | (0.14, 0.108) |
| Example 8 | ADN | Compound 44 | 700 | 13 | 4.2 | (0.14, 0.099) |
| Example 9 | ADN | Compound 69 | 700 | 12 | 4.3 | (0.14, 0.101) |
| Example 10 | ADN | Compound 87 | 700 | 14 | 4.2 | (0.14, 0.102) |
| Example 11 | ADN | Compound 90 | 700 | 12 | 4.3 | (0.14, 0.107) |
| Comparative Example A | ADN | Compound A | 700 | 16 | 4.6 | (0.16, 0.20) |
| Comparative Example B | ADN | Compound B | 700 | 44 | 6.0 | (0.16, 0.10) |

From Table 1, it may be seen that the organic light-emitting diodes of Examples 1 to 11 exhibited lower driving voltages, higher current density, and better color purity characteristics than the organic light-emitting diodes of Comparative Examples A and B.

An organic light-emitting diode and an organic light-emitting apparatus each including the pyrene-based compound according to an embodiment may have a low driving voltage, a high current density, and excellent color purity characteristics, and a long lifespan.

By way of summation and review, an OLED may have a structure including a substrate, and an anode, a hole transport layer, an emission layer, an electron transport layer, and a cathode which are sequentially stacked on the substrate. The hole transport layer, the emission layer, and the electron transport layer may be organic thin films formed of organic compounds.

An operating principle of an OLED having the above-described structure may be as follows. Holes injected from the anode may move to the emission layer via the hole transport layer, and electrons injected from the cathode may move to the emission layer via the electron transport layer. The holes and electrons (carriers) may recombine in the organic emission layer to generate excitons. When the excitons drop from an excited state to a ground state, light is emitted.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A pyrene-based asymmetrical compound represented by Formula 1, below:

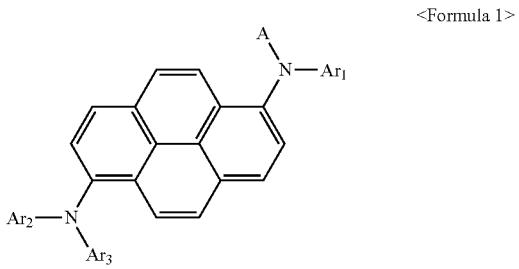

<Formula 1> wherein, in Formula 1,
A is a substituted or unsubstituted $C_2$-$C_{30}$ heteroaromatic group including at least one nitrogen (N); and
$Ar_1$, $Ar_2$, and $Ar_3$ are each independently a substituted or unsubstituted phenyl group or a substituted or unsubstituted naphthyl group.

2. The compound of claim 1, wherein A is selected from a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted isoquinolinyl group, a substituted or unsubstituted quinolinyl group, a substituted or unsubstituted phthalazinyl group, a substituted or unsubstituted quinoxalinyl group, a substituted or unsubstituted quinazolinyl group, a substituted or unsubstituted cinnolinyl group, and a substituted or unsubstituted 1,10-phenanthrolinyl group.

3. The compound of claim 1, wherein A is selected from:
a pyridinyl group, a pyrimidinyl group, a triazinyl group, a pyrazinyl group, a pyridazinyl group, an isoindolyl group, an indolyl group, an indazolyl group, an isoquinolinyl group, a quinolinyl group, a phthalazinyl group, a quinoxalinyl group, a cinnolinyl group, and a 1,10-phenanthrolinyl group; or
a pyridinyl group, a pyrimidinyl group, a triazinyl group, a pyrazinyl group, a pyridazinyl group, an isoindolyl group, an indolyl group, an indazolyl group, an isoquinolinyl group, a quinolinyl group, a phthalazinyl group, a quinoxalinyl group, a cinnolinyl group, and a 1,10-phenanthrolinyl group, each substituted with at least one of:

a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$aryl group, a $C_6$-$C_{60}$ aryloxy group, a $C_6$-$C_{60}$ arylthio group, and a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group, or —Si($Q_{11}$)($Q_{12}$)($Q_{13}$), in which $Q_{11}$ to $Q_{13}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group.

4. The compound of claim 1, wherein A is a group represented by one of Formulae 2A to 2K below:

Formula 2A

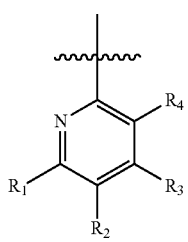

Formula 2B

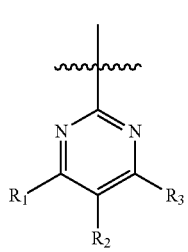

Formula 2C

Formula 2D

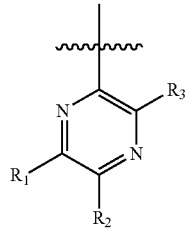

Formula 2E

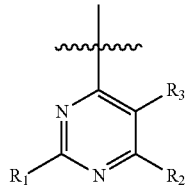

Formula 2F

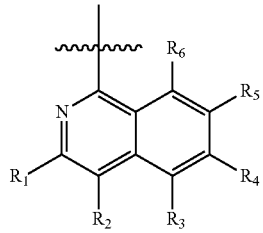

Formula 2G

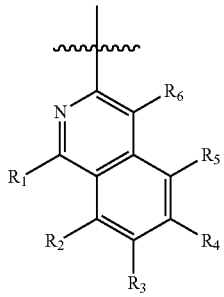

Formula 2H

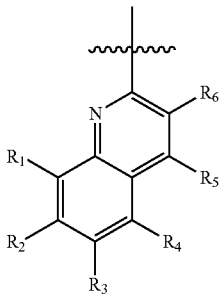

-continued

Formula 2I

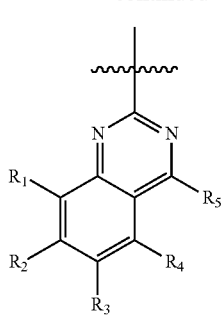

Formula 2J

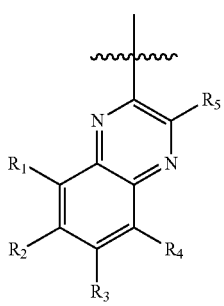

Formula 2K

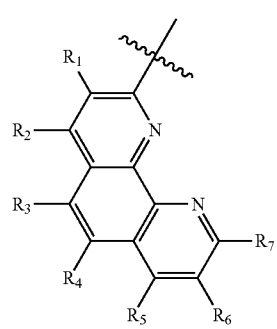

wherein, in Formulae 2A to 2K, $R_1$ to $R_7$ are each independently selected from:

a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group; and —$Si(Q_{11})(Q_{12})(Q_{13})$, in which $Q_{11}$ to $Q_{13}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group.

5. The compound of claim 4, wherein $R_1$ to $R_7$ are each independently selected from:

a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a $C_1$-$C_{10}$ alkyl group;

a $C_1$-$C_{60}$ alkyl group substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof;

a $C_6$-$C_{16}$ aryl group, and a $C_2$-$C_{16}$ heteroaryl group;

a $C_6$-$C_{16}$ aryl group or a $C_2$-$C_{16}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{10}$ alkyl group, phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group; and —$Si(Q_{11})(Q_{12})(Q_{13})$, in which $Q_{11}$ to $Q_{13}$ are each independently a $C_1$-$C_{10}$ alkyl group, a $C_6$-$C_{16}$ aryl group, or a $C_2$-$C_{16}$ heteroaryl group.

6. The compound of claim 4, wherein $R_1$ to $R_7$ are each independently selected from:

a hydrogen atom, a deuterium atom, F, Cl, Br, I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a methyl group, an ethyl group, a propyl group, a butyl group, a pentyl group, and a hexyl group;

a phenyl group, a naphthyl group, and an anthracenyl group; and a phenyl group, a naphthyl group, and an anthracenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a methyl group, an ethyl group, a propyl group, a butyl group, a pentyl group, a hexyl group, phenyl group, a naphthyl group, an anthracenyl group, a fluorenyl group, a dimethylfluorenyl group, a diphenylfluorenyl group, a carbazolyl group, and a phenylcarbazolyl group.

7. The compound of claim 1, wherein A has a structure selected from one of the following structures:

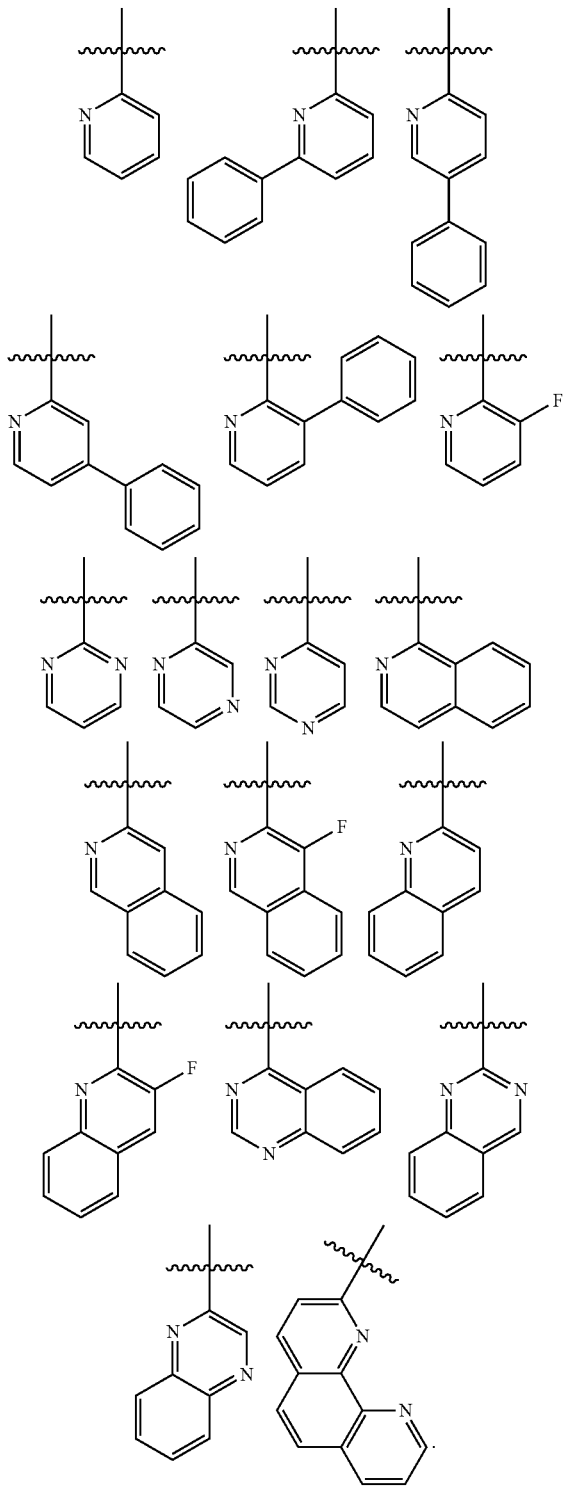

8. The compound of claim 1, wherein $Ar_1$, $Ar_2$, and $Ar_3$ are each independently selected from:
 a phenyl group and a naphthyl group; and
 a phenyl group and a naphthyl group, each substituted with at least one of:
  a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group,
  a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof,
  a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group,
  a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group, and
  —Si($Q_{11}$)($Q_{12}$)($Q_{13}$), in which $Q_{11}$ to $Q_{13}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group.

9. The compound of claim 1, wherein $Ar_1$, $Ar_2$, and $Ar_3$ are each independently selected from:
 a phenyl group and a naphthyl group; and
 a phenyl group and a naphthyl group, each substituted with at least one of:
  a deuterium atom, F, Cl, Br, I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof and a methyl group, an ethyl group, a propyl group, a butyl group, a pentyl group, and a hexyl group,
  a phenyl group, a naphthyl group, and an anthracenyl group, and
  a phenyl group, a naphthyl group, and an anthracenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a methyl group, an ethyl group, a propyl group, a butyl group, a pentyl group, a hexyl group, phenyl group, a naphthyl group, an anthracenyl group, a fluorenyl group, a dimethylfluorenyl group, a diphenylfluorenyl group, a carbazolyl group, and a phenylcarbazolyl group.

10. The compound of claim 1, wherein $Ar_1$ is selected from one of the following structures:

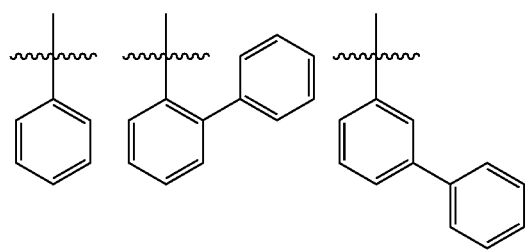
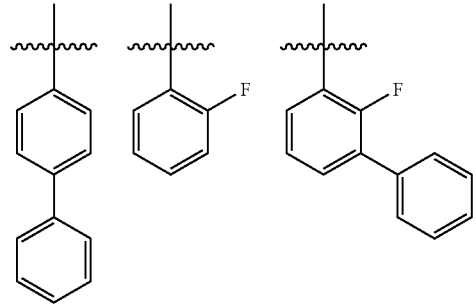
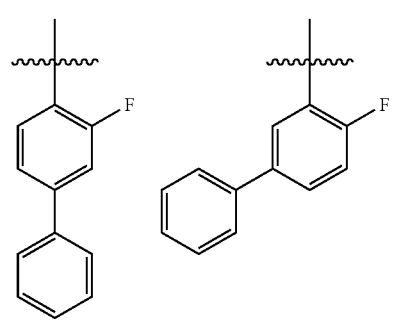
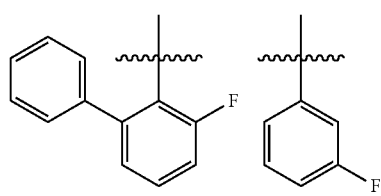
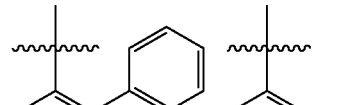
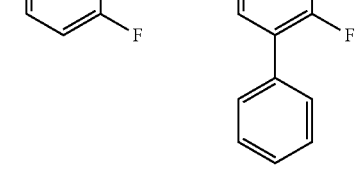
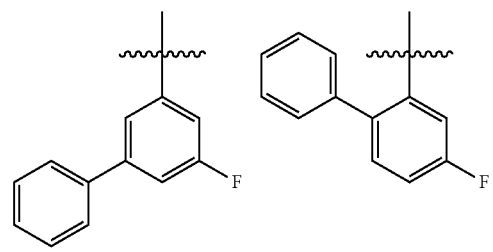
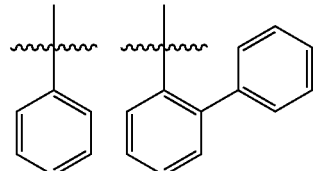
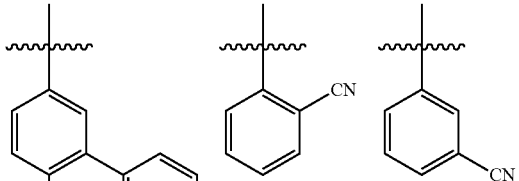
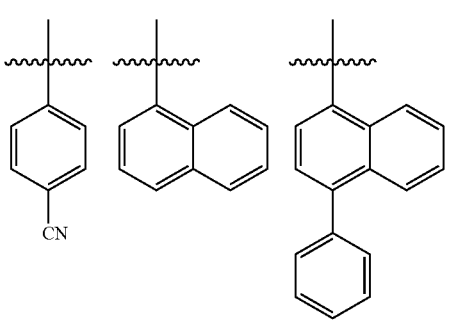
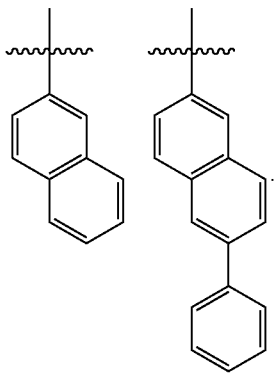
11. The compound of claim 1, wherein Ar$_2$ and Ar$_3$ are each independently selected from one of the following structures:
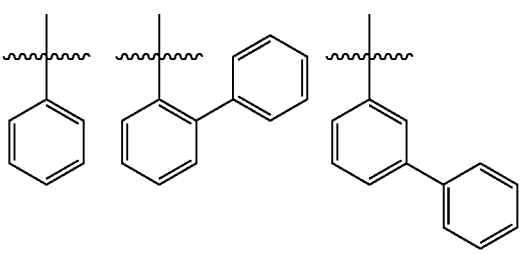

-continued
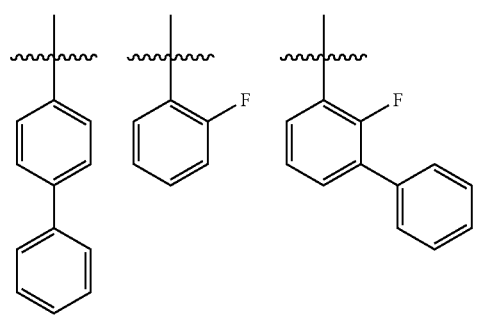
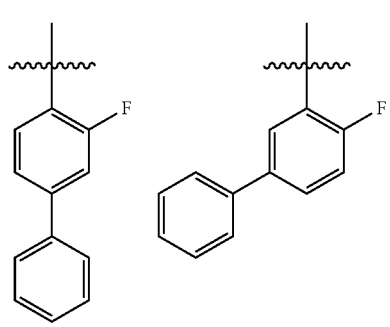
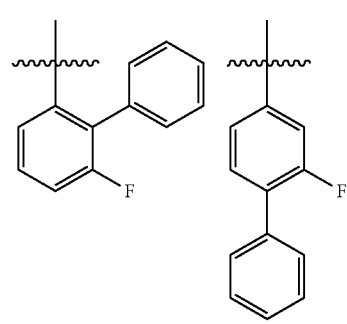
-continued
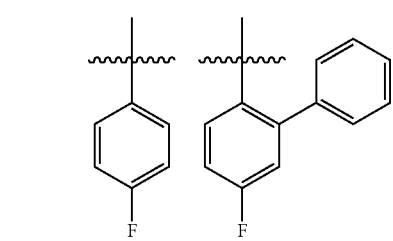
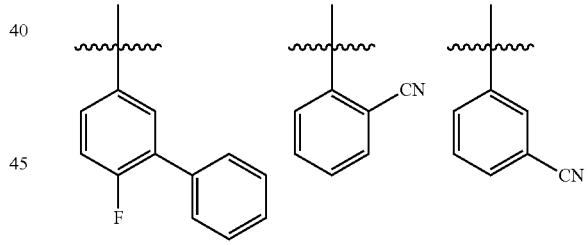
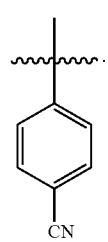
12. The compound of claim 1, wherein Ar₁ is a substituted or unsubstituted phenyl group or a substituted or unsubstituted a naphthyl group, and Ar₂ and Ar₃ are a substituted or unsubstituted phenyl group.
13. The compound of claim 1, wherein the pyrene-based compound is represented by one of Formulae 1A, 1B, or 1C, below:

<Formula 1A>

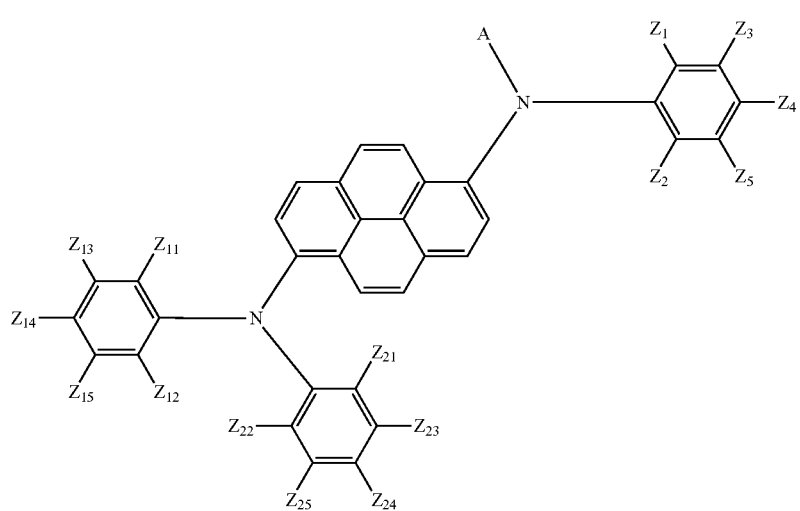

<Formula 1B>

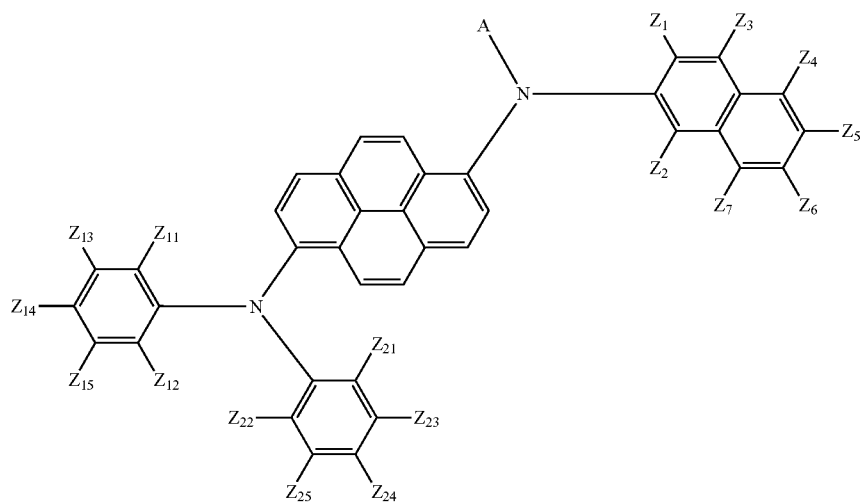

<Formula 1C>

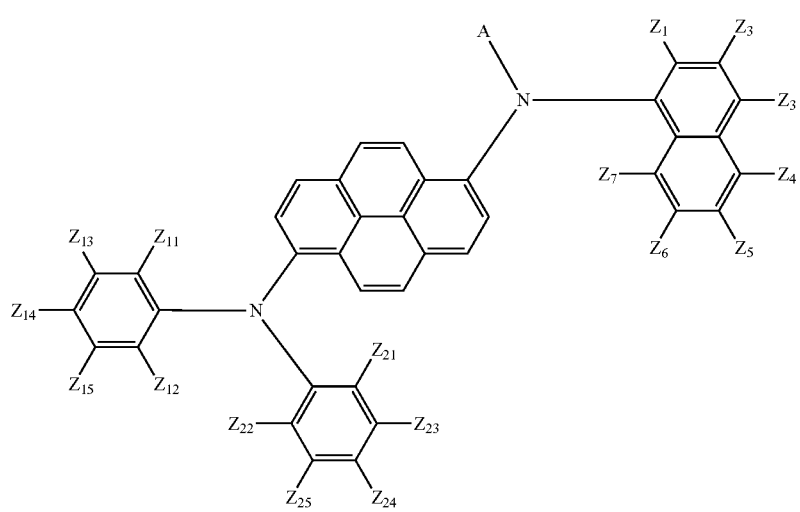

wherein, in Formulae 1A, 1B, and 1C,

A is a substituted or unsubstituted $C_2$-$C_{30}$ heteroaromatic group including at least one nitrogen (N); and $Z_1$ to $Z_7$, $Z_{11}$ to $Z_{15}$ and $Z_{21}$ to $Z_{25}$ are each independently selected from:

a hydrogen atom, a deuterium atom, F, Cl, Br, I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a methyl group, an ethyl group, a propyl group, a butyl group, a pentyl group, and a hexyl group;

a phenyl group, a naphthyl group, and an anthracenyl group; and a phenyl group, a naphthyl group, and an anthracenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a methyl group, an ethyl group, a propyl group, a butyl group, a pentyl group, a hexyl group, phenyl group, a naphthyl group, an anthracenyl group, a fluorenyl group, a dimethylfluorenyl group, a diphenylfluorenyl group, a carbazolyl group and a phenylcarbazolyl group.

14. The compound of claim 13, wherein A is represented by one of Formulae 2A to 2K, below:

Formula 2A

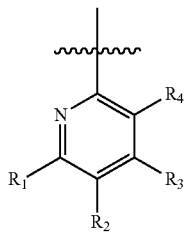

Formula 2B

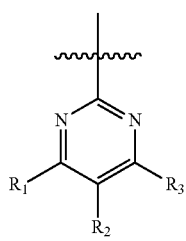

Formula 2C

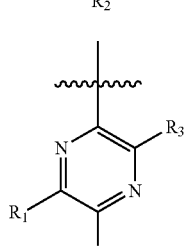

Formula 2D

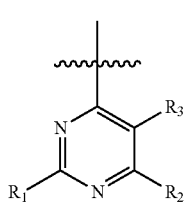

Formula 2E

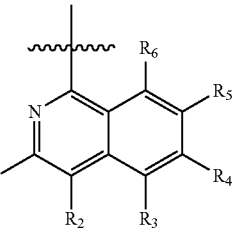

Formula 2F

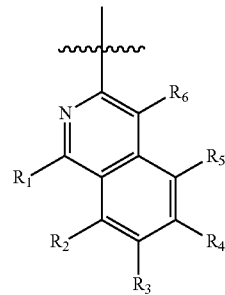

Formula 2G

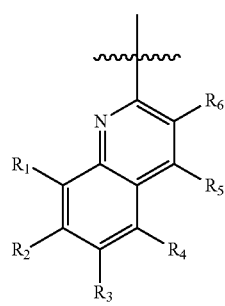

Formula 2H

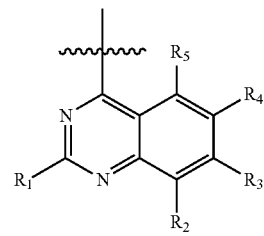

Formula 2I

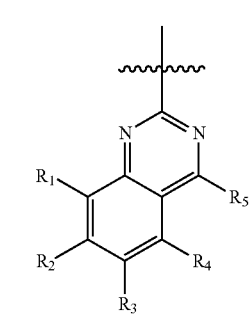

Formula 2J

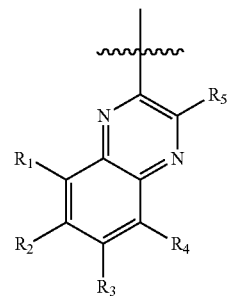

Formula 2K

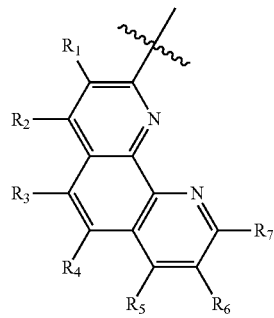

wherein, in Formulae 2A to 2K, $R_1$ to $R_7$ are each independently selected from:
a hydrogen atom, a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a $C_1$-$C_{10}$ alkyl group;
a $C_1$-$C_{60}$ alkyl group substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, and a phosphoric acid or a salt thereof;
a $C_6$-$C_{16}$ aryl group and a $C_2$-$C_{16}$ heteroaryl group;
a $C_6$-$C_{16}$ aryl group and a $C_2$-$C_{16}$ heteroaryl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid or a salt thereof, a $C_1$-$C_{10}$ alkyl group, phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolinyl group, and an isoquinolinyl group; and
—Si($Q_{11}$)($Q_{12}$)($Q_{13}$), in which $Q_{11}$ to $Q_{13}$ are each independently a $C_1$-$C_{10}$ alkyl group, a $C_6$-$C_{16}$ aryl group, or a $C_2$-$C_{16}$ heteroaryl group.

15. The compound of claim 14, wherein $R_1$ to $R_7$, $Z_1$ to $Z_7$, $Z_{11}$ to $Z_{15}$ and $Z_{21}$ to $Z_{25}$ are each independently a hydrogen atom, a F atom, a cyano group, or a phenyl group.

16. The compound of claim 1, wherein the compound is one of Compounds 1 to 96, below:

1

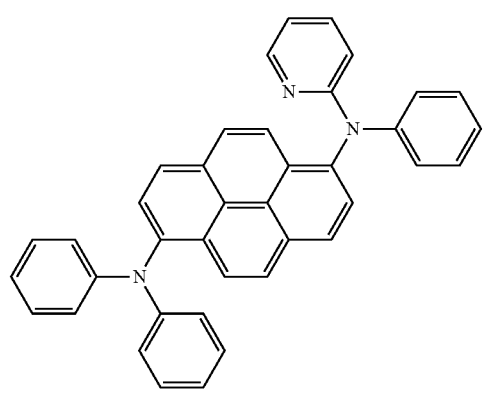

2

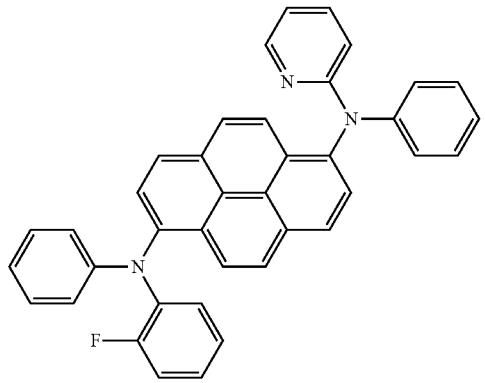

3

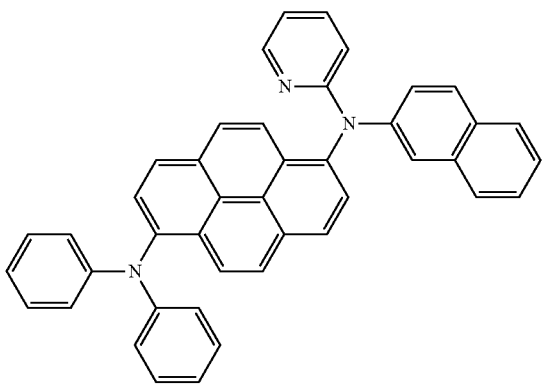

4

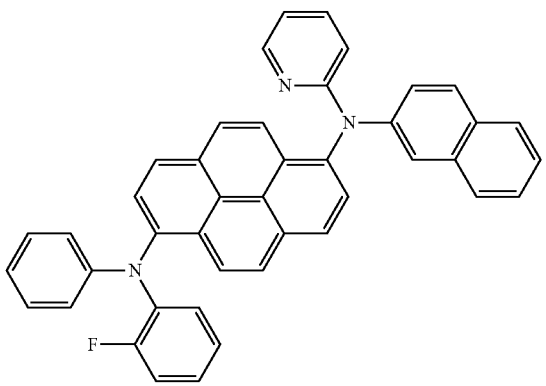

5

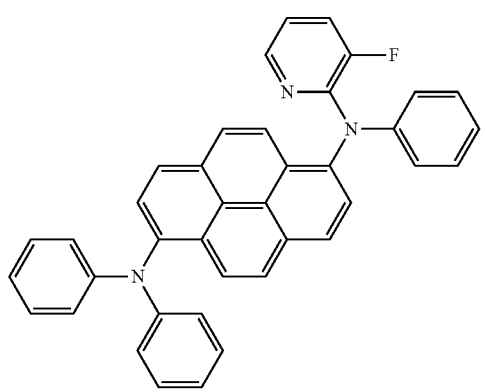

6
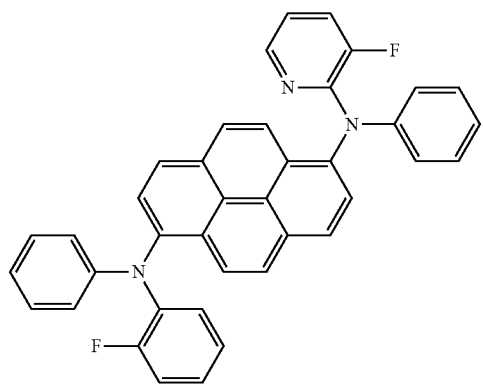
7
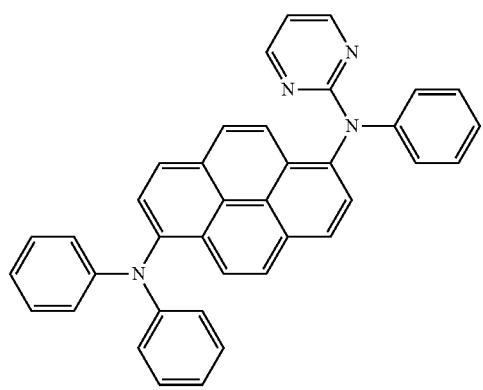
8
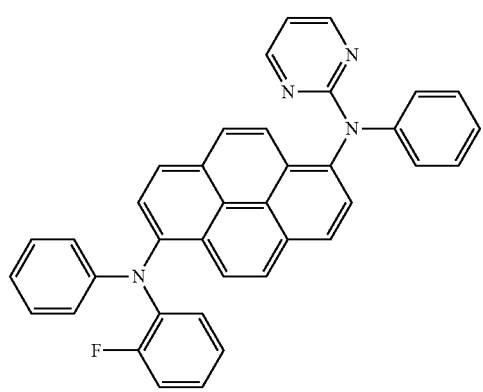
9
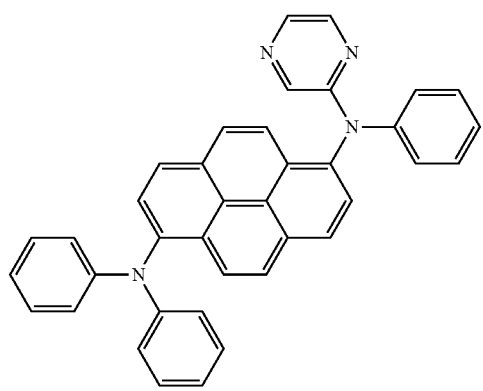
10
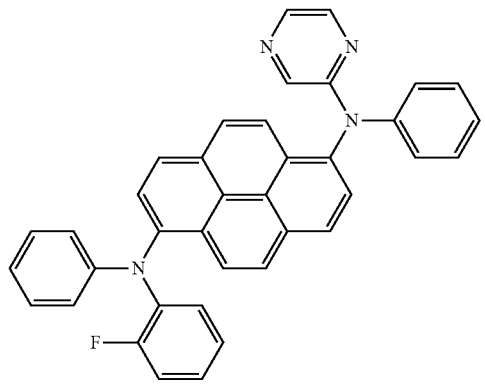
11
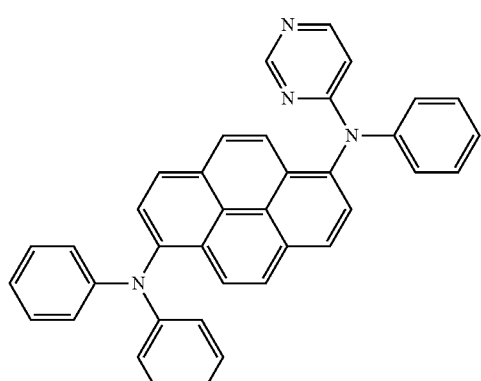
12
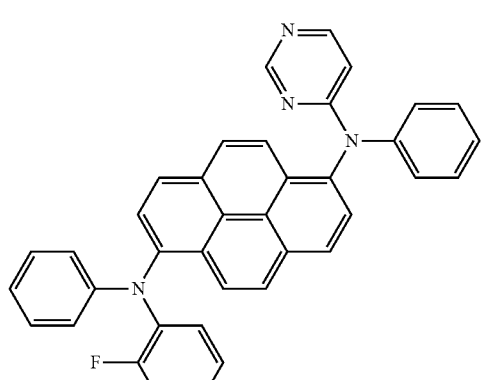
13
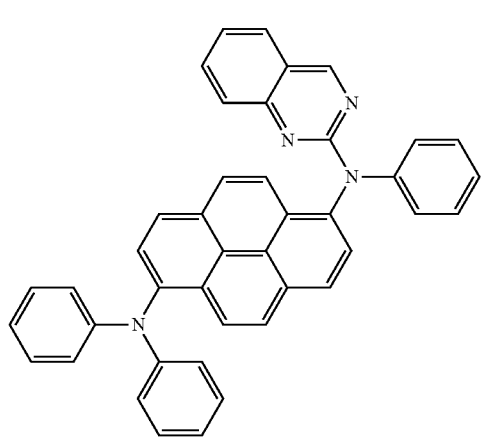

14
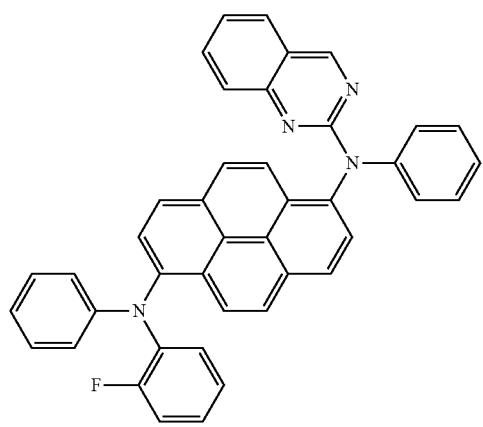
15
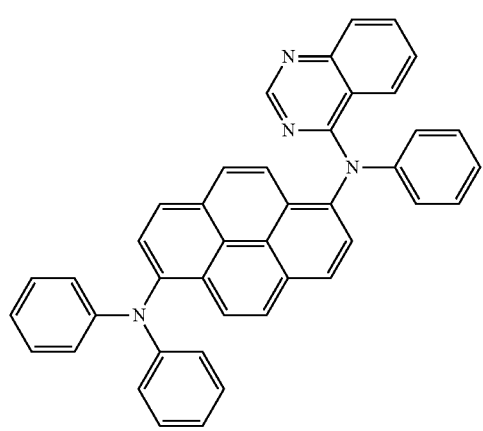
16
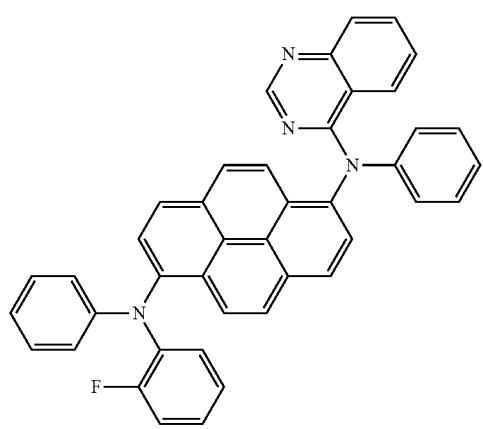
17
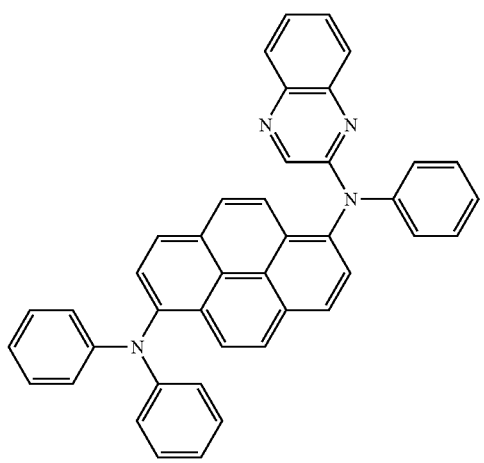
18
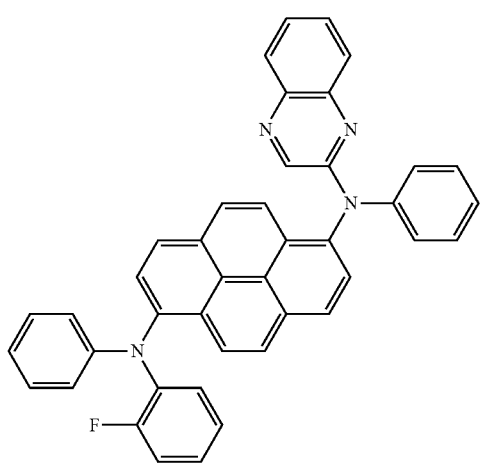
19
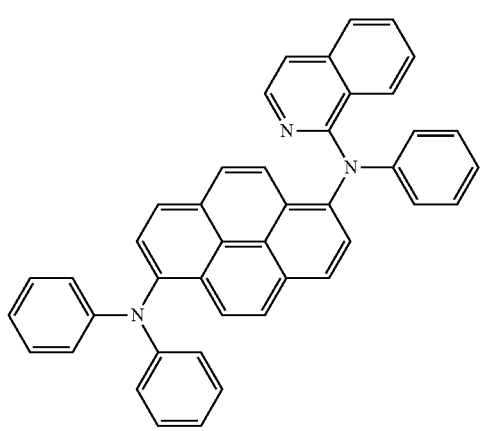

-continued
20
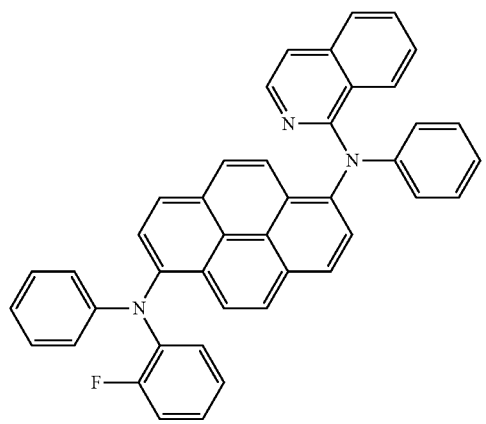
21
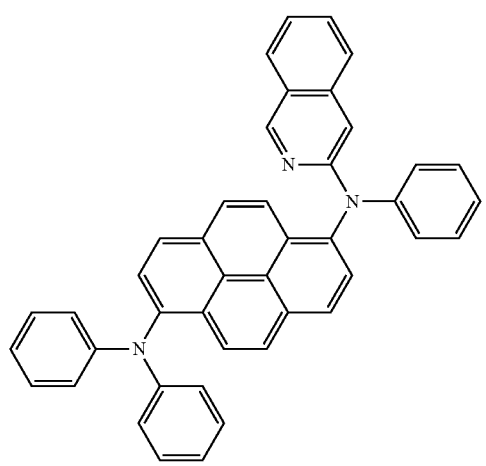
22
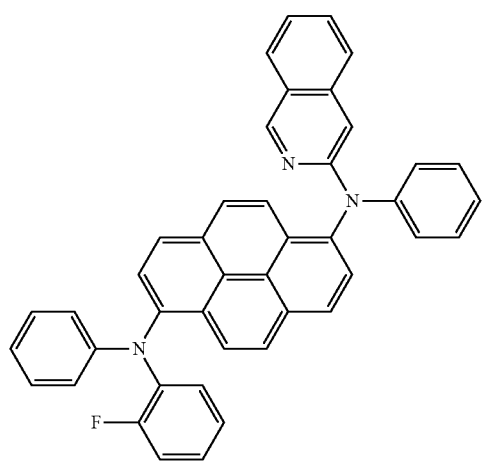
-continued
23
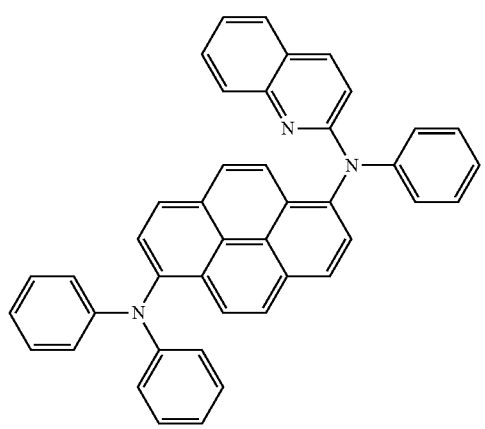
24
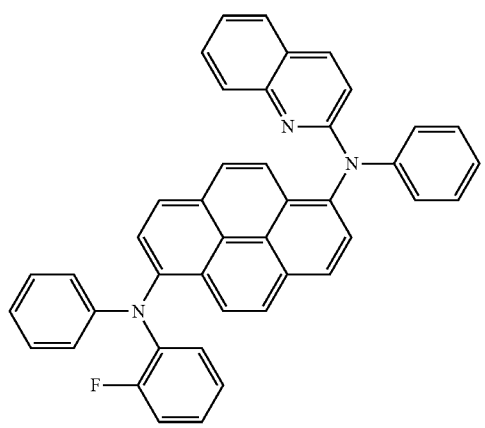
25
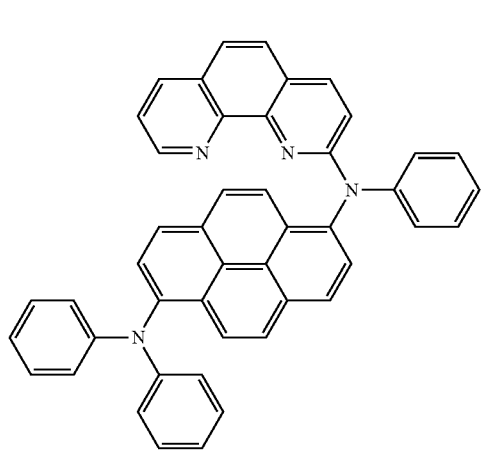

26
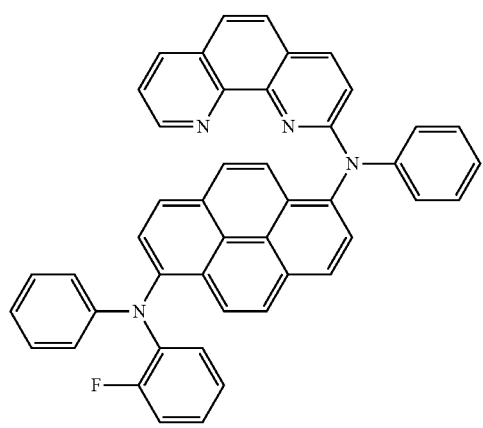
27
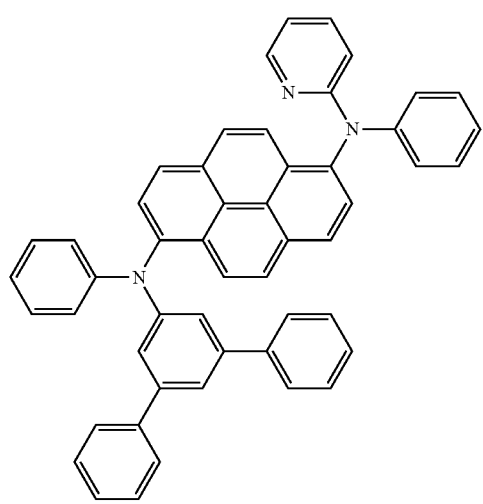
28
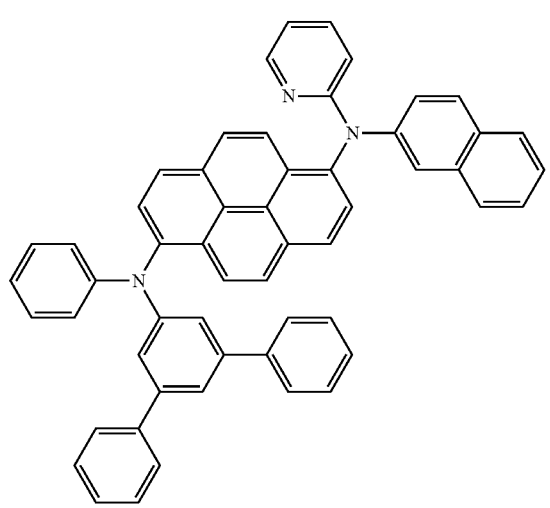
29
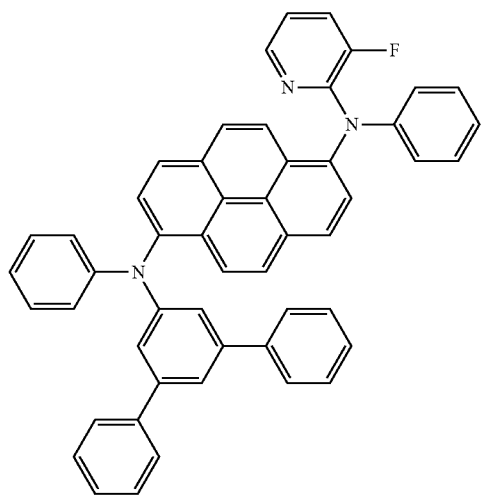
30
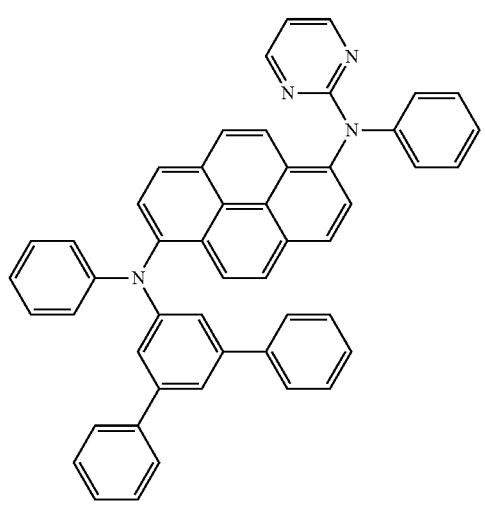
31
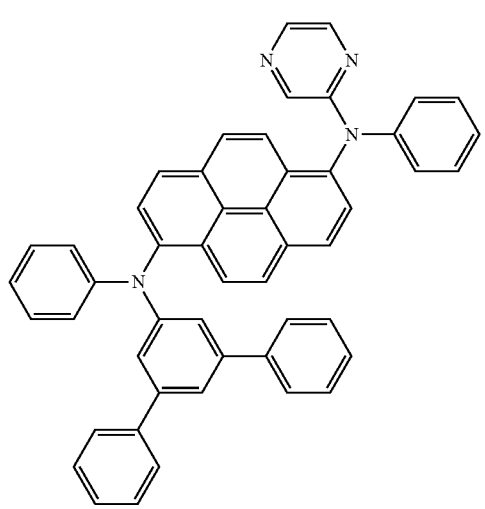

189
32
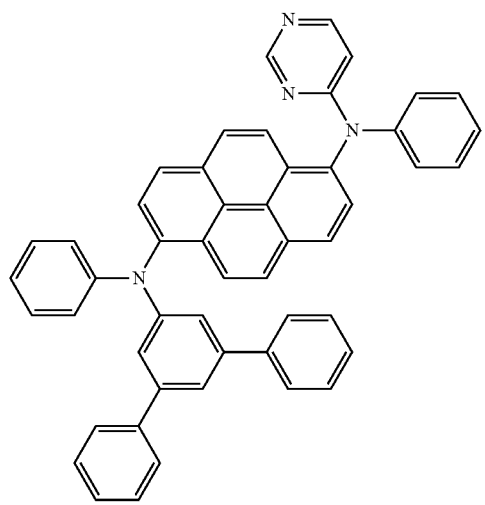
33
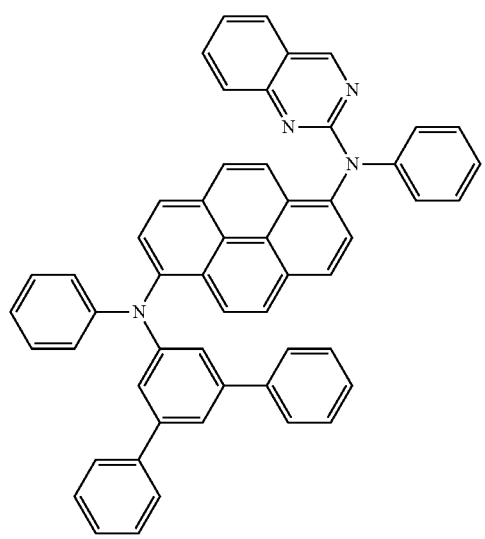
34
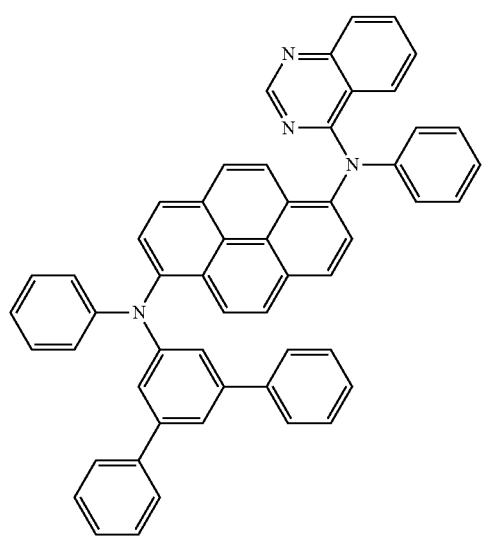
190
35
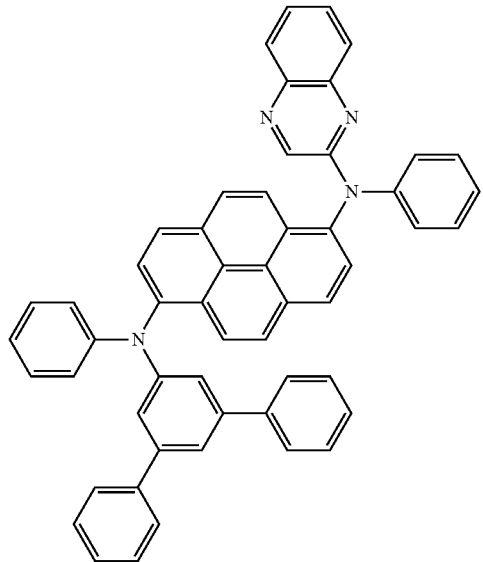
36
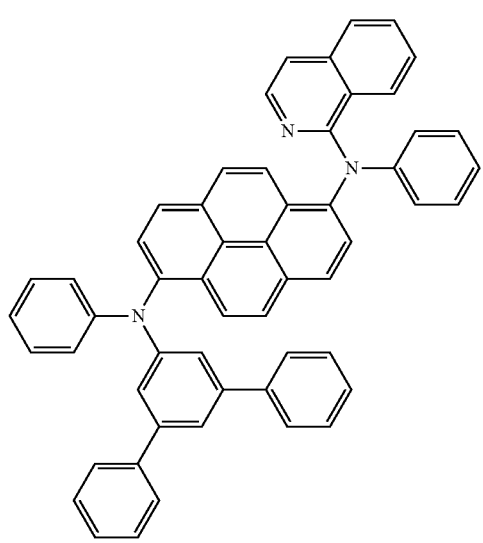
37
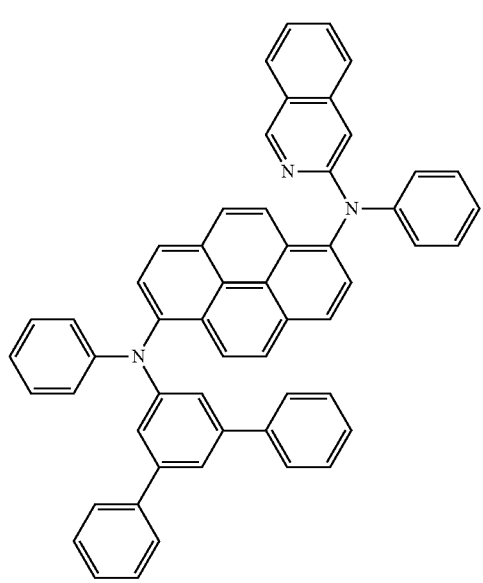

38
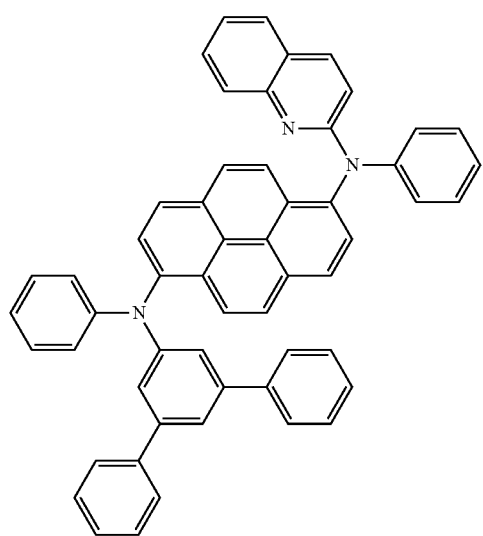
39
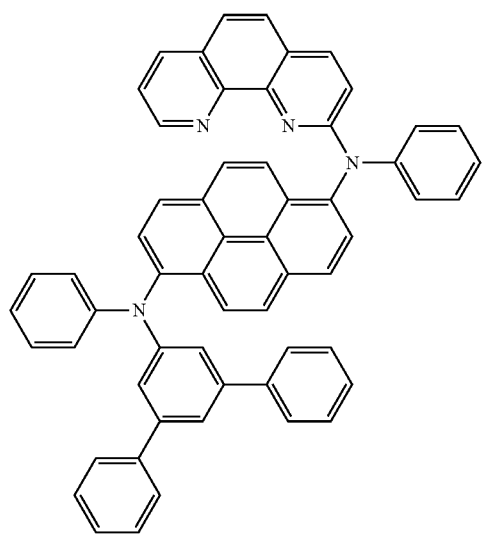
40
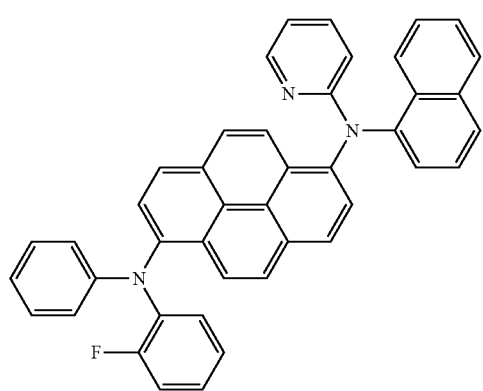
41
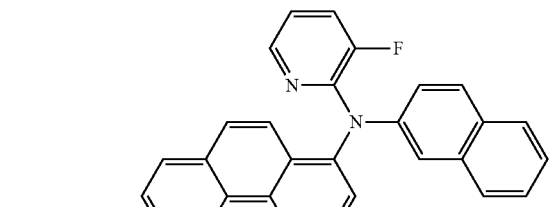
42
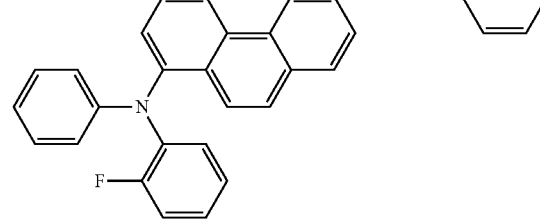
43
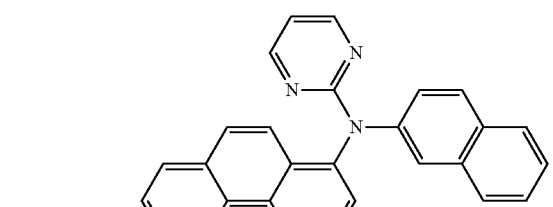
44
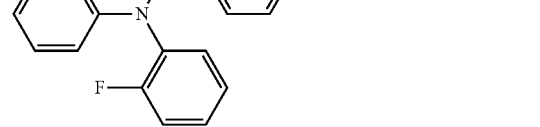

45
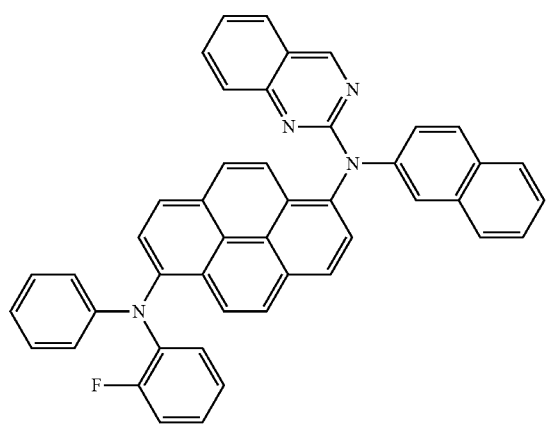
46
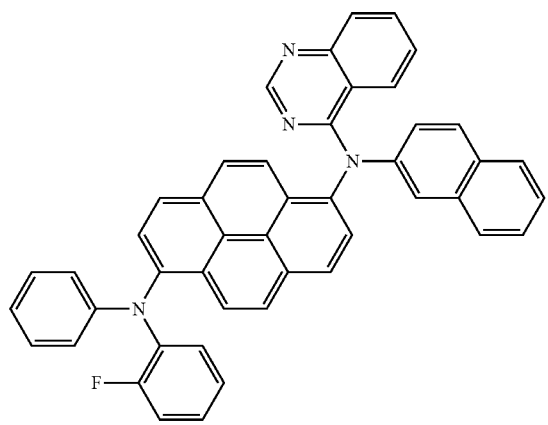
47
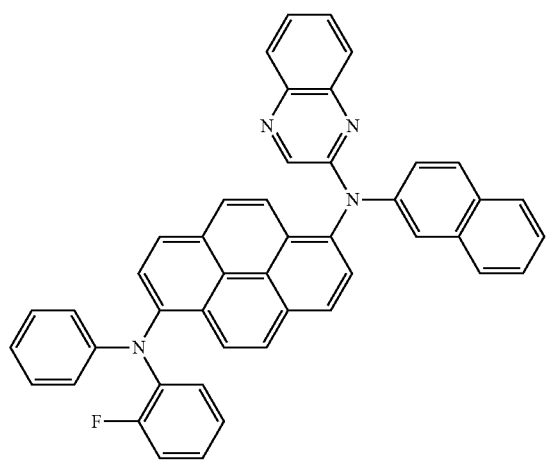
48
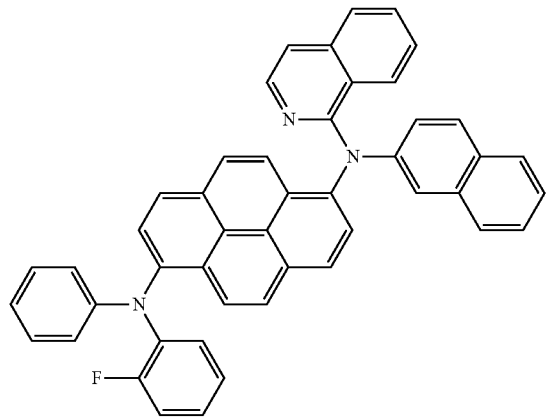
49
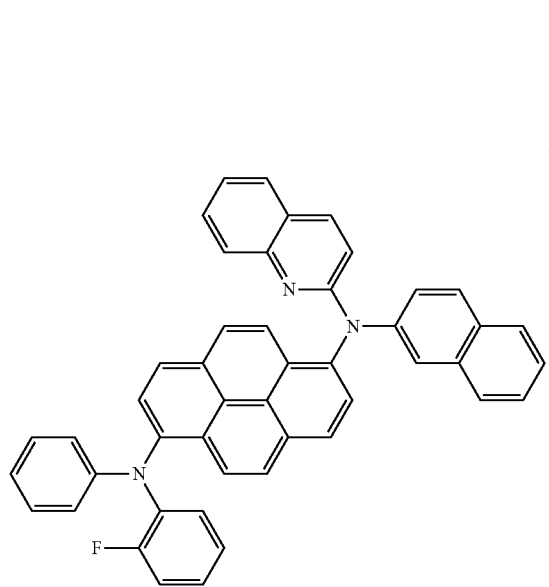
50

51
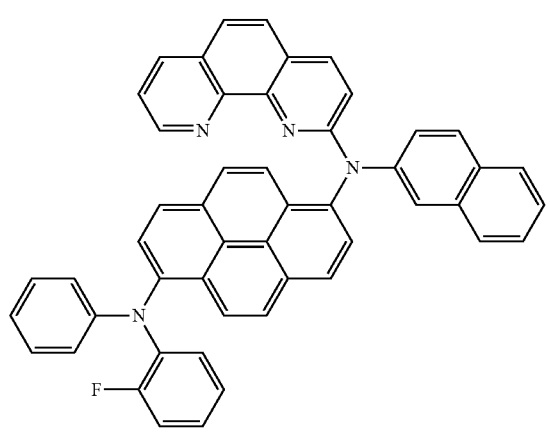
52
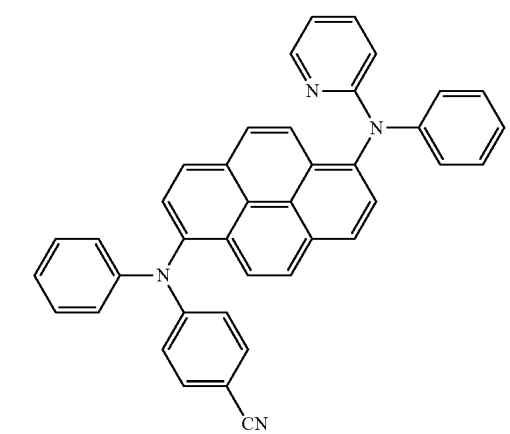
53
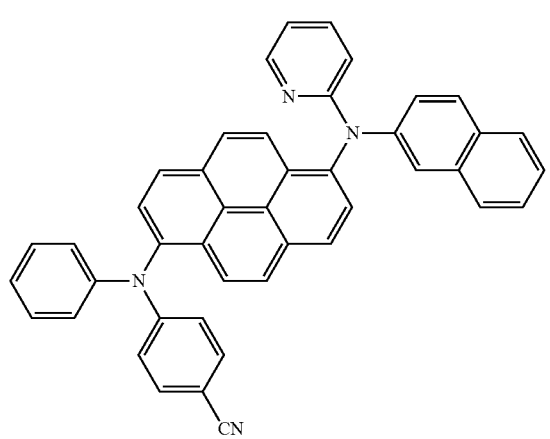
54
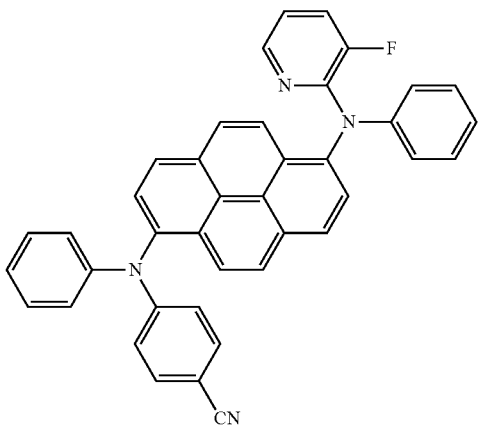
55
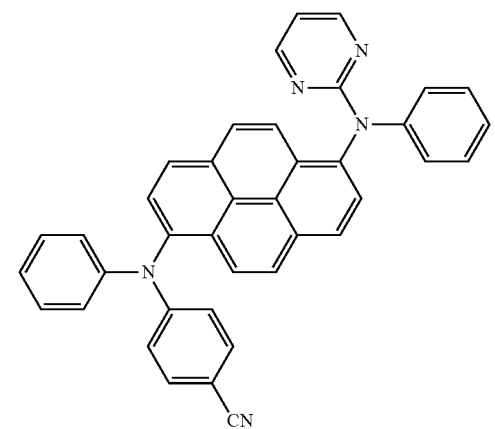
56
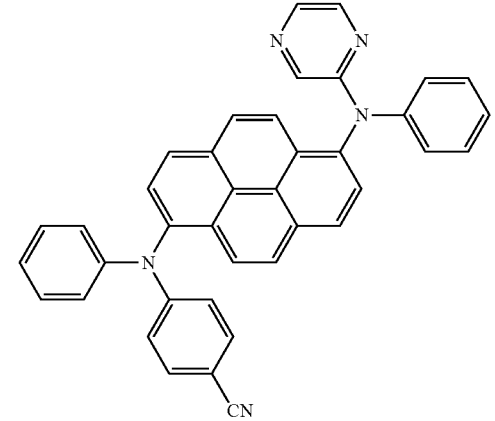

-continued
57
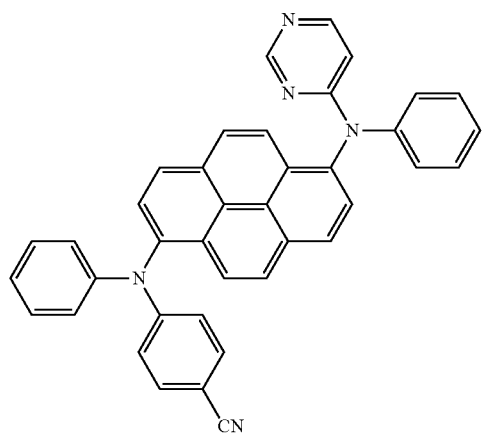
58
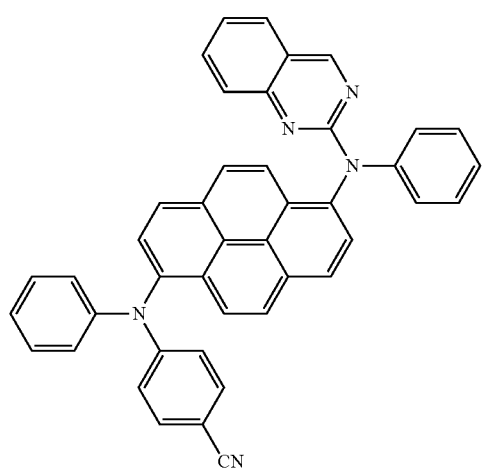
59
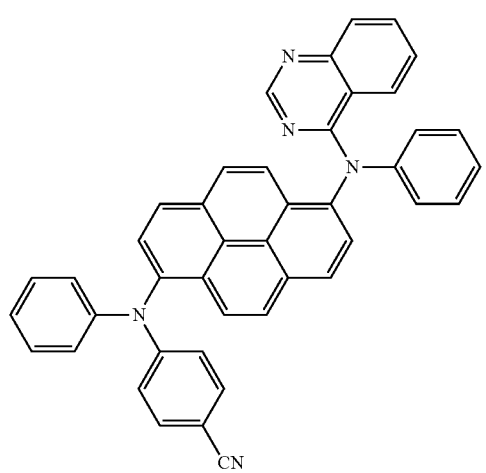
-continued
60
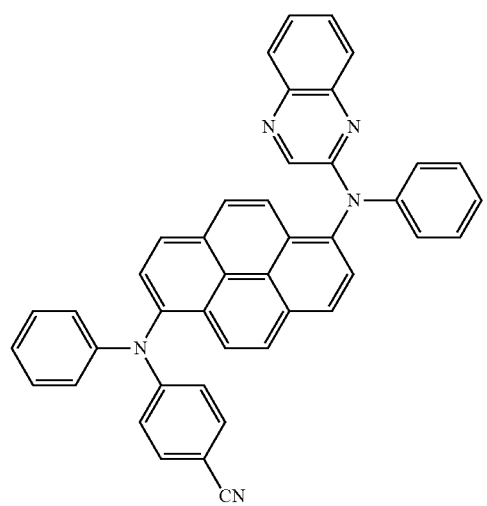
61
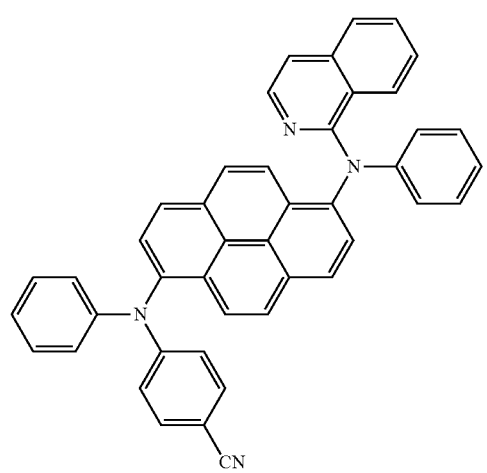
62
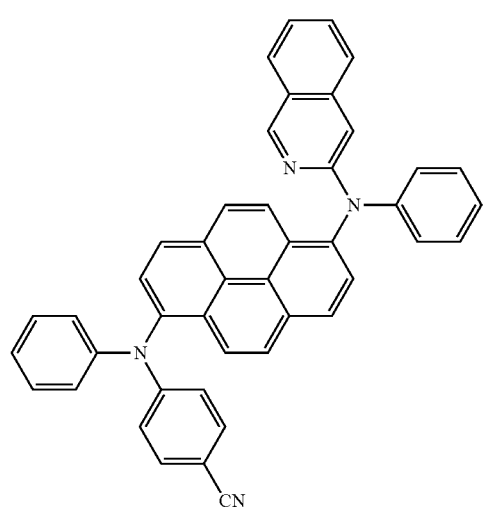

199
-continued
63
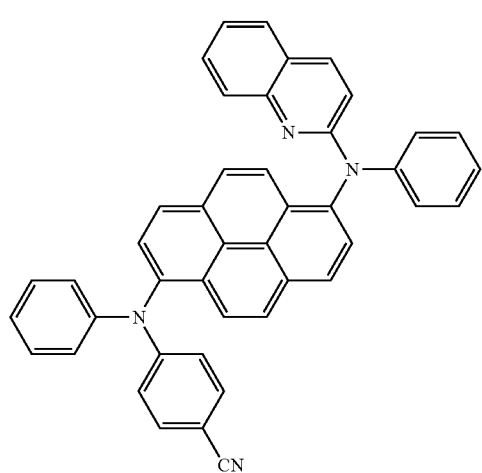
64
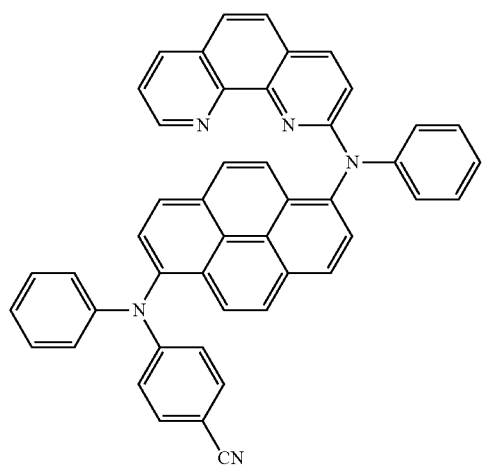
65
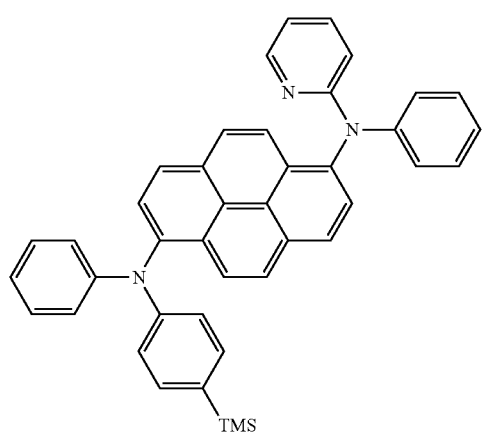
200
-continued
66
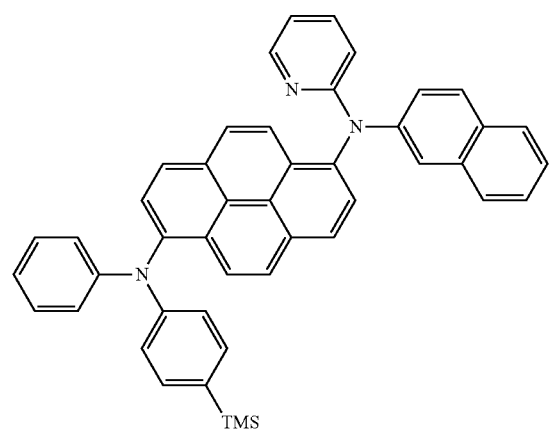
67
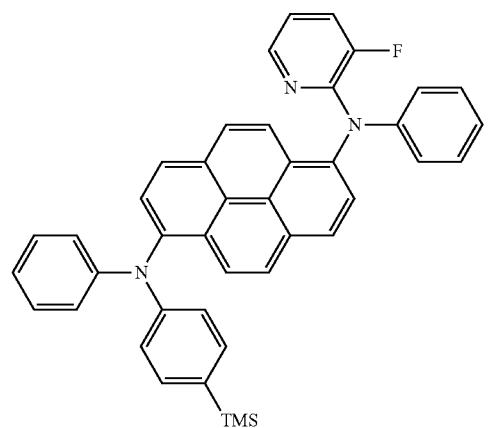
68
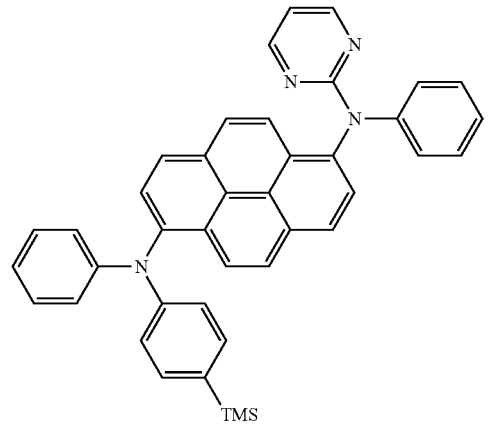

-continued
69
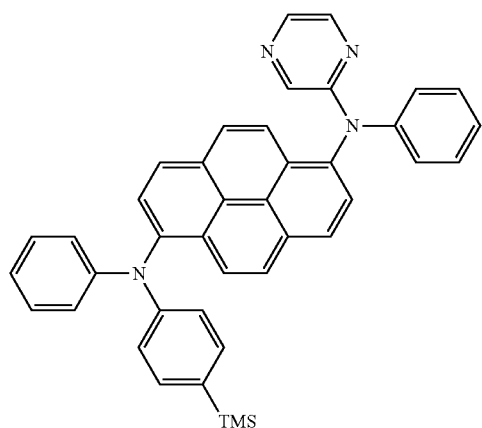
70
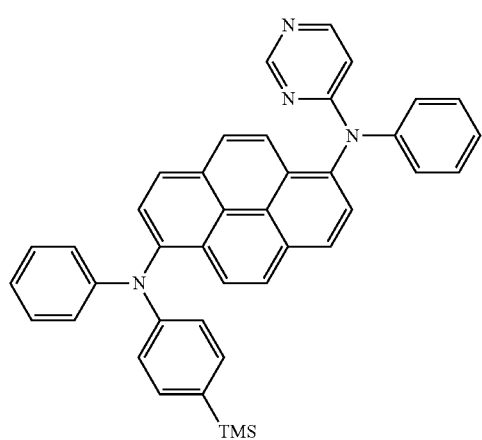
71
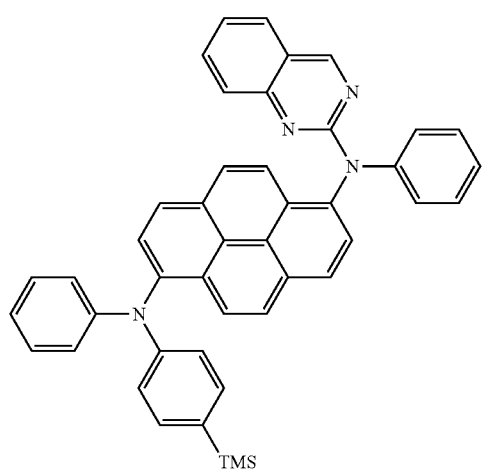
-continued
72
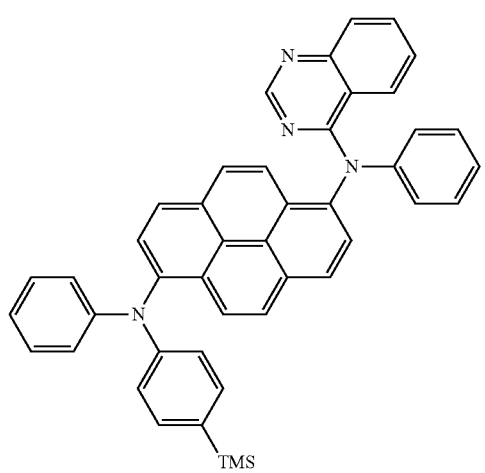
73
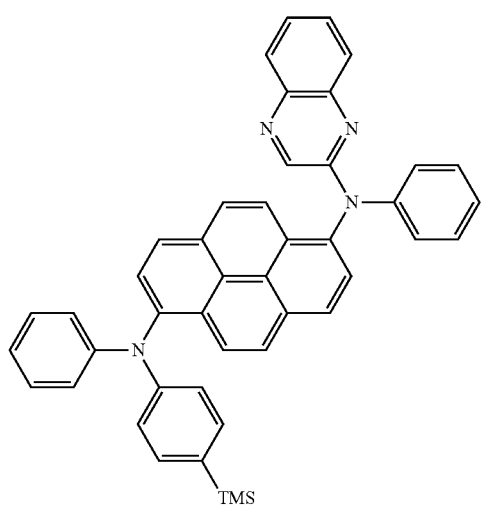
74
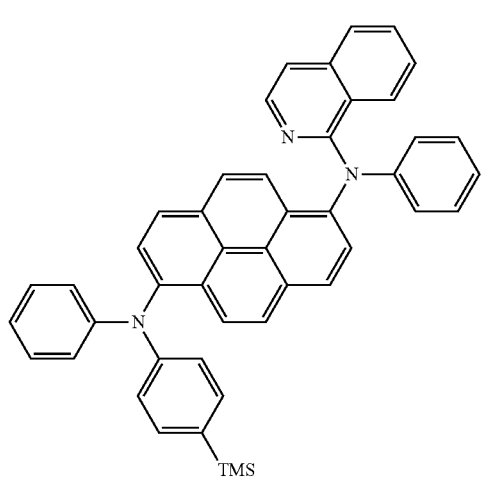

-continued
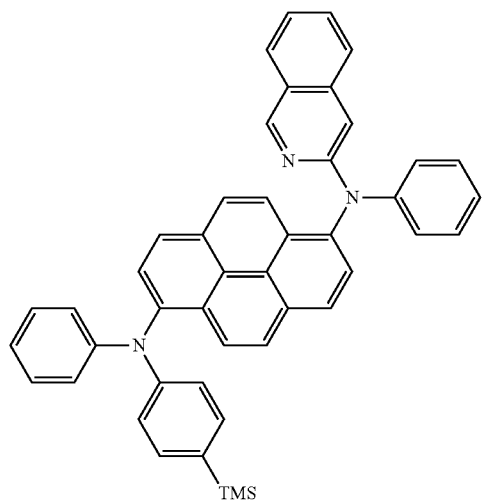
75
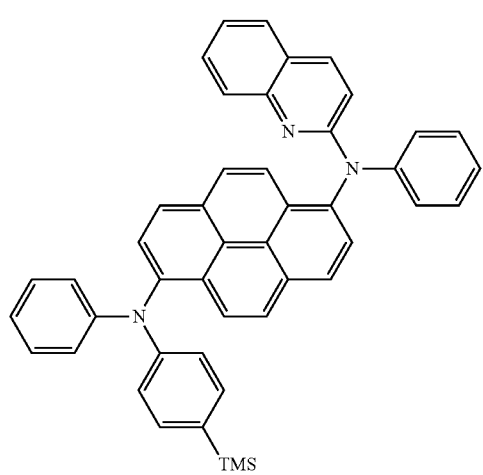
76
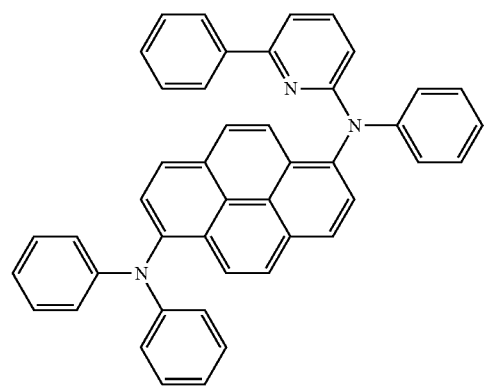
78
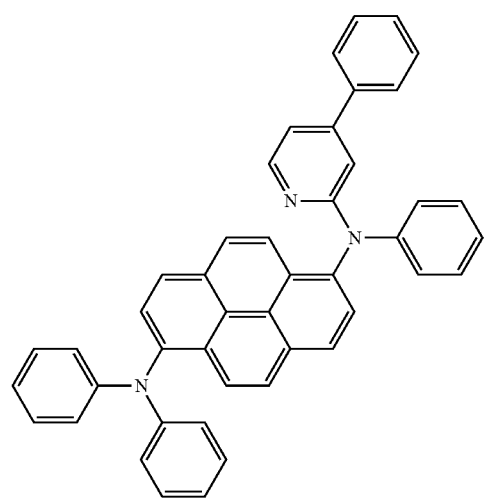

205
-continued
81
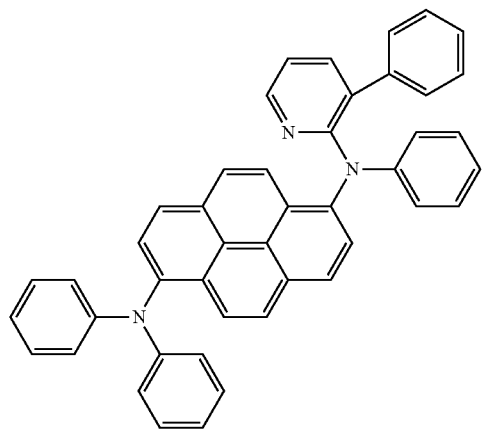
82
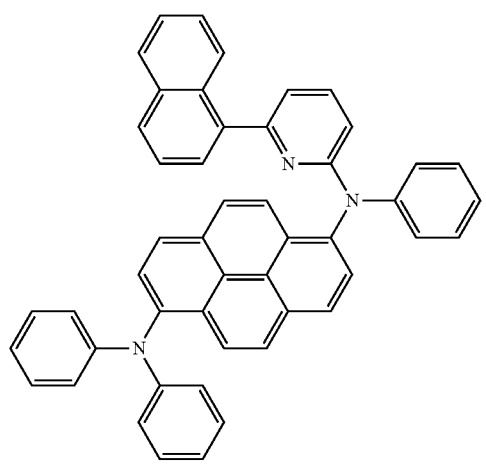
83
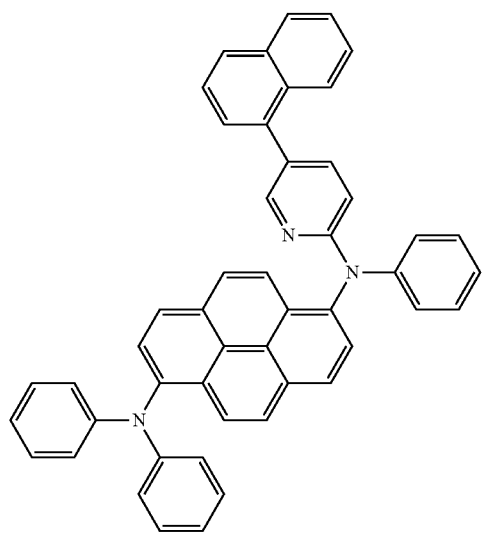
206
-continued
84
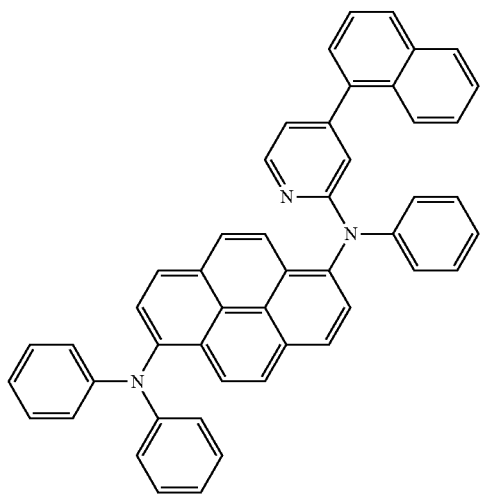
85
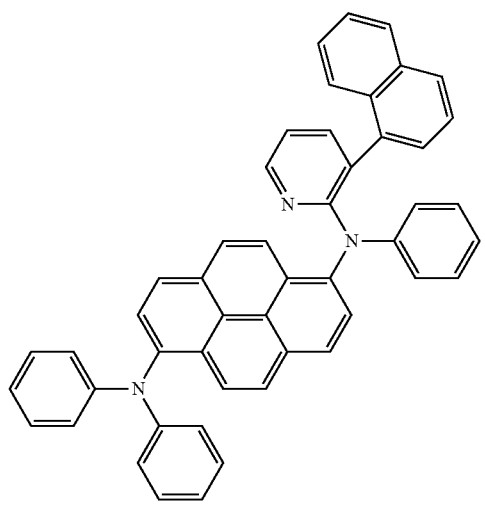
86
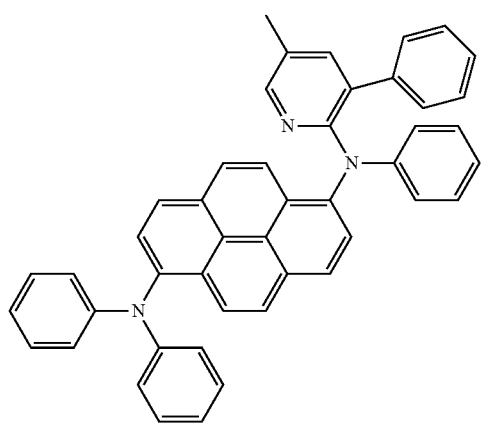

87
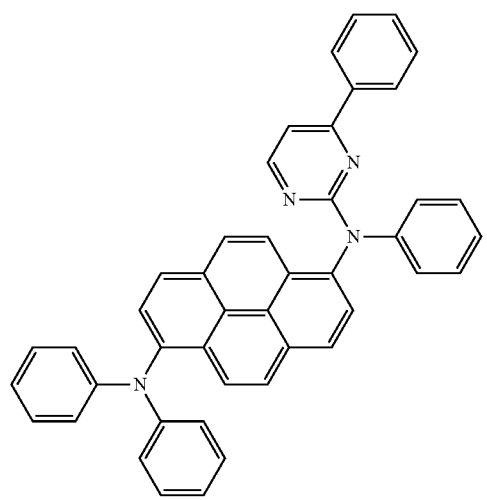
88
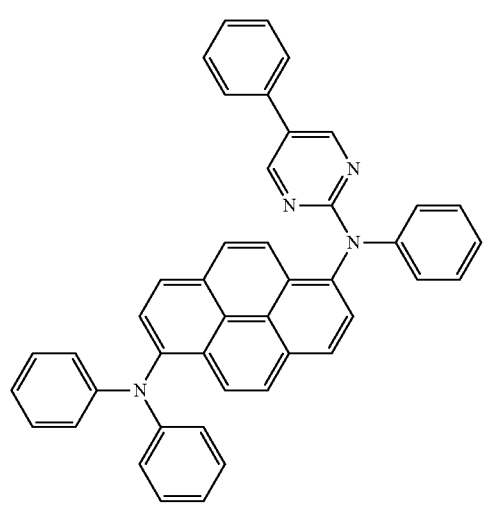
89
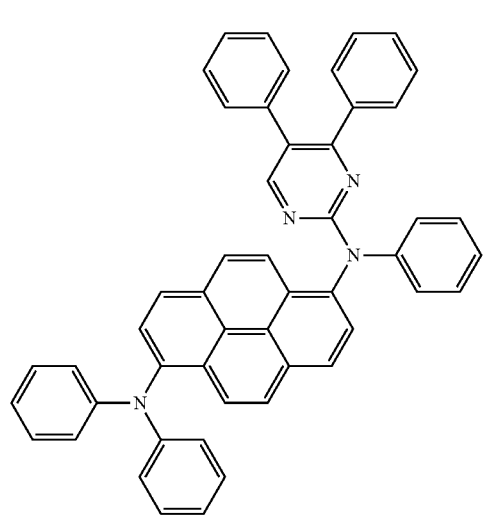
90
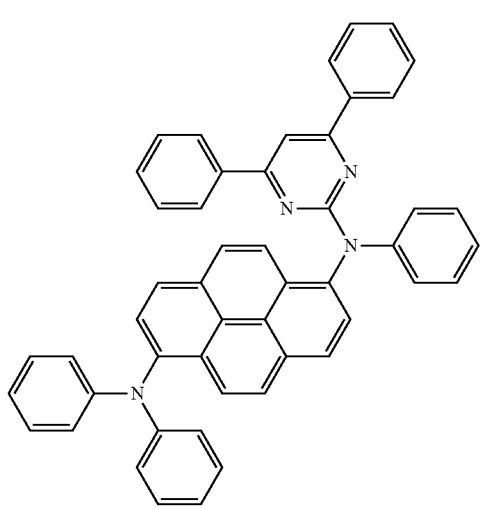
91
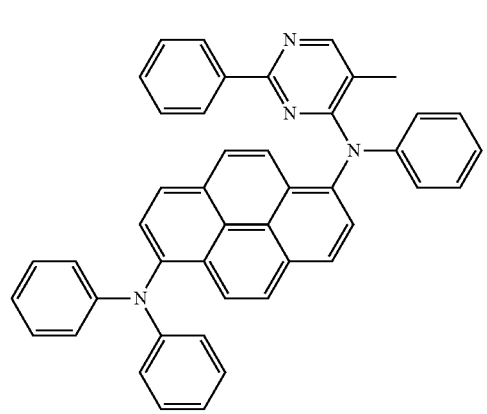
92
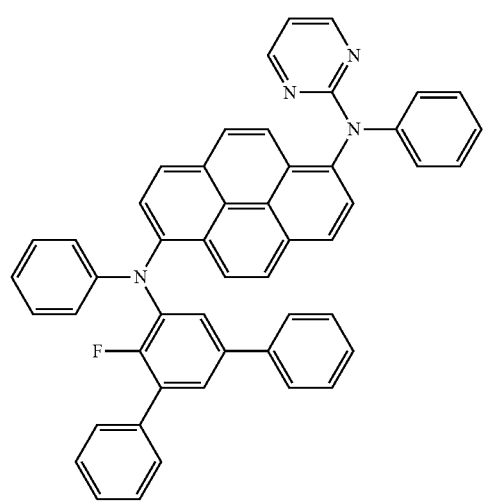

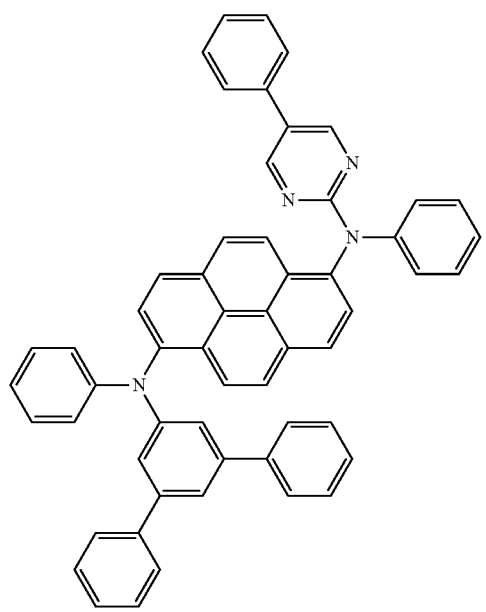

93

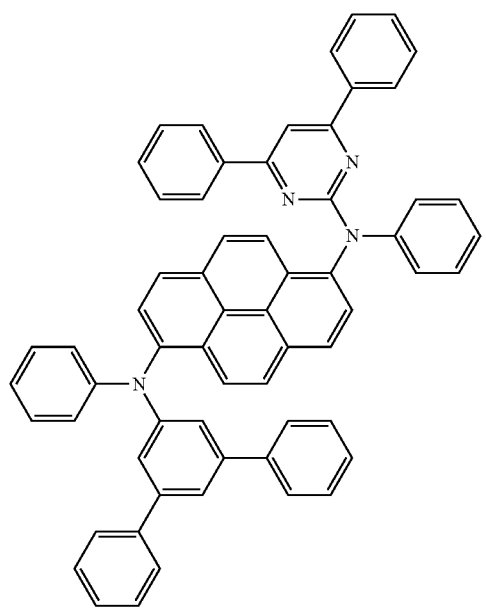

94

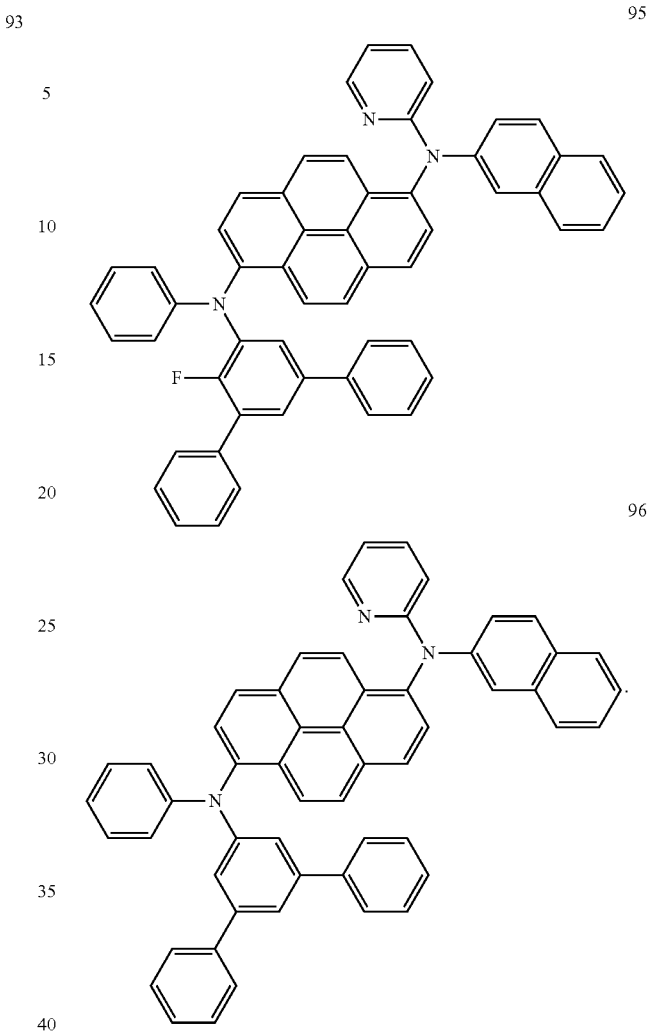

95

96

17. An organic light-emitting diode, comprising:
a first electrode;
a second electrode facing the first electrode; and
an organic layer between the first electrode and the second electrode and including an emission layer, wherein the organic layer includes the compound of claim 1.

18. The organic light-emitting diode of claim 17, wherein the organic layer further includes:
a hole transportation region between the first electrode and the emission layer, the hole transportation region including at least one of a hole injection layer, a hole transportation layer, a functional layer having a hole injection capability and a hole transport capability, a buffer layer, and an electron blocking layer, and
an electron transportation region between the emission layer and the second electrode, the electron transportation region including at least one of a hole blocking layer, an electron transportation layer, and an electron injection layer.

19. The organic light-emitting diode of claim 17, wherein the compound is:
in the emission layer, and
a fluorescent dopant that emits light according to a fluorescence emission mechanism, the emission layer further including a host.

20. The organic light-emitting diode of claim 19, wherein the host includes at least one of an anthracene-based compound represented by Formula 400, below, or an anthracene-based compound represented by Formula 401, below:

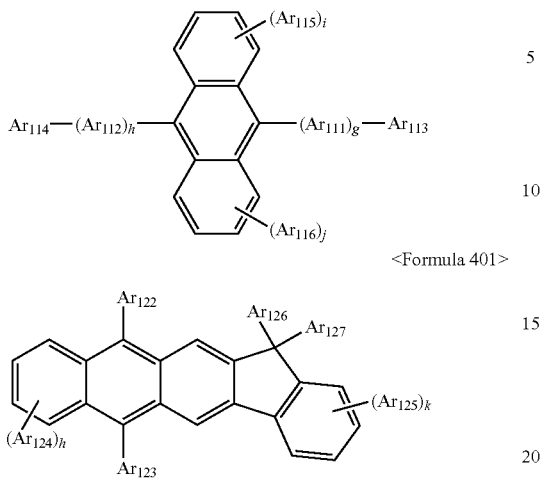

<Formula 400>

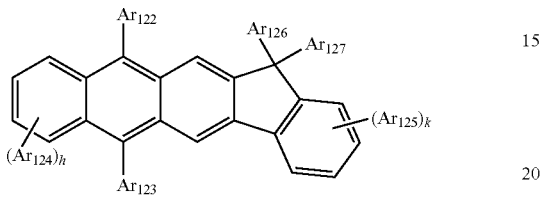

<Formula 401> wherein, in Formulae 400 and 401, $Ar_{111}$ and $Ar_{112}$ are each independently a substituted or unsubstituted $C_6$-$C_{60}$ arylene group;

$Ar_{113}$ to $Ar_{116}$ and $Ar_{122}$ to $Ar_{125}$ are each independently a substituted or unsubstituted $C_1$-$C_{10}$ alkyl group or a substituted or unsubstituted $C_6$-$C_{60}$ aryl group;

$Ar_{126}$ and $Ar_{127}$ are each independently a $C_1$-$C_{10}$ alkyl group; and g, h, i, j, k, and l are each independently an integer of 0 to 4.

* * * * *